US010519519B2

(12) United States Patent
Kouwen et al.

(10) Patent No.: US 10,519,519 B2
(45) **Date of Patent: *Dec. 31, 2019**

(54) **PHAGE INSENSITIVE *STREPTOCOCCUS THERMOPHILUS***

(71) Applicant: DSM IP ASSETS B.V., Heerlen (NL)

(72) Inventors: Roelof Hendrik Matthijs Kouwen, Echt (NL); Pim Van Hee, Echt (NL); Douwe Van Sinderen, Carrigrohane (IE); Brian McDonnell, Cork (IE); Jennifer Mahony, Cork (IE)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,700

(22) Filed: Jul. 2, 2018

(65) Prior Publication Data

US 2018/0305777 A1 Oct. 25, 2018

Related U.S. Application Data

(62) Division of application No. 15/119,708, filed as application No. PCT/EP2015/053601 on Feb. 20, 2015, now Pat. No. 10,041,135.

(30) Foreign Application Priority Data

Feb. 20, 2014 (EP) .................................... 14155872

(51) Int. Cl.

| | |
|---|---|
| ***A23C 9/123*** | (2006.01) |
| ***C12N 15/01*** | (2006.01) |
| ***A23C 19/032*** | (2006.01) |
| ***C12N 1/20*** | (2006.01) |
| ***C12R 1/46*** | (2006.01) |
| ***G16B 30/00*** | (2019.01) |
| ***C12N 1/04*** | (2006.01) |
| ***C12Q 1/689*** | (2018.01) |

(52) U.S. Cl.

CPC .............. *C12R 1/46* (2013.01); *A23C 9/1238* (2013.01); *A23C 19/0323* (2013.01); *C12N 1/04* (2013.01); *C12N 1/20* (2013.01); *C12N 15/01* (2013.01); *C12Q 1/689* (2013.01); *G16B 30/00* (2019.02); *A23Y 2240/75* (2013.01)

(58) Field of Classification Search

CPC .. C12R 1/46; G06F 19/22; C12N 1/20; C12N 1/04; C12N 15/01; A23C 19/0323; A23C 9/1238; C12Q 1/689; A23Y 2240/75

See application file for complete search history.

(56) References Cited

FOREIGN PATENT DOCUMENTS

| | | | |
|---|---|---|---|
| WO | 01/07566 | A2 | 2/2001 |
| WO | 01/16329 | A2 | 3/2001 |
| WO | 01/70990 | A1 | 9/2001 |
| WO | 2004/085607 | A2 | 10/2004 |
| WO | 2008/108989 | A2 | 9/2008 |
| WO | 2011/092300 | A1 | 8/2011 |

OTHER PUBLICATIONS

Dupuis et al., Nature Communications 4:2087, pp. 1-7, Jul. 2, 2013.*

Mills, S. et al., "Crispr Analysis of Bacteriophage-Insensitive Mutants (BIMS) of Industrial *Streptococcus thermophilus*—Implications for Starter Design", Journal of Applied Microbiology, vol. 108, No. 3, pp. 945-955, Mar. 1, 2010.

Mills, S. et al., "Efficient Method for Generation of Bacteriophage Insensitive Mutants of *Streptococcus thermophilus* Yoghurt and Mozzarella Strains", Journal of Microbiological Methods, vol. 70, No. 1, pp. 159-164, Apr. 24, 2007.

Larbi, D. et al., "Different Bacteriophage Resistance Mechanisms in *Streptococcus salivarius* Subsp. Thermophilus", Journal of Dairy Research, vol. 59, pp. 349-357, 1992.

Allison, G E et al., "Phage Resistance Mechanisms in Lactic Acid Bacteria", International Dairy Journal, vol. 8, No. 3, pp. 207-226, Mar. 1, 1998.

Labrie, Simon J. et al., "Bacteriophage Resistance Mechanisms", Nature Reviews Microbiology, vol. 8, No. 5, pp. 317-327, Mar. 29, 2010.

Giedrius, Gasinunas et al., "Molecular Mechanisms of Crispr-Mediated Microbial Immunity", Cellular and Molecular Life Sciences, vol. 71, No. 3, pp. 449-465, Aug. 20, 2013.

Klieve, A V et al., "Phage Resistance and Altered Growth Habit in a Strain of *Streptococcus Bovis*", Fems Microbiology Letters, vol. 80, No. 2-3, pp. 155-159, May 15, 1991.

International Search Report of International Application No. PCT/EP2015/053601 dated May 8, 2015.

Andersen, Astrid B. et al., "Storage Stability of Freeze-dried Started Cultures (*Streptococcus thermophilus*) as Related to Physical State of Freezing Matrix", Lebensm.-Wiss. u.-Technol., 1999, pp. 540-547, vol. 32.

* cited by examiner

*Primary Examiner* — Delia M Ramirez

(74) *Attorney, Agent, or Firm* — McBee Moore Woodward & Vanik IP, LLC

(57) ABSTRACT

Bacteriophage Insensitive Mutants (BIMs) of three *Streptococcus thermophilus* parent strains were generated and characterized for phage sensitivity, sedimentation rate, cell chain length, phage adsorption and CRISPR loci alterations. Several BIMs showed an altered sedimentation phenotype as well as an increase cell chain length, reduced phage sensitivity, reduced phage adsorption and 100% identity in three CRISPR loci. The results show that the derived BIMs have become phage-resistant through a mechanism other than CRISPR.

20 Claims, 9 Drawing Sheets

Specification includes a Sequence Listing.

Tube A Tube B Tube C Tube D

Tube A Tube B

A

B

SEQUENCE LISTING

```
<160> NUMBER OF SEQ ID NOS: 25

<210> SEQ ID NO 1
<211> LENGTH: 34580
<212> TYPE: DNA
<213> ORGANISM: Streptococcus phage
<220> FEATURE:
<221> NAME/KEY: source
<222> LOCATION: (1)..(34580)
<223> OTHER INFORMATION: /organism="Streptococcus phage" /mol_type=
      "unassigned DNA"

<400> SEQUENCE: 1

ggttcgaatc cactatgagt cattaattcc agaaagtttg gaggtgataa cagcgtaact      60

gtcgctataa ttcaaattct ttattcttgt agcttgtgag ggttcgactc cctcgctcgc     120

tgttagtctg tcatgactag gtaatttttt tgacactcgc atcgctgaca gaccgatgca     180

caaacccagt aaatatttta tagaaacgag ggaaccaata catacttttt ttagtccagc     240
```

-continued

```
cttgcattgc tggtagcaag actggaattt aaaataaagg gggtgataaa aggaccaaga    300
acaaacactc ttatcttttc atgaaacctc ttaatgtttg tttattggtt taaaaaacaa    360
aaaagaccga cataatggcc ggcactcttt gaaagtcaac actactatta taccagagag    420
ggcagaacaa tgctattgcc ggaaattgat gagaaagcaa caatcaaacg ttgcaagcgc    480
aaacttcgag aatatccacg ttggcgagag attgcacacg acggagctga gcagaaaata    540
acacaggaat tcacatttat gccacggggt ggtagtggaa tgagtagacc agtggaaaat    600
attgcagtta ggcgtgttga tgcaatgaac gagctagaag ctatagagca agcagttagc    660
ggtctatatc gtccagacta tcgcagaata ttgatagaaa aatatctaga gtttccaccc    720
aaacccaact ggcagatagc tcaatcaatc ggctttgaac gcactgcatt ccaagagctt    780
ttaaacaact ctatcctagc tttcgcagaa ttgtatcgtg atggtcggtt aattgtggag    840
cgttgaaaaa aatggtattt tagcggaatt ttaacggtct ctattaactg ttttaagtgg    900
tattattata ttatcgaaga agaaagaaaa gacggctcat ttgtgggttg tctttttttg    960
atcaagtaat gaaggaggtg gacatattgg gctaaatcaa cgacagaaaa tatttgcgga   1020
tgaatacttg atttctggca tagcttacaa tgcggctctt aaagctggat attctgaaaa   1080
ttactctaaa actagagctc ataaattgtt agaaaatgac agaattaagg cttatatcga   1140
agaacgactg aaagagcttg agaagaagaa aatagcaaaa caagacgaag ttatgcaagt   1200
cttcacttcg attctgaggc aggaactcgt ggaagaagtc gtagagctaa atgccgctac   1260
aggtcagttt gtcaagacta aaaaaccccc gtccatctct gaggtcatca aggcaggaag   1320
cgaactcatg aaacgctatc caacagctaa gcaagctgag aaactagagc ttgagatgag   1380
aaaactaaga gaacagcttg atagcggtat tgaaggcaca atgaatctca acattgtcaa   1440
caagtgggag gatatcccag atgataacga ttgatattca gaaaaacgtc aacccacatt   1500
ttaaatcggt ttggcagtct aacaaacctt acaacgtctt aaagggaggt cgtaactctt   1560
tcaagtcctc ggtcatcgct cttaaacttg tctatatgat gattaagtac atagcaaagg   1620
acgataaggc aaatgtggta gttattcgga aagtagctaa cacaatccgt gacagcgtgt   1680
ttaataagat tcaatgggcc attagtatgt ttggactaga gagtcagttt agagctactg   1740
tgagcccgtt taagattgtt cacaagcaaa caggttcgac attctatttc tacggacagg   1800
acgatttcca gaaactgaaa tcaaatgaca tcgggaacat tattgctgtt tggtatgaag   1860
aagcggctga gtttaccagt gctgaagact tcgaccaatc aaatgtcacc tttatgcggc   1920
aaaaacacga gaacgctcaa tttgtgcaat ttttttggtc atacaaccca cctcgaaacc   1980
cttatagctg gataaatgag tggtttgaag aaatcaagac aaatgataac tatctaacgc   2040
attcaagtac ttatcttgat gatgaattag gtttcgttac tgatcaaatg cttgaagata   2100
tagaacgtat taagcagaac gactatgatt attaccgtta tctatattta ggtgaagcgg   2160
tagggcttgg taatcaagtg tataacatga gtacattcca tgctatcgat agcttaccga   2220
cagacgatag acttattggt atatcttttg caatggacac agggcatcaa caatcagcta   2280
cagcttgctg tgcttatgga ctaactgcaa agggcaatgt gattctgtta gatacgttct   2340
attacagccc agctggtcaa gttgttaaga aggcacctag cgagctaact gtcatggtta   2400
gcaatttcat tgataaggta cttaataaat accgagttcc taaactacgc atgaccatcg   2460
atagtgcaga gggcgcattg aggaatcaat atttcaaaga ttttggcgaa cgatggcatc   2520
cagtagctaa gaagaagaat cagaccatga tagacatggt taccagtctg ttagctgagg   2580
```

-continued

```
gtcgattcta ctaccttgac attccagcta ataagatatt ctacgaggag cataaaatgt   2640
atcgatatga cgagaagacg atacatacag acgatccaaa agtaattaaa gaggatgacc   2700
actgttgcga ctctatgaaa tattttgtct tagacaacgc tagagaacta gatttgaaag   2760
cttaaaggag caactaatgg gaatcataca gaccattaag aactttataa aaaggagcaa   2820
ttacgtgata actaaccaaa gtttaaacag tatcacagac catccaaaga ttgctatctc   2880
acctgaagaa tacaaccgta tcatggataa tctccgatat tttgctggag atttcgacag   2940
tgtaacttac cgagatagta acgggtcaca agttaagcga gacttcaacc acttgcctct   3000
tggacgtaca gcttcgaaga aggttgctag tctggtattt aatgagcaag ctactattcg   3060
agttgataat gaagttgccg acgcttttat caatgagaca ctgaaaaatg acaaatttag   3120
caagaacttt gaacgctact tagagtcatg tctggctctt ggtggtcttg caatgcgtcc   3180
ttatattgac ggtgatcaaa taagagtgtc gtttgtgcaa gcaacggtat tctttccatt   3240
gcgagcaaac actcaagacg tatcaagtgc tgccattgtc actaaatcga taaaaacgga   3300
agggcagaaa gtaaaatact acagtctgat tgaatttcat gagtggaaca aagagactta   3360
cacgataagt aatgagcttt atgagtctga atccaaaacc attatcggtc aacgtgttcc   3420
tctatcaaca ctctatgaag atttagaaga gactgttacc ctaaacggac ttacaagacc   3480
actatttacg tatttgaaac cgcctggtat gaataacaag gacattaaca gtcctttggg   3540
cttatctatt ttcgacaacg ctaagactac tatggacttc atcaatacca cttatgacga   3600
attcatgtgg gaagtcaaga tgggtcagcg tagggttgca gtaccgactc aaatgattaa   3660
gactgagtat gatacaaacg gtgagaaggt cacagtcaaa cgtgagtttg agactggtca   3720
caatgtttac gaacaattcg atagcggtga tatggataaa ggaatcggta ttactgatct   3780
tacgacagat atccgctcag acgattacat taaagccatt aacaaaggac tcagtctatt   3840
tgaaatgcaa ctaggtgtgt ccgctggaat gtttagcttc gacggtaaga gcatgaagac   3900
tgctactgag gtagtgtcag aacaagcaga cacatatcaa atgcggaact ctattgctac   3960
tcttgttgag aagtcattaa aagagcttgt aatttcaatc ctagagcttg ctaaagtcta   4020
caatctctac actggtgaga ttccaacaat ggatgaagtt agtgttgatt tagatgatgg   4080
tgtattcaca gaccgaaatg ctgagtttga ttactggtct aagatggttg ccgctgggtt   4140
tgctccaaaa acgatggcta ttgaaaagac actcaacgta acaaaagaac aagcacaaga   4200
gatttaccaa aaaatcaatg atgaaactat ggtaagcact gatagtttta ggacaagtga   4260
agaggttgac atctacgggg agtgataggc tatgactaag aaaaaaccta tcaaattaaa   4320
cgaccaacaa ctaacgcttg acgctagtag agtagctgac atctatcatc aactaaccgt   4380
ggaattattc gaccaagtaa ttgatcgagt gagagaacgt gggacagcaa gccttgaaga   4440
aaatccctat ctttggcaac tcgaaaaaat gagtgagatg ggattgctca acaatgctaa   4500
tattaagctt attgcagagt attctgggat tgctgaagaa caattgagat acgttatcga   4560
gaacgaagga tataaggtat ataaggacac caagagtcaa ctgatagagg atttgggagg   4620
taaaaacgac ttcattacaa acaaccttat tcaaaccagt ctagcaaact acgtcaatca   4680
aacgatggga gatattgata accttattaa tactactctt ccaaagagta tcaggaaagt   4740
ctatcaagga atcgttgagg agactgtggc taaagttgta acaggtttag aaacacctca   4800
aaaagctata tcaacaactg ttatcaaatg ggctgataaa ggcttctatg gttttacaga   4860
taagcaaggc aagcagtgga gagctgatac ttacgcaaga acagtcatta actcgacttc   4920
ttggcgtgtc tatcgtgaag caagaacggc accagcaaaa gaattgggaa ttgatacatt   4980
```

-continued

```
ctattactca atgaagccag cggctcgtga aatgtgtgct cctatccagc ataaaattgt   5040
aacgtttgga aagtcaaggg ttgaagaagg agagaagatt tattctcttt tagactacgg   5100
atatgggagt gctagtggat gccttggtat taactgccac catacattga cgccatatat   5160
tgtaggtgtt aactacaaaa ctgaacttcc cgaacacctc gaccacataa caccagaaga   5220
ggcgatagag aacgccaacg ctcaatctaa acagagagct atagaacgct ctatcagaaa   5280
gtctaaagag cttcttcatg ttgctaacaa gctagatgat gacgatctaa taagcaaata   5340
cagagagcaa gttagaaaac aacaagcagc aatgagagac tatctgaaac gacatccatt   5400
cctatataga gattattcga aagagaggta ttacgatgat ccattcaatc aagctaaagc   5460
agaaatcgaa atgcggaagc ggagaaaaaa gaaaggtgat gatccaaaat cttgactgat   5520
aggaattaga ctatcatgac ctgccaaacg tcgtaaaact gggcaaatta agtccaccgg   5580
acgtaaaaca aaggagtttt aaacatgagt ttgaaacgtg atatgttagt tgaagctggt   5640
attacagata agagtgtgat tgacaatatc atgcaagcgt acggtgcagg tattgagaac   5700
gctaaatcac aagctaagtc tgaattacaa gctgaaaacg aaagccttaa acaacaactt   5760
gagcaacaaa gccaagcact caatgacttg caagctaagg aaggagcgag cgaagaactc   5820
aaacaacaat tgacggactt acaagctaaa ttcgacactt acaagtcaga gtatgaagca   5880
aaccttgcta aagttactaa atcaaatgct attcgtctag ctttgaaaga cgtgaacgct   5940
cacaattcag atgaccttgc taaattcatc aattttgacg aaattgaact tgatgaagct   6000
ggtaaaccca aactagacaa agtcgttgaa gagttgaaga caacaagccc atatcttttc   6060
aagcaagaag aacaagcatc acaacctaaa atctttgccg gtgggaatcc cactgctagt   6120
cagagcggac ttaccaaaga agatttcaga cgtatgggta tcaatgagcg tcaagcactc   6180
tttgataaag acccagagtt atatcaaaaa ttgaaaggat aattttaaat gacaacaggt   6240
attacaacaa ctgcacaggt gatcaatccg caggtaatgg ctgacatggt ttcagctaaa   6300
ttgcctaaac taatcaaatt cacacctcta gcattcatcg acactaatct agtaggtcgt   6360
ccgggtgatc aacttacagt tcctcaatgg acatattcag gagatgctac agatatcact   6420
gagggaactg caattccaat tgaccaattg ggaactaaag tgacacagat gaaaatcaaa   6480
caagctggta aagctattga aatcacagac aaagccgcct tagtcggaca tggaaatgtc   6540
tatggtgaag ctaccaacca gattgctttg gctattgcta acaaagttga caatgaccta   6600
gttgaagttg ctaaaactgc cactcaaaac attgctgaag cccctgtttc agttgcaaat   6660
atcgataaag ccttgtcagt atttgcagac gaagaagatg ctcgctatgt ggctcttatc   6720
aaccctaaag acgctatcaa attgcgtgct gatgctggac aaaactggct caaaggatca   6780
gaaattggag ctgaagctgt agtgtctggc actttcggtg aagtttctgg tgtgcaaatc   6840
gtccgcacta agaaagttga tgaaggaaaa ggattccttg ttaaaatttc ttcacttcaa   6900
acagatacag atgatgacgc caaatatggt gcattcgtca tcgctttaaa acgtgatgtc   6960
atgattgaaa acgaccgtga cattttgaaa aagacaactg tttattcagg cgatgaatac   7020
tacggtgttt atctctacga cgactctaaa gttgttaaat tcggaggtgc ttaatgggaa   7080
tgctaatgcg tcgtcattac agcggcgata aagcatcacc cgataatgac gttcaaaaac   7140
aatcgtctga aacgctagaa gacaagactg tcgctgattt gcgtattatc gcacagcaac   7200
gtggtctcac tggcttttca acacttacta aagcggagct tttagacctc ctaaaatgac   7260
gaaaggaggc ggttgaatga catatttaac caaagaagaa tttctaaaac ttggtttcga   7320
```

agacgtagaa gactttgaaa aactattagc tagagctagt ctcactattg atttatattt 7380
aaaaaacttc tacgatttta atgattttga aacggacttt gaccaacgca agcaatcggt 7440
caaaaaagca gtagcttatc aaattgctta cttagattcg agcggtttgt tgactgctga 7500
ggataagacg tcgttgtcaa gcatgactgt tggacgtact catgtaagct atcagaacgg 7560
ttctaaatcg tcccatgatg gaaaacggtt caatctatcc cttgacgctc taaactggct 7620
gacattagct ggatttggct gtaaggcggt ggactatgat agataagcgt atgttagttg 7680
atgctgtcac tatcaagaag ttgacgggag aaacggatgt ttggggaaaa gtaacatatg 7740
atgagcccac aaccctaaaa cccgttagat ttgatagaca gttcaatgtt agcgggtcaa 7800
ctaacaatcg taacgaatcg aagcccagta ttttatttgt ctatccgaaa tattgtccag 7860
tggttcttga cgaaagcttt gaaaacggat tgattaatga cggaaaacga gattataaga 7920
ttcgttccat tattccagtt tattatccaa gacaaaataa agtgttttgc tatgaaattg 7980
aggtgatcta atgggaacta cagtatcggt taaagttgac cttcatggtc tcgaaaagaa 8040
atgcagtccc gaagcggtca aacgtggaaa agttgctatg attggtcaaa tgattactga 8100
tatggagcca ttcatccctc gtagagatgg aactttgagt gctagcggtt caccttttag 8160
cgatggcatt agatatccgg gaccttatgc aagagctcaa ttctatggat caagttacaa 8220
caaaaataga agcttcgttt tcaggaatta tactacgccc ggaactggta aacgttggga 8280
catgaaggca tctgctaaat attctaaaca atggggcgaa gtcgctttaa gagctatggg 8340
agttaaataa tgaacgacaa cgatttttca gaagttctcg caaacttcat caacacactt 8400
ggactaccgt taaaatgcaa acttgattat ctttcagaaa acgagagtct ttcagtctat 8460
ccattgcctg gtgggaaggt tgaagacgaa gacatggctg gcacccagat tctatcacta 8520
ccttatgaga tagcgattaa atcaaaggat cagcaaaaac taaatgctat tctttggaaa 8580
attaacacag aactttccaa aattggattc gagttaccaa gtttaaataa ttcttacact 8640
tttatatcct tgaccgtcga gacaccgagc ctaaacgatg ccgacgagca gggtttttat 8700
atttacttgc ttgatttaaa tgcaagatta gaagtagaaa ggaactttaa ttaatggcta 8760
aatttaaaaa cgctattcga aaacactata tcgcacctta cgacccaaag aatccagata 8820
aagtcccaac agacgacaaa tatatgtgga ttgctaaagg tatcaaagag tctgctccag 8880
aaaacgacac agaagacgat gatgtagcat attttgatgg tgatggcact aaagaaacgg 8940
ttatcacttc aaaatctcgc ggtcgctcat ttgaaggtca tcgtgactat gatgataaag 9000
ctcaaaactt tgtcgttgac aaagaagacg cattaggtga tgaccttatt gtttggtaca 9060
aagaagtagc tgcagatggt aagacttaca aagaaggtct tgctcgactt tctgaaattg 9120
aggttggtga cggtgaagct tcagagcttg aaactattaa atttcaagtc aactggtcac 9180
gcacaccaga gaaacacgaa gtcgctccat caactactgt tcgtacagtt gcatcttcac 9240
cgggaatcgg tggataatca ctaaattaaa taaattaaat agaaaagata agacaactaa 9300
gagggtgggg gtttgccctt accctctttt tttcgtaaag gagaacaaac atggtagtaa 9360
ttaaaaaacg tagcaatgtc atccccgtcg atttcggtga gtttaaactt gagtttcctg 9420
tatctgatag caatatcaaa cgtatgaagg cagttggtga ggacttgcaa gccaaaggga 9480
aagcgttcca agaaacaagc gatgaagaag ctcttggagc gttgaaagca ttggtagaag 9540
atggctttaa tcaaatattt gacgataaag aagcctttaa tcaagtctat gcgtttgctg 9600
gcaattcaac aattaatgct atgttctatc tgattgaagc catcaaaggc atttctgagg 9660
aatttgaaaa ccaaaactca aaagctgccc tcgataagta tttgaatgat tgatttatca 9720

-continued

```
cgaaaactaa cagataagtt agttattgat gataaagagt acgcccttga cttgtccttt   9780
gacaatattt tgaaaatgtt tgaaatgatg cgggatgatg atattcctga atacatcaaa   9840
cctcatttag ctattcggat gctgattagc aaaagcctag ttggtaacac tagagaggaa   9900
aaatcagaat catttaacaa agcttttgag aattactcag tagaagagat gtcaaaagtg   9960
ttcaaatcag tctttgagga gcatatcagc ttatccgatg tcgaggacaa tcatgttgag  10020
tatgacttgg ctggtaatcc tatgaagaca acagcaagca atgacacgaa gcagagagca  10080
ccatatgaca tccgatatga tggtgactat atctattcgt cattcttaca agcatacggc  10140
attgatctat tcgatgcaca aggtaaactg cattggcgaa aattcaacgc tctactgtct  10200
gggctaccag agggaacgaa gttgatggaa gtcattaaaa ttcgcaaatg gaagccacaa  10260
aagggcgact cttcagaata caaagaggaa atgcgtaggc ttcagaaaga ttatgctctc  10320
cctaacgatg ttatcgagga agaagaaaat gaagaagaat tttagaaagg agggataatc  10380
tatggcagat ggtacagtca ccatcaaggc gttatttgat ggtaaagacg ccgaaagcgg  10440
tgcacaacgt attaagagct cgctagaagg tttaaaaggt tcagctggta aggttggttc  10500
ggtgtttaag tctgtactcg gtgctaactt ggtcggtagt gctatcatgg gaggtattag  10560
tgcccttggc aatggcatga agtcaatggt tggtgagttg aataattcag ctaaggcatg  10620
gaagaccttt gaaggcaaca tgcaacaaat taacattcca accgaccaga taaagcaggt  10680
taaaagcgag ttgcaagact atgcaacaaa aacagtctat tcagcttccg atatggcttc  10740
tacatactca cagctagcag ctgttgggac aaaaaaataca actgagcttg ttaaaggttt  10800
cgggggactt gcggcagcag ctgaaaaccc ccaacaagcc atgaagacct tgagtcaaca  10860
agcaacacag atggcagcta aacctaaggt tcaatggcaa gatttcaagc taatgatgga  10920
acaaacgcct gctggtattg ctgcaattgc gaaagaaatg ggcatgagca ctgctgaaat  10980
ggtgcaagct gtccaagatg gcaagattaa gaccgaggat ttctttgatg ccatcgcaaa  11040
ggtcggtaac aacgaaactt tcagcaagat ggcgacagag ttcaagactg ttgaccaagc  11100
aatcgatggg atgaaagaat ctctagcaaa taagctaatg cctcagtttg aaaaactcaa  11160
tcaaataggt ataaaggcag ttgttggtct taccgacgca atcgaaagga ttgacatcaa  11220
cgccattgcg gacaagattg gcagtggatt gtcttcgctt tggaaaggtt tctcaaacac  11280
gggagcttta aagaaccttg gtgcgacctt taattatata tcaaaatcaa tcaagcaact  11340
atttagcaag attgatggta gcaagatcat gcagggcatt ggctcggtgt ttggcgatat  11400
tgcaaacggt atctcacaag ctctaaacat tgctacgaca tcggttaaaa atttcataaa  11460
atcatttgct gatactggag catttcagtc atttaaagct gctgttcaag acacttggaa  11520
cgccattaag actatcggtt catcattcgg cgaagtactt ggtagctcac aaatgcagtc  11580
aatcatttca ggtattggat cagctcttgg aacgcttgta aactggatat ctcaagccat  11640
ttcagcagtg tctaagtttg tcagctcatt accgccggag gttctaaacg gtatcaccag  11700
tgggattttg gcaatggtag caggttttgc tactgccaag gctggtattt cagtattagg  11760
tgttgcaatg aaagggttgg acttcatcaa tagtttaaat cctttcaaga agtttggaaa  11820
ggacgctgca gaaggaactg aacaagctgc caagagtgct aaacgttcta aatcaactat  11880
cactcaatta ttcagtggga tggccaatgt cattaaatca acagggacta gcatttcaac  11940
agctacaaaa ggcatcggaa cagggctatc aactgctttt aaaggctttg gccaaggaat  12000
taaatcagct ttacaaggtc ttaaagggtt gaaccccgca accttgctat catttggtgc  12060
```

-continued atccgtagct atcgcagcag tcggaatcgg tgctggtatt ggtattatcg ttgcttcatt 12120
cactttgcta gccactcaat cccaaggcgt ttctcaaatc ttaaacgctt tgggttcagc 12180
atttagcaca gtcgtccaag gtattggcaa agctgcagga actatcattg aagcattcgg 12240
aactgctttt ggaattgtcg tcaaggcagt cggtgaagct gcgcccggac ttgcacgatt 12300
atctccattg gttgaagcta tcggcactgc tctaggcaat gcagcaccat ttattacagc 12360
atttggtaat gcttggactt ctattttagg aacgtttcca gctattatca gtgcatttag 12420
tggattagca accgctatcg gtactgcaat tagtgcagta gttaccgcaa ttactccaat 12480
tattcaaatc attggaaata caataacagc agtaactcaa atcatcgcta acgctattat 12540
tgcaatcgct ccggtaatag caaactgcat cattcaagtt actcaagtaa ttggtcaatt 12600
cggaccacag attgcaatga taatcagtgc tatcactcaa gcgatagcag cttcagcacc 12660
tatcatcata tccttgattc aaggtattgt tacagtcgtt cagcttatgg ctccggtcat 12720
tagtcaagtg atctctgcca tcattgcggt tgttcaaacg ttagcaccta tcatcagtca 12780
aatcatttca gcgattgtta cagcgataac acaaattgtg cctattatca cctcaattgg 12840
tagtgtgatt agtgctgcat tgagtggtat cgcatcggtt gtgtcagctg caggaatggc 12900
aattgctacc gcagctatgg gtatcggtac ggctattagt acggctctaa gtggtgtggc 12960
tagtattata agtgctactg gtgctgtaat tggtgcagcc ttgcaaggta ttgctagcgt 13020
ggttcaatca gttggaacat caatcagtac agctgctcaa ggtatcggaa acggtattaa 13080
gtcagcgttt gaaggcattt caagcgtgat tacttccgca ggcaatgcaa tcagtagtat 13140
attgaatagc cttgctaatg tattcaactc aattggtaca gctgctcaaa aagcagggat 13200
tggtttcaat cagttagcaa atggtgtggt taagattact aatacaaatc tcggtgacat 13260
ggctgcatct cttgcagcag tggctcatgg tattggttcg attggggata actcagcagg 13320
gcttgctcaa gctggttctg gtatggctca acttgggaat ggtatgagca aagtgtcaac 13380
atcagcggct agcgctgttt caggattgag tcttttctca agcatgatta caagtattca 13440
atcagcgttt actagcttac agtcaatgct aactatcgca ggaacagcgt tcagcacgtt 13500
ctcaattcaa gccatgcaat cactaactgg attgtctgct attgcagtac ctatcacaat 13560
cttccaaact cagattatga tgatagtgcc agcattaatg caagcaacag caggattaac 13620
tatgttcagc gcagtagcta tggcattagc aactagcttg acctcaattg gtgctgtcat 13680
gactatgttg actaccaaca tgactatgtt agctacacaa ctaacaatga taacaacaag 13740
cttcacgatg attgctaata gctcagctat gctaggaaca agcttcgtta tggttggtac 13800
atcgctaact atgttgaata gtcaatttat gatgtttgct acaggaatca tgcaaatgac 13860
atcacagctc atgatgtcag gtgcagcggt agctatgttt ggtgctcaac tcattgcagc 13920
acaaactggt ttcagtatgg tttccatgat ggctactatg gtatctagtc agcttgctat 13980
gcttactagc tcggctcaaa ttgcaggagc tggatttgca acagtaagtg ctcaagtcat 14040
gatgcttgct agtgtattcg ctaccgttgg agcgtcagca atgacactac aatctgcaat 14100
ggtgtcatta ggtatggcag taagaactgg cattatgtca gcggttcaat cggtaatgtc 14160
aggttctatg caaatgactg ctgctctacg ttctagtgga actcaaatga ttgctattac 14220
acaagcctct atgaatcaaa tagttacggt ggtgagaaat ggcatgaatt caatcgttgc 14280
tgcggtaagg gttggcggtg gtcaaatggt ttcagcaatg cagtcaagcg gacagaaatt 14340
agtggtaatt actcaagcag cggttaacca agcagccgca gcagcgagat caggttacgg 14400
tgctttctac tcagcaggag cttacatggg acaaggtctt gcagcaggta tgaattcagc 14460

-continued

```
tcttggatcg gttacagcag cagctaacca actggtagca caagctgaaa gagcggcaca  14520
agctaaagcc aaaatcaact caccatcaca cctattccgt gacgaagtcg gttggtggat  14580
tggtcttggt attgctcgag gtatcgacga atcagctcca gaggttgcga acagtctcga  14640
ttatatccgt gaacaagtca acggattcaa tgttcgagct aacgccatgc taacgggtgc  14700
cacttcaaat atggctagtc agttgaagat ggaagtactc agagataaaa ccccagacgc  14760
tacgatttca gcacgtcaag aagcctatgc tgcacattca gccggtttgc ttagtgatgt  14820
gattgatgct cttggagaac tcaaatacca agtagcacaa ggtcaaaaca tggtattaga  14880
taccggtact cttgtcggtg gcacagttaa taatttcaac agtgctatcg atacgattaa  14940
aacattgaaa ggacgtcaca gattatgatt actaaaatca aagaatatat agcgtttggc  15000
gattttaata gtcgtgacgc tggttggtac ttacagaaac gtgaagcacc aacgccaggc  15060
gagaaagaga ttgtcgagtc tatcccttac atgcaagggg agcttgattt ctctagtgtt  15120
cttggtgagc gtgtctttga gcctagagag attacatacg agtttaagtt accgtttaaa  15180
gagtacgaag accgtaagac agcagagcgt atgattaagt ctcaaatggt cactaaaaca  15240
gaacagaaac tgtttgatac gcatgataga cgttattact ggatgggcaa ggttaaacac  15300
atcaaagtag cagacgatcc tattaagaag aatctggtag ctaccattgt ttttaagtgc  15360
tatccattcg cattccacga agatgaatac tttgatgatg tttgggatac attcgatttt  15420
aataacgatt tttcagtgtg gacaaagtgg gaagtttcag gagaaaaaag tatttatttt  15480
gtaaattgtg gagacacatc tattagccca aagattaaat gtagtagtaa tttcaatctg  15540
attgatgaca atggaacaat ttataacttt aaaaaaggtg aaaatacaga tttcacctta  15600
attttaaaac ccggagtcaa ctattttact gctcaaggag atggctatat atctatgcat  15660
ttttctattg aggtaatggc atgacaaatt taaaaagtgg aggatttgaa gtttatcact  15720
ggccaagttt taatgataga ctatcagata aattatctaa aaaaactatt catagacagg  15780
ttatccacga accgtattca cgaacagcga ataaagtttt atcaggtcag attactcaag  15840
ctttgaatgc aatacatgaa tttactttta caattccaat gactaatccg ctatatcaaa  15900
atatagtacc ttttcaatca attattgaag tagttaatct tagagatggt gaagttgaat  15960
ttaaaggacg tgtgctagct atgtctaata agatgacaag aaatggcttt gttcaagaag  16020
ttatctgtga agattttcta tcattctttc atgattctag tcaatatttt caaaagctaa  16080
gaaatgaagg aactagacca tacttagaag aaattttaag agtagcaaat agtcaggtag  16140
agccttacaa acggatagcg ttaggtaatg taactgtcga aagtaggact gatagacctt  16200
atcggtattt agggtatgaa actacatggg atacaattcg ggagcgtata attacaagta  16260
taggagggta tttaacgcta cgtgaagaaa atgatggctt ttatttagat tggactgcag  16320
atgtaggaga aactaaaaaa agccctatcc aattgggtag gaatatcaaa tctgctagcc  16380
gtgatattga ctttgatggt cttgctactc agattatgcc aattggcgct gatcttgata  16440
cacaaggaag tcaagaagaa caaggtcatg atgtaacacg cgctcaattg gatatttcaa  16500
gtgttaatgg cggtaatata tggcttcaag atgatgagtt agtaaaacaa ttcggaatta  16560
ttcgtaaacc tgtcatttgg acagaaattg atgaccctaa tattttattg gctcgtggaa  16620
aacaatactt gagagatcaa aaagtttcat tagctaaatg gacagtctct gtagttgaaa  16680
gatatctgat tgatgatcgt tatgggaaat tcaaaatcgg taataaacat cctattttaa  16740
atgccccaat atccgatata gcgacattac agataataga gaagaaaata gatatattga  16800
```

-continued aacctcaaat atctgaattg acgatagggt ctcagtatca atcattatat gaatatcaat 16860
tacagttgcg tgaagcaaca aagtctatcg ctaaattgaa ggaagattct tcagttgcga 16920
ataagcgaaa acgattagag agcttaaaat atcaattaga tagcttgaaa aaagatactg 16980
aaacaccacc agttagaccg tctgcaccaa ctccgctatc agataaagca accgatgcag 17040
aacgttctgc atatgaacaa tctttatatg tttatgaaat tgcaaaaacg acatatgaag 17100
aacatctggc tacttataat aagaaccaag aagaaaaagc aaaaactatt tcaaatcttg 17160
agtctgaaat tgctagattg caacaagaac taaagggagg taattaaata tgcaacaaac 17220
agaagcagag ggacgtttga acctctacga tgatgtgacg ccgttggaaa aaaccaaaaa 17280
cattaatgtt ttgacagcgg ctatcagaaa aaaaacaaga ggggcagatg tccgtgaagc 17340
catcgctacg tctattgaaa cgacttacgc agatagtatc gctaacggaa ataccaacat 17400
ggaagtcgct aaggcaagag gaacatataa tactctagga gatagacttg aaaattttga 17460
tactgaaatc aggaatattg taagttgttc accaaaagga atatatgcta atctatcaga 17520
gctacaatcg gctaagccga acggagattc cggaatctat ctcacaacag acaacggcca 17580
ttggtactat tatgctaacg gttggaaaga tggtggcatg tatcaggcgg cggggattgc 17640
tgatggaagc gtgaagtttt cttcaatcga taaaaaagat tttaacgttc agtttgaccc 17700
gaaattgaaa gtcgtatata agccaaattt aaattcttgg atgaatgcag ataatcccac 17760
cgagaacgcc acaaaaattt atatgattcc atttagaggc gcaggcaaag tgaccgttag 17820
tttttatgga tccctgtttc ctggcgtaaa atcgcaaata aagttagtca aaaaggctac 17880
taattcaagt aattattgtg tgtctctcaa tgaaaaaacc ataactgaaa cgacagaagg 17940
cggatataca acaattacgt tcaatcatcc agttcctaaa ggcgaatatt ttatcgcttt 18000
ttgtggaatt aatttcagat ggaattttgg atatagttat tggttagaaa gctcttcagg 18060
ttacaatcag tcgatttttt tacaaagaaa gacagaaaat agatgcatag atgctgttat 18120
tgcttgtgat ttttctgttg attctagcgg tgagaaatta ttagacgaaa atatgcactt 18180
tgattcaggt atattttcgt ttcacactga acctatttta tatattccta attacgaatt 18240
gcctatcgga acaaaatcta taattcttgg gactaaaaac aatacacctg ttttcatttt 18300
tagaaaaaat gaaaataata cgtttgaaaa aataaaacaa atatacacag aagaaatagg 18360
tgaaggagca cgttatagaa aatacttttt agacattgtt gctgaaaaag atatgtatgt 18420
cggagttttt ggaaatgttt attatgatac ttctggtgat gtttctgcaa agaaaggaca 18480
tttcgaaaaa gatatttcgg cttcagattc tgaaaatata gggtcaatgt atttcaatcc 18540
acatacaaat attcacatgg ttcctatttt atattatgat gaaaatttaa ttaatgttgc 18600
acaaaaaaat gcgaattcat ttgaggaaat aaatggatcg ctaattgata tcaccaataa 18660
aataaataaa ataaataaaa aaacaataac attaacaaac ataatcagaa aaatgaaaag 18720
agggaatgca gtcactattt cgctttacgg agactcaacg tactatggtc ataagtcagg 18780
cgctgtccct ttaggcacta gaacaagcga gcctgtttct gaaagtttgc aaaaatatct 18840
acgtgcttat tttttgaacg aaaatataac agtaaacaac tatgcaacta acggaagaca 18900
agcacaacaa gattcagatg attgggacac aaaaatggct aatgacaaag cggacgttat 18960
ttttataaat ttcgggataa acgattcaaa ttccggtaaa acagcagaaa ctttttacag 19020
tcaaatggaa actttagtac aaggtgcgct gaaaacgaac aaagcagtca tcttagaaac 19080
tgctaatcaa gtcttaactt ttgacaaagg aagtcaaggg atgggagact atacgaaagc 19140
ttttaacatt aaagaatttg ttgatgtaac aagacagtta gttaagagtt ataatattta 19200
tttgcttgat ggatataaac gttcattaag ctacattaac gaatttttta atcccacaat 19260
agctttgccg gacggcatgc atccgtcaga cgatatgtat aagtataaag ctgttcaaat 19320
gatgtctatg tttactaata cgagtttttc aaaattaaaa tcaggacaga cattatctat 19380
tttagaagct aattttaata caacaacacc aaattcagta gcggatagca gttctaaatt 19440
cggttttaaa tatacggtta aagacatctc ggtatcattt ggactagaaa aacaatcaga 19500
tattaaaatt tatatcaaaa gcacagcatc aatgaaagtt tatgttaatg gtttagatac 19560
tcaatatatt agctctgatg gatatatcgt aataaaaaat attcactcta acgatgtatt 19620
cattcagatc acttcagacg aagcgacaga tgtttatggt ttagaagtgg tttaaacacg 19680
atcattgagt gtgctttttt tagaaaagat tattttgagc gctagcttac tattgcaata 19740
tacagcttat gcggctgtcg gcgcccaagt gcaaaaattt cttgatttat ccatacagga 19800
ttgcaagatg acaatactgc tgaataagct tagaaagtga aatttatgtt gaatcctgaa 19860
attattagaa tgattcttag tatatcttta tcattgttaa cgctatttac atttttccaa 19920
agtcgtatga ctttaacaga aaaacgttta acgattcttg aagagaataa taaacaacaa 19980
gataaacgac tggcagaaaa caaatctata ttggataatc acgatcaaca aatgaaagtt 20040
cttatccaaa tgaccgaaca aatcaaaaat ttgtcggaaa aaattgaaaa aatcgataac 20100
aaattggagg aagtcaaatg attaatttaa aattacgatt acaaaacaaa gctacattag 20160
tagctctcat ttcagcagtg ttcttgatgc tgcaacaatt cgggcttaat atcccaagca 20220
acattcaaga aggtattaat acattggtta ccatcttggt tattcttgga attgttaccg 20280
acccaaccac taaggggatt gcagacagcg aacgagcatt gaactatgat gtaccactaa 20340
acgaaaagga aagaaaatag tatgagcgta caacaatcta ttgtaaattg gtttgttaac 20400
catcgaggca aattgaccta ttcaatgtat gggtcacgca acggagcaga cggtacagct 20460
gactgctctg gttcgatttc gcaagcctta aaagaagctg gtattggtat tcaaggacta 20520
ccatcaacag taacccttgg tcaacaactt gccaaaaatg gattctatcg agtaagtatt 20580
aatcaagatt gggatgcttt gacaggtgat attgtgttaa tgtcatgggg tgctgatatg 20640
tccacatctg gcggagctgg agggcacgtt ggtgtcatga tggatgctac atactttatt 20700
agttgcgatt attcaactca aggggcacct gggcaagcta tcaatactta cccgtggaat 20760
gactactatg cagcgaacaa gccttcctat atcgaggttt ggcgttattc tgattcagca 20820
ccacagacga ataaccaagc aaatacagca gtagcaccac aacaaaaggc ttactatgaa 20880
gccaatgaag tcaaatatgt taacggtatc tggcagatta agtgcgacta tctatgtcca 20940
attgggttcg actgggttaa ctaattttcg gctcagtata aactaagtga acgcaaacaa 21000
agcggtgtca tgcaaaagca tggctaacgg tggacaccca gaacgggcaa taccgtgcca 21060
agtctggtat aatagtatca gaaaggtgta acgactatcc ttttgaggag tacactcact 21120
atttgtacgc gagtggaagt gcttagactt tagaaagatg gtgtcataag atgagtaaaa 21180
ccaaacgtgg cgtttgtgcc aattgtcata cagtatttga agtttctaaa aaacaaagat 21240
ataaaatcaa aaacggtaaa tcggtttttt gttcccaaac ttgttcttta gaaaaatacg 21300
gaaaaactaa aattactatt tctgaaattc ctttaagtat gacagaaaat atctaaagta 21360
agatatagtc taatcccact aggaatagtg ggtagtaatg agaaaatggg atcccagtag 21420
acatggttaa ctgggtggat gctaacggta atgatattcc agatggcaag tctgaagatt 21480
tcaaacctgg aatgttcttt agttttgcag gtgatgaagt caacatcaca gacacaggag 21540

-continued

```
aaggtggcta ttatggtggc tattactacc gacgtttcga gtttggtcag tttggtacgg  21600
tttggctttc ttgttggaat aaagatgatt tggtaaacta ttaccaatag accacgcaaa  21660
ctaaaaaata aaaaaggagt atatcacctc acctcacact gcagtaggga taccatggca  21720
gtagtggtcg aagccccagc ataatgctga ggcttttttg tttgcttttt ttaaaataaa  21780
tgctactata ttaatgaata cagttaaaag ctgagtcttc gataaactct ctctcaccct  21840
gacttgaatt agtcagggtt tttgttttgc aaaaaaatat atattttttt ataaaaacag  21900
tttccgtctg gtcaccaaaa tagactagaa tggattgaga gcaacttgga aaacattcga  21960
taaaaaataa aaaaacgagg taaaaacaat ggatacatac aaagaacaat atatagtatg  22020
ttttactaat tttcaagtaa atatataata aaatcaaaaa aacttaaaaa aaatcaagaa  22080
aactgttgac attgaatttt atttaagcta taatatgttt gtaagttagt taggaaggag  22140
gaacaaaaat gatagaaaca gttccaaaga ttacaattaa agaacttcga gcacgtcaca  22200
atttgacaca agaggaattt gctaaaagtg ttggtacgtc agcacaaaca gttagtgctt  22260
gggagaaaaa ccgactttca atttctccta agttcatgtt agccatttgt aaaaaataca  22320
accttaaatc gtctgatttg tatggatttt gattttaaaa cttgaattaa attcaagtta  22380
gaaaggaaca agatgaacga aatagcaaca aatgatttcg actactcttt gctcgatgca  22440
aagacaaaag aattcttaga agagcgtgcc aatatcattt acggcatcca aagcaagagt  22500
gcttacgaaa ttggaaaaca acttgccaaa gctcaaaaag agctttcgac tagaggttat  22560
ggttgcttcg aagaatggta tagaagttta gggtttaaaa aaaccaaagc ttatgaatat  22620
atcaatcatt acaatttcgt ttgttcgcaa aacgaacaag caaatattga aaaattcgaa  22680
agtttaccaa aagtgttgca agcccaagtg tctaaaccat ccgccaatcc agaggttaat  22740
caagcagtat tcgacggaga tatcaaaact cacaaagaat acaaagagct tgagcgtcgc  22800
ctaaaactca aagaccaagc actagaagcg gtcaagggag agttggaacg tgtcaaacaa  22860
accaaaacta ctgaaaagat aatcgaaaag gaagtcattc cgcaagatta caaagcaacg  22920
caagacctca acaagcaatt gctaggaaag aataaagacc tagcggaaga gcttgattca  22980
gtcaaacgta gcttgcgact taaagaagcg tcttatgaaa tgctcgaaaa ggaaacatca  23040
gaggcattag ccttgaaaga gtctattgag cacttacgag ctgataaaga aaagctagaa  23100
aacagcgtta ctaatatctt taacctaagc aagctcgtaa ctaagtttga aaacttcttt  23160
gacgaagaaa tggcaccgct tagatttaaa acccttatcc aaggcattgg aaaagacgct  23220
cagattgaaa aactcagaga tatcttgaca ctaactgaaa attggctaga cgaaatgaac  23280
aagattatcc cagaagacgg aagaacaatt atcgaaggag aaatcataaa tgagtaagaa  23340
gaaatataag aaaaaagaaa atctactcgc tgaaacagta gaaatgcaga agaaacaagc  23400
tatgaatctg gttgctcaaa gcaccgttaa ccaacagctt ttggaagaaa tcatcggaat  23460
taaggaagaa atggacagaa atgttaaaaa gacaaatcaa aaactcactg acattgagtt  23520
gcttgttgag gaagtcaata agaaagtcca tattgacgat ggtgaagctt ctaaaatcaa  23580
gagtattgtt ttcaaaaaag ctggcgtgtt cgcagatatg tacttcgata atcagaaatc  23640
aaaccctagt gataatctgt ttgcttcaaa gaaaggccaa tttattcgct tgatgtactc  23700
acatttgaag aaagcattta acgtgactaa gtacactaac atcaaacacg ttgaagctga  23760
gaaggcggtt aaattcttgg aaagtctatc ttatgacgat ttcacaccgt ttgaaatccg  23820
tgagacacca aagcaaaaag aaattatagc tcttgaaaaa aatgagtgac tgaaagcatt  23880
ataacgtgga agtttcaata aaagataaaa aaactttaaa aaatagaata aaattgttga  23940
```

caaaataaaa aatatgattt aaaatagaaa cataaagtta agaaaggaga gtttgatgga 24000
atttaaatac gataaattaa aaggacgtat caaagaaaaa tacggaactc aagaaaattt 24060
tgcaaaagct atcggaaaaa ctcaaaccac aacatctttt aaaatcaatg gaaaaagatt 24120
gtggaatcaa gatgaaatca ttaaagctat tgagctatta gaactttcaa aagatgatat 24180
tgttgaatat tttttcaact actaatacaa cttgaatgat atagagagga atcaaaaatg 24240
aaaaaactat ttaattttat ttggtcaaac aagcaaacag aaacacaaga agttccaaaa 24300
tggacttttg aaaaaaatgc atctgagcct agccgtgatc gatacaacaa gattcacgga 24360
ttaggaaaga cattaattta aactaactaa agctgtttca gtccgtagcc aaccctcggt 24420
gtgcggagtg caactaaata ccttataccc caaaaataaa tataaataaa agccaaaact 24480
accttcttat gaaattgaat attaacgaag cacgtcgggg gctgggtgcg gattgaagca 24540
ctaaaaaaca cgggtaattg cccgtgtcgt ataaaaatct aatgatatta tactatgaca 24600
tttaaacaaa aaaagcaact ggagagggtg agtctaaaat gtctgataat caaaaatact 24660
attatatgag gctcaaacaa gacttctttg agacggaaga aatgataata cttgagtcta 24720
tgcaagacgg ctatttgtat agcaacatct tgttgaaact atatttgaga agtttaaagc 24780
gtgacggtaa attgatgttt aacgacacaa tcccatacag tgctgaggtt ttagctacag 24840
ttacacgtca cagcgtcgga acaatcgaga aagctatgga tgtcttccaa aagctaggac 24900
tagtcgaggt aatggatgac ggagctatct atatgttaca aattcaggaa tatataggca 24960
aaagctctac tgaagctgaa cgaaagaagc gttatcgaga tagaatcaag ttcgaaaaac 25020
gtgagaaaaa tgaggctttg gaaaatttgg gacatttgtc caccaaagaa gtgggacatt 25080
tgtccggaca ttcgtccacc agagatagag atagagatag agatagaata gatataaaga 25140
cagaagtaga agtagaagag agaaatggac agatgtcttc tgctactgct gctgataatt 25200
ctaatttgaa tatctttgaa tattatcaag aaaggattgg actactagat ggattccaac 25260
ttcaaaaact agaagagtat caaattatcg atggaattga acctgaatta atcaagatag 25320
ccattgataa agcagctgat aactctaaac gttcttttgg gtatgttaac tctatcttga 25380
aatcatgggc tcaaaatgga atcaagacag tagctcaaca acaagaggaa cagaataact 25440
acttttctaa caagccaaac agcgataaac ctaagtttgg tccagcttgt agcaaatact 25500
aaaggggttg actatgagtt tagaaaagac agctaagcaa atgagacaga tgtatatgac 25560
tactagtgat aaatactgcg agaagcacaa tcgaaacttt gtcactattc agctaccaaa 25620
cagcaagcca tacactgtat gtgagacgtg ccatcgtgaa gagcaagagc gacagaattc 25680
tattaaagca caagaacagt ttgagcgtga gcaagagcag aagcgtctct acttcctcaa 25740
agatttcagc ttactggatg acgatttaaa aactgccagt tttgacaact acaaggcggt 25800
aaccagagag cagaaagaag acttgaaaaa tgttagaagt caacttaaag gctatctaga 25860
cggacaagaa tacaacattg tcttaatagg agacacagga gtaggcaaga gtcatctagc 25920
ttattcagcg ctcaaagcct tgtccaatca tacgaaaaag atggggctat tcatcaatgt 25980
tgttgaccta ttagccaaaa taaaagagga tttcaccctc gaagctgaat atatcagacg 26040
aatttccgaa gctgaatggt tggtgttgga tgacttagga actgaaaaag tgacagagtg 26100
gtctaacggt atcttgtaca gcattttgaa caagcgcaca aagacaatca taacgacaaa 26160
cctaagccca caggacatca tgggcacata tggtaaacgt gtatattcaa ggatttttaa 26220
gaagacagga cttggaacta ctaacgaaca cgtttacaag tttaaaacac agcaagacaa 26280
gaggatgatg ctatgacaga aacagaagtt aaactaaagc tctttgagga ctacgagagc 26340
attcatggac ttgtatactc ggaggaatat aagcagaaaa tgatggatga gctagatact 26400
tattcattca taagtaaaat gaacgaattg atgtacaaag ctaagaatcc aattcaggtt 26460
tttagcgtac aataaaaccc ctctaaaatc gattttaagg cgtgtatttt gctctatagt 26520
acaaatatac taggatacat ttaaaattgc actacacccc cttaaattga gaattagggc 26580
atatgaaagg gaaatgatat gaagaatgaa ttacaaagta caaaaggaga gtatttgacc 26640
gacttgcaac atcttgatgg cgaaacgttg aggaatttcg tcgatcccaa acatcaagca 26700
agtccacaag aactccaaac attgctagca atcgttaaga accgcaatct taaccctttt 26760
actaaagagg tctatttcat taagtatgga aacaatcctg ctcaaatcgt agtatcaaaa 26820
gacgcattca tgaagcgagc tgaacaaaat ccgaattacg acggatttga aagtggcgta 26880
atctacgagg atgaaaaagg tgagcttaaa actaaaaaag gtgtaatctt gccacgcaaa 26940
ggaacattaa ttggcggttg gtgtgcagtg tatcgaaaag atagaagtcg tccaatatat 27000
cgtgaagttg aattgtcagc ttataacacg cataaaaatt ggtggcagaa agcacctggt 27060
caaatgattg aaaaggtggc aatcgtggca gccgttcgag atgcattctc cgagaatgtg 27120
ggcggtcttt acactgcaga tgaaatggaa caagctgcac ctgtcgacgt tacacaacga 27180
gaaacgcaag aggatgttaa gattcgtaaa atagcacaag ttgagcaata cagacaagag 27240
caatctcaac cagttcaatc agagccagaa ctagttgaag acgtagctga agctgaagaa 27300
caacaagaag tcaatcctaa tttcattagt atcgagcaac atgacattat cgagaaacaa 27360
atcaatgaat tagctttaat cacgggaaag ccagccgaaa cagtagctaa ttactatttg 27420
aataagtaca aactcaacga ttttcatgaa ttacttgtgt ctggatttga aattgtgacc 27480
aacgacattc aaacacagat aaataataga aaggcgaact agatatgaag gatataacaa 27540
acaattttat tgaaacaatc gagccagtat atacgccggg aataattagg tttgattttg 27600
acaaattcga tgcagctatc caagcggcag ttagcgaatt atcagacgaa caactagaca 27660
atcttgaata taacgatatt aagaatgaat ttacacgttt caacagcttg ctgacgaaac 27720
ttgaaactaa acgaaaagaa attgcgaaag tttataaaaa ccctttgaca gagtttgaat 27780
ctaatttcaa gtcatctaaa gagccactca aagaaattat tgacaaattg cgtgccaaac 27840
gagatgagat tgacgaacat catagaatgc tacgagttga ccacgttaga tcggtctttg 27900
aagaaaagtg tgagcttgca gggttggaca aagatgcttt caaggacaag tacgacggct 27960
attctttgaa gaagtgtttc aaagacaaaa agatggaact caaaaaagaa accatcgaag 28020
aaatcgacgc tttgatttta gctgaatacg accgacttga agaatacaag gccaacattg 28080
caatgattga ggaacaagcc cttgattatg agttgccagc ggaacattac actagagcgt 28140
tgcagaacga cacacctata gttgaaatat tgaagcaaat gaaaaaagat cgtgatgcag 28200
ctattgaacg caaacagcaa gcagaagcta aacgacaagc ggaagctgag cgccttgcag 28260
aaattgaagc gatggctaaa cagtcagcta acgaggagat taaggcggta aatgctgaaa 28320
caggtgaggt tatcgaaaaa tcaaaacaag cagatgaaac tccaatcaaa ccagttgagc 28380
catataaaat cgatatttct ctaaccttcc acggtggtga aaagcaatgg catcaatttg 28440
ctaaattatt ggaagataac tttataaact atgaaatcaa aggagaaaac aaatgatgaa 28500
ctcagtatgt ctagttggtc gcatgaccaa agatgcagaa ctaaaataca ctgggaacaa 28560
tatcgcagta gcatctttca gccttgcggt taaccgtaac tttaaggatg ctaatggtga 28620
gcgtgaaact gactttatca attgcgttat ctggagacag caagctgaaa acttggctaa 28680

-continued

```
ctgggctaag aaaggagcat tgattggtat tactggacgt attcagactc gtagctatga  28740
aaatcaacaa ggtcaacgtg tttacgtgac tgaagttgtt gctgaaaact tccagatgtt  28800
ggaaagtcgt gcagcgcgtg agggtggtaa tgctaatgtt ggttataatc aaccacaaca  28860
gcaagcacca aactttgcaa gagaaagcgg accttacggg aactcaagcc ctatggacat  28920
cagtgatgat atgctaccgt tctaatttga ggagggttta tggatattaa agaaataaag  28980
gggtatgagg ggctatatga agcacattcg gacgggacga tttggtcttg caaaaataaa  29040
acaacatata gctttgtaag gggaaagaca ataaaaaggg tttgggaaca aagagagata  29100
aaacctcaga tagcaagaag acaaaggagt gatcactacg ataagcgagt gaaattgtgg  29160
aaaaacaaaa agatgacaac tcacctagtg agtaggttga ttgctcagac ttttatacca  29220
aacccagaaa acaaaggcta cgtcaatcac aaaaacggca accctttaga caactcagta  29280
gagaatcttg agtgggtgac aaggtcagaa aacatgagac atgcgttcaa aaacggtttg  29340
ttacaaacaa gtaaaaaagt cactctagta agcaaggcag acggggcaaa ggtaagcttt  29400
tacagtctaa gagctgccag cgagtttcta ggtaaaaaca agggttattt gagcaatatt  29460
ataaaaagcg gaagaacgct tggtaattac gaaattgtgg taggtgaaat atgaaactag  29520
aatttctatt accaaggtca aaaactaaac ctgctcaaaa tttagttatc aacagtaatg  29580
acagatttca ttatcaagca gagggccgga tggtcaagaa actgcgattg atagcgaaag  29640
cagaagcggg gcttaacacc aagccagtat atagccctga taagccttgc aaggtgcttg  29700
taactgtcta cgcaccaacc agaagaagat tagacccacc aaacctatat ccgactgtta  29760
aagctattat agatggcttg acggacgcta atttgtggcc agacgacaac cacgaagtta  29820
tcaaaatgat gtcgtttcag tatggcgggc taagtggtga gtctgggaaa tttaagattg  29880
tgttagacat tgaggaaacg ttaaatgaaa agcaaagtta aagacaaact ggtcggtata  29940
tatgctccag caagctacgg acatacaagt gtgttagagg agacacaaga gttttcgaag  30000
tggttctggg aaaaccacaa agatatagat tttatcagct caaagttaga aattagcact  30060
aagaaattaa atcgcatcct aacgctggag cagttaccag atgaggaatt attgaaagag  30120
atgatagagc tatgcgaaat aaagaatacg ctttgtacaa aggcgaagaa atcatagcta  30180
tgggtacaaa acgtgaaata gctgaacagt taggaatttc agtacacgcc gttacttgct  30240
atgggacacc atcatacgcc agaagaacta gcgaaaacgc aaggagatta gtagagttat  30300
gaaatataaa attatcgtct attacgacaa tatggaagac gatgtggaaa cttattacag  30360
caaggatgaa gcaatcaaaa gactgcatca tttgagaggt gttaaatata ggaattcgag  30420
aatgtataca gtagagatga aagaggaagc agatgaataa acaggaagca attagatcac  30480
taaaggaaat ggctcaagag tcgtttgaag ttgtaaaaat aaatgcagtg catattgaca  30540
atatcgtgga agtcataaac caaatagacg aaccgcagaa agtgactata cctaagtttg  30600
tagcggagtg gttggaagag aacgactggc gaaaagatac attgggaagg caaactatct  30660
ttgacgcttt cgacaatttg actctggacg caagcaatgg attatatgtt gacgtaaaaa  30720
aatgggtcga agagaacggg aacatttttt tacaagcgtg ggtctttggc tacgaggttg  30780
agaaggagaa gctgtataca gcgaggttaa aactacttag ttttaaaaag tacagctata  30840
ttaataaaaa taaagataaa aaaacactat gtttatctga ttcagatgat cttacagatg  30900
tgtatcaaac tcattttacg caagcagaac ttgaaggact tggtgtttgg gataacccag  30960
catttgaaat cgaagaggtg gaagcatgat tagaacgaag tatttagtaa ccagaagaag  31020
```

-continued

```
caggttatac atcgaggaaa ttgatgaatt gattaatcgt tttttcgaag aaaacccaag  31080
tatagaactc attgatatta aatatcagtc aaatatatca gccgtagcta atggaggagt  31140
aagtgctact cattttaaca actcagcgct ggttatttat aaagaggtgg aagatgaata  31200
aaaaagaagg aatcggaaaa tataaagtag gtcaacaagt tgcaatttgc gggtttatcg  31260
aagaaataaa tattgagaat ttgcgagata tagaaaatac tactcatcta gtaattaata  31320
cacttactag gacaattgat gttaatccaa aatatgaaac agtcataaca gacatcaaca  31380
aacctaaacc agtagtgcca caatatgttg ctgattggta tgaggaacac aaggataatt  31440
taaatgagtc aatttgggag catctcgtta attgggacga cgcaaattgg gatgatttcc  31500
accgctggat gtcccagcct gatgtgaatg gggttatcac tactctagtc aatatgcatc  31560
aatttagcta tgaggttgag gaagagatta gatatacagt gagaattaga aatttaaacg  31620
ttgaaaaccg tttcttgtct tataataatt tcaatgataa gtggttattt agtgaacgat  31680
atatttcaaa tgatcgcttc aggataaccc acacacgcaa agagctagaa gaaggtggat  31740
ttggctgggt atttgattgt gaaggtattg aagttaagga ggtatgatag atgaataggc  31800
ttaaagaatt aagagaatta cgaaaaatga caagagttga gttatccgaa aagattggtg  31860
tgacaaaatt gaccatcctt aattgggaac atggcaccca tgaaatcaaa ggaagtaatg  31920
ctaagaagtt agctgattat ttcaatgtat caattccata cttgctaggt tacgataccg  31980
ataacacatt ctcggaccta gttgccaaga ttaacgagtg ggcggacgaa cgcaatttaa  32040
agcaagctga ccctaagatt cagtggatgc gtatcacgga agaagtcgga gaaattcggg  32100
atgtactctt gaaaccgact aaattcaatg aaccacaaac agcactcaag gatgcaatag  32160
gagacacgct agtaacgatt atcgtgttgg cacatcaatt agaccttgat gtcactgagt  32220
gtttaaatat tgcatataga gaaattaggg accgaaaggg aaaaatgata aatggaacgt  32280
ttgttaagga ggaagacctt tgaaatttct tgacttattt gcaggtattg gcggttttcg  32340
tcttggaatg gaaagtgcag gacatgaatg tgtaggtttt tgtgaaatag acaaatttgc  32400
tagagcaagt tataaagcaa tccataacac tgaaggagaa atagagctac atgatgcaac  32460
aggaatcaca aagaaagaaa tcaaagcaat cggacaagtc gatgttatct gcgcaggatt  32520
tccgtgtcag cctttcagcg ctgctggtgc aagacgaggt tttgaagata caaacggaac  32580
tctcttcttt gaaatcgcaa ggttcgcttc cattctcaaa cctaagtatc tattcctcga  32640
gaacgtcaag gggcttatta gccatgataa agggtacacc tttgagacaa tcatcggatc  32700
gttggatgag ttggggtatg atgtcgaatg gcaagtgctt aacagcaagg attttggagt  32760
cccccaaaac agagaacgag tgttcattat cggacatctt agaggaacaa gtggaagaca  32820
aatatttcct atcgctgaaa caagatcaga taaatcaatt atgcaactag gaaatatcaa  32880
aaaaaccgaa agttttggtg gaaatcctca atgcggaaga atttacagca tagacggatt  32940
agcgccttgc ctaaatacga tgcaaggtgg acaaagagaa cccaaaatcc ttattgacgg  33000
taaggtacgc aagctgacac ctcgtgaatg ttggagattg caaggattcc ctgattgggc  33060
ttttgataaa gcacaagaag tcaattctaa cagtcagcta tacaagcaag ctggtaatag  33120
cgtgactgtc aatgtaatta aagaaattgc gaggtattta tgaaacataa ggatctaacg  33180
atagccacaa ttctactact ggtctcgcta gcgattaacg tgactactgt tctgcgagtg  33240
gttaatagac ctatcgagac cgtggtgatc cacaaggcag ataatgcagt ggaactacac  33300
ggcaaggtta ctggaaaatc tacggttggc aagctctaca cgatcgattg tggggcgcat  33360
ggtaagtttc tagtgacaaa ggaacaatac gatagtgtca gtgtaggtga tgatattcca  33420
```

agctatttga aaggaagagg acaatgaagt acgtcgagta cgcaggactg accaaagaat 33480
tacattcaag gttcgtggtt gaatttaaca atttgaaaga gcaacaccat agaacattaa 33540
caaagtacgt gatggaaaca aagcagtgcg accgattgca agctagaaaa tattgtcaaa 33600
gatttgataa tgtgatcaaa gagcgttcta agttatcacc cgcgacatta aacgatatgc 33660
gtgagtatat cactgacgga ctcgcaaacg acttagagaa ctatctgtca aaacactgtt 33720
ttagtagctc cgcaaagtgt cggccagata ccgacaagag aaatgctgga ctgcctgagg 33780
aactctttaa acagtattgc gaggaaatca aatcattaaa agctaaatac ccaaacagct 33840
tcaccgccta catcatggat gttaaagggt gcaaatatca aaaagccaat aacatacgga 33900
cagcgataaa tacaatctat acagagattg ggataatgac acctcgcaag gtaatccaac 33960
ttgaaggtct tctatctaga gagctattcg gtaagatagc gaagtacgtc tttaataagt 34020
atgaatggcc agaaagccta gatgaagagg ttaatagaat ctttttagag tatcgcacaa 34080
aaggtaatct aggcagtgac aaagaaagtg ttaaacgtgt gttatataaa gcgatttata 34140
tgggcttata gcggtctttt gtatttggtc taaataaagc agtcaacaca aaattaacag 34200
aagatgaagg agaaatagat gaaaaaaaat aaatatactt tgccagaagt aataattgcc 34260
atatgtgtac tgtttccgat ttccgttgtt ttatcaggat ttactattac ttatggctgg 34320
aacaatattt tagcttcaat tgcaggagtc cctaaaatta caattattca agcaattggt 34380
ttatatgtcc ttgttagttt tattgtcagc agtggacgtg actcagcagt ggaaaatttt 34440
gttgaacttt gttttagagt acttttaaca cctgtcacta ctttactagc cttttggatg 34500
gtaacattat ttatgtgatg gatacgtgtt ttaaaactta taaattttta atttggtgcc 34560
cacgcttgga gctttaagac 34580

<210> SEQ ID NO 2
<211> LENGTH: 34932
<212> TYPE: DNA
<213> ORGANISM: Streptococcus phage
<220> FEATURE:
<221> NAME/KEY: source
<222> LOCATION: (1)..(34932)
<223> OTHER INFORMATION: /organism="Streptococcus phage" /mol_type=
"unassigned DNA"

<400> SEQUENCE: 2
gaagaaagaa aagacggctc atttgtgggt tgtctttttt tgatcaagta atgaaggagg 60
tggacatatt gggctaaatc aacgacagaa aatatttgcg gatgaatact tgatttctgg 120
catagcttac aatgcagctc ttaaagctgg atattctgaa aattactcta aaactagagc 180
tcataaattg ttagaaaatg acagaattaa ggcttatatc gaagaacgac tgaaagagct 240
tgagaagaag aaaatagcaa aacaagacga agttatgcaa gtcttcactt cgattctgag 300
gcaggaactc gtggaagaag tcgtagagct aaatgccgct acaggtcagt ttgtcaagac 360
taaaaaaccc ccgtccatct ctgaggtcat caaggcagga agcgaactca tgaaacgcta 420
tccaacagct aagcaagctg agaaactaga gcttgagatg agaaaactaa gagaacagct 480
tgatagcggt attgaaggca caatgaatct caacattgtc aacaagtggg aggatatccc 540
agatgataac gattgatatt cagaaaaacg tcaacccaca ttttaaatcg gtttggcagt 600
ctaacaaacc ttacaacgtc ttaaagggag gtcgtaactc tttcaagtcc tcggtcatcg 660
ctcttaaact tgtctatatg atgattaagt acatagcaaa ggacgataag gcaaatgtgg 720
tagttattcg gaaagtagct aacacaatcc gtgacagcgt gtttaataag attcaatggg 780

-continued

```
ccattagtat gtttggacta gagagtcagt ttagagctac tgtgagcccg tttaagattg    840
ttcacaagca aacaggttcg acattctatt tctacggaca ggacgatttc cagaaactga    900
aatcaaatga catcgggaac attattgctg tttggtatga agaagcggct gagtttacca    960
gtgctgaaga cttcgaccaa tcaaatgtca cctttatgcg gcaaaaacac gagaacgctc   1020
aatttgtgca atttttttgg tcatacaacc cacctcgaaa cccttatagc tggataaatg   1080
agtggtttga agaaatcaag acaaatgata actatctaac gcattcaagt acttatcttg   1140
atgatgaatt aggtttcgtt actgatcaaa tgcttgaaga tatagaacgt attaagcaga   1200
acgactatga ttattaccgt tatctatatt taggtgaagc ggtagggctt ggtaatcaag   1260
tgtataacat gagtacattc catgctatcg atagcttacc gacagacgat agacttattg   1320
gtatatcttt tgcaatggac acagggcatc aacaatcagc tacagcttgc tgtgcttatg   1380
gactaactgc aaagggcaat gtgattctgt tagatacgtt ctattacagc ccagctggtc   1440
aagttgttaa gaaggcacct agcgagctaa ctgtcatggt tagcaatttc attgataagg   1500
tacttaataa ataccgagtt cctaaactac gcatgaccat cgatagtgca gagggcgcat   1560
tgaggaatca atatttcaaa gattttggcg aacgatggca tccagtagct aagaagaaga   1620
atcagaccat gatagacatg gttaccagtc tgttagctga gggtcgattc tactaccttg   1680
acattccagc taataagata ttctacgagg agcataaaat gtatcgatat gacgagaaga   1740
cgatacatac agacgatcca aaagtaatta aagaggatga ccactgttgc gactctatga   1800
aatattttgt cttagacaac gctagagaac tagatttgaa agcttaaagg agcaactaat   1860
gggaatcata cagaccatta agaactttat aaaaaggagc aattacgtga taactaacca   1920
aagtttaaac agtatcacag accatccaaa gattgctatc tcacctgaag aatacaaccg   1980
tatcatggat aatctccgat attttgctgg agatttcgac agtgtaactt accgagatag   2040
taacgggtca caagttaagc gagacttcaa ccacttgcct cttggacgta cagcttcgaa   2100
gaaggttgct agtctggtat ttaatgagca agctactatt cgagttgata atgaagttgc   2160
cgacgctttt atcaatgaga cactgaaaaa tgacaaattt agcaagaact ttgaacgcta   2220
cttagagtca tgtctggctc ttggtggtct tgcaatgcgt ccttatattg acggtgatca   2280
aataagagtg tcgtttgtgc aagcaacggt attctttcca ttgcgagcaa acactcaaga   2340
cgtatcaagt gctgccattg tcactaaatc gataaaaacg gaagggcaga aagtaaaata   2400
ctacagtctg attgaatttc atgagtggaa caaagagact tacacgataa gtaatgagct   2460
ttatgagtct gaatccaaaa ccattatcgg tcaacgtgtt cctctatcaa cactctatga   2520
agatttagaa gagactgtta ccctaaacgg acttacaaga ccactattta cgtatttgaa   2580
accgcctggt atgaataaca aggacattaa cagtcctttg ggcttatcta ttttcgacaa   2640
cgctaagact actatggact tcatcaatac cacttatgac gaattcatgt gggaagtcaa   2700
gatgggtcag cgtagggttg cagtaccgac tcaaatgatt aagactgagt atgatacaaa   2760
cggtgagaag gtcacagtca aacgtgagtt tgagactggt cacaatgttt acgaacaatt   2820
cgatagcggt gatatggata aaggaatcgg tattactgat cttacgacag atatccgctc   2880
agacgattac attaaagcca ttaacaaagg actcagtcta tttgaaatgc aactaggtgt   2940
gtccactgga atgtttagct tcgacggtaa gagcatgaag actgctactg aggtagtgtc   3000
agaacaagca gacacatatc aaatgcggaa ctctattgct actcttgttg agaagtcatt   3060
aaaagagctt gtaatttcaa tcctagagct tgctaaagtc tacaatctct acactggtga   3120
```

-continued

```
gattccaaca atggatgaag ttagtgttga tttagatgat ggtgtattca cagaccgaaa   3180

tgctgagttt gattactggt ctaagatggt tgccgctggg tttgctccaa aaacgatggc   3240

tattgaaaag acactcaacg taacaaaaga acaagcacaa gagatttacc aaaaaatcaa   3300

tgatgaaact atggtaagca ctgatagttt taggacaagt gaagaggttg acatctacgg   3360

ggagtgatag gctatgacta agaaaaaacc tatcaaatta aacgaccaac aactaacgct   3420

tgacgctagt agagtagctg acatctatca tcaactaacc gtggaattat tcgaccaagt   3480

aattgatcga gtgagagaac gtgggacagc aagccttgaa gaaaatccct atctttggca   3540

actcgaaaaa atgagtgaga tgggattgct caacaatgct aatattaagc ttattgcaga   3600

gtattctggg attgctgaag aacaattgag atacgttatc gagaacgaag gatataaggt   3660

atataaggac accaagagtc aactgataga ggatttggga ggtaaaaacg acttcattac   3720

aaacaacctt attcaaacca gtctagcaaa ctacgtcaat caaacgatgg gagatattga   3780

taaccttatt aatactactc ttccaaagag tatcaggaaa gtctatcaag gaatcgttga   3840

ggagactgtg gctaaagttg taacaggttt agaaacacct caaaaagcta tatcaacaac   3900

tgttatcaaa tgggctgata aaggcttcta tggttttaca gataagcaag gcaagcagtg   3960

gagagctgat acttacgcaa gaacagtcat taactcgact tcttggcgtg tctatcgtga   4020

agcaagaacg gcaccagcaa aagaattggg aattgataca ttctattact caatgaagcc   4080

agcggctcgt gaaatgtgtg ctcctatcca gcataaaatt gtaacgtttg gaaagtcaag   4140

ggttgaagaa ggagagaaga tttattctct tttagactac ggatatggga gtgctagtgg   4200

atgccttggt attaactgcc accatacatt gacgccctat gttgtaggtg tcaactacaa   4260

gcccgaactt cccgaacacc tagcaaacat aacaccagat gaagcaataa agaacgccaa   4320

cgctcaatct aagcagagag ctatagaacg ctctatcaga aagtctaaag agcttcttca   4380

tgttgctaac aagctagatg atgacgatct aataagcaaa tacagagagc aagttagaaa   4440

acaacaagca gcaatgagag actatctgaa acgacatcca ttcctatata gagattattc   4500

gaaagagagg tattacgatg atccattcaa tcaagctaaa gcagaaatcg aaatgcggaa   4560

gcggagaaaa aagaaaggtg atgatccaaa atcttgactg ataggaatta gactatcatg   4620

acctgccaaa cgtcgtaaaa ctgggcaaat taagtccacc ggacgtaaaa caaaggagtt   4680

ttaaacatga gtttgaaacg tgatatgtta gttgaagctg gtattacaga taagagtgtg   4740

attgacaata tcatgcaagc gtacggtgca ggtattgaga acgctaaatc acaagctaag   4800

tctgaattac aagctgaaaa cgaaagcctt aaacaacaac ttgagcaaca aagccaagca   4860

ctcaatgact tgcaagctaa ggaaggagcg agcgaagaac tcaaacaaca attgacggac   4920

ttacaagcta aattcgacac ttacaagtca gagtatgaag caaaccttgc taaagttact   4980

aaatcaaatg ctattcgtct agctttgaaa gacgtgaacg ctcacaattc agatgacctt   5040

gctaaattca tcaattttga cgaaattgaa cttgatgaag ctggtaaacc caaactagac   5100

aaagtcgttg aagagttgaa gacaacaagc ccatatcttt tcaagcaaga agaacaagca   5160

tcacaaccta aaatctttgc cggtgggaat cccactgcta gtcagagcgg acttaccaaa   5220

gaagatttca gacgtatggg tatcaatgag cgtcaagcac tctttgataa agacccagag   5280

ttatatcaaa aattgaaagg ataattttaa atgacaacag gtattacaac aactgcacag   5340

gtgatcaatc cgcaggtaat ggctgacatg gtttcagcta aattgcctaa actaatcaaa   5400

ttcacacctc tagcattcat cgacactaat ctagtaggtc gtccgggtga tcaacttaca   5460

gttcctcaat ggacatattc aggagatgct acagatatca ctgagggaac tgcaattcca   5520
```

-continued

```
attgaccaat tgggaactaa agtgacacag atgaaaatca aacaagctgg taaagctatt   5580
gaaatcacag acaaagccgc cttagtcgga catggaaatg tctatggtga agctaccaac   5640
cagattgctt tggctattgc taacaaagtt gacaatgacc tagttgaagt tgctaaaact   5700
gccactcaaa acattgctga agcccctgtt tcagttgcaa atatcgataa agccttgtca   5760
gtatttgcag acgaagaaga tgctcgctat gtggctctta tcaaccctaa agacgctatc   5820
aaattgcgtg ctgatgctgg acaaaactgg ctcaaaggat cagaaattgg agctgaagct   5880
gtagtgtctg gcactttcgg tgaagtttct ggtgtgcaaa tcgtccgcac taagaaagtt   5940
gatgaaggaa aaggattcct tgttaaaatt tcttcacttc aaacagatac agatgatgac   6000
gccaaatatg gtgcattcgt catcgcttta aaacgtgatg tcatgattga aaacgaccgt   6060
gacattttga aaaagacaac tgtttattca ggcgatgaat actacggtgt ttatctctac   6120
gacgactcta aagttgttaa attcggaggt gcttaatggg aatgctaatg cgtcgtcatt   6180
acagcggcga taaagcatca cccgataatg acgttcaaaa acaatcgtct gaaacgctag   6240
aagacaagac tgtcgctgat ttgcgtatta tcgcacagca acgtggtctc actggctttt   6300
caacacttac taaagcggag cttttagacc tcctaaaatg acgaaaggag gcggttgaat   6360
gacatattta accaaagaag aatttctaaa acttggtttc gaagacgtag aagactttga   6420
aaaactatta gctagagcta gtctcactat tgatttatat ttaaaaaact tctacgattt   6480
taatgatttt gaaacggact ttgaccaacg caagcaatcg gtcaaaaaag cagtagctta   6540
tcaaattgct tacttagatt cgagcggttt gttgactgct gaggataaga cgtcgttgtc   6600
aagcatgact gttggacgta ctcatgtaag ctatcagaac ggttctaaat cgtcccatga   6660
tggaaaacgg ttcaatctat cccttgacgc tctaaactgg ctgacattag ctggatttgg   6720
ctgtaaggcg gtggactatg atagataagc gtatgttagt tgatgctgtc actatcaaga   6780
agttgacggg agaaacggat gtttggggaa aagtaacata tgatgagccc acaaccctaa   6840
aacccgttag atttgataga cagttcaatg ttagcgggtc aactaacaat cgtaacgaat   6900
cgaagcccag tattttattt gtctatccga aatattgtcc agttgttctt gacgaaagct   6960
ttgaaaacgg attgattaat gacggaaaac gagattataa gattcgttcc attattccag   7020
tttattatcc aagacaaaat aaagtgtttt gctatgaaat tgaggtgatc taatgggaac   7080
tacagtatcg gttaaagttg accttcatgg tctcgaaaag aaatgcagtc ccgaagcggt   7140
caaacgtgga aaagttgcta tgattggtca aatgattact gatatggagc cattcatccc   7200
tcgtagagat ggaactttga gtgctagcgg ttcacctttt agcgatggca ttagatatcc   7260
gggaccttat gcaagagctc aattctatgg atcaagttac aacaaaaata gaagcttcgt   7320
tttcaggaat tatactacgc ccggaactgg taaacgttgg gacatgaagg catctgctaa   7380
atattctaaa caatggggcg aagtcgcttt aagagctatg ggagttaaat aatgaacgac   7440
aacgattttt cagaagttct cgcaaacttc atcaacacac ttagactacc gttaaaatgc   7500
aaacttgatt atctttcaga aaacgagagt ctttcagtct atccattgcc tggtgggaag   7560
gttgaagacg aagacatggc tggcacccag attctatcac taccttatga gatagcgatt   7620
aaatcaaagg atcagcaaaa actaaatgct attctttgga aaattaacac agaactttcc   7680
aaaattggat tcgagttacc aagtttaaat aattcttaca cttttatatc cttgaccgtc   7740
gagacaccga gcctaaacga tgccgacgag cagggttttt atatttactt gcttgattta   7800
aatgcaagat tagaagtaga aaggaacttt aattaatggc taaatttaaa aacgctattc   7860
```

-continued gaaaacacta tatcgcacct tacgacccaa agaatccaga taaagtccca acagacgaca 7920
aatatatgtg gattgctaaa ggtatcaaag agtctgctcc agaaaacgac acagaagacg 7980
atgatgtagc atattttgat ggtgatggca ctaaagaaac ggttatcact tcaaaatctc 8040
gcggtcgctc atttgaaggt catcgtgact atgatgataa agctcaaaac tttgtcgttg 8100
acaaagaaga cgcattaggt gatgacctta ttgtttggta caaagaagta gctgcagatg 8160
gtaagactta caaagaaggt cttgctcgac tttctgaaat tgaggttggt gacggtgaag 8220
cttcagagct tgaaactatt aaatttcaag tcaactggtc acgcacacca gagaaacacg 8280
aagtcgctcc atcaactact gttcgtacag ttgcatcttc accgggaatc ggtggataat 8340
cactaaatta aataaattaa atagaaaaga taagacaact aagagggtgg gggtttgccc 8400
ttaccctctt tttttcgtaa aggagaacaa acatggtagt aattaaaaaa cgtagcaatg 8460
tcatccccgt cgatttcggt gagtttaaac ttgagtttcc tgtatctgat agcaatatca 8520
aacgtatgaa ggcagttggt gaggacttgc aagccaaagg gaaagcgttc caagaaacaa 8580
gcgatgaaga agctcttgga gcgttgaaag cattggtaga agatggcttt aatcaaatat 8640
ttgacgataa agaagccttt aatcaagtct atgcgtttgc tggcaattca acaattaatg 8700
ctatgttcta tctgattgaa gccatcaaag gcatttctga ggaatttgaa aaccaaaact 8760
caaaagctgc cctcgataag tatttgaatg attgatttat cacgaaaact aacagataag 8820
ttagttattg atgataaaga gtacgccctt gacttgtcct ttgacaatat tttgaaaatg 8880
tttgaaatga tgcgggatga tgatattcct gaatacatca aacctcattt agctattcgg 8940
atgctgatta gcaaaagcct agttggtaac actagagagg aaaaatcaga atcatttaac 9000
aaagcttttg agaattactc agtagaagag atgtcaaaag tgttcaaatc agtctttgag 9060
gagcatatca gcttatccga tgtcgaggac aatcatgttg agtatgactt ggctggtaat 9120
cctatgaaga caacagcaag caatgacacg aagcagagag caccatatga catccgatat 9180
gatggtgact atatctattc gtcattctta caagcatacg gcattgatct attcgatgca 9240
caaggtaaac tgcattggcg aaaattcaac gctctactgt ctgggctacc agagggaacg 9300
aagttgatgg aagtcattaa aattcgcaaa tggaagccac aaaagggcga ctcttcagaa 9360
tacaaagagg aaatgcgtag gcttcagaaa gattatgctc tccctaacga tgttatcgag 9420
gaagaagaaa atgaagaaga attttagaaa ggagggataa tctatggcag atggtacagt 9480
caccatcaag gcgttatttg atggtaaaga cgccgaaagc ggtgcacaac gtattaagag 9540
ctcgctagaa ggtttaaaag gttcagctgg taaggttggt tcggtgttta agtctgtact 9600
cggtgctaac ttggtcggta gtgctatcat gggaggtatt agtgcccttg gcaatggcat 9660
gaagtcaatg gttggtgagt tgaataattc agctaaggca tggaagacct ttgaaggcaa 9720
catgcaacaa attaacattc caaccgacca gataaagcag gttaaaagcg agttgcaaga 9780
ctatgcaaca aaaacagtct attcagcttc cgatatggct tctacatact cacagctagc 9840
agctgttggg acaaaaaata caactgagct tgttaaaggt ttcgggggac ttgcggcagc 9900
agctgaaaac ccccaacaag ccatgaagac cttgagtcaa caagcaacac agatggcagc 9960
taaacctaag gttcaatggc aagatttcaa gctaatgatg gaacaaacgc ctgctggtat 10020
tgctgcaatt gcgaaagaaa tgggcatgag cactgctgaa atggtgcaag ctgtccaaga 10080
tggcaagatt aagaccgagg atttctttga tgccatcgca aaggtcggta acaacgaaac 10140
tttcagcaag atggcgacag agttcaagac tgttgaccaa gcaatcgatg ggatgaaaga 10200
atctctagca aataagctaa tgcctcagtt tgaaaaactc aatcaaatag gtataaaggc 10260

-continued

```
agttgttggt cttaccgacg caatcgaaag gattgacatc aacgccattg cggacaagat  10320
tggcagtgga ttgtcttcgc tttggaaagg tttctcaaac acgggagctt taaagaacct  10380
tggtgcgacc tttaattata tatcaaaatc aatcaagcaa ctatttagca agattgatgg  10440
tagcaagatc atgcagggca ttggctcggt gtttggcgat attgcaaacg gtatctcaca  10500
agctctaaac attgctacga catcggttaa aaatttcata aaatcatttg ctgatactgg  10560
agcatttcag tcatttaaag ctgctgttca agacacttgg aacgccatta agactatcgg  10620
ttcatcattc ggcgaagtac ttggtagctc acaaatgcag tcaatcattt caggtattgg  10680
atcagctctt ggaacgcttg taaactggat atctcaagcc atttcagcag tgtctaagtt  10740
tgtcagctca ttaccgccgg aggttctaaa cggtatcacc agtgggattt tggcaatggt  10800
agcaggtttt gctactgcca aggctggtat ttcagtatta ggtgttgcaa tgaaagggtt  10860
ggacttcatc aatagtttaa atcctttcaa gaagtttgga aaggacgctg cagaaggaac  10920
tgaacaagct gccaagagtg ctaaacgttc taaatcaact atcactcaat tattcagtgg  10980
gatggccaat gtcattaaat caacagggac tagcatttca acagctacaa aaggcatcgg  11040
aacagggcta tcaactgctt ttaaaggctt tggccaagga attaaatcag ctttacaagg  11100
tcttaaaggg ttgaaccccg caaccttgct atcatttggt gcatccgtag ctatcgcagc  11160
agtcggaatc ggtgctggta ttggtattat cgttgcttca ttcactttgc tagccactca  11220
atcccaaggc gtttcacaga tattaaaagc tttgggttca gcatttagca cagtcgtcca  11280
aggtattggc aaagctgcag gaactatcat tgaagcattc ggaactgctt ttggaattgt  11340
cgtcaaggca gtcggtgaag ctgcgcccgg acttgcacga ttatctccat tggttgaagc  11400
tatcggcact gctctaggca atgcagcacc atttattaca gcatttggta atgcttggac  11460
ttctatttta ggaacgtttc cagctattat cagtgcattt agtggattag caaccgctat  11520
cggtactgca atcagtgcag tagttaccgc aattactcca attattcaaa tcattggaaa  11580
tacaataaca gcagtaactc aaatcatcgc taacgctatt attgcaatcg taccagttat  11640
cgcgaattgt atcgttcaag ttgctcaagt tatcggacaa tttgggccac agattgcaat  11700
ggtaatcagt actattgctc aagctatatc agcttcagca cctatcatca taaccttgat  11760
tcaaggtatt gttaccgtcg ttcagacaat ggctcctgta atgagtcaag tgatctctgc  11820
catcgttacg gttgttcaaa ctcttgcgcc tatcataagc caaaccattt cagctattgt  11880
tacagcgata acgcaaattg tacctattat tacatcaatc ggtggtgtga ttagtgctgc  11940
attgagtggt attgcatcta ttgtgtcagc tgcaggaatg gcaattgcta ccgcagctat  12000
gggtatcggt acggctatta gtacggctct aagtggtgtg gctagtatta taagtgctac  12060
tggtgctgta attggtgcag ccttgcaagg tattgctagc gtggttcaat cagttggaac  12120
atcaatcagt acagctgctc aaggtatcgg aaacggtatt aagtcagcgt ttgaaggcat  12180
ttcaagcgtg attacttccg caggcaatgc aatcagtagt atattgaata gccttgctaa  12240
tgtattcaac tcaattggta cagctgctca aaaagcaggg attggtttca atcagttagc  12300
aaatggtgtg gttaagatta ctaatacaaa tctcggtgac atggctgcat ctcttgcagc  12360
agtggctcat ggtattggtt cgattgggga taactcagca gggcttgctc aagctggttc  12420
tggtatggct caacttggga atggtatgag caaagtgtca acatcagcgg ctagcgctgt  12480
ttcaggattg agtcttttct caagcatgat tacaagtatt caatcagcgt ttactagctt  12540
acagtcaatg ctaactatcg caggaacagc gttcagcacg ttctcaattc aagccatgca  12600
```

-continued atcactaact ggattgtctg ctattgcagt acctatcaca atcttccaaa ctcagattat 12660
gatgatagtg ccagcattaa tgcaagcaac agcaggatta actatgttca gcgcagtagc 12720
tatggcatta gcaactagct tgacctcaat tggtgctgtc atgactatgt tgactaccaa 12780
catgactatg ttagctacac aactaacaat gataacaaca agcttcacga tgattgctaa 12840
tagctcagct atgctaggaa caagcttcgt tatggttggt acatcgctaa ctatgttgaa 12900
tagtcaattt atgatgtttg ctacaggaat catgcaaatg acatcacagc tcatgatgtc 12960
aggtgcagcg gtagctatgt ttggtgctca actcattgca gcacaaactg gtttcagtat 13020
ggtttccatg atggctacta tggtatctag tcagcttgct atgcttacta gctcggctca 13080
aattgcagga gctggatttg caacagtaag tgctcaagtc atgatgcttg ctagtgtatt 13140
cgctaccgtt ggagcgtcag caatgacact acaatctgca atggtgtcat taggtatggc 13200
agtaagaact ggcattatgt cagcggttca atcggtaatg tcaggttcta tgcaaatgac 13260
tgctgctcta cgttctagtg gaactcaaat gattgctatt acacaagcct ctatgaatca 13320
aatagttacg gtggtgagaa atggcatgaa tcaaatcgtt gctgcggtaa gggctggcgg 13380
tgctcaaatg gtttcagcaa tgcagtcaag cggacagaaa ttagtggtaa ttactcaagc 13440
agcggttaac caagcagccg cagcagcgag atcaggttac ggtgctttct actcagcagg 13500
agcttacatg ggacaaggtc ttgcagcagg tatgaattca gctcttggat cggttacagc 13560
agcagctaac caactggtag cacaagctga aagagcggca caagctaaag ccaaaatcaa 13620
ctcaccatca cacctattcc gtgacgaagt cggttggtgg attggtcttg gtattgctcg 13680
aggtatcgac gaatcagctc cagaggttgc gaacagtctc gattatatcc gtgaacaagt 13740
caacggattc aatgttcgag ctaacgccat gctaacgggt gccacttcaa atatggctag 13800
tcagttgaag atggaagtac tcagagataa aaccccagac gctacgattt cagcacgtca 13860
agaagcctat gctgcacatt cagccggttt gcttagtgat gtgattgatg ctcttggaga 13920
actcaaagac caagtagcac aaggtcaaaa catggtatta gataccggta ctcttgtcgg 13980
tggcacagtt aataatttca acagtgctat cgatacgatt aaaacattga aaggacgtca 14040
cagattatga ttactaaaat caaagaatat atagcgtttg gcgattttaa tagtcgtgac 14100
gctggttggt acttacagaa acgtgaagca ccaacgccag gcgagaaaga gattgtcgag 14160
tctatccctt acatgcaagg ggagcttgat ttctctagtg ttcttggtga gcgtgtcttt 14220
gagcctagag agattacata cgagtttaag ttaccgttta aagagtacga agaccgtaag 14280
acagcagagc gtatgattaa gtctcaaatg gtcactaaaa cagaacagaa actgtttgat 14340
acgcatgata gacgttatta ctggatgggc aaggttaaac acatcaaagt agcagacgat 14400
cctattaaga agaatctggt agctaccatt gtttttaagt gctatccatt cgcattccac 14460
gaagatgaat actttgatga tgtttgggat acattcgatt ttaataacga tttttcagtg 14520
tggacaaagt gggaagtttc aggagaaaaa agtatttatt ttgtaaattg tggagacaca 14580
tctattagcc caacgattaa atgtagtagt aatttcaatc tgattgatga caatggaaca 14640
atttataact ttaaaaaagg tgaaaataca gatttcacct taattttaaa acccggagtc 14700
aactatttta ctgctcaagg agatggctat atatctatgc atttttctat tgaggtaatg 14760
gcatgacaaa tttaaaaagt ggaggatttg aagtttatca ctggccaagt tttaatgata 14820
gactatcaga taaattatct aaaaaaacta ttcatagaca ggttatccac gaaccgtatt 14880
cacgaacagc gaataaagtt ttatcaggtc agattactca agctttgaat gcaatacatg 14940
aatttacttt tacaattcca atgactaatc cgctatatca aaatatagta ccttttcaat 15000

-continued

```
caattattga agtagttaat cttagagatg gtgaagttga atttaaagga cgtgtgctag  15060
ctatgtctaa taagatgaca agaaatggct ttgttcaaga agttatctgt gaagattttc  15120
tatcattctt tcatgattct agtcaatatt ttcaaaagct aagaaatgaa ggaactagac  15180
catacttaga agaaatttta agagtagcaa atagtcaggt agagccttac aaacggatag  15240
cgttaggtaa tgtaactgtc gaaagtagga ctgatagacc ttatcggtat ttagggtatg  15300
aaactacatg ggatacaatt cgggagcgta taattacaag tataggaggg tatttaacgc  15360
tacgtgaaga aaatgatggc ttttatttag attggactgc agatgtagga gaaactaaaa  15420
aaagccctat ccaattgggt aggaatatca aatctgctag ccgtgatatt gactttgatg  15480
gtcttgctac tcagattatg ccaattggcg ctgatcttga tacacaagga agtcaagaag  15540
aactaggtaa tgatgtaaca cgcgctcaat tggatatttc aagtgttaat ggcggtaata  15600
tatggcttca agatgatgag ttagtaaaac aattcggaat tattcgtaaa cctgtcattt  15660
ggacagaaat tgatgaccct aatattttat tggctcgtgg aaaacaatac ttgagagatc  15720
aaaaagtttc attagctaaa tggacagtct ctgtagttga aagatatctg attgatgatc  15780
gttatgggaa attcaaaatc ggtaataaac atcctatttt aaatgcccca atatccgata  15840
tagcgacatt acagataata gagaagaaaa tagatatatt gaaacctcaa atatctgaat  15900
tgacgatagg gtctcagtat caatcattat atgaatatca attacagttg cgtgaagcaa  15960
caaagtctat cgctaaattg aaggaagatt cttcagttgc gaataagcga aaacgattag  16020
agagcttaaa atatcaatta gatagcttga aaaaagatac tgaaacacca ccagttagac  16080
cgtctgcacc aactccgcta tcagataaag caaccgatgc agaacgttct gcatatgaac  16140
aatctttata tgtttatgaa attgcaaaaa cgacatatga agaacatctg gctacttata  16200
ataagaacca agaagaaaaa gcaaaaacta tttcaaatct tgagtctgaa attgctagat  16260
tgcaacaaga actaaaggga ggtaattaaa tatgcaacaa acagaagcag agggacgttt  16320
gaacctctac gatgatgtga cgccgttgga aaaaaccaaa aacattaatg ttttgacagc  16380
ggctatcaga aaaaaaacaa gaggggcaga tgtccgtgaa gccatcgcta cgtctattga  16440
aacgacttac gcagatagta tcgctaacgg aaataccaac atggaagtcg ctaaggcaag  16500
aggaacatat aatactctag gagatagact tgaaaatttt gatactgaaa tcaggaatat  16560
tgtaagttgt tcaccaaaag gaatatatgc taatctatca gagctacaat cggctaagcc  16620
gaacggagat tccggaatct atctcacaac agacaacggc cattggtact attatgctaa  16680
cggttggaaa gatggtggcc tgtatcaggc ggcggggatt gctgatggaa gcgtgaagtt  16740
ttcttcaatc gataaaaaag attttaacgt tcagtttgac ccgaaattga aagtcgtata  16800
taagccaaat ttaaattctt ggatgaatgc agataatccc accgagaacg ccacaaaaat  16860
ttatatgatt ccatttagag gcgcaggcaa agtgaccgtt agtttttatg gatccctgtt  16920
tcctggcgta aaatcgcaaa taaagttagt caaaaaggct actaattcaa gtaattattg  16980
tgtgtctctc aatgaaaaaa ccataactga aacgacagaa ggcggatata caacaattac  17040
gttccatcat ccagttccta aaggcgaata ttttatcgct ttttgtggaa ttaatttcag  17100
atggaatttt ggatatagtt attggttaga aagctcttca ggttacaatc agtcgatttt  17160
tttacaaaga aagacagaaa atagatgcat agatgctgtt attgcttgtg atttttctgt  17220
tgattctagc ggtgagaaat tattagacga aaatatgcac tttgattcag gtatattttc  17280
gtttcacact gaacctattt tatatattcc taattacgaa ttgcctatcg gaacaaaatc  17340
```

-continued

```
tataattctt gggactaaaa acaatacacc tgttttcatt tttagaaaaa atgaaaataa  17400
tacgtttgaa aaaataaaac aaatatacac agaagaaata ggtgaaggag cacgttatag  17460
aaaatacttt ttagacattg ttgctgaaaa agatatgtat gtcggagttt ttggaaatgt  17520
ttattatgat actgctggtg atgtttctgc aaagaaagga catttcgaaa aagatatttc  17580
ggcttcagat tctgaaaata tagggtcaat gtatttcaat ccaaatacaa atattcacat  17640
ggttcctatt ttatattatg atgaaaattt aattaatgtt gcacaaaaaa atgcgaattc  17700
atttgaggaa ataaatggat cgctaattga tatcaccaat aaaataaata aaataaataa  17760
aaaaacaata acattagcaa acataatcag aaaaatgaaa agagggaatg cagtcactat  17820
ttcgctttac ggagactcaa cgtactatgg tcataagtca ggcgctgtcc ctttaggcac  17880
tagaacaagc gagcctgttt ctgaaagttt gcaaaaatat ctacgtgctt attttttgaa  17940
cgaaaatata acagtaaaca actatgcaac taacggaaga caagcacaac aagattcaga  18000
tgattgggac acaaaaatgg ctaatgacaa agcggacgtt atttttataa atttcgggat  18060
aaacgattca aattccggta aaacagcaga aactttttac agtcaaatgg aaactttagt  18120
acaaggtgcg ctgaaaacga acaaagcagt catcttagaa actgctaatc aagtcttaac  18180
ttttgacaaa ggaggtcaag ggatgggaga ctatacgaaa gcttttaaca ttaaagaatt  18240
tgttgatgta acaagacagt tagttaagag ttataatatt tatttgcttg atggatataa  18300
acgttcatta agctacatta acgaattttt tgatcccaca atagctttgc cggacggcat  18360
gcatccgtca gacgatatgt ataagtataa agctgttcaa atgatgtcta tgtttactaa  18420
tacgagtttt tcaaaattaa aatcaggaca gacattatct attttagaag ctaattttaa  18480
tacaacaaca ccaaatgcag tagcggatag cagttctaaa ttcggtttta aatatacggt  18540
taaagacatc tcggtatcat ttggactaga aaaacaatca gatattaaaa tttatatcaa  18600
aagcacagca tcaatgaaag tttatgttaa tggtttagat actcaatata ttagctctga  18660
tggatatatc gtaataaaaa atattcactc taacgatgta ttcattcaga tcacttcaga  18720
cgaagcgaca gatgtttatg gtttagaagt ggtttaaaca cgatcattga gtgtgctttt  18780
tttagaaaag attattttga gcgctagctt actattgcaa tatacagctt atgcggctgt  18840
cggcgcccaa gtgcaaaaat ttcttgattt atccatacag gattgcaaga tgacaatact  18900
gctgaataag cttagaaagt gaaatttatg ttgaatcctg aaattattag aatgattctt  18960
agtatatctt tatcattgtt aacgctattt acatttttcc aaagtcgtat gactttaaca  19020
gaaaaacgtt taacgattct tgaagagaat aataaacaac aagataaacg actggcagaa  19080
aacaaatcta tgttggataa tcacgatcaa caaatgaaag ttcttatcca aatgaccgaa  19140
caaatcaaaa atttgtcgga aaaaattgaa aaaatcgata acaaattgga ggaagtcaaa  19200
tgattaattt aaaattacga ttacaaaaca aagctacatt agtagctctc atttcagcag  19260
tgttcttgat gctgcaacaa ttcgggctta atatcccaag caacattcaa gaaggtatta  19320
atacattggt taccatcttg gttattcttg gaattgttac cgacccaacc actaagggga  19380
ttgcagacag cgaacgagca ttgaactatg atgtaccact aaacgaaaag gaaataaaat  19440
agtatgagcg tacaacaatc tattgtaaat tggtttgtta accatcgagg caaattgacc  19500
tattcaatgt atgggtcacg caacggagca gacggtacag ctgactgctc tggttcgatt  19560
tcgcaagcct taaaagaagc tggtattggt attcaaggac taccatcaac agtaaccctt  19620
ggtcaacaac ttgccaaaaa tggattctat cgagtaagta ttaatcaaga ttgggatgct  19680
ttgacaggtg atattgtgtt aatgtcatgg ggtgctgata tgtccacatc tggcggagct  19740
```

ggagggcacg ttggtgtcat gatggatgct acatacttta ttagttgcga ttattcaact 19800
caaggggcac ctgggcaagc tatcaatact tacccgtgga atgactacta tgcagcgaac 19860
aagccttcct atatcgaggt ttggcgttat tctgattcag caccacagac gaataaccaa 19920
gcaaatacag cagtagcacc acaacaaaag gcttactatg aagccaatga agtcaaatat 19980
gttaacggta tctggcagat taagtgcgac tatctatgtc caattgggtt cgactgggtt 20040
aactaatttt cggctcagta taaactaagt gaacgcaaac aaagcggtgt catgcaaaag 20100
catggctaac ggtggacacc cagaacgggc aataccgtgc caagtctggt ataatagtat 20160
cagaaaggtg taacgactat ccttttgagg agtacactca ctatttgtac gcgagtggaa 20220
gtgcttagac tttagaaaga tggtgtcata agatgagtaa aaccaaacgt ggcgtttgtg 20280
ccaattgtca tacagtattt gaagtttcta aaaaacaaag atataaaatc aaaaacggta 20340
aatcggtttt ttgttcccaa acttgttctt tagaaaaata cggaaaaact aaaattacta 20400
tttctgaaat tcctttaagt atgacagaaa atatctaaag taagatatag tctaatccca 20460
ctaggaatag tgggtagtaa tgagaaaatg ggatcccagt agacatggtt aactgggtgg 20520
atgctaacgg taatgatatt ccagatggca agtctgaaga cttcaaacct ggaatgttct 20580
ttagttttgc aggtgatgaa gtcaacatca cagacacagg agaaggtggc tattatggtg 20640
gctattacta ccgacgtttc gagtttggtc agtttggtac ggtttggctt tcttgttgga 20700
ataaagatga tttggtaaac tattaccaat agaccacgca aactaaaaaa taaaaaagga 20760
gtatatcacc tcacctcaca ctgcagtagg gataccatgg cagtagtggt cgaagcctca 20820
gcattatgct ggggcttttt tgtttgcttt ttttaaccta acagcccgta attcccccac 20880
ctctaaggtg gcgggatgta agggcttcgg tctagtgcag tgacttgctc cctgtgcgtt 20940
accgacaata aagaggattg gcaagttttt gactttcctt ttgtcttatg ataaaataaa 21000
gtcagttata tttagtaaaa ggttgttata tcaatgaaat tagatacaaa tgctcattca 21060
gtctttctgc ttcattacca tctcattctt gttgtgaaat atcgccgcca agtattcact 21120
gatgagattt cggaacgtgc aaaagaaata ttttcttaca tagcacccag ttacaaaatt 21180
gagttagtgg aatggaatca cgataaagac cacgttcaca ttctattcaa aggacaacct 21240
aaaacagaaa tgagtaaatt catcaatgct tacaaatctg ctagtagtcg attactaaag 21300
aaagagttcc ctattattcg ccaaaaactc tggaaagaaa tgttctggtc tcaatctttc 21360
tgtctcctat ctagtggtgg agcccctatt gaagttatca aagaatatat cgaaaatcaa 21420
ggacaaaaga aatgacagtt aggcaaaaat cttataagtt cagaatatat ccaactagag 21480
aacaaactgt tatgttctct aaaacatttg gctgttgtag ggctatctgg aatatgatgt 21540
tagctgataa aatcaagcac tatgaagaaa caggacaaac actaaaaaat acgccagctc 21600
aatacaagaa agagttcgag tggctaaaag aagttgatag ccttgcatta gctaatgtac 21660
aactcaatct ccaaaaagcc tataaatctt tcttccaatc tggatttggt tttccaaaat 21720
tcaagaaaaa acgtcatcgt caatcttaca aaacaaacaa ccaaaacggg acaattactg 21780
tacttgatgg aaaagtcaag ctccctaaaa ttgggtgggt gaaactcaac caacatagag 21840
aaatgtctgg tgttatcaag agtgctacta tctcaatgac agaaacaggt aaatacttta 21900
tttcgatttt gtgtgaaact gaaatctatc cactcccaaa aacaggggag catgtaggga 21960
ttgaccttgg gttgtctgat ttcgctattc tatcaactgg agaaaagatt ggaaatgaga 22020
aatttctcca aaatctctcc aagaaactag ctaaagagca gaaaatcctt tctcgtagag 22080

-continued

```
ccttggttgc taaaaaatct ggtaagaagt tatctgaaag tatgaactat cagaaacaac  22140
gtatcaaggt agctaatatc cacgagaaga tagctaacaa acgcagagat tttctcaata  22200
agttaagtac ggaaattgtc aagaaccacg atattatctg tattgaagac ttatccagta  22260
aaaatctgat gaaaaatcat aaattggcta gggctatcgg agatgtctct tggtctgaat  22320
ttgtgagaat gttagagtac aaggctgaat ggtacgaaaa acaagtatca aaaattagcc  22380
gttggtatgc ttcatctcaa atctgttcag attgtggctt cgcttcaggt aaaaagccac  22440
tctcaatcag agaatggact tgtgaaaatt gtggtagtca tcacgataga gacatcaatg  22500
caagtatcaa tattctaaac gaagggctac gcttagccta acaaataaag tgaaccgtag  22560
gaactacggg gatagcttgg taaacttgtg taaccgctgt tggttagaaa gctaatcatc  22620
aagtaagcac attacccaag aagctcctac atctaagcga tagcgtaggt aggagtggtt  22680
cacaataaat gctactatat taatgaatac agttaaaagc tgagtcttcg ataaactctc  22740
tctcaccctg acttgaatta gtcagggttt ttgttttgca aaaaaaatat ataatttttt  22800
ataaaaacag tttccgtctg gtcgcaaaaa tcgacttgaa tggattgaaa acaatctgga  22860
aaatattcga taaaaaataa aaaaacgagg taaaaacaat ggatacatac aaagaacaat  22920
atatagtatg ttttactaat tttcaagttg tttaataata aaatcaaaaa aactttaaaa  22980
aaaatcaaga aaactgttga cgttgaattt tgtttaagct ataatatgtt tgtaagttag  23040
ttaggaagga ggaacaaaat gacagaagta gttccaaaga ttacaattaa agaacttcga  23100
gcacgtcaca atttgacaca agaggaattt gctaaaagtg ttggtacgtc agcacaaaca  23160
gttagtgctt gggagaaaaa ccgactttca atctctccta agttcatgtt agccatttgt  23220
aaaaaataca accttaaatc gtctgatttg tatggctttt gattttaaaa cttgaattaa  23280
attcaagtta gaaaggaaca atatgaacga aatagcaaca aatgatttta attactcttt  23340
agtcgatgca aaaacgaaag aatttctgga agagcgtgcc aatatcattt acggcatcca  23400
aagcaagagt gcttacgaaa ttggaaaaca acttgccaaa gctcaaaaag agctttcgac  23460
tagaggttat ggttgcttcg aagaatggta tagaagttta gggtttaaaa aaaccaaagc  23520
ttatgaatat atcaatcatt acaatttcgt ttgttcgcaa aacgaacaag caaatattga  23580
aaaattcgaa agtttgccta aaacgttaca agctcaagta tctaaaccat ctgccaatcc  23640
agaggttaat caagcagtgt tcaacggaga tatcaaaact cacaaagaat ataaagagct  23700
tgagcgtcgt ctcaaactca aagaccaagc actggaagcg gtcaagggag agttggaacg  23760
tgtcaaacaa accaaaacta ctgaaaagat aatcgaaaaa gaagtcattc cgcaagatta  23820
caaagcaacg caagacctta acaagcaatt gctaggaaag aataaagacc tagcagacga  23880
gcttgattca gtcaaaagga gcttgcgact taaggaagca gcttatgaaa tgctcgaaaa  23940
agaaacatca gaagcattag ccttgaaaga gtctattgag cacttacgag ctgataagga  24000
agagctagaa aatagcgtga ctaatatctt taatctcagt aagcttgtta ccaagtttga  24060
agacttcttt gacgaagaaa tggcaccgct cagatttaaa acgcttattc aaggcattgg  24120
aaaagacgct cagattgaaa aactcagaga tatcttgaca ctaactgaaa attggctaga  24180
cgaaatgaac aagattatcc cagagaatgg aagaacaatt atagaaggag aaatcataaa  24240
tgagtaagaa gaaaagtaag aaagacaacg ttcttatcga gacagtaaaa atgcaaggcg  24300
aacaagctat gcaactcgtc aaacaagcga aatttaacca aaacttattg gatgaagtga  24360
ttggtttgaa agacgaaatg gatagaaatg ttagaaagac taatcaaaag ctaactgaca  24420
ttgagttgct tgtagaggaa gtcaataaga aggtccatat tgacgacggt gaagcttcta  24480
```

-continued

```
aaatcaagag tattattttc aaaaaagctg gcgtgtttgc tgacttctac tttaaagaac  24540
agaaaacaca tccaagtgat aacttgttcg catctaagaa ggggcagttt attcgcttga  24600
tgtactcgca tttgaagaaa gaatttaacg tgacaaaata cactaacatc aagcacgttg  24660
aagctgagaa ggcagttaag tttttggaag atttatctta cgacgatttt acaccgtttg  24720
agattcgtga aacgccaaaa caaaaagaga ttatagctct tgaaaaaaat gagtgactga  24780
aagcattata acgtttgagt ttcaataaaa gataaaaaac tttaaaaaaa tagaataaaa  24840
ttgttgacaa aataaaaaat atggtttaaa atagaaccat aaagttaaga aaggagagtt  24900
tgatggaatt taactattct aaattaaagg gacgtattaa agaaaaatac ggaactcaag  24960
agaattttgc gaaagctatc ggaaaaactc aaaccacaac atcttttaaa attaacggaa  25020
aaagattgtg gaatcaagat gaaatcatta aggctattga gctattagat ctttcaaaag  25080
atgatattgt agaatacttc tttaactatt aatagaaagg tatttaaaat gaaaaactta  25140
tttaaatgga ttttagctaa agatgagaaa gaacaaaaac cagtatggac accatacgaa  25200
gaaaacgaaa agaaatatga agaaattcat aaacaactat caatgaaata aaatagctaa  25260
accgttcttc aatccgtagc cacacctcga tgtgctgagt gcaacttaat accccaaaaa  25320
taaatataaa taaaaaccaa aactaccttc ttagaaaatt gaatattaac gagtacatcg  25380
ggggctgggt gcggattgaa gcactaaaaa aacacgggta aaagcccgtg tcatataaaa  25440
atctaatgat gttatagtat cacatttaaa caaaaaaagc aactggagag ggtgagtcta  25500
aaatgtctga taatcaaaaa tactattata tgaggctcaa acaagacttc tttgagacgg  25560
aagaaatgat aatacttgag tctatgcaag acggctattt gtatagcaac atcttgttga  25620
aactatattt gagaagttta aagcgtgacg gtaaattgat gtttaacgac acaatcccat  25680
acagtgctga ggttttagct acagttacac gtcacagcgt cggaacaatc gagaaagcta  25740
tggatgtctt ccaaaagctc ggactagtcg aggtaatgga tgacggagct atatatatgt  25800
tacaaattca ggaatatata ggcaaaagct ctactgaagc tgaacgaaag aagcgttatc  25860
gagatagaat caagctcgaa aaacgtgaga aaaatgaggc tttggaaaat ttgggacatt  25920
tgtccaccaa agaatcggga catttgtccg gacattcgtc caccagagat agagatagag  25980
atagagatag agatagaata gatataaaga cagaagtaga agtagaagag agaaatggac  26040
agatgtcttc tgctactgct gctgataaat ctaatttaaa tatctttgaa tactatcaag  26100
aaagaatcgg tcttctagat ggattccaat tacaaaagtt agaagagtat caagttatcg  26160
atagacttga acctgaatta atcaagatag ccattgataa agcagctgat aactctaaac  26220
gttcttttgg gtatgttaac tctatcttga aatcatgggc tcaaaatgga atcaagacag  26280
tagctcaaca aatagaagag cagaataatt tcacttctaa caagtcaaat agtgacaaac  26340
ccaagtttgg accagcttgc agtaaatact gaggggattt cctatgagtt tagatcaaac  26400
agctagacag atgcgacagc tatatatgac tactagtgat aaatactgcg agaagcacaa  26460
tcgaaacttt gtcactattc agctaccaaa cagcaagcca tacactgtat gtgagacgtg  26520
ccatcgtgaa gagcaagagc gacagaattc tattaaagca caagaacagt ttgagcgtga  26580
gcaagagcag aagcgtctct actttctcaa agatttcagt ttgatggatg atgatttaaa  26640
aagtgctagc tttgaaactt accatgctgt taccaaagag caaaaggaag acttgaagaa  26700
tgttcgaagt caactcagag gctatctcga tggccaggac tacaacattg tcctcattgg  26760
tgatactgga gtaggcaaga gtcatctagc ttattcagcg ctcaaagcct tgtctgatca  26820
```

-continued

```
tacgaagaag atgggcctat tcatcaacat cgttgacttg ctagccaaaa tcaaagagga  26880
tttcagccta gaagcagaat acatcagacg tatatctgaa tctgagtggc ttgtattgga  26940
tgatgttggc actgaaaaag taacagagtg gtctaatggt atcttgtaca gcattttgaa  27000
caagcgcaca aagacaatca taacgacaaa cctaagccca caggacatca tgggcacata  27060
tggtaaacgt gtatattcaa ggatttttaa gaagacagga cttggaacta ctaacgaaca  27120
cgtttacaag tttaaaacac agcaagacaa gaggatgatg ctatgacaga aacagaagtt  27180
aaactaaagc tctttgagga ctacgagagc attcatggac ttgtatactc ggaggaatat  27240
aagcagaaaa tgatggatga gctagatact tattcattca taagtaaaat gaacgaattg  27300
atgtacaaag ctaagaatcc aattcaggtt tttagcgtac aataaaaccc ctctaaaatc  27360
gattttaagg cgtgtatttt gctctatagt acaaatatac taggatacat ttaaaattgc  27420
actacacccc cttaaattga gaattagggc atatgaaagg gaaatgatat gaagaatgaa  27480
ttacaaagta caaaaggaga gtatttgacc gacttgcaac atcttgatgg cgaaacgttg  27540
aggaatttcg tcgatcccaa acatcaagca agtccacaag aactccaaac attgctagca  27600
atcgttaaga accgcaatct taaccctttt actaaagagg tctatttcat taagtatgga  27660
aacaatcctg ctcaaatcgt agtatcaaaa gacgcattca tgaagcgagc tgaacaaaat  27720
ccgaattacg acggatttga aagtggcgta atctacgagg atgaaaaagg tgagcttaaa  27780
actaaaaaag gtgtaatctt gccacgcaaa ggaacattaa ttggcggttg gtgtgcagtg  27840
tatcgaaaag atagaagtcg tccaatatat cgtgaagttg aattgtcagc ttataacacg  27900
cataaaaatt ggtggcagaa agcacctggt caaatgattg aaaaggtggc aatcgtggca  27960
gccgttcgag atgcattctc cgagaatgtg ggcggtcttt acactgcaga tgaaatggaa  28020
caagttgcac ctgtcgacgt tacacaacga gaaacgcaag aggatgttaa gattcgtaaa  28080
atagcacaag ttgagcaata cagacaagag caatctcaac cagttcaatc agagccagaa  28140
ctagttgaag acgtagctga agctgaagaa caacaagaag tcaatcctaa tttcattagt  28200
atcgagcaac gtgacattat cgagaaacaa atcaatgaat tagctttaat cacgggaaag  28260
ccagccgaaa cagtagctaa ttactatttg aataagtaca aactcaacga ttttcatgaa  28320
ttacttgtgt ctggatttga aattgtgacc aacgacattc aaacacagat aaataataga  28380
aaggcgaact agatatgaag gatataacaa acaattttat tgaaacaatc gagccagtat  28440
atacgccggg aataattagg tttgattttg acaaattcga tgcagctatc caagcggcag  28500
ttagcgaatt atcagacgaa caactagaca atcttgaata taacgatatt aagaatgaat  28560
ttacacgttt caacagcttg ctgacgaaac ttgaaactaa acgaaaagaa attgcgaaag  28620
tttataaaaa ccctttgaca gagtttgaat ctaatttcaa gtcatctaaa gagccactca  28680
aagaaattat tgacaaattg cgtgccaaac gagatgagat tgacgaacat catagaatgc  28740
tacgagttga ccacgttaga tcggtctttg aagaaaagtg tgagcttgca gggttggaca  28800
aagatgcttt caaggacaag tacgacggct attctttgaa gaagtgtttc aaagacaaaa  28860
agatggaact caaaaaagaa accatcgaag aaatcgacgc tttgatttta gctgaatacg  28920
accgacttga agaatacaag gccaacattg caatgattga ggaacaagcc cttgattatg  28980
agttgccagc ggaaccttac actagagcgt tgcagaacga cacacctata gttgaaatat  29040
tgaagcaaat gaaaaaagat cgtgatgcag ctattgaacg caaacagcaa gcagaagcta  29100
aacgacaagc ggaagctgag cgccttgcag aaattgaagc gatggctaaa cagtcagcta  29160
acgaggagat taaggcggta aatgctgaaa caggtgaggt tatcgaaaaa tcaaaaccag  29220
```

-continued

```
cagatgaaac tccaatcaaa ccagttgagc catataaaat cgatatttct ctaaccttcc  29280
acggtggaga gaaacaatgg tatcaatttg ccaagatgct tgaagacaac tttgtaaact  29340
atgaaatttt aggagaaaat aaatgattaa ttcaaccgtt cttgttggtc gcatgaccaa  29400
agatgcagaa ctaaaataca ctggaaacaa tatcgcagta gcatctttca gccttgcggt  29460
taaccgtaac tttaaggatg ctaatggtga gcgtgaagca gattttataa attgcgttat  29520
ctggcgccag caagctgaaa atttggctaa ttgggctaaa aaaggcgcat taataggaat  29580
tactggacgt attcagactc gtagctatga aaatcaacag gggcaacgag tgtatgtgac  29640
agaggttgtc gctgagaatt ttcaaatgct agaaagccgt gcagcgcgtg aggggggtaa  29700
tgctaacaac agttatagcc aacagcaagg gccaaacttt gcaagagaaa gcggacctta  29760
cgggaactca agccctatgg acatcagtga tgatatgcta ccgttctaat ttgaggaggg  29820
tttatggata ttaaagaaat aaaggggtat gaggggctat atgaagcaca ttcggacggg  29880
acgatttggt cttgcaaaaa taaaacaaca tatagctttg taagggaaaa gacaataaaa  29940
agggtttggg aacaaagaga gataaaacct cagatagcaa gaagacaaag gagtgatcac  30000
tacgataagc gagtgaaatt gtggaaaaac aaaaagatga caactcacct agtgagtagg  30060
ttgattgctc agacttttat accaaaccca gaaaacaaag gctacgtcaa tcacaaaaac  30120
ggcaaccctt tagacaactc agtagagaat cttgagtggg tgacaaggtc agaaaacatg  30180
agacatgcgt tcaaaaacgg tttgttacaa acaagtaaaa aagtcactct agtaagcaag  30240
gcagacgggg caaaggtaag cttttacagt ctaagagctg ccagcgagtt tctaggtaaa  30300
aacaagggtt atttgagcaa tattataaaa agcggaagaa cgcttggtaa ttacgaaatt  30360
gtggtaggtg aaatatgaaa ctagaatttc tattaccaag gtcaaaaact aaacctgctc  30420
aaaatttagt tatcaacagt aatgacagat ttcattatca agcagagggc cggatggtca  30480
agaaactgcg attgatagcg aaagcagaag cggggcttaa caccaagcca gtatatagcc  30540
ctgataagcc ttgcaaggtg cttgtaactg tctacgcacc aaccagaaga agattagacc  30600
caccaaacct atatccgact gttaaagcta ttatagatgg cttgacggac gctaatttgt  30660
ggccagacga caaccacgaa gttatcaaaa tgatgtcgtt tcagtatggc gggctaagtg  30720
gtgagtctgg gaaatttaag attgtgttag acattgagga aacgttaaat gaaaagcaaa  30780
gttaaagaca aactggtcgg tatatatgct ccagcaagct acggacatac aagtgtgtta  30840
gaggagacac aagagttttc gaagtggttt tgggagaaca gtaaagacat agacttaatc  30900
agcgataagt taggaattag cactaagaaa ttaaatcgca tcctaacgct ggagcagtta  30960
ccagatgagg aattattgaa agagatgata gagctatgcg aaataaagaa tacgctttgt  31020
acaaaggcga agaaatcata gctatgggta caaaacgtga aatagctgaa cagttaggaa  31080
tttcagtaca cgccgttact tgctatggga caccatcata cgccagaaga actagcgaaa  31140
acgcaaggag attagtagag ttatgaaata taaaattatc gtctattacg acaatatgga  31200
agatgaagta gaaatttatg ataacaagga tgaggctctc aaaagactgc atcatttgag  31260
aggtgttaaa tatcgcaatt caagaatgta tacagtagag atgaaagagg aagcagatga  31320
ataaacagga agcaattaga tcactacagg aaatggctca agagtcgttc gaagttgtaa  31380
aaataaatgc agtgcatatt gacaatatcg tggaagtcat aaaccaaata gacgaaccgc  31440
agaaagtgac tattccgaag tttgtagcgg agtggattga gtattgtaaa tctaataaat  31500
tgacattgtt gggtgctttt gaccaagtat cagaacatgg tattggactt gctgatacat  31560
```

-continued

```
ttacaggggt agtgcggaaa ggtattgatt gggcaaaacg taaccaagaa accttcgccc  31620
gtgcttggtt ggacagttat gaggttgaat aggtgaatag aattaaacag ttacgaaaag  31680
aaaaaaagct atcgatagtc gatgtagctg aacacatggg agtgcaaaaa ctgaatgttt  31740
taaaatggga acacggaaca agtcaaataa gtataaggga agccaaaaaa ctagcagact  31800
ttttcggtgt tagcgttggt tatctgttag gtcttgatac aactgaaaat gacagtatca  31860
ctgatctaat cgcaaaaatc aatcactggg cggacgaacg caatttaaag caagcagacc  31920
caaaaattca gtggatgcgt atcactgagg aggtcggaga aattcgtgat gtactattga  31980
aaccgactaa attcaatgaa ccacaaacag cactcaagga cgcaatagga gacacgctag  32040
taacgattat cgtgttggca catcaattag accttgatgt cactgagtgt ttaaatattg  32100
catatagaga aattagggac cgaaagggaa aaatgataaa tggaacgttt gttaaggagg  32160
aagacctttg aaatttcttg acttatttgc aggtattggc ggttttcgtc ttggaatgga  32220
aagtgcagga catgaatgtg taggtttttg tgaaatagac aaatttgcta gagcaagtta  32280
taaagcaatc cataacactg aaggagaaat agagctacat gatgcaacag gaatcacaaa  32340
gaaagaaatc aaagcaatcg gacaagtcga tgttatctgc gcaggatttc cgtgtcagcc  32400
tttcagcgct gctggtgcaa gacgaggttt tgaagataca aacggaactc tcttctttga  32460
aatcgcaagg ttcgcttcca ttctcaaacc taagtatcta ttcctcgaga acgtcaaggg  32520
gcttattagc catgataaag ggtacacctt tgagacaatc atcggatcat tggatgagtt  32580
ggggtatgat gtcgaatggc aagtgcttaa cagcaaggat tttggagtcc cccaaaacag  32640
agaacgagtg ttcattatcg gacatcttag aggaacaagt ggaagacaaa tatttcctat  32700
cgctgaaaca agatcagata aatcaattat gcaactagga aatatcaaaa aaaccgaaag  32760
ttttggtgga aatcctcaat gcggaagaat ttacagcata gacggattag cgccttgcct  32820
aaatacgatg caaggtggac aaagagaacc caaaatcctt attgacggta aggtacgcaa  32880
gctgacacct cgtgaatgtt ggagattgca aggattccct gattgggctt ttgataaagc  32940
acaagaagtc aattctaaca gtcagctata caagcaagct ggtaatagcg tgactgtcaa  33000
tgtaattaaa gaaattgcga ggtatttatg aaacataagg atctaacgat agccacaatt  33060
ctactactgg tctcgctagc gattaacgtg actactgttc tgcgagtggt taatagacct  33120
atcgagaccg tggtgatcca caaggcagat aatgcagtgg aactacacgg caaggttact  33180
ggaaaatcta cggttggcaa gctctacacg atcgattgtg gggcgtatgg caagtttcta  33240
gtgacaaaag aacaatatga aagtgttcag gtaggagatg atatacctag ctatttgaaa  33300
ggaagaggac aatgaagtac gtcgagtacg caggactgac caaagaatta cattcaaggt  33360
tcgtggttga atttaacaat ttgaaagagc aacaccatag aacattaaca aagtacgtga  33420
tggaaacaaa gcagtgcgac cgattgcaag ctagaaaata ttgtcaaaga tttgacaatg  33480
tgatcaaaga gcgttctaag ttatcacccg cgacattaaa cgatatgcgt gagtatatca  33540
ctgacggact cgcaaacgac ttagagaact atctgtcaaa acactttttt agtagctccg  33600
caaagtgtcg gccagatacc gacaagagaa atgctggact gcctgaggaa ctctttaaac  33660
agtattgcga ggaaatcaaa tcattaaaag ctaaataccc aaacagcttc accgcctaca  33720
tcatggatgt taaagggtgc aaatatcaaa aagccaataa catacggaca gcgataaata  33780
cactctatac agagattggg atagtgacac ctcgcaaggt aatccaatta gagggacttc  33840
tttctagaga attattcgga aagatagcta agtacgtctt taataagtat gaatggccgg  33900
aaagcctaga tgaagaggtt gatcggattt atttagagta tcgcactaaa ggtgatatag  33960
```

gtcgtgataa agaaagtgtt aaacggacgc tattcaaagc gatttcaatg ggcttatagt 34020
ggttcgaatc cactatgagt tgttaattcc agtaagtttg gaggtgataa cagcgtaact 34080
gtcttttcaa attctttatt cttgtagcgt tcgagggttc gactccctcg ctcgctgtta 34140
gtctgtcgtg actaggtaac ttttttcgac actcgtatcg ctgacagacc gatacacaaa 34200
cccagtaaat attttataga aatgaggatc caatacatac tttttgctct agtcttgcat 34260
tactggtagc aagactggaa tttaagatag aggaggtgat aaaaggacca agaacaaaca 34320
ctcttatctt ttcatgaaac ctcttaatgt ttgtttattg gtttaaaaaa caaaaaaaga 34380
ccgacataat ggccggcact ctttgaaagt caacactact attataccag agagggcaga 34440
acaatgctat tgccggaaat tgatgagaaa gcaacaatca aacgttgcaa gcgcaaactt 34500
cgagaatatc cacgttggcg agagattgca cacgacggag ctgagcagaa aataacacag 34560
gaattcacat ttatgccacg gggtggtagt ggaatgagta gaccagtgga aaatattgca 34620
gttaggcgtg ttgatgcaat gaacgagcta gaagctatag agcaagcagt tagcggtcta 34680
tatcgtccag actatcgcag aatattgata gaaaaatatc tagagtttcc acccaaaccc 34740
aactggcaga tagctcaatc aatcggcttt gaacgcactg cattccaaga gcttttaaac 34800
aactctatcc tagctttcgc agaattgtat cgtgatggtc ggttaattgt ggagcgttga 34860
aaaaaatggt attttagcgg aattttaacg gtctctatta actgttttaa gtggtattat 34920
tatattatcg aa 34932

<210> SEQ ID NO 3
<211> LENGTH: 33335
<212> TYPE: DNA
<213> ORGANISM: Streptococcus phage
<220> FEATURE:
<221> NAME/KEY: source
<222> LOCATION: (1)..(33335)
<223> OTHER INFORMATION: /organism="Streptococcus phage" /mol_type=
"unassigned DNA"

<400> SEQUENCE: 3
gaagaaagaa aagacggctc atttgtgggt tgtctttttt tgatcaagta atgaaggagg 60
tggacatatt gggctaaatc aacgacagaa aatatttgcg gatgaatact tgatttctgg 120
catagcttac aatgcagctc ttaaagctgg atattctgaa aattactcta aaactagagc 180
tcataaattg ttagaaaatg acagaattaa ggcttatatc gaagaacgac tgaaagagct 240
tgagaagaag aaaatagcaa aacaagacga agttatgcaa gtcttcactt cgattctgag 300
gcaggaactc gtggaagaag tcgtagagct aaatgccgct acaggtcagt ttgtcaagac 360
taaaaaaccc ccgtccatct ctgaggtcat caaggcagga agcgaactca tgaaacgcta 420
tccaacagct aagcaagctg agaaactaga gcttgagatg agaaaactaa gagaacagct 480
tgatagcggt attgaaggca caatgaatct caacattgtc aacaagtggg aggatatccc 540
agatgataac gattgatatt cagaaaaacg tcaacccaca ttttaaatcg gtttggcagt 600
ctaacaaacc ttacaacgtc ttaaagggag gtcgtaactc tttcaagtcc tcggtcatcg 660
ctcttaaact tgtctatatg atgattaagt acatagcaaa ggacgataag gcaaatgtgg 720
tagttattcg gaaagtagct aacacaatcc gtgacagcgt gtttaataag attcaatggg 780
ccattagtat gtttggacta gagagtcagt ttagagctac tgtgagcccg tttaagattg 840
ttcacaagca aacaggttcg acattctatt tctacggaca ggacgatttc cagaaactga 900
aatcaaatga catcgggaac attattgctg tttggtatga agaagcggct gagtttacca 960

-continued gtgctgaaga cttcgaccaa tcaaatgtca cctttatgcg gcaaaaacac gagaacgctc 1020
aatttgtgca attttttgg tcatacaacc cacctcgaaa cccttatagc tggataaatg 1080
agtggtttga agaaatcaag acaaatgata actatctaac gcattcaagt acttatcttg 1140
atgatgaatt aggtttcgtt actgatcaaa tgcttgaaga tatagaacgt attaagcaga 1200
acgactatga ttattaccgt tatctatatt taggtgaagc ggtagggctt ggtaatcaag 1260
tgtataacat gagtacattc catgctatcg atagcttacc gacagacgat agacttattg 1320
gtatatcttt tgcaatggac acagggcatc aacaatcagc tacagcttgc tgtgcttatg 1380
gactaactgc aaagggcaat gtgattctgt tagatacgtt ctattacagc ccagctggtc 1440
aagttgttaa gaaggcacct agcgagctaa ctgtcatggt tagcaatttc attgataagg 1500
tacttaataa ataccgagtt cctaaactac gcatgaccat cgatagtgca gagggcgcat 1560
tgaggaatca atatttcaaa gattttggcg aacgatggca tccagtagct aagaagaaga 1620
atcagaccat gatagacatg gttaccagtc tgttagctga gggtcgattc tactaccttg 1680
acattccagc taataagata ttctacgagg agcataaaat gtatcgatat gacgagaaga 1740
cgatacatac agacgatcca aaagtaatta aagaggatga ccactgttgc gactctatga 1800
aatattttgt cttagacaac gctagagaac tagatttgaa agcttaaagg agcaactaat 1860
gggaatcata cagaccatta agaactttat aaaaaggagc aattacgtga taactaacca 1920
aagtttaaac agtatcacag accatccaaa gattgctatc tcacctgaag aatacaaccg 1980
tatcatggat aatctccgat attttgctgg agatttcgac agtgtaactt accgagatag 2040
taacgggtca caagttaagc gagacttcaa ccacttgcct cttggacgta cagcttcgaa 2100
gaaggttgct agtctggtat ttaatgagca agctactatt cgagttgata atgaagttgc 2160
cgacgctttt atcaatgaga cactgaaaaa tgacaaattt agcaagaact ttgaacgcta 2220
cttagagtca tgtctggctc ttggtggtct tgcaatgcgt ccttatattg acggtgatca 2280
aataagagtg tcgtttgtgc aagcaacggt attctttcca ttgcgagcaa acactcaaga 2340
cgtatcaagt gctgccattg tcactaaatc gataaaaacg gaagggcaga aagtaaaata 2400
ctacagtctg attgaatttc atgagtggaa caaagagact tacacgataa gtaatgagct 2460
ttatgagtct gaatccaaaa ccattatcgg tcaacgtgtt cctctatcaa cactctatga 2520
agatttagaa gagactgtta ccctaaacgg acttacaaga ccactattta cgtatttgaa 2580
accgcctggt atgaataaca aggacattaa cagtcctttg ggcttatcta ttttcgacaa 2640
cgctaagact actatggact tcatcaatac cacttatgac gaattcatgt gggaagtcaa 2700
gatgggtcag cgtagggttg cagtaccgac tcaaatgatt aagactgagt atgatacaaa 2760
cggtgagaag gtcacagtca aacgtgagtt tgagactggt cacaatgttt acgaacaatt 2820
cgatagcggt gatatggata aaggaatcgg tattactgat cttacgacag atatccgctc 2880
agacgattac attaaagcca ttaacaaagg actcagtcta tttgaaatgc aactaggtgt 2940
gtccactgga atgtttagct tcgacggtaa gagcatgaag actgctactg aggtagtgtc 3000
agaacaagca gacacatatc aaatgcggaa ctctattgct actcttgttg agaagtcatt 3060
aaaagagctt gtaatttcaa tcctagagct tgctaaagtc tacaatctct acactggtga 3120
gattccaaca atggatgaag ttagtgttga tttagatgat ggtgtattca cagaccgaaa 3180
tgctgagttt gattactggt ctaagatggt tgccgctggg tttgctccaa aaacgatggc 3240
tattgaaaag acactcaacg taacaaaaga acaagcacaa gagatttacc aaaaaatcaa 3300

-continued

```
tgatgaaact atggtaagca ctgatagttt taggacaagt gaagaggttg acatctacgg   3360
ggagtgatag gctatgacta agaaaaaacc tatcaaatta aacgaccaac aactaacgct   3420
tgacgctagt agagtagctg acatctatca tcaactaacc gtggaattat tcgaccaagt   3480
aattgatcga gtgagagaac gtgggacagc aagccttgaa gaaaatccct atctttggca   3540
actcgaaaaa atgagtgaga tgggattgct caacaatgct aatattaagc ttattgcaga   3600
gtattctggg attgctgaag aacaattgag atacgttatc gagaacgaag gatataaggt   3660
atataaggac accaagagtc aactgataga ggatttggga ggtaaaaacg acttcattac   3720
aaacaacctt attcaaacca gtctagcaaa ctacgtcaat caaacgatgg gagatattga   3780
taaccttatt aatactactc ttccaaagag tatcaggaaa gtctatcaag gaatcgttga   3840
ggagactgtg gctaaagttg taacaggttt agaaacacct caaaaagcta tatcaacaac   3900
tgttatcaaa tgggctgata aaggcttcta tggttttaca gataagcaag gcaagcagtg   3960
gagagctgat acttacgcaa gaacagtcat taactcgact tcttggcgtg tctatcgtga   4020
agcaagaacg gcaccagcaa aagaattggg aattgataca ttctattact caatgaagcc   4080
agcggctcgt gaaatgtgtg ctcctatcca gcataaaatt gtaacgtttg gaaagtcaag   4140
ggttgaagaa ggagagaaga tttattctct tttagactac ggatatggga gtgctagtgg   4200
atgccttggt attaactgcc accatacatt gacgccctat gttgtaggtg tcaactacaa   4260
gcccgaactt cccgaacacc tagcaaacat aacaccagat gaagcaataa agaacgccaa   4320
cgctcaatct aagcagagag ctatagaacg ctctatcaga aagtctaaag agcttcttca   4380
tgttgctaac aagctagatg atgacgatct aataagcaaa tacagagagc aagttagaaa   4440
acaacaagca gcaatgagag actatctgaa acgacatcca ttcctatata gagattattc   4500
gaaagagagg tattacgatg atccattcaa tcaagctaaa gcagaaatcg aaatgcggaa   4560
gcggagaaaa aagaaaggtg atgatccaaa atcttgactg ataggaatta gactatcatg   4620
acctgccaaa cgtcgtaaaa ctgggcaaat taagtccacc ggacgtaaaa caaaggagtt   4680
ttaaacatga gtttgaaacg tgatatgtta gttgaagctg gtattacaga taagagtgtg   4740
attgacaata tcatgcaagc gtacggtgca ggtattgaga acgctaaatc acaagctaag   4800
tctgaattac aagctgaaaa cgaaagcctt aaacaacaac ttgagcaaca aagccaagca   4860
ctcaatgact tgcaagctaa ggaaggagcg agcgaagaac tcaaacaaca attgacggac   4920
ttacaagcta aattcgacac ttacaagtca gagtatgaag caaaccttgc taaagttact   4980
aaatcaaatg ctattcgtct agctttgaaa gacgtgaacg ctcacaattc agatgacctt   5040
gctaaattca tcaattttga cgaaattgaa cttgatgaag ctggtaaacc caaactagac   5100
aaagtcgttg aagagttgaa gacaacaagc ccatatcttt tcaagcaaga agaacaagca   5160
tcacaaccta aaatctttgc cggtgggaat cccactgcta gtcagagcgg acttaccaaa   5220
gaagatttca gacgtatggg tatcaatgag cgtcaagcac tctttgataa agacccagag   5280
ttatatcaaa aattgaaagg ataattttaa atgacaacag gtattacaac aactgcacag   5340
gtgatcaatc cgcaggtaat ggctgacatg gtttcagcta aattgcctaa actaatcaaa   5400
ttcacacctc tagcattcat cgacactaat ctagtaggtc gtccgggtga tcaacttaca   5460
gttcctcaat ggacatattc aggagatgct acagatatca ctgagggaac tgcaattcca   5520
attgaccaat tgggaactaa agtgacacag atgaaaatca aacaagctgg taaagctatt   5580
gaaatcacag acaaagccgc cttagtcgga catggaaatg tctatggtga agctaccaac   5640
cagattgctt tggctattgc taacaaagtt gacaatgacc tagttgaagt tgctaaaact   5700
```

```
gccactcaaa acattgctga agcccctgtt tcagttgcaa atatcgataa agccttgtca   5760
gtatttgcag acgaagaaga tgctcgctat gtggctctta tcaaccctaa agacgctatc   5820
aaattgcgtg ctgatgctgg acaaaactgg ctcaaaggat cagaaattgg agctgaagct   5880
gtagtgtctg gcactttcgg tgaagtttct ggtgtgcaaa tcgtccgcac taagaaagtt   5940
gatgaaggaa aaggattcct tgttaaaatt tcttcacttc aaacagatac agatgatgac   6000
gccaaatatg gtgcattcgt catcgcttta aaacgtgatg tcatgattga aaacgaccgt   6060
gacattttga aaaagacaac tgtttattca ggcgatgaat actacggtgt ttatctctac   6120
gacgactcta aagttgttaa attcggaggt gcttaatggg aatgctaatg cgtcgtcatt   6180
acagcggcga taaagcatca cccgataatg acgttcaaaa acaatcgtct gaaacgctag   6240
aagacaagac tgtcgctgat ttgcgtatta tcgcacagca acgtggtctc actggctttt   6300
caacacttac taaagcggag cttttagacc tcctaaaatg acgaaaggag gcggttgaat   6360
gacatattta accaaagaag aatttctaaa acttggtttc gaagacgtag aagactttga   6420
aaaactatta gctagagcta gtctcactat tgatttatat ttaaaaaact tctacgattt   6480
taatgatttt gaaacggact ttgaccaacg caagcaatcg gtcaaaaaag cagtagctta   6540
tcaaattgct tacttagatt cgagcggttt gttgactgct gaggataaga cgtcgttgtc   6600
aagcatgact gttggacgta ctcatgtaag ctatcagaac ggttctaaat cgtcccatga   6660
tggaaaaacgg ttcaatctat cccttgacgc tctaaactgg ctgacattag ctggatttgg   6720
ctgtaaggcg gtggactatg atagataagc gtatgttagt tgatgctgtc actatcaaga   6780
agttgacggg agaaacggat gtttggggaa aagtaacata tgatgagccc acaaccctaa   6840
aacccgttag atttgataga cagttcaatg ttagcgggtc aactaacaat cgtaacgaat   6900
cgaagcccag tattttattt gtctatccga aatattgtcc agttgttctt gacgaaagct   6960
ttgaaaacgg attgattaat gacggaaaac gagattataa gattcgttcc attattccag   7020
tttattatcc aagacaaaat aaagtgtttt gctatgaaat tgaggtgatc taatgggaac   7080
tacagtatcg gttaaagttg accttcatgg tctcgaaaag aaatgcagtc ccgaagcggt   7140
caaacgtgga aaagttgcta tgattggtca aatgattact gatatggagc cattcatccc   7200
tcgtagagat ggaactttga gtgctagcgg ttcacctttt agcgatggca ttagatatcc   7260
gggaccttat gcaagagctc aattctatgg atcaagttac aacaaaaata gaagcttcgt   7320
tttcaggaat tatactacgc ccggaactgg taaacgttgg gacatgaagg catctgctaa   7380
atattctaaa caatggggcg aagtcgcttt aagagctatg ggagttaaat aatgaacgac   7440
aacgattttt cagaagttct cgcaaacttc atcaacacac ttagactacc gttaaaatgc   7500
aaacttgatt atctttcaga aaacgagagt ctttcagtct atccattgcc tggtgggaag   7560
gttgaagacg aagacatggc tggcacccag attctatcac taccttatga gatagcgatt   7620
aaatcaaagg atcagcaaaa actaaatgct attctttgga aaattaacac agaactttcc   7680
aaaattggat tcgagttacc aagtttaaat aattcttaca cttttatatc cttgaccgtc   7740
gagacaccga gcctaaacga tgccgacgag cagggttttt atatttactt gcttgattta   7800
aatgcaagat tagaagtaga aaggaacttt aattaatggc taaatttaaa aacgctattc   7860
gaaaacacta tatcgcacct tacgacccaa agaatccaga taaagtccca acagacgaca   7920
aatatatgtg gattgctaaa ggtatcaaag agtctgctcc agaaaacgac acagaagacg   7980
atgatgtagc atattttgat ggtgatggca ctaaagaaac ggttatcact tcaaaatctc   8040
```

-continued gcggtcgctc atttgaaggt catcgtgact atgatgataa agctcaaaac tttgtcgttg 8100
acaaagaaga cgcattaggt gatgacctta ttgtttggta caaagaagta gctgcagatg 8160
gtaagactta caaagaaggt cttgctcgac tttctgaaat tgaggttggt gacggtgaag 8220
cttcagagct tgaaactatt aaatttcaag tcaactggtc acgcacacca gagaaacacg 8280
aagtcgctcc atcaactact gttcgtacag ttgcatcttc accgggaatc ggtggataat 8340
cactaaatta aataaattaa atagaaaaga taagacaact aagagggtgg gggtttgccc 8400
ttaccctctt tttttcgtaa aggagaacaa acatggtagt aattaaaaaa cgtagcaatg 8460
tcatccccgt cgatttcggt gagtttaaac ttgagtttcc tgtatctgat agcaatatca 8520
aacgtatgaa ggcagttggt gaggacttgc aagccaaagg gaaagcgttc caagaaacaa 8580
gcgatgaaga agctcttgga gcgttgaaag cattggtaga agatggcttt aatcaaatat 8640
ttgacgataa agaagccttt aatcaagtct atgcgtttgc tggcaattca acaattaatg 8700
ctatgttcta tctgattgaa gccatcaaag gcatttctga ggaatttgaa aaccaaaact 8760
caaaagctgc cctcgataag tatttgaatg attgatttat cacgaaaact aacagataag 8820
ttagttattg atgataaaga gtacgccctt gacttgtcct ttgacaatat tttgaaaatg 8880
tttgaaatga tgcgggatga tgatattcct gaatacatca aacctcattt agctattcgg 8940
atgctgatta gcaaaagcct agttggtaac actagagagg aaaaatcaga atcatttaac 9000
aaagcttttg agaattactc agtagaagag atgtcaaaag tgttcaaatc agtctttgag 9060
gagcatatca gcttatccga tgtcgaggac aatcatgttg agtatgactt ggctggtaat 9120
cctatgaaga caacagcaag caatgacacg aagcagagag caccatatga catccgatat 9180
gatggtgact atatctattc gtcattctta caagcatacg gcattgatct attcgatgca 9240
caaggtaaac tgcattggcg aaaattcaac gctctactgt ctgggctacc agagggaacg 9300
aagttgatgg aagtcattaa aattcgcaaa tggaagccac aaaagggcga ctcttcagaa 9360
tacaaagagg aaatgcgtag gcttcagaaa gattatgctc tccctaacga tgttatcgag 9420
gaagaagaaa atgaagaaga attttagaaa ggagggataa tctatggcag atggtacagt 9480
caccatcaag gcgttatttg atggtaaaga cgccgaaagc ggtgcacaac gtattaagag 9540
ctcgctagaa ggtttaaaag gttcagctgg taaggttggt tcggtgttta agtctgtact 9600
cggtgctaac ttggtcggta gtgctatcat gggaggtatt agtgcccttg gcaatggcat 9660
gaagtcaatg gttggtgagt tgaataattc agctaaggca tggaagacct ttgaaggcaa 9720
catgcaacaa attaacattc caaccgacca gataaagcag gttaaaagcg agttgcaaga 9780
ctatgcaaca aaaacagtct attcagcttc cgatatggct tctacatact cacagctagc 9840
agctgttggg acaaaaaata caactgagct tgttaaaggt ttcgggggac ttgcggcagc 9900
agctgaaaac ccccaacaag ccatgaagac cttgagtcaa caagcaacac agatggcagc 9960
taaacctaag gttcaatggc aagatttcaa gctaatgatg gaacaaacgc ctgctggtat 10020
tgctgcaatt gcgaaagaaa tgggcatgag cactgctgaa atggtgcaag ctgtccaaga 10080
tggcaagatt aagaccgagg atttctttga tgccatcgca aaggtcggta acaacgaaac 10140
tttcagcaag atggcgacag agttcaagac tgttgaccaa gcaatcgatg ggatgaaaga 10200
atctctagca aataagctaa tgcctcagtt tgaaaaactc aatcaaatag gtataaaggc 10260
agttgttggt cttaccgacg caatcgaaag gattgacatc aacgccattg cggacaagat 10320
tggcagtgga ttgtcttcgc tttggaaagg tttctcaaac acgggagctt taaagaacct 10380
tggtgcgacc tttaattata tatcaaaatc aatcaagcaa ctatttagca agattgatgg 10440

```
tagcaagatc atgcagggca ttggctcggt gtttggcgat attgcaaacg gtatctcaca  10500
agctctaaac attgctacga catcggttaa aaatttcata aaatcatttg ctgatactgg  10560
agcatttcag tcatttaaag ctgctgttca agacacttgg aacgccatta agactatcgg  10620
ttcatcattc ggcgaagtac ttggtagctc acaaatgcag tcaatcattt caggtattgg  10680
atcagctctt ggaacgcttg taaactggat atctcaagcc atttcagcag tgtctaagtt  10740
tgtcagctca ttaccgccgg aggttctaaa cggtatcacc agtgggattt tggcaatggt  10800
agcaggtttt gctactgcca aggctggtat ttcagtatta ggtgttgcaa tgaaagggtt  10860
ggacttcatc aatagtttaa atcctttcaa gaagtttgga aaggacgctg cagaaggaac  10920
tgaacaagct gccaagagtg ctaaacgttc taaatcaact atcactcaat tattcagtgg  10980
gatggccaat gtcattaaat caacagggac tagcatttca acagctacaa aaggcatcgg  11040
aacagggcta tcaactgctt ttaaaggctt tggccaagga attaaatcag ctttacaagg  11100
tcttaaaggg ttgaaccccg caaccttgct atcatttggt gcatccgtag ctatcgcagc  11160
agtcggaatc ggtgctggta ttggtattat cgttgcttca ttcactttgc tagccactca  11220
atcccaaggc gtttcacaga tattaaaagc tttgggttca gcatttagca cagtcgtcca  11280
aggtattggc aaagctgcag gaactatcat tgaagcattc ggaactgctt ttggaattgt  11340
cgtcaaggca gtcggtgaag ctgcgcccgg acttgcacga ttatctccat tggttgaagc  11400
tatcggcact gctctaggca atgcagcacc atttattaca gcatttggta atgcttggac  11460
ttctatttta ggaacgtttc cagctattat cagtgcattt agtggattag caaccgctat  11520
cggtactgca atcagtgcag tagttaccgc aattactcca attattcaaa tcattggaaa  11580
tacaataaca gcagtaactc aaatcatcgc taacgctatt attgcaatcg taccagttat  11640
cgcgaattgt atcgttcaag ttgctcaagt tatcggacaa tttgggccac agattgcaat  11700
ggtaatcagt actattgctc aagctatatc agcttcagca cctatcatca taaccttgat  11760
tcaaggtatt gttaccgtcg ttcagacaat ggctcctgta atgagtcaag tgatctctgc  11820
catcgttacg gttgttcaaa ctcttgcgcc tatcataagc caaaccattt cagctattgt  11880
tacagcgata acgcaaattg tacctattat tacatcaatc ggtggtgtga ttagtgctgc  11940
attgagtggt attgcatcta ttgtgtcagc tgcaggaatg gcaattgcta ccgcagctat  12000
gggtatcggt acggctatta gtacggctct aagtggtgtg gctagtatta taagtgctac  12060
tggtgctgta attggtgcag ccttgcaagg tattgctagc gtggttcaat cagttggaac  12120
atcaatcagt acagctgctc aaggtatcgg aaacggtatt aagtcagcgt ttgaaggcat  12180
ttcaagcgtg attacttccg caggcaatgc aatcagtagt atattgaata gccttgctaa  12240
tgtattcaac tcaattggta cagctgctca aaaagcaggg attggtttca atcagttagc  12300
aaatggtgtg gttaagatta ctaatacaaa tctcggtgac atggctgcat ctcttgcagc  12360
agtggctcat ggtattggtt cgattgggga taactcagca gggcttgctc aagctggttc  12420
tggtatggct caacttggga atggtatgag caaagtgtca acatcagcgg ctagcgctgt  12480
ttcaggattg agtcttttct caagcatgat tacaagtatt caatcagcgt ttactagctt  12540
acagtcaatg ctaactatcg caggaacagc gttcagcacg ttctcaattc aagccatgca  12600
atcactaact ggattgtctg ctattgcagt acctatcaca atcttccaaa ctcagattat  12660
gatgatagtg ccagcattaa tgcaagcaac agcaggatta actatgttca gcgcagtagc  12720
tatggcatta gcaactagct tgacctcaat tggtgctgtc atgactatgt tgactaccaa  12780
```

-continued

```
catgactatg ttagctacac aactaacaat gataacaaca agcttcacga tgattgctaa  12840
tagctcagct atgctaggaa caagcttcgt tatggttggt acatcgctaa ctatgttgaa  12900
tagtcaattt atgatgtttg ctacaggaat catgcaaatg acatcacagc tcatgatgtc  12960
aggtgcagcg gtagctatgt ttggtgctca actcattgca gcacaaactg gtttcagtat  13020
ggtttccatg atggctacta tggtatctag tcagcttgct atgcttacta gctcggctca  13080
aattgcagga gctggatttg caacagtaag tgctcaagtc atgatgcttg ctagtgtatt  13140
cgctaccgtt ggagcgtcag caatgacact acaatctgca atggtgtcat taggtatggc  13200
agtaagaact ggcattatgt cagcggttca atcggtaatg tcaggttcta tgcaaatgac  13260
tgctgctcta cgttctagtg gaactcaaat gattgctatt acacaagcct ttattaatca  13320
aatagttacg gtggtgagaa atggcatgaa tcaaatcgtt gctccggtaa gggttggcgg  13380
tgctcaaatg gtttcagcaa tgcagtcaag cggacagaaa ttagtggtaa ttactcaagc  13440
agcggttaac caagcagccg cagcagcgag atcaggttac ggtgctttct actcagcagg  13500
agcttacatg ggacaaggtc ttgcagcagg tatgaattca gctcttggat cggttacagc  13560
agcagctaac caactggtag cacaagctga aagagcggca caagctaaag ccaaaatcaa  13620
ctcaccatca cacctattcc gtgacgaagt cggttggtgg attggtcttg gtattgctcg  13680
aggtatcgac gaatcagctc cagaggttgc gaacagtctc gattatatcc gtgaacaagt  13740
caacggattc aatgttcgag ctaacgccat gctaacgggt gccacttcaa atatggctag  13800
tcagttgaag atggaagtac tcagagataa aaccccagac gctacgattt cagcacgtca  13860
agaagcctat gctgcacatt cagccggttt gcttagtgat gtgattgatg ctcttggaga  13920
actcaaagac caagtagcac aaggtcaaaa catggtatta gataccggta ctcttgtcgg  13980
tggcacagtt aataatttca acagtgctat cgatacgatt aaaacattga aaggacgtca  14040
cagattatga ttactaaaat caaagaatat atagcgtttg gcgattttaa tagtcgtgac  14100
gctggttggt acttacagaa acgtgaagca ccaacgccag gcgagaaaga gattgtcgag  14160
tctatccctt acatgcaagg ggagcttgat ttctctagtg ttcttggtga gcgtgtcttt  14220
gagcctagag agattacata cgagtttaag ttaccgttta aagagtacga agaccgtaag  14280
acagcagagc gtatgattaa gtctcaaatg gtcactaaaa cagaacagaa actgtttgat  14340
acgcatgata gacgttatta ctggatgggc aaggttaaac acatcaaagt agcagacgat  14400
cctattaaga agaatctggt agctaccatt gtttttaagt gctatccatt cgcattccac  14460
gaagatgaat actttgatga tgtttgggat acattcgatt ttaataacga tttttcagtg  14520
tggacaaagt gggaagtttc aggagaaaaa agtatttatt ttgtaaattg tggagacaca  14580
tctattagcc caacgattaa atgtagtagt aatttcaatc tgattgatga caatggaaca  14640
atttataact ttaaaaaagg tgaaaataca gatttcacct taattttaaa acccggagtc  14700
aactatttta ctgctcaagg agatggctat atatctatgc atttttctat tgaggtaatg  14760
gcatgacaaa tttaaaaagt ggaggatttg aagtttatca ctggccaagt tttaatgata  14820
gactatcaga taaattatct aaaaaaacta ttcatagaca ggttatccac gaaccgtatt  14880
cacgaacagc gaataaagtt ttatcaggtc agattactca agctttgaat gcaatacatg  14940
aatttacttt tacaattcca ataactaatc cgctatatca aaatatagta ccttttcaat  15000
caattattga agtagttaat cttagagatg gtgaagttga atttaaagga cgtgtgctag  15060
ctatgtctaa taagatgaca agaaatggct ttgttcaaga agttatctgt gaagattttc  15120
tatcattctt tcatgattct agtcaatatt ttcaaaagct aagaaatgaa ggaactagac  15180
```

-continued

```
catacttaga agaaatttta agagtagcaa atagtcaggt agagccttac aaacggatag  15240
cgttaggtaa tgtaactgtc gaaagtagga ctgatagacc ttatcggtat ttagggtatg  15300
aaactacatg ggatacaatt cgggagcgta taattacaag tataggaggg tatttaacgc  15360
tacgtgaaga aaatgatggc ttttatttag attggactgc agatgtagga gaaactaaaa  15420
aaagccctat ccaattgggt aggaatatca aatctgctag ccgtgatatt gactttgatg  15480
gtcttgctac tcagattatg ccaattggcg ctgatcttta tacacaagga agtcaagaag  15540
aactaggtaa tgatgtaaca cgcgctcaat tggatatttc aagtgttaat ggcggtaaga  15600
tatggcttca agatgatgag ttagtaaaac aattcggaat tattcgtaaa cctgtcattt  15660
ggacagaaat tgatgaccct aatattttat tggctcgtgg aaaacaatac ttgagagatc  15720
aaaaagtttc attagctaaa tggacagtct ctgtagttga aagatatctg attgatgatc  15780
gttatgggaa attcaaaatc ggtaataaac atcctatttt aaatgcccca atatccgata  15840
tagcgacatt acagatagta gagaagaaaa tagatatatt gaaacctcaa atatctgaat  15900
tgacgatagg gtctcagtat caatcattat atgaatatca attacagttg cgtgaagcaa  15960
caaagtctat cgctaaattg aaggaagatt cttcagttgc gaataagcga aaacgattag  16020
agagcttaaa atatcaatta gatagcttga aaaaagatac tgaaacacca ccagttagac  16080
cgtctgcacc aactccgcta tcagataaag caaccgatgc agaacgttct gcatatgaac  16140
aatctttata tgtttatgaa attgcaaaaa agacatatga agaacatctg gctacttata  16200
ataagaacca agaagaaaaa gcaaaaacta tttcaaatct tgagtctgaa attgctagat  16260
tgcaacaaga actaaaggga ggtaattaaa tatgcaacaa acagaagcag agggacgttt  16320
gaacctctac gatgatgtga cgccgttgga aaaaaccaaa aacattaatg ttttgacagc  16380
ggctatcaga aaaaaaacaa gaggggcaga tgtccgtgaa gccatcgcta cgggtattga  16440
aacgacttac gcagatagta tcgctaacgg aaataccaac atggaagtcg ctaaggcaag  16500
aggaacatat aatactctag gagatagact tgaaaatttt gatactgaaa tcaggaatat  16560
tgtaagttgt tcaccaaaag gaatatatgc taatctatca gagctacaat cggctaagcc  16620
gaacggagat tccggaatct atctcacaac agacaacggc cattggtact attatgctaa  16680
cggttggaaa gatggtggcc tgtatcaggc ggcggggatt gctgatggaa gcgtgaagtt  16740
ttcttcaatc gataaaaaag attttaacgt tcagtttgac ccgaaattga aagtcgtata  16800
taagccaaat ttaaattctt ggatgaatgc agataatccc accgagaacg ccacaaaaat  16860
ttatatgatt ccatttagag gcgcaggcaa agtgaccgtt agtttttatg gatccctgtt  16920
tcctggcgta aaatcgcaaa taaagttagt caaaaaggct actaattcaa gtaattattg  16980
tgtgtctctc aatgaaaaaa ccataactga aacgacagaa ggcggatata caacaattac  17040
gttccatcat ccagttccta aaggcgaata ttttatcgct ttttgtggaa ttaatttcag  17100
atggaatttt ggatatagtt attggttaga aagctcttca ggttacaatc agtcgatttt  17160
tttacaaaga aagacagaaa atagatgcat agatgctgtt attgcttgtg atttttctgt  17220
tgattctagc ggtgagaaat tattagacga aaatatgcac tttgattcag gtatattttc  17280
gtttcacact gaacctattt tatatattcc taattacgaa ttgcctatcg gaacaaaatc  17340
tataattctt gggactaaaa acaatacacc tgttttcatt tttagaaaaa atgaaaataa  17400
tacgtttgaa aaaataaaac aaatatacac agaagaaata ggtgaaggag cacgttatag  17460
aaaatacttt ttagacattg ttgctgaaaa agatatgtat gtcggagttt ttggaaatgt  17520
```

```
ttattatgat actgctggtg atgtttctgc aaagaaagga catttcgaaa aagatatttc  17580
ggcttcagat tctgaaaata tagggtcaat gtatttcaat ccaaatacaa atattcacat  17640
ggttcctatt ttatattatg atgaaaattt aattaatgtt gcacaaaaaa atgcgaattc  17700
atttgaggaa ataaatggat cgctaattga tatcaccaat aaaataaata aaataaataa  17760
aaaaacaata acattagcaa acataatcag aaaaatgaaa agagggaatg cagtcactat  17820
ttcgctttac ggagactcaa cgtactatgg tcataagtca ggcgctgtcc ctttaggcac  17880
tagaacaagc gagcctgttt ctgaaagttt gcaaaaatat ctacgtgctt attttttgaa  17940
cgaaaatata acagtaaaca actatgcaac taacggaaga caagcacaac aagattcaga  18000
tgattgggac acaaaaatgg ctaatgacaa agcggacgtt atttttataa atttcgggat  18060
aaacgattca aattccggta aaacagcaga aactttttac agtcaaatgg aaactttagt  18120
acaaggtgcg ctgaaaacga acaaagcagt catcttagaa actgctaatc aagtcttaac  18180
ttttgacaaa ggaggtcaag ggatgggaga ctatacgaaa gcttttaaca ttaaagaatt  18240
tgttgatgta acaagacagt tagttaagag ttataatatt tatttgcttg atggatataa  18300
acgttcatta agctacatta acgaattttt tgatcccaca atagctttgc cggacggcat  18360
gcatccgtca gacgatatgt ataagtataa agctgttcaa atgatgtcta tgtttactaa  18420
tacgagtttt tcaaaattaa aatcaggaca gacattatct attttagaag ctaattttaa  18480
tacaacaaca ccaaatgcag tagcggatag cagttctaaa ttcggtttta aatatacggt  18540
taaagacatc tcggtatcat ttggactaga aaaacaatca gatattaaaa tttatatcaa  18600
aagcacagca tcaatgaaag tttatgttaa tggtttagat actcaatata ttagctctga  18660
tggatatatc gtaataaaaa atattcactc taacgatgta ttcattcaga tcacttcaga  18720
cgaagcgaca gatgtttatg gtttagaagt ggtttaaaca cgatcattga gtgtgctttt  18780
tttagaaaag attattttga gcgctagctt actattgcaa tatacagctt atgcggctgt  18840
cggcgcccaa gtgcaaaaat ttcttgattt atccatacag gattgcaaga tgacaatact  18900
gctgaataag cttagaaagt gaaatttatg ttgaatcctg aaattattag aatgattctt  18960
agtatatctt tatcattgtt aacgctattt acatttttcc aaagtcgtat gactttaaca  19020
gaaaaacgtt taacgattct tgaagagaat aataaacaac aagataaacg actggcagaa  19080
aacaaatcta tgttggataa tcacgatcaa caaatgaaag ttcttatcca aatgaccgaa  19140
caaatcaaaa atttgtcgga aaaaattgaa aaaatcgata acaaattgga ggaagtcaaa  19200
tgattaattt aaaattacga ttacaaaaca aagctacatt agtagctctc atttcagcag  19260
tgttcttgat gctgcaacaa ttcgggctta atatcccaag caacattcaa gaaggtatta  19320
atacattggt taccatcttg gttattcttg gaattgttac cgacccaacc actaagggga  19380
ttgcagacag cgaacgagca ttgaactatg atgtaccact aaacgaaaag gaaataaaat  19440
agtatgagcg tacaacaatc tattgtaaat tggtttgtta accatcgagg caaattgacc  19500
tattcaatgt atgggtcacg caacggagca gacggtacag ctgactgctc tggttcgatt  19560
tcgcaagcct taaaagaagc tggtattggt attcaaggac taccatcaac agtaaccctt  19620
ggtcaacaac ttgccaaaaa tggattctat cgagtaagta ttaatcaaga ttgggatgct  19680
ttgacaggtg atattgtgtt aatgtcatgg ggtgctgata tgtccacatc tggcggagct  19740
ggagggcacg ttggtgtcat gatggatgct acatacttta ttagttgcga ttattcaact  19800
caaggggcac ctgggcaagc tatcaatact tacccgtgga atgactacta tgcagcgaac  19860
aagccttcct atatcgaggt ttggcgttat tctgattcag caccacagac gaataaccaa  19920
```

-continued

```
gcaaatacag cagtagcacc acaacaaaag gcttactatg aagccaatga agtcaaatat  19980
gttaacggta tctggcagat taagtgcgac tatctatgtc caattgggtt cgactgggtt  20040
aactaatttt cggctcagta taaactaagt gaacgcaaac aaagcggtgt catgcaaaag  20100
catggctaac ggtggacacc cagaacgggc aataccgtgc caagtctggt ataatagtat  20160
cagaaaggtg taacgactat ccttttgagg agtacactca ctatttgtac gcgagtggaa  20220
gtgcttagac tttagaaaga tggtgtcata agatgagtaa aaccaaacgt ggcgtttgtg  20280
ccaattgtca tacagtattt gaagtttcta aaaaacaaag atataaaatc aaaaacggta  20340
aatcggtttt ttgttcccaa acttgttctt tagaaaaata cggaaaaact aaaattacta  20400
tttctgaaat tcctttaagt atgacagaaa atatctaaag taagatatag tctaatccca  20460
ctaggaatag tgggtagtaa tgagaaaatg ggatcccagt agacatggtt aactgggtgg  20520
atgctaacgg taatgatatt ccagatggca agtctgaaga cttcaaacct ggaatgttct  20580
ttagttttgc aggtgatgaa gtcaacatca cagacacagg agaaggtggc tattatggtg  20640
gctattacta ccgacgtttc gagtttggtc agtttggtac ggtttggctt tcttgttgga  20700
ataaagatga tttggtaaac tattaccaat agaccacgca aactaaaaaa taaaaaagga  20760
gtatatcacc tcacctcaca ctgcagtagg gataccatgg cagtagtggt cgaagcccca  20820
gcataatgct gaggcttttt tgtttgcttt ttttaaaata aatgctacta tattaatgaa  20880
tacagttaaa agctgagtct tcgataaact ctctctcacc ctgacttgaa ttagtcaggg  20940
tttttgtttt gcaaaaaaat atatattttt ttataaaaac agttggcaga ctatcatata  21000
tgatatgtaa tgtatacata agataaagag agaggtaaaa actcgcttta gtcaataggt  21060
agaacaaaat tttaaaattc tagaagaagg ttatgatttt acaagtgtag ttggaactac  21120
ggttgtaaaa tcataacctt tctcttgccc tgacttgaat tagtcagggt ttttgttttg  21180
caaaaaaaat atatattttt ttataaaaac agtttccgtc tggtcgcaaa aatcgacttg  21240
aatggattga aaacaatctg gaaaatattc gataaaaaat aaaaaaacga ggtaaaaaca  21300
atggatacat acaaagaaca atatatagta tgttttacta attttcaagt tgtttaataa  21360
taaaatcaaa aaaactttaa aaaaaatcaa gaaaactatt gacattgaat tttatttaaa  21420
ctataatatg tttgtaagtt agttagagag gaggaacaaa aatgacagaa acaattccaa  21480
agattacaat taaagaactt cgagcacgtc acaatttgac acaagaggaa tttgctaaaa  21540
gtgttggtac gtcagcacaa acagttagtg cttgggagaa aaaccgactt tcaatctctc  21600
ctaagttcat gttagccatt tgtaaaaaat acaaccttaa atcgtctgat ttgtatggct  21660
tttgatttta aaacttgaat taaattcaag ttagaaagga acaatatgaa cgaaatagca  21720
acaaatgatt ttaattactc tttagtcgat gcaaaaacga aagaatttct ggaagagcgt  21780
gccaatatca tttacggcat ccaaagcaag agtgcttacg aaattggaaa acaacttgcc  21840
aaagctcaaa aagagctttc gactagaggt tatggttgct tcgaagaatg gtatagaagt  21900
ttagggttta aaaaaaccaa agcttatgaa tatatcaatc attacaattt cgtttgttcg  21960
caaaacgaac aagcaaatat tgaaaaattc gaaagtttgc ctaaaacgtt acaagctcaa  22020
gtatctaaac catctgccaa tccagaggtt aatcaagcag tgttcaacgg agatatcaaa  22080
actcacaaag aatataaaga gcttgagcgt cgtctcaaac tcaaagacca agcactggaa  22140
gcggtcaagg gagagttgga acgtgtcaaa caaaccaaaa ctactgaaaa gataatcgaa  22200
aaagaagtca ttccgcaaga ttacaaagca acgcaagacc ttaacaagca attgctagga  22260
```

-continued aagaataaag acctagcaga cgagcttgat tcagtcaaaa ggagcttgcg acttaaggaa 22320
gcagcttatg aaatgctcga aaaagaaaca tcagaagcat tagccttgaa agagtctatt 22380
gagcacttac gagctgataa ggaagagcta gaaaatagcg tgactaatat ctttaatctc 22440
agtaagcttg ttaccaagtt tgaagacttc tttgacgaag aaatggcacc gctcagattt 22500
aaaacgctta ttcaaggcat tggaaaagac gctcagattg aaaaactcag agatatcttg 22560
acactaactg aaaattggct agacgaaatg aacaagatta tcccagagaa tggaagaaca 22620
attatagaag gagaaatcat aaatgagtaa gaagaaaagt aagaaagaca acgttcttat 22680
cgagacagta aaaatgcaag gcgaacaagc tatgcaactc gtcaaacaag cgaaatttaa 22740
ccaaaactta ttggatgaag tgattggttt gaaagacgaa atggatagaa atgttagaaa 22800
gactaatcaa aagctaactg acattgagtt gcttgtagag gaagtcaata agaaggtcca 22860
tattgacgac ggtgaagctt ctaaaatcaa gagtattatt ttcaaaaaag ctggcgtgtt 22920
tgctgacttc tactttaaag aacagaaaac acatccaagt gataacttgt tcgcatctaa 22980
gaaggggcag tttattcgct tgatgtactc gcatttgaag aaagaattta acgtgacaaa 23040
atacactaac atcaagcacg ttgaagctga gaaggcagtt aagtttttgg aagatttatc 23100
ttacgacgat tttacaccgt ttgagattcg tgaaacgcca aaacaaaaag agattatagc 23160
tcttgaaaaa aatgagtgac tgaaagcatt ataacgtttg agtttcaata aaagataaaa 23220
aactttaaaa aaatagaata aaattgttga caaaataaaa aatatggttt aaaatagaac 23280
cataaagtta agaaaggaga gtttgatgga atttaactat tctaaattaa agggacgtat 23340
taaagaaaaa tacggaactc aagagaattt tgcgaaagct atcggaaaaa ctcaaaccac 23400
aacatctttt aaaattaacg gaaaaagatt gtggaatcaa gatgaaatca ttaaggctat 23460
tgagctatta gatctttcaa aagatgatat tgtagaatac ttctttaact attaatagaa 23520
aggtatttaa aatgaaaaac ttatttaaat ggattttagc taaagatgag aaagaacaaa 23580
aaccagtatg gacaccatac gaagaaaacg aaaagaaata tgaagaaatt cataaacaac 23640
tatcaatgaa ataaaatagc taaaccgttc ttcaatccgt agccacacct cgatgtgctg 23700
agtgcaactt aataccccaa aaataaatat aaataaaaac caaaactacc ttcttagaaa 23760
attgaatatt aacgagtaca tcgggggctg ggtgcggatt gaagcactaa aaaaacacgg 23820
gtaaaagccc gtgtcatata aaaatctaat gatgttatag tatcacattt aaacaaaaaa 23880
agcaactgga gagggtgagt ctaaaatgtc tgataatcaa aaatactatt atatgaggct 23940
caaacaagac ttctttgaga cggaagaaat gataatactt gagtctatgc aagacggcta 24000
tttgtatagc aacatcttgt tgaaactata tttgagaagt ttaaagcgtg acggtaaatt 24060
gatgtttaac gacacaatcc catacagtgc tgaggtttta gctacagtta cacgtcacag 24120
cgtcggaaca atcgagaaag ctatggatgt cttccaaaag ctaggactag tcgaggtaat 24180
ggatgacgga gctatctata tgttacaaat tcaggaatat ataggcaaaa gctctactga 24240
agctgaacga aagaagcgtt atcgagatag aatcaagctc gaaaaacgtg agaaaaatga 24300
ggctttggaa aatttgggac atttgtccac caaagaatcg ggacatttgt ccggacattc 24360
gtccaccaga gatagagata gagatagaga tagagataga atagatataa agacagaagt 24420
agaagtagaa gagagaaatg gacagatgtc ttctgctact gctgctgata aatctaattt 24480
aaatatcttt gaatactatc aagaaagaat cggtcttcta gatggattcc aattacaaaa 24540
gttagaagag tatcaagtta tcgatagact tgaacctgaa ttaatcaaga tagccattga 24600
taaagcagct gataactcta aacgttcttt tgggtatgtt aactctatct tgaaatcatg 24660
ggctcaaaat ggaatcaaga cagtagctca acaaatagaa gagcagaata atttcacttc 24720
taacaagtca aatagtgaca aacccaagtt tggaccagct tgcagtaaat actgagggga 24780
tttcctatga gtttagatca aacagctaga cagatgcgac agctatatat gactactagt 24840
gataaatact gcgagaagca caatcgaaac tttgtcacta ttcagctacc aaacagcaag 24900
ccatacactg tatgtgagac gtgccatcgt gaagagcaag agcgacagaa ttctattaaa 24960
gcacaagaac agtttgagcg tgagcaagag cagaagcgtc tctactttct caaagatttc 25020
agtttgatgg atgatgattt aaaaagtgct agctttgaaa cttaccatgc tgttaccaaa 25080
gagcaaaagg aagacttgaa gaatgttcga agtcaactca gaggctatct cgatggccag 25140
gactacaaca ttgtcctcat tggtgatact ggagtaggca agagtcatct agcttattca 25200
gcgctcaaag ccttgtctga tcatacgaag aagatgggcc tattcatcaa catcgttgac 25260
ttgctagcca aaatcaaaga ggatttcagc ctagaagcag aatacatcag acgtatatct 25320
gaatctgagt ggcttgtatt ggatgatgtt ggcactgaaa aagtaacaga gtggtctaat 25380
ggtatcttgt acagcatttt gaacaagcgc acaaagacaa tcataacgac aaacctaagc 25440
ccacaggaca tcatgggcac atatggtaaa cgtgtatatt caaggatttt taagaagaca 25500
ggacttggaa ctactaacga acacgtttac aagtttaaaa cacagcaaga caagaggatg 25560
atgctatgac agaaacagaa gttaaactaa agctctttga ggactacgag agcattcatg 25620
gacttgtata ctcggaggaa tataagcaga aaatgatgga tgagctagat acttattcat 25680
tcataagtaa aatgaacgaa ttgatgtaca aagctaagaa tccaattcag gtttttagcg 25740
tacaataaaa cccctctaaa atcgatttta aggcgtgtat tttgctctat agtacaaata 25800
tactaggata catttaaaat tgcactacac ccccttaaat tgagaattag ggcatatgaa 25860
agggaaatga tatgaagaat gaattacaaa gtacaaaagg agagtatttg accgacttgc 25920
aacatcttga tggcgaaacg ttgaggaatt tcgtcgatcc caaacatcaa gcaagtccac 25980
aagaactcca aacattgcta gcaatcgtta agaaccgcaa tcttaaccct tttactaaag 26040
aggtctattt cattaagtat ggaaacaatc ctgctcaaat cgtagtatca aaagacgcat 26100
tcatgaagcg agctgaacaa aatccgaatt acgacggatt tgaaagtggc gtaatctacg 26160
aggatgaaaa aggtgagctt aaaactaaaa aaggtgtaat cttgccacgc aaaggaacat 26220
taattggcgg ttggtgtgca gtgtatcgaa aagatagaag tcgtccaata tatcgtgaag 26280
ttgaattgtc agcttataac acgcataaaa attggtggca gaaagcacct ggtcaaatga 26340
ttgaaaaggt ggcaatcgtg gcagccgttc gagatgcatt ctccgagaat gtgggcggtc 26400
tttacactgc agatgaaatg gaacaagttg cacctgtcga cgttacacaa cgagaaacgc 26460
aagaggatgt taagattcgt aaaatagcac aagttgagca atacagacaa gagcaatctc 26520
aaccagttca atcagagcca gaactagttg aagacgtagc tgaagctgaa gaacaacaag 26580
aagtcaatcc taatttcatt agtatcgagc aacgtgacat tatcgagaaa caaatcaatg 26640
aattagcttt aatcacggga aagccagccg aaacagtagc taattactat ttgaataagt 26700
acaaactcaa cgattttcat gaattacttg tgtctggatt tgaaattgtg accaacgaca 26760
ttcaaacaca gataaataat agaaaggcga actagatatg aaggatataa caaacaattt 26820
tattgaaaca atcgagccag tatatacgcc gggaataatt aggtttgatt ttgacaaatt 26880
cgatgcagct atccaagcgg cagttagcga attatcagac gaacaactag acaatcttga 26940
atataacgat attaagaatg aatttacacg tttcaacagc ttgctgacga aacttgaaac 27000

```
taaacgaaaa gaaattgcga aagtttataa aaaccctttg acagagtttg aatctaattt  27060
caagtcatct aaagagccac tcaaagaaat tattgacaaa ttgcgtgcca aacgagatga  27120
gattgacgaa catcatagaa tgctacgagt tgaccacgtt agatcggtct ttgaagaaaa  27180
gtgtgagctt gcagggttgg acaaagatgc tttcaaggac aagtacgacg gctattcttt  27240
gaagaagtgt ttcaaagaca aaaagatgga actcaaaaaa gaaaccatcg aagaaatcga  27300
cgctttgatt ttagctgaat acgaccgact tgaagaatac aaggccaaca ttgcaatgat  27360
tgaggaacaa gcccttgatt atgagttgcc agcggaacct tacactagag cgttgcagaa  27420
cgacacacct atagttgaaa tattgaagca aatgaaaaaa gatcgtgatg cagctattga  27480
acgcaaacag caagcagaag ctaaacgaca agcggaagct gagcgccttg cagaaattga  27540
agcgatggct aaacagtcag ctaacgagga gattaaggcg gtaaatgctg aaacaggtga  27600
ggttatcgaa aaatcaaaac cagcagatga aactccaatc aaaccagttg agccatataa  27660
aatcgatatt tctctaacct tccacggtgg agagaaacaa tggtatcaat ttgccaagat  27720
gcttgaagac aactttgtaa actatgaaat tttaggagaa aataaatgat taattcaacc  27780
gttcttgttg gtcgcatgac caaagatgca gaactaaaat acactggaaa caatatcgca  27840
gtagcatctt tcagccttgc ggttaaccgt aactttaagg atgctaatgg tgagcgtgaa  27900
gcagatttta taaattgcgt tatctggcgc cagcaagctg aaaatttggc taattgggct  27960
aaaaaaggcg cattaatagg aattactgga cgtattcaga ctcgtagcta tgaaaatcaa  28020
caggggcaac gagtgtatgt gacagaggtt gtcgctgaga attttcaaat gctagaaagc  28080
cgtgcagcgc gtgagggggg taatgctaac aacagttata gccaacagca agggccaaac  28140
tttgcaagag aaagcggacc ttacgggaac tcaagcccta tggacatcag tgatgatatg  28200
ctaccgttct aatttgagga gggtttatgg atattaaaga aataaagggg tatgaggggc  28260
tatatgaagc acattcggac gggacgattt ggtcttgcaa aaataaaaca acatatagct  28320
ttgtaaggga aaagacaata aaaagggttt gggaacaaag agagataaaa cctcagatag  28380
caagaagaca aaggagtgat cactacgata agcgagtgaa attgtggaaa aacaaaaaga  28440
tgacaactca cctagtgagt aggttgattg ctcagacttt tataccaaac ccagaaaaca  28500
aaggctacgt caatcacaaa aacggcaacc ctttagacaa ctcagtagag aatcttgagt  28560
gggtgacaag gtcagaaaac atgagacatg cgttcaaaaa cggtttgtta caaacaagta  28620
aaaaagtcac tctagtaagc aaggcagacg gggcaaaggt aagcttttac agtctaagag  28680
ctgccagcga gtttctaggt aaaaacaagg gttatttgag caatattata aaaagcggaa  28740
gaacgcttgg taattacgaa attgtggtag gtgaaatatg aaactagaat ttctattacc  28800
aaggtcaaaa actaaacctg ctcaaaattt agttatcaac agtaatgaca gatttcatta  28860
tcaagcagag ggccggatgg tcaagaaact gcgattgata gcgaaagcag aagcggggct  28920
taacaccaag ccagtatata gccctgataa gccttgcaag gtgcttgtaa ctgtctacgc  28980
accaaccaga agaagattag acccaccaaa cctatatccg actgttaaag ctattataga  29040
tggcttgacg gacgctaatt tgtggccaga cgacaaccac gaagttatca aaatgatgtc  29100
gtttcagtat ggcgggctaa gtggtgagtc tgggaaattt aagattgtgt tagacattga  29160
ggaaacgtta aatgaaaagc aaagttaaag acaaactggt cggtatatat gctccagcaa  29220
gctacggaca tacaagtgtg ttagaggaga cacaagagtt ttcgaagtgg ttttgggaga  29280
acagtaaaga catagactta atcagcgata agttaggaat tagcactaag aaattaaatc  29340
gcatcctaac gctggagcag ttaccagatg aggaattatt gaaagagatg atagagctat  29400
```

```
gcgaaataaa gaatacgctt tgtacaaagg cgaagaaatc atagctatgg gtacaaaacg  29460
tgaaatagct gaacagttag gaatttcagt acacgccgtt acttgctatg ggacaccatc  29520
atacgccaga agaactagcg aaaacgcaag gagattagta gagttatgaa atataaaatt  29580
atcgtctatt acgacaatat ggaagatgaa gtagaaattt atgataacaa ggatgaggct  29640
ctcaaaagac tgcatcattt gagaggtgtt aaatatcgca attcaagaat gtatacagta  29700
gagatgaaag aggaagcaga tgaataaaca ggaagcaatt agatcactac aggaaatggc  29760
tcaagagtcg ttcgaagttg taaaaataaa tgcagtgcat attgacaata tcgtggaagt  29820
cataaaccaa atagacgaac cgcagaaagt gactattccg aagtttgtag cggagtggat  29880
tgagtattgt aaatctaata aattgacatt gttgggtgct tttgaccaag tatcagaaca  29940
tggtattgga cttgctgata catttacagg ggtagtgcgg aaaggtattg attgggcaaa  30000
acgtaaccaa gaaaccttcg cccgtgcttg gttggacagt tatgaggttg aataggtgaa  30060
tagaattaaa cagttacgaa aagaaaaaaa gctatcgata gtcgatgtag ctgaacacat  30120
gggagtgcaa aaactgaatg ttttaaaatg ggaacacgga acaagtcaaa taagtataag  30180
ggaagccaaa aaactagcag actttttcgg tgttagcgtt ggttatctgt taggtcttga  30240
tacaactgaa aatgacagta tcactgatct aatcgcaaaa atcaatcact gggcggacga  30300
acgcaattta aagcaagcag acccaaaaat tcagtggatg cgtatcactg aggaggtcgg  30360
agaaattcgt gatgtactat tgaaaccgac taaattcaat gaaccacaaa cagcactcaa  30420
ggacgcaata ggagacacgc tagtaacgat tatcgtgttg gcacatcaat tagaccttga  30480
tgtcactgag tgtttaaata ttgcatatag agaaattagg gaccgaaagg gaaaaatgat  30540
aaatggaacg tttgttaagg aggaagacct ttgaaatttc ttgacttatt tgcaggtatt  30600
ggcggttttc gtcttggaat ggaaagtgca ggacatgaat gtgtaggttt ttgtgaaata  30660
gacaaatttg ctagagcaag ttataaagca atccataaca ctgaaggaga aatagagcta  30720
catgatgcaa caggaatcac aaagaaagaa atcaaagcaa tcggacaagt cgatgttatc  30780
tgcgcaggat ttccgtgtca gcctttcagc gctgctggtg caagacgagg ttttgaagat  30840
acaaacggaa ctctcttctt tgaaatcgca aggttcgctt ccattctcaa acctaagtat  30900
ctattcctcg agaacgtcaa ggggcttatt agccatgata aagggtacac ctttgagaca  30960
atcatcggat cattggatga gttggggtat gatgtcgaat ggcaagtgct taacagcaag  31020
gattttggag tcccccaaaa cagagaacga gtgttcatta tcggacatct tagaggaaca  31080
agtggaagac aaatatttcc tatcgctgaa acaagatcag ataaatcaat tatgcaacta  31140
ggaaatatca aaaaaaccga aagttttggt ggaaatcctc aatgcggaag aatttacagc  31200
atagacggat tagcgccttg cctaaatacg atgcaaggtg gacaaagaga acccaaaatc  31260
cttattgacg gtaaggtacg caagctgaca cctcgtgaat gttggagatt gcaaggattc  31320
cctgattggg cttttgataa agcacaagaa gtcaattcta acagtcagct atacaagcaa  31380
gctggtaata gcgtgactgt caatgtaatt aaagaaattg cgaggtattt atgaaacata  31440
aggatctaac gatagccaca attctactac tggtctcgct agcgattaac gtgactactg  31500
ttctgcgagt ggttaataga cctatcgaga ccgtggtgat ccacaaggca gataatgcag  31560
tggaactaca cggcaaggtt actggaaaat ctacggttgg caagctctac acgatcgatt  31620
gtggggcgta tggcaagttt ctagtgacaa aagaacaata tgaaagtgtt caggtaggag  31680
atgatatacc tagctatttg aaaggaagag gacaatgaag tacgtcgagt acgcaggact  31740
```

gaccaaagaa ttacattcaa ggttcgtggt tgaatttaac aatttgaaag agcaacacca 31800
tagaacatta acaaagtacg tgatggaaac aaagcagtgc gaccgattgc aagctagaaa 31860
atattgtcaa agatttgaca atgtgatcaa agagcgttct aagttatcac ccgcgacatt 31920
aaacgatatg cgtgagtata tcactgacgg actcgcaaac gacttagaga actatctgtc 31980
aaaacacttt tttagtagct ccgcaaagtg tcggccagat accgacaaga gaaatgctgg 32040
actgcctgag gaactcttta aacagtattg cgaggaaatc aaatcattaa aagctaaata 32100
cccaaacagc ttcaccgcct acatcatgga tgttaaaggg tgcaaatatc aaaaagccaa 32160
taacatacgg acagcgataa atacactcta tacagagatt gggatagtga cacctcgcaa 32220
ggtaatccaa ttagagggac ttctttctag agaattattc ggaaagatag ctaagtacgt 32280
ctttaataag tatgaatggc cggaaagcct agatgaagag gttgatcgga tttatttaga 32340
gtatcgcact aaaggtgata taggtcgtga taaagaaagt gttaaacgga cgctattcaa 32400
agcgatttca atgggcttat agtggttcga atccactatg agttgttaat tccagtaagt 32460
ttggaggtga taacagcgta actgtctttt caaattcttt attcttgtag cgttcgaggg 32520
ttcgactccc tcgctcgctg ttagtctgtc gtgactaggt aacttttttc gacactcgta 32580
tcgctgacag accgatacac aaacccagta aatattttat agaaatgagg atccaataca 32640
tactttttgc tctagtcttg cattactggt agcaagactg gaatttaaga tagaggaggt 32700
gataaaagga ccaagaacaa acactcttat cttttcatga aacctcttaa tgtttgttta 32760
ttggtttaaa aaacaaaaaa agaccgacat aatggccggc actctttgaa agtcaacact 32820
actattatac cagagagggc agaacaatgc tattgccgga aattgatgag aaagcaacaa 32880
tcaaacgttg caagcgcaaa cttcgagaat atccacgttg gcgagagatt gcacacgacg 32940
gagctgagca gaaaataaca caggaattca catttatgcc acggggtggt agtggaatga 33000
gtagaccagt ggaaaatatt gcagttaggc gtgttgatgc aatgaacgag ctagaagcta 33060
tagagcaagc agttagcggt ctatatcgtc cagactatcg cagaatattg atagaaaaat 33120
atctagagtt tccacccaaa cccaactggc agatagctca atcaatcggc tttgaacgca 33180
ctgcattcca agagctttta aacaactcta tcctagcttt cgcagaattg tatcgtgatg 33240
gtcggttaat tgtggagcgt tgaaaaaaat ggtattttag cggaatttta acggtctcta 33300
ttaactgttt taagtggtat tattatatta tcgaa 33335

<210> SEQ ID NO 4
<211> LENGTH: 34123
<212> TYPE: DNA
<213> ORGANISM: Streptococcus phage
<220> FEATURE:
<221> NAME/KEY: source
<222> LOCATION: (1)..(34123)
<223> OTHER INFORMATION: /organism="Streptococcus phage" /mol_type=
"unassigned DNA"

<400> SEQUENCE: 4
ggttcgaaaa ttacattaag tttggaggtg ataacagcgt aattcaaatt ctttattctt 60
gtttgctgtc aggggttcga ctcccttgtc agtcgttagt ctgtcatgac taggtaattt 120
tttcgacaaa acgtcaagct gacagacctt gacaacaaat ccagtaaata ttttatagaa 180
aagaggaaac caattttact ctagtcttgc attgctggta gcagactgga atttaaacta 240
gaggggggtg ataaaaaacc tcttaatgtt tgtttcaaac aaaaaaagac cgacacaatt 300
gcaggcactt tatgaaagtt aacactacta ttatatcaga gaggttagta caatgctatt 360

-continued

```
gccggaaatt gatgaaaaag caacactcaa acgttgcaaa cgcaagcttc gagaatatcc    420
acgctggcga gagattgcac acgatagcgc tgaacagaaa ataacacagg aatttacatt    480
catgccaagg ggtggcggag tgaataaacc tgttgaaaat atcgcagtaa gacgtgtcga    540
tgcattgaat gagctagaag ccatagaaca agcggttaat gggctatatc gtccagacta    600
tcgcagaata ctgatagaga aatatctagc ttatccgccc aaacccaact ggcagatagc    660
tcaatcaatc ggctttgaac gcactgcatt ccaagagctt ttaaacaact ctatcctagc    720
tttcgcagaa ttgtatcgtg atggtcggtt aattgtggag cgttgaaaaa aatggtattt    780
tagcggaatt ttcacggtct ctattaactg ttttaagtgg tattattata ttatcgaaga    840
agaaagaaaa gacggctcat ttgtgggttg tcttttttttg attaagtaat gaaggaggtg    900
gatgtattgg gctaaatcaa cgacaaaaac gatttgcaga cgaatatttg atatctggtg    960
tcgcttacaa tgcagctatc aaagctgggt attctgagaa atacgctaga gcaagaagtc   1020
ataccttgtt ggaaaatgtc ggcatcaagg cttatatcga agaacgactg aaagagcttg   1080
aaaagaaaaa gattgcaaaa caagatgaag tcatgcaagt attcacttcg attttacgtc   1140
aagaactcat ggaagaagtc gtagagctaa atgctgctac tggtcagttt gtcaagacaa   1200
agaagcctcc ggccatctct gaggtaataa aggcaggtag cgagcttatg aaacgctatc   1260
caacaactaa acaagccgag aagttacagc ttgaaataga aaaactcaaa tctcaaattg   1320
gtggagatga aggacaagat gaaaagatat ctggcttcct aaaccttatc aaaggagctg   1380
taaacaatgg acttgagtaa gctctatacc aagcgacagt tagaagtgct taattacatc   1440
tggaatcacg actggttcat ctgtgggctt catggagcta aacgtgctgg taagactgta   1500
gttaataacg acacttttgt aactgagtta agtcgtgtca gaaagattgc tgaccgatta   1560
ggtgtagatg agcctattta cattttggca ggtacgtctt caacagcaat tcagaataac   1620
gtcttacaag aactttataa caagtatggc tttgaaccaa aatacgataa acatggctct   1680
ttcgttttct gtggtgtcaa agtcgtgcag gtctatactg gctctatatc tggtcttaaa   1740
cgtgcccgtg gttttacagc gttcggagct tatgtcaacg aagcgtcgct agccaatgag   1800
tttgttttta aagagattat ctcacgctgt tctggtgatg gtgctcgtgt tgtttgggat   1860
agtaacccag ataatcctaa tcactggctt aaccgagatt atatcggtaa gaacgacgga   1920
aagattatag attttagttt caagctagat gataatactt tcttatcaaa acgctatata   1980
gactctatca aagcagctac gccaaagggt aaattctacg atagagatat tttaggactc   2040
tggacagtag cagagggtgc tatatacgct gattacgaca gtaagataca cgtagttgat   2100
gaactgccag acatgatacg ttatttcggt ggtattgact ggggatatac tcactacgga   2160
tctatcgtga ttgttggcga gggtgtagat gacaactact acctcgttga cggtgtggcg   2220
gcacaattca aagagataga ttggtgggta gagcaagcta ggaagctgac tggcatctat   2280
ggaaacattc cgttctatgc tgatagtgcc cgtccagagc atgtagcaag atttgaaaac   2340
gaaggctttg atattagtaa cgctaacaag tcagtgatag ctggcatcga gcttatcgct   2400
aaattgttca aagaacagag attatacgtt aagcggggat ttgtacctcg atttttcgac   2460
gagatttttc agtaccgatg gaaagagaac agcacgaagg atgagccgtt aaaagaattt   2520
gatgacgtgc tggatagtgt gagatacgct atatattctg attatgtcat cggtagcaca   2580
gagcaagcaa gttatgatga cttgcttagt atttttaggt aggaggaatg atggaacaga   2640
cactatttac ggacagtact ggacaagacc tagttttgaa cttacgcttc catcgagagt   2700
ctcgcattcg ttatcgagcg gacaacttag aggagctcat ggtgaataat tgggaattgt   2760
```

-continued

```
tgaagaattt catcaatcac cataaattga gacaagctcc acggattcaa gagctgttgg   2820
actatgccag aggtgaaaac cacgacgttc tcaagtctgg tcgtcgtaag gataacgaga   2880
tggctgataa acgagctgtg cataactacg gtcgtatgat tagcaaattc aaaacaggct   2940
atttagctgg taatcctatc cgtgtcgaat atgacgatag tgatgataac tcacaaaacg   3000
acgatgcaat taaacgaata ggtcgaatta atgatttaga ttcacttaat agaacgctta   3060
tcagagactt gtctcaaact ggtagagctt atgaagtgat ttatcgaagc gagtatgatg   3120
aaacacgcat taagcgatta agtccgttag aaacatttgt gatttatgac aattcattag   3180
aatataattc aatcgcagct gtcagatact acaatcgagg tacactccaa agtgcaaaag   3240
atgtagttga aatttacact aacgaacaca tctatacgct tgatgcatca gatgacttta   3300
atgaaatttc agttacaact cacgcgtttg gtactgtgcc aattactgag tttcttaaca   3360
acgttgacgg cattggtgat tatgaaactg aactctactt aattgactta tatgacagtg   3420
cagaatccga tacagccaac cacatgagcg acatggcaga tgctatactt gccatttatg   3480
gcgaccttgc cttgcctaaa ggtatacaag ccagtgacac gaaacgcacg cgccttatgc   3540
agcttaaacc tcctaaatca gcagacggca aagagggcac ggtaaaagct gagtacctca   3600
cgaaatctta cgatgtgtct ggtgcagaag catataagac acggttaaac agggatattc   3660
atatatttac taacacccca gacatgtcag atacgaattt cagcggtaac acgtctggtg   3720
aggcgttgaa atataagtta ttcggtctag accaagacag agttgacaca caatcacaat   3780
tcactcaagg attgaaacgt cgctatcgtc ttgctgctcg tattggttct ttggttaacg   3840
aatttaaaga ttttgatgaa agtctattga aaatcacatt cacaccaaac cttccaaaat   3900
cgttaaatga gcaagtatct attttgacag gattgggtgg ccaagtgtcg caagaaactg   3960
cgcttagtct ttcaggattg gtagagagtc ctaacgaaga gttggaaaaa ataaataaag   4020
aagtgtctga aatcgatttt aaggggtatt ctaacgactt taattcacat gtaggcaaat   4080
ataccgacga ggtaaaataa acgcatacag acgattttga gagggaatat gaatgacgta   4140
ctggacgaag cgtaccctac gcgagagaga agcgagcatc aaaaagggtg aagccgagtt   4200
taagaaagaa cttgaagcgc tatataactt gcaactctca cagctccgaa aagagcttga   4260
tgcttttatt caaaaatacg ctaacaaaaa tggattaagc attagtgatg ctaaacgaaa   4320
agcagacagt tttgatgtca aggcttttga aaccaaagct aaacggtacg tagctgacaa   4380
agactttagt ccaaaagcta acagagaact tcgagactat aacttttcta tgtcggttgg   4440
tcgtcaagaa ctgcttattc aagaattaga gctcgaacta ttagctctat ctgagagcga   4500
acgacaattg accgatgatt atctgaagag tggatataag agtgaagttg caagagagag   4560
cttacttgac cagacagtgc cgagtggtaa aactcttgaa aagtatatga aagctgctgt   4620
caacgctaac tttgaaggtg ctgaatggtc agagcgcgtc tggaagaggc aagaacagtt   4680
acgaaaagtt gtaaagaccg aagtaaccag agctctcatt cgaggggaaa acggtttgac   4740
gattgcaaga cgtatcagaa aacatatgga tgcatctcgt acagaagctg aacggttggc   4800
aattacagaa cacgcaagag tgcaaacgtt agcccaggaa agcatcatga aagagaatgg   4860
ctttgagcat ttcaaactca tgccagaatc gagagcgtgt gatatttgca aagatattgg   4920
taaagaaaca gaaaagaatc ctgtcagaat tgctgacatg gaaattggaa cgaatgctcc   4980
acctattcac ccatactgcc gatgtgcagt cgttgaggtc gaatagtaca ccacttttaa   5040
gaaacaaccg aggtcgtgcc tcgggtggtg tatagggcta ttttaagctc taaataaaca   5100
```

-continued

```
atactagcgt ggctcattgg taaatacact agataagact agacagggcg tagctagcct   5160
tgtcgtggct ttgaaagtgt gctgtcgatg agactagata ggagaacata atggaaacag   5220
ataacacaac agtcgaaacg gtcgaaactg aggaagtaag ccatgacgtt gatgaaaatc   5280
aatcgagcga cttccaagcg ccgcaatcac agtcagaacg agatagcatt gttaacaagg   5340
cagtccaaaa agccttgagt aattataaga agggcgaaga aactcgaatc aatgaggcaa   5400
tcgctaaagc gttaaagaaa gaacaagact attctaaatt atcggctgct gagcgggcta   5460
gcaaggaatt tgaagaccaa aaagcagaat ttgagaagca agtggcagag tttgagtttg   5520
agaaactcaa tatggcagtc aaagaagacc ttgtatcaaa gggattacca gttgaactag   5580
ctgaaatgtt tagtcatgct gagaacgcct ctgaagctct taaattggtt ggtacttttg   5640
aaaaagtatt caatgacgca gtagctgaga aagtcaaagc tactatccgt caaaatacac   5700
caaatgcagc aagttttggt ggcactcaga cagataactt cggagctaaa cttgctaaat   5760
ctacgaacgt aacgactgct cgttttatct aaagcagaaa ggaaatttta aatgccaaca   5820
caaacaattt tcgacacatc aaacattgtc cgctcattgc cttataaagc agtgtcagcg   5880
actgtagaca aatcatttcc aggtgtaacc gtagatggta aaaaatatat caaagcaggt   5940
accctcgtag caggtaatgg cggctcgatt tttgacgacc gcacaaaaac tgtcgtggaa   6000
aacaaaactg cacctgaagg aatcgttcta tatgacgtag atttgacaat cgataacact   6060
gtatcagtgc tctatgctgg tgaagtttac aaagacaagg tgaatggtgg ttctgtggac   6120
agcacagtta ctaaagcttt gccactcgtt aaatttatct ctaagaaata agaggaggaa   6180
tattaaaaca tgggacttat ttatgataaa ataaccgctt ctaatatcgc tggttatttc   6240
aacgcgttgc aagagaatgt tgactctact ttgggtgagt atattttccc agctcgcaaa   6300
caacttggga ctaaattgtc ttacatcaaa ggtgcttctg gtcaatctgt tgctttaaaa   6360
gccgctgcat ttgatacgaa tgtaaccatt cgtgaccgtg ttagtgctga aatacacgat   6420
gaacagatgc cattctttaa agaggctatg cttgtcaagg agaatgaccg tcaacaactc   6480
aatcttgtga aagacacagg caatgaagcg ttagttaata caattgtagc gggtattttc   6540
aatgacaatt tgacacttgt taatggtgcg cgtgctcgtc ttgaagctat gcgtatgcaa   6600
gtacttgcta ctggtaaaat tgcatttacg agcgacggag ttaacaaaga tattgattat   6660
ggtgttaaag cagaccataa gaaacaagta tctaagagct gggcagaacc tagtgctaca   6720
cctcttgcag atttggaaga tgctatcgaa acagcgcgtg aacttggtct taatccagaa   6780
cgtgcaatca tgaatgccaa aacattcggt cttattcgca aggctgcatc tacagttaaa   6840
gctattaaac cattggcagg tgatgggtca tcagttacta aagctgaact tcagaattat   6900
gtggctgata attatggtgt ggaaattgtt ctcgaaaacg gtacttaccg aaacgagaaa   6960
ggtgaagttt ctaaattctt ccctgacggc cacttgactc ttatccctaa cggaccactt   7020
gggaacactg ttttcggtac aactccagaa gaatcagact tgttcgctga taacactgtt   7080
aacgctgacg ttgaaatcgt tgacagcggg attgcagtaa caactactaa aactactgac   7140
cctgttaacg ttcaaactaa agtatctatg gtagcattac catcattcga acgtttggac   7200
gatgtttaca tgcttactgt aattccgggg gtttaagagg tactgatatg aatgtcgtac   7260
taaaagcgtt caaagataaa acaaatgaca aagtatactt tgctggtgat gcctacgatg   7320
gtgaacgtac tgaagaactc atcgggctag ggtacgtaca agacgacaag cctaagaaaa   7380
agactagagc taagaaaacc actgaatagc gaggtatggc atggtgacgt tagataaaga   7440
caaagttatt aaaaatgtat cggttgatct caacactaac gatgatggct tgcttgaaat   7500
```

tttattggag cgtgtagtta accacttcaa atcagagtat ggcgtcgaag agattgatga 7560
caagttagca ttcatttttg aggattgtgt catcaaacgt ttcaatcgtc gaggcgctga 7620
aggtgctaaa tctgaatcag tagatggtca ttcaatgtct tactacgata acgaaactga 7680
atttaagcct tacgataata tgcttcagcg tttatatgga acttctggac agtctaaaga 7740
gggagaggtg ttattcctat gagatacgct gataccgtag tgctaaaata tatcgataag 7800
acacaaaagc actacgaccc agacttagga cgtatggttg gcggtaagga agtaactaag 7860
acaacagcat gtaatgtgac tggtgctagc cttgaattgc aagccaaact aggagaccta 7920
ttaaacgcca atagcatcgt cgttaggttt agaagcccta tcaaagatgg aattgacacg 7980
attgaataca acggtggcaa atacaaacct gttactgtca gaagctatct aactggtcta 8040
aacgtcatct atgctaacaa gatggtgaaa taacatggct acaatcgaat ttgaaggatt 8100
ggatgaaatg gctcaaagtc ttcttaaaaa cgcctcttca gaaagacgtt caaaggtttt 8160
gaggaagtat ggttcaaaat taaaagaagc tgctgttaaa agagcacaat tcaataaagg 8220
ttattcaacg ggtgctactc gtagaagtat tactctacaa gttgaaagcg ataaagcaat 8280
tgtcgaagcc ttgactagct attcagggta tctcgaggta ggaactcgta agatggaggc 8340
acagccattt atgaaaccag cccttgaaga ggtagtgccc aagatggttg aagagatggc 8400
gaaatgggat gaaatatgaa acaaccagat cagttacttc atgatgaaat gtatcggatt 8460
agtcatgagt taggatatga cacttacaca tatttaccac cagacgacgt ggcttaccca 8520
ttcgttgtaa tgggggaaac aatggttttg ccacaatcca caaaatcaca cttgataggc 8580
cgtttatcgt ctacggtgca tgtttgggga cgtgtggatg accgaaaaac attatcagat 8640
atggctggac agttaatgtc tagttttttt gctatcaaaa atattggcgg catgcagttt 8700
tcagcagaag tcaacaagtc gtcaattgat agcaatcgag acaatagcac agatgaagtg 8760
ctatatcact tcatcatcta tacttatttt aaatttattt aacaggagga aaaaatggct 8820
gatactaaga aagaagccct tttgggtaaa gataaaatct tgatgttccg aaaattcgga 8880
gacaaaacag cggcagctaa acttgcccta caaacagagc acgaatggga atattcacgt 8940
gatgcagata gcaccaaaac caaagacggt gcagttgttg ccgacggtgg ccttgaaact 9000
aaactatcaa ttaacgctat tggtactaaa gatgacctca acgaaatgct aaaaaaatca 9060
gtagttgacg gttacaaagt ggaagtttgg gaaattgatt tggctgacaa aaaatcaaat 9120
ggtaaatacg gtgctctcta tgcgattgga cgtctgtcta gctggaaagt accggctaat 9180
gtagaagacc ttgtagaaat tgaatcagaa ttgactattg aaggtaagcc acaagctgga 9240
gaagctacat tgactggaga acaaattaaa gaaattcaat acacattcca agacactact 9300
gtaccttcag gcctcggtgt ttaatagtat gtaattatct tgagccaaac taaaaaagtt 9360
tggcttttta ttttagaaaa aataggagta aacaaacaat gcacacaatc actattgata 9420
aaaaagacta cactttgact tttggatttg attttatccg cgaacttgat aaacgctact 9480
ctatttcaga tggtggtgtt tcgttcggtt tcggtgtaca acacgcagtc gttgacttgc 9540
aacagaaaaa tccagtaatt ttgcttgacc ttatccaagc agcaacaatt acagaacgtc 9600
aaaaaccatc tgtaaaaggt attgaagcat acgtcgttga agaagctgag aaaggtcatc 9660
ttgactcact atttgatgat tttttatcag cattgcgaac tcaacctttg acgaaagcaa 9720
caacgaaacg agtggaagaa gccacagagt agaaaagaca acgagtgata accaaagttc 9780
agctgaagta tacgaggagt taatcacgaa tgctatggct gattttggcg tgtcattgct 9840

```
tgaagcacga agaatgacac ttaaagaaat gaaactctat cagaaagcgc ataaaaaacg   9900
ttttcttaat aaagaaagag aaatatatca acttgcttat cttaataggt tagcaaatgc   9960
cacaactaaa gatggcaaga agtattactt tgaaaaattc gatgacttct ataattctaa  10020
agaacgagct cgtgaagttt taggcgaaaa aatcacaaac agtaaactat tagaacgagc  10080
taagaaaaat cttaattaca aactggagag gggcttgcta gatggcagat aaaacattta  10140
acgtccgagc aatattgagt gctcaagaca atggcatgtc tagcgctctc agaaaagcac  10200
aaagaaacgc tgaaaatttg ggtaaaactg gcactaaact agggtcggtt tttaaaagtg  10260
ttttgggtgc taacttagtc agcgctggta tcactaaggg catcggagct ttaactagtg  10320
gtatcggtgg tatgatggcc gagcttaaca attctacgaa ggcttggaaa acatttgatg  10380
gtaacttaag ccaactaggt tggggtaagt cagaaattgc agcggctaag aagtcaatgc  10440
aagattatgc aactcaaaca atctactccg cctcggacat ggggaccaca ttctcgcaaa  10500
tggctgcgat tggtcgtagc gatgctgggg atttggtgaa agccatgggt ggtttagctg  10560
cttctgcaga aaaccctaaa caagcaatga aaaccttaag ccaacaaatg gttcaagcga  10620
tgaccaaacc caaagtttca tgggcagatt ttaagcttat gatggaacaa tcaccagcgg  10680
gtatggctgc agttgctaaa gagatgggta tgtctctcga tgagcttgta accaaaatcc  10740
aaaatggaga aatcaagacc gacgacttca ccgaagcttt caaacgtgct ggtaattcca  10800
tgcaagactt agctacgaga tataaatctg tagatgaagc tgttggtgga ctttatgaaa  10860
cggtttcaaa taaattgcaa cccgtttttg aaaaacttag ttcaaaggca attaaaggaa  10920
ttgaaggcat cattgatgct tttagcaaaa tcgatgacag taagattcag aactttgcta  10980
acaatctgag caaaggcatt gataaagcgg ttaaagaagc aagtcaggct gtgaaggctt  11040
tttgggaagg ctttagcaat actggggcta taaaaggtct tagcaatgct ttcagatatg  11100
ttgctggtca gatagggtta gcgtttaaaa gtatcgactt tgacaaccta ttcaaaggtc  11160
taggtagtgc tctaggagat ataggttatg gaatttcaag agccttaaca cttgccacga  11220
gatcagttag caactttatc agatcattcg ctgatacagg agcattcaag gcgtttaaaa  11280
cagccttaaa agatgtttgg gttgctgtta aaagacttgg ttcgtcactc gctgacgtgt  11340
ttggtagttc tgaaatgcaa acgattatat ctgtactagg tacagcgttt ggaacactaa  11400
ccaagtgggt atcacaagct gcatcagcag tagctaactt tataagttca attcctaaag  11460
gtgttctcaa cggtatcacc agcgggatat tggcaatagc agcaggattt gtaactgcta  11520
aggctggtat ttcagtatta ggtcgtgcat tgaaaggctt ggacttcatc aagagtctta  11580
atcctttcaa gaaattcgga gcggacgctg cagaaggaac agcgcaagct gctaatagcg  11640
ctagtcggtc taagtctatt atcactcaat tgtttaatgg aatatctaac gccattaaat  11700
cttctggtaa tgcaatcaag ggtatcttga caacgatatt caaagggatt gcagaaactt  11760
ttaaaggctt aggtcaaggg gtgaaatatg ctttacaagg tcttaaaggg ttgaacccag  11820
caaccttgtt atcatttggt gcatccgtag ctatcgcagc agtcggaatc ggtgctggta  11880
ttggtattat cgttgcttca ttcgccttat tggctactca atcccaaggc gtttcacaga  11940
tattaaaagc tttgggttca gcgtttagca cagtcgtcca aggtattggc aaagcggcag  12000
gaactatcat tgaagcattc ggtactgctt ttggaattgt cgtcaaggca gtcggtgaag  12060
cagcaccggg gctagccaaa ctttccccat tggttgaagc tatcggcact gctctaggca  12120
atgcatcccc atttattaca gcgtttggta atgcttggac ttctatttta ggaacgcttc  12180
cagctattat cagtgcattt agtggatttg caaccgctct aggtactgca atcagtgcag  12240
```

-continued tagctaccgc aataactccg attattcaaa ttattggaaa cacaataacg gcagtaactc 12300
aaatcattgc taatgctatc gtggcaatcg taccagttat cgcgaattgt atcgttcaag 12360
ttgctcaagt tatcggacaa tttgggccac agattgcaat ggtaatcagt gctatcgctc 12420
aagctatatc agcttcagca cctatcatca tatccttgat tcaaggtatt gttacagtcg 12480
ttcagattat ggctccagtt attagtcaag cgatctctgc catcgttgca gtcgttcaaa 12540
ctcttgcgcc tatcatcagt caaatcattt cagcgattgt tacagcaata acacaaattg 12600
ttcctattat taactcaatc ggtggtgtga ttagtgctgc attgagtggt attgcatcta 12660
ttgtgtcagc tgcaggaatg gcaattgcta ccgcagctat gggtatcggt acggctatta 12720
gtacggctct tagtggtgtg gcaagcatca tcagtgctac tggtagcgct atcggtgctg 12780
cattgcaagg gattgctagc gtggtgcaat cagtcggaac atcaattagc acagcggctc 12840
aaggtatcgg aaacggcatc aagtcagcat ttgaaggtat ttcaagcgtt attacttctg 12900
cagggaatgc aataagtagt gtgttgaata gcctagctaa tgtattcaac tcaatcggta 12960
cagctgctca gaaggctggt gctggtttca atcagctagc tactggtgta gtcaaaatta 13020
ccaatacaaa cttaggagac atggctgcat ctcttgcggc agtggctcat ggtattggtt 13080
cgattagtga taactcagca gggcttgctc aagctggtgc aggtatggct caacttggaa 13140
atggcatgag caaggtgtca gcatcagcaa ctagcgctgt atctggtttg acatcattct 13200
caactgctat ctcaagcatt caatcatcat ttggtagttt gcaagctttg cttgctactg 13260
cagcagctgc gttcagtaca ttctcaagtc aagccctgca atcactagct gggttaacgg 13320
ccattgtagc acctattgcg gtcttccaaa tgcagataat gatgatagtg ccagcattga 13380
tgcaagcggc tgcgggattg actatgttca gtgcagtggc aatggcgttg tcttctagct 13440
tgacctttat cagtacgtcc atgacaatgc tgaccgctgg catgactatg ttagcctctc 13500
agcttactat ggtagcgact ggttttacta ctatggttgc aagctcgacc tcactgggtg 13560
caagtttgac catgatggca gctcaattca tcacgattgg tgcatcatta acaatgctaa 13620
atagtcaatt cattgcattc acagctgcgt tgactatggt taacagtcag ttattggctt 13680
ctgctgtggg cgtgacaatg tttggctcac aatttacaat gctgggatca atcatgtccg 13740
tgttcagcag tcaattaaca atggttggag catctattca aatgatggcc gcacaattca 13800
ccatgatgag tgcaagcctc accgctgttg gttctacagt tgcgatgatt gccagccagt 13860
ttactgtgtt gattgcgagc attatgcagt tgactgcttc aatttcaaca attccgccac 13920
aattcagcat ggttgcaaca agtgctacaa cggccacaac agcgatcatg cgaattggaa 13980
catcggcgcc attgattgct tcagcaatga acagcgcggc ctcacaggtg caatcagcaa 14040
tgcagaatat ggcacaagct gttcagtcta atggccaacg aatgattcaa atgggcagac 14100
aagccgggct acaaacaggg caaggaattg ctagcggtat tcaatcagcg actgtagccg 14160
tatctgctgc agcgggcgca ctggttagcg cagcacaatc acgcgctatg gcaggcgcag 14220
gcgctatgcg ttccgtaggg gcaatgattg gacaaggttt ggccgctggt atgatgtcag 14280
ctcttggagc ggtaacagct gcggccaatg ccctagtcgc tcaagcagag cgcgcggctc 14340
aagctaaggc taaaatccac tcaccttctc ggttgttccg tgatgaggtc ggtatcttta 14400
ttgggcaagg tatggccgta ggtatcgata atagtgttaa atacgtcaga gattccatcg 14460
agaacatggt tgacgtggct agcggttacg cgatagacgc tagagagctc ttggaaggta 14520
atgacctgtt tgatggcttt ggcggtggtt taatccgtgg cagtgttgac ttaactgtta 14580

-continued

```
gagatgacag tcgaatgaac cgccttgagc aagcgatgga cattatcgct ggattaatcg  14640
agcgccctat atcacttaac atagacggta gagaatttgc atacgccaca gtggacgact  14700
tggtatcgta ccaaaacgaa aaggatttta gttacaaacg tatgagaggt attaaataat  14760
ggctgtgttt caattcaacg gatatgattt aaatgattac tttaaactaa tcaaagtgtc  14820
gcacgaaatc gggaatgaac gcgatatcac tacagactca gcccctaaaa tgggggttaa  14880
tattcaacgt gtttcgtttg gtgctaaaaa aatcaagcta actgttagtt tagcaactag  14940
agaccttaat gataatgctt tcgtagaccc aaacgagccc gctcaaattg atagcggtat  15000
gtttcaccat gtaagagagc aagcggctag agtactgcac actgaaacac ctgtagagtt  15060
gaaactacca gatgagccag ataggtacta tttagcgata gtaaagggtg atgttacttt  15120
gaaaggcatc tctgactggt atgaccagac tgaaatagaa ttttttgtgc ctgacggtgt  15180
cgcacattcg actacctatc gcagttttga aacccctaaa atagagaaca acaagatggt  15240
atttgacctt gttaacgatg gatcagttaa tgctaaccca ataattacag tgaagcacaa  15300
cagtgagaat ggctatattg gattagttaa tagcacaggt atctgcgagc ttggggatag  15360
gttagaagca aatacagaag attatagaca ttcagaggta ctgtttgatt acgcttcatc  15420
taatggacag cacagaatcc ctaacggttt atctcaagga ttgaaaaaca ttggcatctc  15480
aaacgatgtc aacgacacca agccaaacgg aactctttac atcgataatg cttggggcag  15540
accacatatt ggtttgcaga gcggtcaagt agcatcggtt acttttgaca taccaaggga  15600
ttcaagcggt gaaaaaggtg cgctatatga atacctttgg tggagacaaa ttttctggtt  15660
agggtctgcg aatcagatgg gctatttaaa aatttgtgtc acagacgcaa gtggtacatt  15720
tttgtatggt gttgaaactt ataaacgtta caatggttta ggctgtgaat ataattttct  15780
agctggtgac ggcaagggag gtttccgtat tgtcgacaga aagaattttc taggaacaca  15840
tatcgagcag cacaacccat ttaatgaacc taggggatgg tcagatatta tgcggtttga  15900
tgatgtcgtt caatactact ggtggggttc atacccaaga tattctattc ctgaaataaa  15960
gggtaaaaaa tcagacaaaa tccatttcat ttttggtaag gtcggcaacg caccacttgt  16020
tacacacatg tatttagatg atttcattta tcgaaaagac tacgtttttg gtgtcaggga  16080
tatccctaat agataccgcg ctggtgggaa agtggtaata gatagtgaaa ctgataccgt  16140
cactgtagat aatattccaa agattgtcga tgttgtgcaa ggctctgact ttctcacgat  16200
tccaccggga aaatcacaat tagaagtcta ctgttcaagc tgggtaacaa ctaaaccatc  16260
cgtatctgtt aaatttgagg agagatatct ataatgttgc taacaattca cgacgctaat  16320
ttgcagaaga ttggcttcat cgataacgag aagcaagaaa cattaaactt ctacgacgac  16380
acttggaccc gtaaccttga gacagcatct agcacgttcg agtttaccgt ttctaagaaa  16440
cagttactta gcgatacagg aaataaacac ctttacaacc aactaaacga gcgctctttt  16500
gtttccttca aatataaggg caagacatat ctttttaaca tcatgaagac ggaagagaat  16560
gagcgatggt tacgatgtta ttgcgaaaac ttaaatctcg agctgataaa tgagtacacg  16620
aacgcctaca aggctgacag gcctaggtct ttcgcggaat atcttgatgt attcgaaatt  16680
cctcagtttg cgatggttaa agtaggtgtt aatgagatct ctgatcagaa gagaatgctc  16740
gagtgggaag ggcaggaaac aaaactggca aggctcttaa gcttggccaa taaatttgac  16800
gctgaagttg aatttgtgac tcaacttaac gatgacagtt caattaagca actcgttttg  16860
aacgtttacc ataaagcgga cgactcgcac actggtgttg gtcggattcg tggcgatatt  16920
cgtcttacgt ttgaaaagaa tatcaaatca atgacgagaa agattgataa gactgaagtc  16980
```

```
tatacgctgg tagttcctta tggcaaatcg aaagagaccc atgaaggcga gcaagaagta  17040
cgtgtctaca ttgacagcct tccgccttgg gaggaaaaga acgatgaagg tattgttatc  17100
ttcaaacaag atggcatagg tctctacgca cctcatgcag ccgacttata cccgtctact  17160
tttggcgtat caactcaatc taataaatgg attcgaaaag acttagaggt tgatagcgac  17220
aatccgagcg ttatccatgc cgcaggaatt gcgaacttgc gtaaacacgc ctatcccgct  17280
atcacttacg aggttgacgg ttttgtagat gtagaaatcg gggataccat aacaatccac  17340
gacaaaggat tcacaccagc gcttgacata agagcgcgtg ccgttgagca aaaaatcagc  17400
ttcagcaatc cgaccaacaa taagaccact ttcggaaact tcaaagagct tgaaaatagg  17460
acgtctggag accttaggag cgttttcgag caaatggttg agaacagtcg accatacaat  17520
atcctagtct caactgataa cggtgttatg tttaagaaca acacagggcg gtcaaccata  17580
agtccaacgt tgaaacgagg aaaccagacc gttcccgcaa catatcgctt tgtaattgat  17640
ggctctattg ttagctctgg tctgacctat accgtcaaag caagcgatat cacaaaacca  17700
actgtggtaa caatttccgc ttgggtagat aacaaagaag tagcttcaga agaagttact  17760
tttctaaacg tatcagatgg gaaacaagga ccacaaggtg accaaggaat accgggacca  17820
aagggtgctg acggaaaaac gcaatataca catatcgctt acgctgacac aatttcaggt  17880
agtggcttta gtcaaacaga tgtcaataaa gcctatattg gtatgtacca agacttcaat  17940
gctgatgata gcaaaaatcc acaagactat cgttggtcta agtggaaagg tagtgatgga  18000
cgagacggga ttcccggtaa agctggggct gacggacgta cgccttacgt ccactttgct  18060
tatgccgata gtgccgatgg tcaaaagggt ttcagtttga cacaaactgg acataagcgc  18120
tatttaggtg tgcttaccaa cttcttcaag gaagacagta ctaatccttc tgactacacg  18180
tggaatgaca cggctggcag tgtgtcggtt ggtggtcgga acttacttgt aaaaaccaat  18240
caaggtatta ctaattggga ctggactctt tctgatggcg acaagagcgt tgaagaagta  18300
aaagttgatg gcattcgtgc tgtaaaacta atcaaaggtt caacaacagc aaacactggt  18360
tggaattaca ttcaatataa cggtttgctg cgtgaactca tacagccgaa gtcaaagtat  18420
gttctttcgt tcgatgttaa accaagcgtt gatgtaactt tctatgcaac gctaacaaat  18480
ggagacttta cagagacgct ggctgatact gccgctatga ctaaagcatt agccaatcag  18540
tggaataagg tatcgtgcgt tttgacaagc aaagaaactt tgccaaatat tgcatggaaa  18600
attgtacact tagcaggtat gccaacaaca aacggtaatt gggtaataat taaaaatatc  18660
aaacttgaag aaggtgacat acctactcag tggacacctg caattgaaga catacaagat  18720
gaaattgatt ccaaagccga tgctgctatg acgactgaac agattaatgc gcttaatgaa  18780
agggctgcaa ttattcaagc agaggtggaa gctagagcaa gcgctgaaat tttgaataaa  18840
tggattaaaa attacaaaga tttcgtcaag gcaaacgaga ccgagagagc tgctgccgag  18900
aaagctttgg ttagctcaag tcagcgggta tcaaccattg ctaaggagtt aggtgaactg  18960
tctgatcgtt ggaatttcat cgatacttac atgagcacat cgaatgatgg gcttgtgatt  19020
ggaaagaatg acggtagctc aagcattatg ttcaacccta acggtcgaat ttcaatgtat  19080
tcagcagggt ctgaagttat gtatatttct caaggtgtaa tccacatcga aaacggtatc  19140
ttctcgaaaa caatccaagt tggtcgatat cgtgaggaac aataccatct caacccagac  19200
atgaatgtca ttcgttatgt aggaggtttt taattggcag aattttggag taataatgat  19260
agaggctata ggattagatt atgggttgac caggttagcc aagacaaagt agctaatacc  19320
```

-continued

```
agtcaggtca gatttcaact agcactgcta aatacgacta cgacttttgc tcaatatcaa  19380
tgtagcgctt atatcgattt cgaaggacaa agattgaatt ggtctggttc acctagtgta  19440
ttagggtggt atcaaacaat tccattgata gatcaaacag ttactattaa tcacgattcc  19500
gacggtaaaa agactttttc tttttcagcg cagtttaatg gcggtggagg ttggagtcct  19560
cgtacattaa caatcagtgg tatctcattt acactaaccg acattccacg gttaagctct  19620
gtcagcgttg atgctggtac tattggtagc tcagtcacta ttaacatcaa ccgtcaaagc  19680
tctagtttta agcacacagt acgttatgct tgggccaata agtcagggac tattgcaagt  19740
aatgtagaca catctacaac atggactatc ccacttgact ttgctaacga ctttccaaac  19800
tcggaaacgg gtacgggaac aatctacgta gatacctact cagaaggaac catgataggg  19860
acacagtcag ctacactgac agcaagtgtg ccagctagca tgaaaccaac tttcacaggg  19920
atttctttat cagactctaa cacagctgct cggaacgtgg tacaaaacgc taacacattc  19980
atccagatta tgtctaacat caaggtatcc ttcaatggtg caagtgggtc ttatggttca  20040
aatatcacgg gctaccgtgc tgagatagtc ggtaagaacc agactaccaa cgtcaatggt  20100
ggcacgctgg gtatcatgaa ctacaacgga accatcacag tcagggcaag tgtatctgat  20160
agtcgtgggc gttggtctga tactaaagat gtcacagtta ctgtacttga gtattttgcc  20220
ccatctctta aaattgacgt aaaacgcgtt ggtgaaacat ctagcacatt agaaattata  20280
agaaatgcac agatagctcc tttgaatatt aatggtattc aaaaaaacac catgaaatta  20340
actttcaagg tgtctcctaa tggaaaagat gattacacaa cggacactgg tcctgcctct  20400
ggtgaatggt taagcatttc aagtcttgtc aattcacctg ctaatttagc tggtatatat  20460
gcagctaata aatcgtggga agttttggca attttggaag acaaattcac atccacgagc  20520
tttaaggcac aagttcctgt tgaaagtgtt gtgctgtcct atgaccgtga tggtcttggt  20580
attggtaaaa tacgcgagtt tggcgctctt gacgtggctg gtgacatcta cgctaacaat  20640
agtcagattc agcaatatca gctaaccagt aataacggcg ctccgaaatg ggtagatgga  20700
aaacctgtcg ctaagaatgc aaatttgata gaccaacctg gacagtatta ccttgaccca  20760
tcggctcaag ggaacccaag cggtcaatgg ggctatttat ttcactacag caattacggt  20820
aagaatacaa atggtcgtaa agaagccatt caaacttttt gggggaaaaa tggtcagctt  20880
tttttcagac atcacagatg gtcttttata atcgacgatt gggagccgtg gaaggaattt  20940
acaagaaacg accacccaaa tctaattaac acgggctggc aaccagcagg atttgaaggt  21000
agttactata aacgcgttgg agatgtgttg accattagat ataactttac tggcacaggt  21060
ggagatatta ctatggctag attaccagca aatattttta aatcaccgca agattatatg  21120
ctaacaatta aagcttggta tcgacttact gaccacgatg gtcacgcaca aattagtgga  21180
ggaacaagtg atattgtcgc tttagcaaca ttaaaaaatt gggattaccg aggtcaacta  21240
acaattatgc tatagaaaga aggaaaattc atgaaatttg aatacgaatc taaatcgaaa  21300
gaatacgatg caagtggcgc agcatacgcc acaaaagtag ttttgagaaa cagggacggg  21360
gcttacgtac ccgtcttttt gccagtcgag aaaatcgact tatcaaacac ttacctccta  21420
aatgaagcgt tagaggtaat ttatcaagag aatttcccac aacgtgctga aaatgagaag  21480
tttaacgagc ttgatacaaa aatcaaagag tacgaagtat taagcaaaaa agctactgat  21540
accattgcta agatggaaga acaaataaag aagcagcaag atgcatcaaa caccgcacaa  21600
gagacattga tgagtattat tgaaaaactt aatgagaaaa aattgttgag tgatgaagac  21660
ttgactgata ataaagaata aagagaaagg ataaaaagat atgtttgcta aactattcgc  21720
```

```
aataaatatt gttaataata actacaaatt taaacgagtt ccaaaagtat taaaaccaaa  21780
agtaaaagaa ttaatcgctg ctatggttaa cgacgaggag ctcttggcaa agcttacaca  21840
agaataaaaa aggaggtata gcgtggtaaa tcaaaacgat ccagatttga tgaactggat  21900
tataacggta attctcccca tttccatttc aagtgcgagt ttctattttt ctagtcaatc  21960
acgcgcctct cgattagaac acagaatcac taaattagag gtcgttgacc atgaaatcga  22020
gaaaattatt gaaacccaca atcagcgcct cgacaaacat caagaggacc aaaaaataat  22080
tctagctcta gtccaaagga tggaccattt taatgagaac attgttgagc taaaaggaaa  22140
tatcgaagaa gttagatcga aacttgagag gataataata aaatgattaa ttttaaactg  22200
cgcttaaaaa acaaagctac tcttgtagca cttatctcag cagtattcct tatgttgcaa  22260
caatttgggc ttcatatccc aaacaacatc caagagggta ttaataccct tgtcggaatc  22320
ttggttattc ttggaattat taccgaccca acaactaagg gcattgctga tagcgaacga  22380
gctttaactt accaagagcc aaaagaataa taaaatataa gaaaggagtg tttagatggc  22440
atggaaaaag gtgattactt tatcgacgtg tcagcgtatc aaccggtaga cttgactggt  22500
atctgtcaag cgtctgggac taataacacg gttatcaaag tgaccgaggg tgtgggctgg  22560
gttagtccag tagccgctca acaaactaac acaagtaatt gtatcgggta ctatcacttt  22620
gctcggtttg gtggggatgt ggcaacggca caagctgaag ctaactactt tatcagcaat  22680
ctgccgtctc acccacgctt tttagtgtgt gactatgagg acggagccag tggagacaag  22740
caagccaata ctaatgcagt attggctttt atggatgtat gtaaatcaga aggctttgag  22800
ccaatttact atagttacaa accatataca ttagctaatg tatatgtaga tcaaatcact  22860
gcacgctacc caaatagctt atggattgca gcgtacccag attatgaggt acgcccagaa  22920
cctttctggg atgtatatcc aaacatggat cacatccgtt ggtggcaatt tactagcacg  22980
ggtttggctg gcggattgga taaaaatgta gtcatcatta atgatagtga taatttagta  23040
gataagaaag aggaagaaga aaatatggat tatgtagttc gaagcgaaag tggaagccaa  23100
ggataccttg gtgtagttaa cggtcatgtg ttcggtatca gctcaatggg gacagtggat  23160
gccttgcgct cagcgggtgc gaaacacttg atgttgccag atgatgattt tgaacgtttc  23220
ttgaatagcc aatcaaacga cactgcgcaa gtcgctaaag ccattgatga agctagcgcc  23280
tcagtagtta aggctatcga agaacgtgca caagctacac aaggtcaaac tggaaaataa  23340
ttagaccacg aaaactataa attgaaaaga agtatatcac ctcccctcag actgcaatag  23400
ggatatcatg gcagtagtgg tcgaagcctc agcattttgc tggggctttt ttgtttgact  23460
tataaatgat aattttataa aatgtaattg ggtaacctag atacaattta tctagcgcaa  23520
aagctgatag actgattaag ttcagatccc ttgaaaaagg gaacattttg ttgggggtta  23580
agaccccctt ttgtttttg tgttataata tatatgaaac gacaaaccct ctgcatccac  23640
atggacagat acgctctgac gcagggcttt ttttgtttgc ttttttaaa taaatgctac  23700
tatattaatg gatacagtta aaagctgagt cttcgataaa ctctctcttg ccctgacttg  23760
aattagtcag ggtttttgtt ttgcaaaaaa atatatattt ttttataaaa acagtttccg  23820
tctggtcgcc aaaatagact agaatggatt gagagcaact tggaaaacat tcgataaaaa  23880
ataaaaaaac gaggtaaaaa caatggatac atacaaagaa caatatatag tatgttttac  23940
taattttcaa gatgtttaat aataaaatca aaaaaacttg aaaaaaaatc aagaaaactg  24000
ttgacattga attttgttta agctataata tgtttgtaag ttagttagga aggaggaaca  24060
```

-continued aaatgacaga agtagttcca aaaattacaa tcaaagaact ccgagcgcgt cacaatttga 24120
cgcaagagga gtttgctaaa accgttggca ctacacctca aacggtgagt gcatgggaga 24180
agaatgtact ttctatttct cctaagaata tggcaaatat ttgtaataaa taccaccttc 24240
aagcgtctga tttgtatggc ttttgatttt tattacaaca aaacttggat taaattcaag 24300
ttagaaagga actagatgaa cgaaatagca acaaatgatt ttgactactc tttgctcgat 24360
gcaaagacga aagaattctt agaagaacgt gccaatatca tctacggcat ccaaagcaag 24420
agtgcttacg aaatcggaaa acaacttgct aaagctcaag aggagctttc aactagaggt 24480
tatggttgct tcgaagaatg gtatagaagt ttagggttta aaaaaaccaa agcttatgaa 24540
tatatcaatc attacaattt cgtttgttcg caaaacgaac aagcaaatat tgaaaaattc 24600
gaaagtttgc ctaaaacgtt acaagctcaa gtatctaaac catctgccaa tccagaggtt 24660
aatcaagcag tattcaacgg agatatcaaa actcacaaag aatataaaga gcttgagaac 24720
cgcctaaaac tcaaagacca agcactggaa gcggtcaagg gagagttgga acgtgtcaaa 24780
caaaccaaaa ctactgaaaa gataatcgaa aaggaagtca ttccgcaaga ttacaaagca 24840
acgcaagacc ttaacaagca attgctagga aagaataaag acctagcaga cgagcttgat 24900
tcagtcaaaa ggagcttgcg acttaaggaa gcagcttatg aaatgctcga aaaagaaaca 24960
tcagaagcat tagccttgaa agagtctatt gagcacttac gagctgataa agagaagcta 25020
gaaaacagcg ttactaatat ctttaaccta agcaagctcg taactaagtt tgaaaacttc 25080
tttgacgaag aaatggcacc gcttagattt aaaaccctta tccaaggcat tggaaaagac 25140
gctcagattg aaaagctcag agacatcttg acgcttactg aaaactggtt agatgaaatg 25200
aacaagatta ttccagaaga tggaagaaca atcatagaag gagaaatcat aaatgagtaa 25260
gaagaaatat aagaaaaaag aaaatctact cgctgaaaca gtagaaatgc agaagaaaca 25320
agctatgaat ctggttgctc aaagcaccgt taaccaacag cttttggaag aaatcatcgg 25380
aattaaggaa gaaatggaca gaaatgttaa aaagacaaat caaaaactaa ctgacattga 25440
gttgcttgta gaggaagtca ataagaaggt ccatattgac gacggtgaag cttctaaaat 25500
caagagtatt attttcaaaa aagctggcgt gttcgcagat atgtacttca ataatcagaa 25560
atcacaccct agtgataatc tgtttgcttc aaagaaaggc caatttattc gcttgatgta 25620
ctcacatttg aagaaagcat ttaacgtgac caagtacact aacatcaaac acgttgaagc 25680
tgagaaagct gtgcaattct tgagagattt gtcttacgat gattttacac cttttgaaat 25740
tcgtgaaaca ccaaaacaaa aagagattat agctcttgaa aaaaatgagt gactgaaagc 25800
attataacgg tttattttaa ataaaagata aaaactttaa aaaaatcgag aaaaaatatt 25860
gacaaataaa aatatatagt ttaaaataaa aacataaagt taagaaagga gaacttaatg 25920
aattatgact attctaaatt gaaaggacgt atcatagaaa aatacgattc tcaaagaagt 25980
tttgctgaag ctattggcaa aacgcaaacc acaacgtctt tcaaaataaa tgggaaagcg 26040
tcgtggaatc aagatgaaat tgtaaaagcc attgaagtat taggtctctc aaaagatgat 26100
attgtagaat acttctttaa ctattaatag aaaggtattt aaaatgaaaa acttatttaa 26160
atggatttta gctaaagatg agaaagaaca aaaaccagta tggacaccat acgaagaaaa 26220
cgaaaagaaa tatgaagaaa ttcataaaca actatcaatg aaataaaata gctaaaccgt 26280
tcttcaatcc gtagccaacc cctgatgtgt ggagtgcaac taaatacctt ataccccaaa 26340
actaaaaata aatataaata aaataccaaa aaactacctt cttaaaattg aataatttga 26400
agcacatcag ggactgggtg cggattgaag cgctaaaaaa acacgggtaa aagcccgtgt 26460

-continued

```
cgtaaaaaaa acattctatg gagattataa cataaatgac taagaataaa actaaaacaa  26520
aagtctattt ttggcttaaa tttgataaaa aattctttga caacttgttt attaaaagac  26580
ttagggacat gagcggtggc tatgcaatga ccgtaattta tatccgactc atgcttgaga  26640
gtttagaaac tgattgcgtt ctgtattatg aaggctattt ggacaactta attcaagagc  26700
tagcacttaa gttagatgtt agcgaggatg atgtcaacat gacaatggct tactttacaa  26760
aatgtggtct tatccaaatc gacacagacg gaaatgctag gtttccacaa gctgaagccc  26820
tcctcgaaca agagacaaac tggtcacaat acaagcgcaa acaacgcaaa gttggacaat  26880
gtccaaccaa attggacaat gtccaaccga tgtccaacca gtgtccaaca gagatagaga  26940
tagagaaaga gatagagata gagaaagaga tagagataga gaaagagata gagatagaga  27000
aagagataga gataaagaca gaagtagaag aagagaatag aaagacttct tctgctgctg  27060
ctgataattc caattttaat atctttgaat actatcaaga aagaatcggt cttctagatg  27120
gatttcaatt acagaagtta gaagagtatc aagtcataga tggactagaa ccagaattaa  27180
tcaagatagc cattgataaa gcagctgata actctaaacg ttcttttggg tatgttaact  27240
ctatcttgaa atcatgggct caaaatggaa tcaagacagt agctcaacaa atagaagagc  27300
agaataattt cacttctaac aagtcaaata gtgacaaacc caagtttgga ccagcttgca  27360
gtaaatacta agaggttctt tatatgagtt tagatcaaac agctagacag atgcgacagg  27420
tatatatgac tactagtgat aaatactgcg agaagcacaa tcgaaacttt gtcactattc  27480
agctaccaaa tagtaagcct tatactgtat gtgaaatgtg tcaccgtgaa gagcaagaaa  27540
aacagaattc tattaaagcg caggaacaat acgaacgtga gcaagaacaa aaacgtctat  27600
acttcctaaa ggattttagt ttgatggatg atgatttgag aaacgctagt ttcgacaact  27660
atcaagcatc aaccagagag caaagagaag acttgagaaa tgttagaagc cagcttaaag  27720
gatatcttga cggtcaagac tataacattg ttcttatcgg cgatactgga gtgggcaaaa  27780
gccatctagc ttattcagcg ctaaaagcct tgtctaatca cacaaaaaag atggggctat  27840
ttataaacgt ggttgatttg ctagccaaaa tcaaagagga tttcaccctc gaagctgaat  27900
atatcagacg aatatccgaa gccgaatggc tagtgctaga cgatctagga acagaaaaag  27960
tgactgagtg gtctaacggc atcttgtaca gtattttgaa caagcgcacc aagactatta  28020
tcacaaccaa cttaagccca caggatatca tgggcactta tggtaaacgt gtctattcga  28080
gggttttcaa aaagacagga ctgggaacga cgaatgaaca cgtttatcaa ttcaaaacac  28140
agcaagacaa gaggatgatg ttatgactga aacagaagta aagctaaaac tatttgaaga  28200
ctacgagtgc attcatggcc ttgtattctc acaagagcat aagcaaaaaa tgatggatga  28260
tttggacttg tattcattca tcgagaaatt aaacgaatat atggcatttg gctactgctc  28320
gaaggtggta tttaatcagc acgttcgata acacgcctaa aatcgtctgc aatcaattta  28380
aaagtgtggg tggtataaat tatctagtta ccacttaaaa acgataagag accccttaaa  28440
ttgagaatta ggggcattca aaacaaaaat atgtattttg ctaaaaaatc aacgcaagtt  28500
tttagcaacg ctagaaaacc cctctaaaat agattttaag gagtgtgttt tggtaggtgg  28560
tataaataga ctaggaaacc gttaaagttg cactacacac ccttaaattg agaattaggg  28620
gcattcaaaa caaaaaagga agacaaagac atgacaaatc aactatcaca caaagatttt  28680
ttcaacacac cagcagttaa acagaaattt caagaggtgt tgaacggcaa tgaacgacaa  28740
tttacagcaa gtttgctatc aatcgtcaat aacaacaacc tactggcacg agcaagtaat  28800
```

-continued gcctcaatca tgacggcagc aatgaaagca gcggtattaa acctgcctat cgagccaagt 28860
ttgggttttg cttacattgt tccatacggg caagatgcac aatttcaatt gggttataaa 28920
ggacttattc agctagctat ccgctccggt caatttaagg ccatcaattc tggaaaagtt 28980
tacaaagcac aattcaaatc gtatgacccg ctatttgaaa cattggacat tgatttcact 29040
caaccagaag atgaggttta tggctatttt gccacattcg agcttgtgaa tggatttaag 29100
aaattgacat tctggacgaa agagcaagca gaaagccacg gaaaacgctt ttcaaagacc 29160
tatgcaagag ggccttggtc aacagacttt gatgcaatgg ctcaaaaaac cgtactcaag 29220
agcattttga gcaagtatgc cccactatcg actgaaatgc aagaagggct tatctcagac 29280
aatcaaactg aggaagttga gactgaccct atcgatgtta caccaaaaaa cgatgacacc 29340
cagacacttt tgggtgacct catgagcgat gaagctgaac cagataaaag cgtagacgct 29400
gaaaccggtg aaatcatcga agaagttagc ttattcgaag gtgattcaac caaaatcaaa 29460
gaggtagaaa atgactgaac taacaatctt gacggattat aattattatt ctgacaaaac 29520
ctatatgtct gtaagtcgtt tcaaggaata catgaaatgc gaagctagag ctaaagctat 29580
cgatgatggt gtttgggatg atgaacgaga tcaaaaacct ctactgttcg gcaactatgt 29640
tcatagctac tttgagagtg aagaagcaca cgagaaattc aaagaagata acaaaaaagc 29700
tatgttctca agtcgcaaac cttatgggct gttatctgat ttcaagttag ctgagaaagt 29760
tatcgacacg cttaaggatg acacgctttt caataactta taccacggta agaaaggtga 29820
caaggttgaa aaagaaaaga ttgtcactgg ttttatcgcc ggcgtgccgt tcaaagggaa 29880
gttggatagc atcaactttt caaagggcta tgtggtcgat ttaaaaacca tgaaatctat 29940
ctggactaag gaatggtcag aggaattgcg taccaaagta ccaacggcag tcaataacat 30000
tctaggattt caataccatg tccaactagg gacttattta gaattgttgc gacaaatgga 30060
ttatccaaca ttcaagccgt ttatcgtggc cgtatcgaaa gagaaacagc cagataagga 30120
aattattgaa ttgactgaag aatggctgga agaagggctt aaatacatta cagagcacgc 30180
ccctagagtg tatcaagtat cgcttggaaa caaagaacct aagaagtgtg gacattgtga 30240
ttattgcaag tctcaaaaga aattgcatga ggttctaaca ttggatgatt tcttaaatag 30300
agagtagaaa aggaaaaaca aatgatcaat aacgtcgtat tggttggtcg catgaccaaa 30360
gatgcagaac taaaatacac tggaaacaat atcgcagtag ctacatttaa ccttgcggtt 30420
aaccgtaact ttaaggatgc taacggagag cgtgaaactg actttattaa ctgcgtcatc 30480
tggcgacaac aggctgaaaa tctggctaac tgggccaaaa aaggggcatt gattggcatt 30540
actggacgca ttcagactcg tagctatgaa aatcaacaag gtcaacgtgt ttacgtgact 30600
gaagtagtcg ctgaaaactt tcagatgttg gaaagtcgtt cggcgcgtga ggggggtaat 30660
gctaacaaca gttatagcca acagcaaggg ccaaactttg caagagaaag cggaccttac 30720
cataatagca atcctataga tatcagtagt gatgatttgc cattctgagg tgaagcatga 30780
gaataacttt aaacatcgag ccaaaaccac aaacaagacc acgatttagc aaattcggaa 30840
cttatgaaga ccctaaaatg aaagcttggc gtcgtcagtg ctcacaactt atcgagcaag 30900
agtatgacgg gcaattcttc gacgggccga ttatggttga tgtcactttc tacatgaaag 30960
ctcctttaaa tgtttcaaaa aagcccacgc caaaagctag agctaaaacg tgggacgcat 31020
tcaaaaaatt catggatgaa agactttggc atgcgaaaaa acccgatctt gacaacctaa 31080
tcaaagcgct ctttgatagc atttcaaacg ctggatacaa caaggttgat aagaagggta 31140
tcgtttggac ggatgacagc atcgtttgtg gtttaatagc tcgcaagaag tacagtacta 31200
acccacgcat tgaattagaa atcaaggagc ttggatgaaa agcaagtaca aagataagtt 31260
agtcggtata tatgctccag gaagctacgg acacacaagt gtgttaggtc aaacacaaga 31320
gttttcgaag tggttctgga aaaaccacaa agacatagat ttaatcagta ataaactagg 31380
gataagcaca aagaaactca atcgtattct gacgcttgag cagttaccag atgagaagct 31440
attgaaagag atgatagaac tatgcaaatg aaggagatta gtagagttat gaaatataaa 31500
gtaattacat attttgacaa catggaagat gatgtagaag tatttgacag aaaggatgaa 31560
gctattaaca gattgcatca tctacgaggt gttaaatata gaaattcaag attatataaa 31620
gtagaaatgg ttgaggtgga atagatgacg ctatccacag accaaatcca aactttacta 31680
ggaattgatg aagcgttcaa agctcctaac agattgattt taacaaatca gatcgtgagg 31740
acttattcag acagttttta aaatacgaaa aagacatgtc tatggttact tagtaactgt 31800
aggttatcgc aacatgtaac cgtcaaacac tttgaaaata aaggttttcg gttgctttag 31860
ttacttagtt actactttta tatatattta taataaataa ataaatatat atatagagag 31920
agagccatca aaataacgtg taactaagta actaaagtgg ccagaaacct tgatatataa 31980
gggtttgtag tggttacgag taaacgtaac tgttactgta atcgagtaac aaaaggagaa 32040
aaaatggaaa ttcaatactt agagattaaa tgaaagtccg tttattgatt ggagaaaata 32100
aaatgactag agatgaagca gttaagaaga ttgcaagaga aggatacata tcaatagaac 32160
acgctgagga attatatggt gaaattattc ctaaacctgt agtgccacaa tatgtggctg 32220
attggtatga ggaacataaa gatagctttg aagaatacct atttcaatgt atccatgatg 32280
ttgtagattt taataacaga gacgaagtaa aatattttaa agattggcta tctattgttg 32340
atggttttat gaaggacgaa ttcaaagctt ggatgtctca ggcttatgag aatggagcta 32400
tcaaaacact catcaatatg caccagtttg gatatgaggt agagaaagtt cctagataca 32460
aggttacttt taaagggtta aatattaata aacatttatg ttgcaacttg acacgtgaaa 32520
attggtattt gtggtatgag aaagaaagta aaatgtgcca tacgagccac actcgcaaag 32580
aactagaaga agctggtttt gggtgggtat ttgactgtga gggagtagag gttaaagagg 32640
tggaataagt gaatagactt tatctgttaa gagaatcacg gaaaattaca agagtcgagt 32700
tggctgaaaa aattggggtt acaaaattaa ccattcttaa ttgggaacat ggcacccatg 32760
aaatcaaagg aagtaacgct aagaagttag ctgaatactt caacgtatca gttccttact 32820
tgcttggcta cgataataca ttcactgact taatcgcaaa gattaacgag tgggctatca 32880
gtcacggact ggataaagga aatcctaaaa tcgaatggat gaaagtcact gaagaagttg 32940
gagagattag agatgtattt ctaaaaccaa acgattttga taacccagaa atggctctaa 33000
aagacgctat aggcgattct attgttaccc tagtggtatt atgcctacaa ctcggttacg 33060
acgttgagga gtgccttaaa atcgcttata acaacattaa ggacaggcaa ggagtaatga 33120
ttgatgacaa ctttgtcaaa acgagataac cagctaaggt ttttactact aatttcaata 33180
gtaatcaatg tgactaccat cataagagtg acaaatagac ctgtggaagc tatcgtggta 33240
cataaggttg ataacgctac tgtattgcat gggaaaatca caggtaagca gatgataggg 33300
aagctctaca caatcgattg tggagcgtat ggtaagtttc tagtcaccaa ggaacagtat 33360
gacaacgtac aggttggaga tgatattcca agttatttga ggagttatta agacatgaag 33420
aaatatgaat acgctgcatt aactaaagag ctacatcaaa ggttaactct agagtttgat 33480
gcattgaggg aagaacatcg cagaacactc actaaatata taatggaaac caagaaatgc 33540

```
aatagaatgg aagctagaaa atattttcaa aggtttgata acgtggttaa agagcgttcg  33600

aaactatcac cttcaacatt ggacgatatg cgcgaatatc ttacggacgg tctagttaat  33660

gacttacaag agtatctatt aaagaactat tcagtaagac gtgggtcatg taaaccagat  33720

gctgataaaa ctaatgcagg tcttacaaga gagctcttcc ttcaatatcg caaggaaatc  33780

caagagttaa gagcagcaca ccctaaccgt aacgcagaat atattatgga agtgaaagga  33840

tgctcaaaaa atcaagctca aacaatcata acagccatca atacaatata tacagaaatt  33900

ggcgttttaa cacctcggaa ggtaatccaa ttagaagggc ttctgtctag agagctattc  33960

ggtaagatag ctaagtacgt ctttaataag tatgagtggc ctgaaagcct agatagcgaa  34020

gttgatcgta tctatttaga atatcgcacc aaaggtgatc taggtcttga aaaggaaagc  34080

gtcaagcgtg tgctatataa agcgatttca atgggcttgt agt                    34123


<210> SEQ ID NO 5
<211> LENGTH: 37594
<212> TYPE: DNA
<213> ORGANISM: Streptococcus phage
<220> FEATURE:
<221> NAME/KEY: source
<222> LOCATION: (1)..(37594)
<223> OTHER INFORMATION: /organism="Streptococcus phage" /mol_type=
      "unassigned DNA"

<400> SEQUENCE: 5

tcgctgacag accgacaatc tttgggaggt gataaggcgt aagctgttca attctcatct     60

aaattcttgt agcgtgcgtg ggttcgaatc cctcgttcgt tgttagtctg tcatgactag    120

gtaatttttt cgacaaaacg tcaagctgac agaccttgac aacaaatcca gtaaatataa    180

tagaaaagag gaaaccaata catacttttt ttactctagt cttgcattgc tggtagcaag    240

actggaattt aaaataaagg gggtggtaaa taaaaaaagc ccaaggcaaa gcttgccgag    300

aactgtataa taatctgaca atattattat accagagagg tcagaataat gctattaccg    360

gaaattgatg agaaagcaac actcaaacgt tgcaaacgca agcttcgaga atatccacgc    420

tggcgagaga ttgcacacga tagcgctgaa cagaaaataa cacaggaatt tacattcatg    480

ccaaggggtg gcggagtgaa taaacctgtt gaaaatatcg cagtaagacg tgtcgatgca    540

ttgaatgagc tagaagccat agaacaagcg gttaatgggc tatatcgtcc agactatcgc    600

agaatactga tagagaaata tctagagttt ccacccaaac ccaactggca gatagctcaa    660

tcaatcggct ttgaacgcac tgcattccaa gagcttttaa acaactctat cctagctttc    720

gcagaattgt atcgtgatgg tcggttaatt gtggagcgtt gaaaaaaatg gtattttagc    780

ggaattttca cggtctctat taactgtttt aagtggtatt attatattat cgaagaagaa    840

agaaaagacg gctcatttgt gggttgtctt tttttgatta agtaatgaag gaggtggaca    900

tattgggcta aatcaacgac agaaaatatt tgcggatgaa tacttgattt ctggcatagc    960

ttacaatgcg gctcttaaag ctggatattc tgaaaattac tctaaaacca gagctcacaa   1020

gttgttagaa aatgacagaa tcaaggctta tatcgaagaa cgactgaaag atcttgaaaa   1080

gaagaaaata gcaaaacaag acgaagttat gcaagtcttc acttcgattt tacgtcaaga   1140

actcatggaa gaagtcgtag agctgaacgc cgctacaggt cagtttgtta aaactaagaa   1200

gcctccgtca atctccgaag tcatcaaggc aggaagcgaa ctcatgaaac gctatccaac   1260

agctaagcaa tctgagaaaa tgcaacttga gattgaaaaa ctcaaatcac aaattggtgg   1320

cgatgaaggt caagatgaaa aaatcgctgg tttccttaat attatcaaag gagctgtaag   1380
```

-continued

```
cgatggactt gagtaaactc tataccaaga gacagttgga agtgcttaac tacatttgga   1440
atcatgattg gtttatctgt gggcttcatg gagctaaacg agcaggtaag accgttgtta   1500
acaatgatac atttgtaacc gaattaagtc gtgtcagaaa aattgctgac cgattaggtg   1560
tagatgagcc tatttacatt ttggcaggta cgtcttcaac agcaattcag aataacgtct   1620
tacaagaact ttataacaag tatggctttg aaccaaaata cgataagcat ggctcttttg   1680
ttttctgtgg tgtaaaagtc gtgcaggtct atactggctc tatatctggt cttaagcgcg   1740
cccgtggttt cacagctttt ggagcttacg ttaacgaagc atcactagca aatgagttag   1800
tgttcaaaga gattatctca cgctgttctg gagaaggtgc tcgtatcgtt tgggatagta   1860
acccagacaa tcctaatcac tggcttaacc gagattatat cggaaagaac gacggcaaga   1920
ttatagattt tagtttcaag cttgatgaca acactttctt atcgaaacgc tatatagact   1980
ctatcaaagc agctacgcca aagggtaaat tctacgatag agatattttg ggtaaacact   2040
tgccccgctg ttgagtgatc aacagatgaa aaactgggtt aaaattggaa ggctaagttt   2100
tgcaaaacgc atgaatttgt agaataagct aatcaattac cactactggc agaaatgtca   2160
gtaaggttta acgactagat aaagtaagct aagttgaatc ggcaccggtt tttaatatgc   2220
ctaaatatcc acgaaatcca gctctcttaa caagagatga agagatagtc tgaacttatg   2280
ggaaaccata agaagcaggg gataaagagc ccttgcgata acaaataatg aagtggacgg   2340
ttgcagaagg cgctatttat gacgattatg acagcaagat acacgtagta gatgaattgc   2400
cagaaatgaa acgatacttt ggtggcatcg actggggata tactcactac ggatctatcg   2460
ttattgttgg cgagggtgta gatggaaact tctatcttct cgatggcgta gcagcgcaat   2520
tcaaagagat tgactggtgg gtagaacaag caaggaaact gactggcatc tatagaaaca   2580
ttccgttcta tgctgatagt gcccgtcctg aacacgtagc aagatttgag agtgaaggat   2640
ttgatattag taacgctaac aagtcagtaa ttgctggtat cgaacttatc gctaaattat   2700
ttaaagaaga aaaattatat gtaaagcgtg gatttgtacc tcgctttttt gatgagatat   2760
accagtaccg atggaaagag aacagcacga aggatgagcc gttaaaagaa tttgatgacg   2820
tgctggatag tgtgagatac gctatatatt ctgattatgt catcggtagc acagagcaag   2880
caagctatga tgacttgctt agtatgttta ggtaggagga atgatggaac agacactatt   2940
tacggacagc actggtcagg aacgagtttt aaacttacgc ttccatcgag agtctcgcat   3000
tcgttatcga gcggacaact tagaggagct catggttaat aattgggagt tgctgaagaa   3060
tttcatcaat caccataaat tgagacaagc cccacgcatt caagagctgt tggactatgc   3120
cataggtgaa aaccacgacg ttctcaagtc tggtcgtcgt aaggacaacg agatggctga   3180
taaacgagct gtgcataact acggtcgtat gattagcaaa tttaaaacag gctatttagc   3240
tggcaatcct atccgtgtcg aatatgacga taatgatgat aactcacaaa acgacgatgc   3300
tattaaacga ataggtcgaa ttaatgattt agattcactc aatagaacgc ttatcagaga   3360
cttgtctcaa actggtagag cttatgaagt gatttatcga agcgagtatg atgaaacacg   3420
aattaagcga ttaagcccgt tagagacatt tgtgatttac gacaactcat tagaagataa   3480
ttcaattgca gctgtcagat actacaatcg aggcacgctc caaagcgcaa aagatgtagt   3540
tgaaatttac acagacgaac acatctatac gcttgatgca tcagatgact ttaatgaaat   3600
ttcagttaca actcatgcat tcggtacagt accgattacg gaatatttaa ataatattga   3660
tggcattggt gattatgaga ctgaactcta cttaattgac ttatatgata gtgcagaatc   3720
tgacacagct aaccatatga gcgacatggc ggacgctatc ctcgccattt atggcgacct   3780
```

-continued

```
tgccttgcct aaaggtatgc aagctagtga catgaaacgc acgcgcctta tgcagcttaa   3840
acctcctaaa tcagcagacg gcaaagaggg cacggtcaaa gctgaatacc tcacgaagtc   3900
ttacgatgtg tctggtgcag aagcatataa gacacggtta aacagggata ttcatatatt   3960
tactaatacc ccagacatgt cagatacgaa tttcagcggt aacacgtctg gtgaggcgtt   4020
gaaatataag ttattcggtc tagaccaaga cagagttgac acacaatcac aattcactaa   4080
agggttgaaa cgtcgctatc gtcttgctgc tcgtattggt tctttggtta acgaatttaa   4140
agattttgat gaaagtctat tgaaaatcac attcacacca aaccttccaa aatcgttaaa   4200
tgagcaagta tctattttga caggcttggg tggccaagta tcgcaagaga ctgcacttag   4260
tctttcagga ttggtagaga gtcctaacga agagttagac aagataaaca aagaaatgtc   4320
tgaaatcgat tttaaggggt attctaacga ctttaacgaa cacgtaggca aatataccga   4380
cgaggtaaaa gaaacgcata cagacgattt tgagagggaa tatgaatgac gtactggacg   4440
aagcgtaccc tacgcgagag agaagcgagc atcaaaaagg gtgaagctga gtttaagaaa   4500
gaacttgaag cgctatataa ctttcaacta tcacagctcc gaaaagaact agacgcgtat   4560
attcaaaaat acgctaacaa aaacggatta agcgttagtg atgctaaacg aaaagcagac   4620
agttttgatg tcaaggcttt tgaaacaaaa gctaaacggt atgtagctga caaagacttt   4680
agtccaaaag ctaacagaga acttcgagac tataactttt ctatgtcggt tggtcgtcaa   4740
gaactgctta ttcaagaatt agagctcgaa ctattagctc tatctgagag cgaacgacaa   4800
ttgaccgatg attatctgaa gaatggatat aagagtgaag ttgcaagaga gagcttgctt   4860
gaccagacag taccaagtgg taaaactctt gaaaagtata tgaaagctgc tgtcaatgct   4920
aactttgaag gtgctgaatg gtcagagcgt atctggaaaa ggcaagaaca gttacgaaaa   4980
gttgtaaaga ccgaagtaac aagagctctc attcgaggtg aaaacggcat aacaatcgcc   5040
cgacggattc gaaagcatat ggatgtctct cgtacagaag ctgaacggtt ggcaattaca   5100
gaacacgcaa gagtgcaaac gttagctcag gagagcatca tgaaagagaa tggctttgag   5160
catttcaaac tcatgccaga atcgagagcg tgtgatattt gcaaagatat tggtaaagag   5220
acagaaaaga atcctgtcaa aatttctgac atgcaaatcg gaactaacgc gccgcctata   5280
catccttatt gcaggtgtgc aatagttgag gttgaatagt gcaccatgtt tttttaagaa   5340
accgcagagg gcgagcctct gatggtgcat agggctattt taagccctaa ataaacaata   5400
ctaacgtggc tcattggtaa atacactaga caagactaga taaggagtag ctaaccatat   5460
cgtggcttag aaagtgtttt acttgtgaga ctagatagga gaaataatgg aaacagataa   5520
cacaacagtt gaaacggtcg aagatgtaga agtaagccaa gacgttgaaa gcaatcaacc   5580
gagcgacttc caagctccgc aatcacagtc agaattggat agcattgtga acaaagcagt   5640
ccaaactgct ttgaagaatc agaaaaagag cgaagaaact cgaatcaatg aggcaatcgc   5700
taaagcgtta caaaaagaac aagactattc aaaattatct gctgctgagc gggctagcaa   5760
ggaatttgaa gaccaaaaag cagaatttga gaagcaagtg gcagagtttg aacttgaaaa   5820
actcaacatg gccgttaaac aagaccttgt ttcgaaaggt ttaccagttg agttggctga   5880
tatgtttagc catgctgaga acgcctccga ggctcttaaa ttggttggta cttttgaaaa   5940
agtatttaat gatgcagtag ctgagaaagt aaaagctact atccgtcaaa atgcaccaaa   6000
agccgcaagt gctggaggta ctcagacgga taattttggc gctcaacttg ctaagtctac   6060
aaacgttacg actgctcgtt ttatctaaaa cagaaaggaa tattttaaat gtcaacacaa   6120
```

-continued

```
acaatttttg acacttcaaa cattgtccgc tcacttcctt acaaggctgt gagtgctact   6180
gtagactcat cttatccggg tgtattggta gatggtaaga aatacatcaa agcaggtaca   6240
ctcgtagcag gtaatggcgg ctcaattttc gatgaccgca caaaaactgt cgtggaaaac   6300
aaaacagcac ctgagggaat cgtactctat gacgtagact tgacaatcga taacactgta   6360
tcagtgctct acgctggtga agtttacaaa gaaaaagtta atggtggaac tgtggacgac   6420
acaatcacta aagctttgcc acttgttaaa tttatctcta ataaataaag gaggaatgtt   6480
aaaacatggg acttatttat gataaagtaa ccgcatctaa tattgcgggt tatttcaaca   6540
cgttgcaaga aaatgttgac tctactttgg gtgagttaat cttccctgca cgcaaacaac   6600
ttgggactaa attgtcttac atcaaaggtg cttctggtca atctgttgca ttgaaagctg   6660
cagcttttga tactaatgta accattcgtg accgtgttag cgctgaaatg cacgacgaac   6720
aaatgccttt cttcaaagaa gctatgctcg ttaaagaaaa cgaccgtcaa cagcttaacc   6780
ttgttaaaga ttctggcaac gcagcattgg ttaacacaat tgtagcgggt attttcaacg   6840
ataatttgac acttgttaat ggtgcacgcg ctcgtcttga agctatgcgt atgcaagtgc   6900
ttgccacagg taaaattgca tttacaagcg atggtgttaa caaagatatc gattatggcg   6960
ttaaagccga ccataagaaa caagtagcta agagctgggc tgaaccagat gctacacctc   7020
tcgctgattt ggaagatgct atcgaaacag cgcgtgaact tggtcttaat ccagaacgtg   7080
caatcatgaa tgccaaaaca ttcggtctta ttcgcaaggc tgcatctaca gttaaagcta   7140
ttaaaccatt ggcaggtgat gggtcatcag ttactaaagc tgaacttgaa aactatatcg   7200
ctgataattt tggtgtatct atcgttcttg aaaacggtac ttaccgaaac gagaaaggtg   7260
aagtttctaa attcttccca gacggtcact tgactcttat ccctaacgga ccacttggga   7320
acactgtttt cggtacaact ccagaagaat cagacttgtt cgctgataac actgttaacg   7380
ctgacgttga aatcgttgac agcgggattg cagtaacaac tactaaaact actgacccag   7440
tcaacgttca aactaaagtt tcaatggtag cattgccatc attcgaacgt ttggacgatg   7500
tttatatgct tactgtaatt cctgcggttt aagaggtact actatgaatg tcgtactaaa   7560
agcttttaag gataaaacag acggaaaagt atacttcgct ggtgatttgt acgatggaga   7620
acgtactgag gaactcattg agttaggaca cgtccaagac gacaaaccaa agaaaaagac   7680
taaagctaaa aagaccactg aatagcgagg tatggcatga tgacgttaga taaagacaaa   7740
gttataaaaa atgtctctgt tgaccttaat actaatgatg atgccttgct taaaattcta   7800
ttagagcgtg tcattaatca cttcaaatca gagtatggtg tcgaagagat tgatgacaag   7860
ttagctttta ttttcgagga ctgtgtcatt aaacgtttca accgtcgagg tgcagaaggt   7920
gctaaatctg agacggttga cggtcattca atgtcttatt atgacaacga aaacgaattt   7980
aagccttatg atgatatgct tcagcgtcta tacggaactt ctggacaagc taaagaggga   8040
gaggtgttat tcctatgaga tacgctgata ccgtagtgct aaaatatatc gataagacac   8100
aaaagcacta cgacccagac ttaggacgta tggttggcgg taaggaatgg tctaagacag   8160
taccatgcaa tgtgactggt actagccttg aattgcaagc caaactagga gacctgttaa   8220
acgccaatag catcgtcgtt aggtttagaa gccctatcaa agatggaatt gacacgattg   8280
aatacaacgg tggcaaatac aaacctgtta ctgtcagaag ctatctaact ggtctaaacg   8340
tcatctatgc taacaagatg gtgaaataac atggctacaa tcgaatttga aggattggat   8400
gaaatggctc aaagtcttct taaaaacgcc tcttcagaaa gacgttcaaa ggttttgagg   8460
aagtatggtt caaaattaaa agaagctgct gttaaaagag cacaattcaa taaaggctat   8520
```

-continued tcaacgggtg ctactcgtag aagtattact ctacaagttg aaagtgataa agcgattgtc 8580
gaagccttga ctagctattc agggtatctc gaggtaggaa ctcgtaagat ggaggcacag 8640
ccatttatga aaccagccct tgaagaggta gtgcccaaga tggttgaaga gatggcaaaa 8700
tgggatgaaa catgaagcaa cctgatcaat taattcatga tgaaatgttt cgtattagtc 8760
atgagttagg atatgacact tacacatatt tgccaccaga cgacgtggct tacccattcg 8820
ttgtaatggg ggaaacaatg gtcttgccac aatccacaaa atcacacttg ataggtcgtt 8880
tatcgtctac ggtgcatgtt tggggacgtg tggatgaccg aaaaacatta tcagatatgg 8940
ctggacagtt aatgtctagt ttttttgcta tcaaaaatat tggcggaatg cagttttcag 9000
cagaagtcaa cgagtcgtca attgatagca atcgagataa tagcacagat gaagtgctat 9060
atcacttcat catttatact tattttaaat ttatttaatt aggaggaaaa aatggctgat 9120
actaataaag aagccctttt ggggaaagat aaaatcttga tgttccgaaa atttggagac 9180
aaaaaagcgg cagctaaact tgccctacaa acagagcacg aatgggaata ttcacgtgat 9240
gcagatagca ccaaaaccaa agacggtgca gttgttgccg acggtggcct tgaaactaaa 9300
ctatcaatta atgctattgg tactaaagat gagctcaatg aaatgctaaa aaaatcagta 9360
gttgacggtt ataaagtaga agtttgggaa attgatttgg ctgacaaaaa atcaaatggc 9420
aaatacggtg ctctctatgc aattggacgt ctgtctaact ggaaagtacc ggctaatgta 9480
gaagaccttg tagaaattga atcagaattg actattgaag gtaagccaca agctggagaa 9540
gctactttga ctggagacca aattaaagaa attcaataca cattccaaga cacaactgca 9600
ccttcaggcc tcggtgttta atagtatgta attatcttga gccaaactaa aaaagtttgg 9660
ctttttattt tagaaaaaat aggagtaaac aaacaatgca cacaatcact attgataaaa 9720
aagactacac tttgactttt ggatttgatt ttatccgcga acttgacaaa cgctactcta 9780
tttcagatgg tggggtttcg ttcggtttcg gtgtacaaca cgcagtcgtt gacttgcaac 9840
agaaaaatcc agtaattttg cttgacctta tccaagcagc aacaattaca gaacgtcaaa 9900
aaccatctgt aaaaggtatt gaagcatacg tcgttgaaga agctgagaaa ggtcatcttg 9960
actcactatt tgatgatttt ttatcagcat tgcgaactca acctttgacg aaagcaacaa 10020
caaaacgagt ggaagaagcc acagagtaga agaaacaacg agtgataacc aaaattcagc 10080
cgaagtatac gaggagttaa tcacgaatgc tatggctgac tttggcgtgt cattgcttga 10140
agcacgaaga atgacactta aagagatgaa actctatcag aaagcatata agaaacgttt 10200
tttgaacaaa gaaagagaaa tatatcaact tgcttatctg aataggttgg ctaatgccac 10260
aactaaagat ggcaaaaagt attatttcga aaaatttgac gacttctata atgctaaaga 10320
acgtgctcgt gaagttttgg gcgaaaaaat cactaacagc aaactgttag aacgagctcg 10380
aaataatctt aattataaga aagaaagagg gttgctagat ggcagataaa acgtttaatg 10440
taagagcaat attgagtgct caagacaatg gtctgtctag cgcgctcaaa aaagcacaac 10500
aaaacgctga aaatttggga aaaacaagca ctaagttagg atcagttttc aaaagtgttt 10560
tgggtgctaa tttagttagt gctggtatca ctaagggcat cagagcttta accagcggta 10620
tcggtggcat gatgaccgag cttaacaatt caacaaaggc ttggaaaacg tttgacggaa 10680
acttaagcca gttgggttgg gggaaaaaag aaattgcatc agctaagaaa gcgatgcaag 10740
attatgcaac tcaaaccatc tattcagcgt ctgacatggg aacaacattc tcgcaaatgg 10800
cagcaatcgg tcgtagtgat gctggggatt tggtgaaagc tatgggtgga cttgcagctt 10860

-continued

```
ccgctgaaaa ccctaaacaa gcgatgaaaa cattgagtca acaaatggtc caagcgatga  10920
ccaaacctaa ggttcaatgg gcagatttta agttgatgat ggaacaatca ccagctggta  10980
tgtctgctgt cgctagagag atgggaatgt ctcttgatga gcttgtcacc aaaatccaaa  11040
acggagaaat aaagaccgaa gattttacag aagcattcaa gcgagctgga aattccatgc  11100
aagacttggc tactaggtat aaatcagtag atgaagctgt tggtggtctt tacgaaacgg  11160
tttcaaataa attgcaacca gtttttgaaa agttaagcgc aaaggcaatt aaaggaatcg  11220
agagcatcat tgatgctttt agcaaaattg atgacagtaa gattcagaac tttgcaaaca  11280
acctaaccaa aggtattgat aaagcggtta aagaagcaag tcagactgtt aaagcttttt  11340
gggaaggttt tagcaataca agtgcaataa aaggtcttag caatgctttc aaatacgttg  11400
ctagtcaaat aagtttggca tttgaaggaa tcgattttaa aaacctattt aaaggtttag  11460
gtagtgtgtt tggtgacata gcttatggca tttcaagaac cttaacaatt gccactaaat  11520
cagttaagaa tttcattgac tcattctccg acacaggagc attcaaggcg tttaaaacag  11580
ccttagagga tgtctggggt gctgttaaga aagttggctc atcaattgct gacgtattta  11640
acagctctga ggttcaaacg atcatatcag ctttaggtac agcgtttgga acactagcta  11700
aatggatatc acaagctgct tcagcaatag ctaaatttgt aagctcaatt cctaaaggtg  11760
tgctcaacgg tatcactagc ggtgttttgg caatggtaac agcattaatg actgccaagg  11820
ttggcatatc agctgttagc tcagctatgc aaggattgaa ttttcttaaa agtcttaatc  11880
cattcaagaa attcggagcg gatgcagcta aaggcatggc tgaagcctcc acaagtgcaa  11940
gtaatggcaa gagcaagatt gcccaagtgt ttgaaagtat tggcggcgta attaaaaacg  12000
ctggttcagc aatttcacaa gctgcaaagg gtatcggaat gggtatctct acagctttta  12060
agggagttgg tacagctatc aatatcgcct tacaaggttt gagagggtta aacccagcca  12120
ctttactttc attcggtgca gccgtggcta ttgccgcagt cggaatcgga gctggtattg  12180
ctattatcgt agcttcattc actttgctag ccactcaatc acaaggcgtt tctcaaatct  12240
taaaagcttt gagtacagca tttagcactg tcgtccaagg tgttggcaaa gctgcaggaa  12300
ttatcattga agcattcgga actgcttttg gaattgtcgt caaggcagtc ggtgaagctg  12360
cgcccggact ggctaagtta tcaccattag tagaagcgtt tggcactgct ctaggcaatg  12420
catcaccatt cattactgcg tttggtaatg cttggacttc tattttagga acgcttccag  12480
ccattatcag tgcatttagt ggatttgcaa ccgctctagg ttctgcaatc agtgcagtag  12540
ctaccgcaat aactccgatt attcaaatta ttggaaacac aatcacggca gtaactcaaa  12600
tcatcgctaa cgctatcgtg gcaatcgctc cgataattgc cgattgcatt gtccaagtaa  12660
ctcaagtaat tggcaattc ggtccacaaa ttgcaatgat tttacaagtt atcgtgcaag  12720
ccatccaagc atcagcacca gtcatcatga ccttgattca aggtattgta accgttgttc  12780
agacaatggc accagttatg agtcaagtag tttctgccat cgttacggtt gttcaaacat  12840
tagcgccaat tcttcaatct gtcgttaatg gcatcatcgc cgtattcggt caaatcgtgc  12900
cagccatttc agcaattggt agtgtgattg cttctgcctt gcaaggtatt gctaacgtgg  12960
tgcaatcagt cggaacatca attagcacag cggctaaagg tatcggaaat ggtattaagt  13020
cagcatttga aggtatttca agcgtgatta cttccgcagg aaatgcaatc agtaatgtac  13080
tgaatagctt agctaatgta ttcaactcaa tcggtacagc tgctcaaaaa gcgggtattg  13140
gtttcaatca gttagccaac ggtgtagtta agattaccaa tacaaactta ggagacatgg  13200
ctgcatctct tgcggcagtc gctcatggta ttggttcgat tagtgatagc tcagcagggc  13260
```

-continued

```
ttgctcaagc tggtgcaggt atggctcaac ttggaaacgg tatgagcaaa gtgtcagcat  13320
cagcatctag tgctgttgca ggtttgagtc gtttcgcaag cgtgactaca agtatacaat  13380
cagcatttac tagcttacaa tcactgctag cttcagcagg aacagcgttc agcacgttct  13440
caattcaagc tatacaatca ctaactggat tgtctgctat cgcagggcct atcacaacgt  13500
tcagaacgca aattatgatg atagtaccat cacttatgca agcagctgct ggattgacca  13560
tgttcagcac agtagctatg ggattgacta ctagcttgac ctcaatcggt gctatcgtga  13620
atatgttagc tacacaacta acaatgttaa caactagctt tacgatgatg gcttctatct  13680
cagctatgtt aggaacaagc ttcaccatga tggctactag ctcatctatg ctaggaacta  13740
gcttcaatat ggttggtgca tcactaacta tgttgaatag tcaattcatg atgtttgctt  13800
catctctcat gcagttaaca acacaattca tgacagcgtc aataccactt aaaatgttca  13860
acgtggcact aacaatgatg acaccagcct tgatgatggg agctgctggg ttcgtgcgat  13920
ttaacgctca agtcatgcaa tctacagctg gtatgtccac actatcagct gctatctcta  13980
ctattccagc aaaacttaca tctgtagcaa gctcagctaa tactacaaca ttatcaatca  14040
tgcgtattgc aactagcgca ccacgaatcg ctagtgctat gagtagtgca gctggacaag  14100
tacagtcagc tatgcaacga atggctcaat ctgtgcagtc tagtagtcaa agcatgattc  14160
aaatgggtcg tcaagcagga actcagactg ggcaaaatat cgcaaatggt attaaatcgt  14220
ccgttggtgc tgtatcttct gcagttgatt cgttagtaaa tgctgcgaga gcacgcgcaa  14280
tgggtggcgt tggtgctatg caaatagtag gagcgatgat tggtaaaggt ttggctaatg  14340
gtatgatagc ttctcttggt gcggtaacag ctgctgctaa cgctcttgta gctcaagcag  14400
aacgtgcagc tcaagcaaaa gcgatgattc attcaccatc acggttattc cgtgatgaag  14460
ttggtatcta tatcggtcaa ggtatggcag ttggtattga tagaagtgtt aaatacgtca  14520
agtcatcaat tgaaaacatg gttgacactg ctagtcgtta cgctatcagc tcacgtgaat  14580
tgtttgaaga caataatgta tttgatagct ttggttgggg taatattcga ggtagcgttg  14640
atttagcatt gagagacgac gatagaatgg atagattaga acaagcactt gatcttatca  14700
ctgaattagt aggacgtcca atatcactca atatcaatgg tcgtgagttt gcttacgcaa  14760
ccgcagatga cattagtggt tatcaaaaat cacaggaatt tacttacaaa cgaatgagag  14820
gacttgatta atggctttgt ttcaatttaa cggatatgat ttaaccaact atttcaagct  14880
aatcaaagta gagcatgaaa taggaaatga acggtctatc tcaacagatt cagcgccagc  14940
aattggggtt aatgtccaaa atgttgatat cggtgcaaag aagataaaac ttacagtcag  15000
cctagcaact agagacttgg ctgatatgac atttattgac ccaaacgaac cagcaccagt  15060
tgacaatgtg cagttttatc gagttagaga agaagctgcc agagtcctac acaccaaaaa  15120
agcggttaaa ctctacttac caacagaacc tgaccgctat tatttggcac tcgttaaagg  15180
cgaggtcagt ctcaaaggta tttcagactg gtatgacgaa gccacgattg aatttttagt  15240
gcctgacgga gtagcacatt cgactacata caagcgcgtt acagattacc aagaaaaaga  15300
tgggaaaatg atttttttcta tcgacaacga aggttcgacg gacgcttatc caataatcac  15360
cctgaaatca aactctgaca atggctatta tggtcttgtt agcgataaat ttgcttttga  15420
aactggagat acagaagaag tagacttaga accttacaaa cattctgaaa ttctgttaga  15480
ttatgcttct tacgattgga tcaccaaagc tttatctgat ggcaaaaaaa acgtcgcaat  15540
tttaaatgat gctagtcaaa gcctcaatgg aacattagga atagaaaacg tttggggtag  15600
```

accacacttg gtattgacaa atcgtggaac tggtttaata aacaaagcgg catctcttac 15660
ctttgatatt ccagcagata gcacaggaga acgtggtgcc ttgaatgaat atatatggtg 15720
gagacagatt ttttgggtaa acccagctga ccaagttggg tttatcaaaa tttcagtctc 15780
atcagaaagt ggtgagtttc tctacggtgt cgaaacaatc aagcgtggta atggcttgac 15840
taccgaatac aatttactaa catctaacgg gatgggtgga tttaacctgc gcaatttggg 15900
gactttttgg tcaacacatt acccgcatga aaatccgttt tctaaagatg gcggacaggc 15960
tgacttacag cgatacaacg atgaaataca agttttctgg cgtggaagct atccaaaatt 16020
tacggttcct gaaattagag acaaaaagtc agcccaagta catatagcgt taggagctct 16080
tgatgacaga ccactaccaa cgcatatgta tgtggatgct tttgtttatg caaaacattt 16140
cgtaacatca atgaaagata taccaaacag atactttcaa ggcagctcat tagttattaa 16200
cagcgagaca gatactgttt acctcaacaa tctacccaat ttagatcaga ttgttgacgg 16260
ttctatgtgg ccagtgtttc caccagggca atcagaattg gaaatcattc aatctaattg 16320
ggctaagaag aagcctagtg taacaattga atttgaggaa aggtggattt aatgttacta 16380
acaatacatg acaataattt gcagaaagtt gcatatatag ataacgaaaa acaatccacg 16440
ctaaattttt tcaacgacaa atggactcga tcacttgaaa gcggaacatc tgtttttgag 16500
ttttcggttt ttaagaaaag cattaaatct aaatcgaatg tagattttgc ttataaatat 16560
cttaacgaga gatcttttgt cagcttcaaa cacaagagac gctcttacct tttcaatgtt 16620
atgaaagttg aagaggatga gcatattatt cgatgctact gtgaaaactt gagccttgaa 16680
ttacttttag agtatcgagg tgcttacaaa gcatcaaaac ctatgacatt caaagagtat 16740
tttgacgatt ggggaatgga acgattcgct aaattgacta ttggtgtcaa cgaggtttct 16800
gatcaaaaga ggactctaga gtgggaagga caagaaacaa ctcttgctcg actgatttcg 16860
ttagctagga actttgatgc tgaaatagaa tttgagacaa agctacaagc taatagtcaa 16920
cttgatgagt ttgttttaaa cgtttacaag tctcatgatg ataaaaatca aggtgttggt 16980
ctcagacgct cagatattgt tctgaagtat gataagaaca taaaaagcat taagcgtagc 17040
gttgacaaga ctcagattta taacatgata acaccttatg gtagaaaaac tgagacgaat 17100
aaagaaacca aaagaatctc cgatccagtt actattcaaa atccagttgt tgttccatct 17160
actagagttg aaaaaaggta tactggaggt gacttgactt atgcaggcca tacgttgagt 17220
gctagtttgg ttcaaaccat ctttaatctt tgtatacagc gaaatctttt gccatcaggc 17280
gtcatatctc agctctatct tgaatcgttc tgggggtctt ctaatgtagc tagacgagac 17340
aataactgga gcggcatgac tggtggtgca caaactcgcc catctggtgt cattgtaaca 17400
acgggtagtc ctagaccagc tagcgaaggt ggaacgtaca tgcactatgc tagcgttgac 17460
gacttcatga aagactacac ttatctacta gcagagcaga cgagtggtgg tcgtaagatg 17520
tacggtgtca aaggcaagca gaacattgaa gaatacacaa aagggctctt ccgaattgga 17580
ggagctcttt atgattatgc tgctgctgga tacaaccact atatctatct tatgcgagat 17640
attcgaaatg gtatcaaccg ttcaaatgga aacattttgg ataagttaga tgatttgtgg 17700
agacagccag acaatcaaat cactcaacca aaccaaccag taacgagaac tgttaaggca 17760
gataaagtta tcgccgtcct caatgaaatg caagggttga aaggtcgtcg agtaggtaac 17820
ggtcaatgtt atgcattagc agcttggtat tctatgaaat taggtggtcc aggtctcggt 17880
gctggagtta ctggcaagtc tggtgcaatt ggttctggta tgtgtgcatc caatattggt 17940
actgactacg cttgggataa gttcggttgg agtgttgtta gacctagcag tgttaaccaa 18000

```
ttaaaagctg gggctattgc taatatcaag gcatacaata gttatatagg tacgtctgtt  18060
tggggacacg tttcaattat catcgctaac aacggtagca ctgttacggt tctagaacaa  18120
aactacgctg gccgtcaata cgttgtccaa aatagctatc ctgctagtgc ttatttagga  18180
tctattgaaa cattatgtta tcctcctgaa ttgaaagagg gtaaaacggt tgagggtagg  18240
actgaaacag ttagcgctct aaacgttgaa gttcaaaagg tagagattcc acctatcgac  18300
gttgaagtaa catctgaaag cacagatgca cttactattg atagcaaacg aaagcaagaa  18360
tggaagaacg ataaaggtca agttgagttt tatcttgaaa acggttcgct atatgctccg  18420
atttcaaaag aactatatcc atccatttta accggtaaag agaatggcga taactggata  18480
cggaaagata tggaaataga cacggacagc gaagacgtgc ttatttcgac agctcttaga  18540
aacctacgaa aattctgtta tccagctatt acttatgagg ttgatggttt cattgattta  18600
gatattgggg acacagttaa aatccaagac actgggttct cgcctatttt gatgcttgaa  18660
gctcgtgtca gcgaacaaca gattagtttc actaatcccg tcgagaataa gacggtattc  18720
gctaactacc aagcacttca aaacaaagtt tcagacagtt tattatcccg aatgactaaa  18780
ttggctgagc aagctattcc ttacgagttg aaactttcaa ccgataatgg gactacattt  18840
aagaatagtg ttggtcaaag cgtactaaaa gcttcgcttg aaaagaacgg tgtagtttat  18900
caaccaatat tcttctataa aaatggcgat gctatcatcg gtactggcaa tcagttagtt  18960
gttaaaccaa cagattttga aaatacttta caggtaactg ttgaagcgta ccttgacgac  19020
gagttagtag caagtacaga aatcacattc acagatgtct cagatggcga acaaggacca  19080
caaggtccac aaggtataga cggtaaaacg ccttacgttc acacggcttg gtcttacagt  19140
gcagatggta cagatagatt cactacggtt tatccgaatt tgaacttgat tgatggtaca  19200
agagatttca gtggtaattg ggatagagat tgggcttggt caaatgatgg atcatacaaa  19260
ggattaaccg ttaaaaaaag aactgatgaa tggcagggta ttaataaaga attcaaggca  19320
ccaaaagatg gtacttatac tttctcagct tatattaaaa cttcaggaaa cactgctaat  19380
atagccagac atattcattt aaacggatct tggaataaag atacttataa gacttttaga  19440
aataactttg attggttaag agatagcttc tctgtaaacc taaaaactgg agatactatt  19500
tctgcaagat acgaattacc aggagaaggt attttatgga ccgcaggcca taaatgggaa  19560
gaaggtccag tagctactcc atggatgcct tccgcttccg aagtcacaac tgctgattat  19620
ccaaaataca ttggtcaata tacgaactat atggaagtag atagtcctaa tcctcaagat  19680
tatacttgga gtctaattcg agggaacgat ggcaagcaag gtccacaagg tcctaaaggt  19740
gaaagtggtc ctcaaggttt acagggccct aaaggcgacc aaggaatccc gggaccaaag  19800
ggtgaagatg gtaaaacgca gtatacccat atagcttacg ctgatactat ttctggtagt  19860
ggatttagtc aaacagatgt caataaacca tacatcggaa tgtaccaaga cttcaatgct  19920
gttgatagcc aaaacccaca agattatcgt tggagcaagt ggaaaggtag cgatggacga  19980
gatggtattc cgggaaaacc gggagctgac ggacgaacac cttatgttca ctttgcctat  20040
gccgatagtg ccgatggtca aaagggtttc agtttaaccc agactggcgc caagcgctat  20100
ttaggtgtgc ttacaaactt cttcaaagaa gacagtacta atccttctga ttacacgtgg  20160
aatgacacgg ctggcagtat atccgttggt ggtcggaact tacttgtaaa aaccaatcaa  20220
ggtattacta attggaattg gcagctttcc gatggcgaca agagcgttga agaagtaaaa  20280
gttgatggca ttcgtgctgt aaaactaatc aaaggttcaa caacagcaaa cactggttgg  20340
```

```
aatttcattg aatataatgg cttgctgcgt gaactcatac agccgaagtc aaagtatgtt  20400
ctttcgttcg atgttaaacc aagtgttgat gtaactttct atgcaacgct aacaaatgga  20460
gactttacag agacgctgac tgatactgtc gctatgcata aagcattagc caatcagtgg  20520
aataaggtat cgtgcgtttt gacaagcaaa gaaactttgc caaatattgc atggcagact  20580
gtatacttag caggtatgcc aacaacaaac ggcaattggg taataattaa aaatatcaaa  20640
cttgaagaag gtgacatacc tactcagtgg acacctgcaa ttgaagacat acaagatgaa  20700
attgattcca aagccgattc tgctatgacg actgaacaga ttaatgcgct taatgaaagg  20760
gctgcaatta ttcaagcaga gacggaagct agagcaagcg ctgaaatttt gaataaatgg  20820
attaaaaatt accaagattt cgtcaaggca aacgagaccg agagagctgc tgccgagaaa  20880
gctttggtta gctcaagtca gcgggtatca accattgcta aggagttagg tgaactgtct  20940
gatcgttgga atttcatcga tacttacatg aacacatcga atgatgggct tgtgattgga  21000
aagaatgacg gtagctcaag cattgtgttc aaccctaacg gtcgaatttc aatgtattca  21060
gcagggtctg aagttatgta tatttctcaa ggtgtaatcc acatcgaaaa cggtatcttc  21120
tcgaaaacaa tccaagttgg tcgatatcgt gaggaacaat accatctcaa cccagacatg  21180
aatgtcattc gttatgtagg aggtttttaa ttggcagaat tttggagtaa taatgataga  21240
ggctatagga ttagattatg ggttgaccag gttagccaag acaaagtagc taataccagt  21300
caggtcagat ttcaactagc actgctaaat acgactacga cttttgctca atatcaatgt  21360
agcgcttata tcgatttcga aggacaaaga ttgaattggt ctggttcacc tagtgtatta  21420
gggtggtatc aaacaattcc attgatagat caaacagtta ctattaatca cgattccgac  21480
ggtaaaaaga ctttttcttt ttcagcgcag tttaatggcg gtggaggttg gagtcctcgt  21540
acattaacaa tcagtggtat ctcatttaca ctaaccgaca ttccacggtt aagctctgtc  21600
agcgttgatg ctggtactat tggtagctca gtcactatta acattaaccg tcaaagctct  21660
agttttaagc acacagtacg ttatgcttgg gccaataagt cagggactat tgcaagtaat  21720
gtagacacat ctacaacatg gactatccca cttgactttg ctaacgactt tccaaactcg  21780
gaaacgggta cgggaacaat ctacgtagat acctactcag aaggaaccat gatagggaca  21840
cagtcagcta cactgacagc aagtgtgcca gctagcatga aaccaacttt cacaggaatt  21900
tctttatcag actctaacac agctgctcgg aacgtggtac aaaacgctaa cacattcatc  21960
cagattatgt ctaacatcaa ggtatccttc aatggtgcaa gtgggtctta tggttcaaat  22020
atcacgggct accgtgctga gatagtcggt aagaaccaga ctaccaacgt caatggtggc  22080
acgctgggta tcatgaacta caacggaacc atcacagtca gggcaagtgt atctgatagt  22140
cgtgggcgtt ggtctgatac tagagatgtc acagttactg tacttgagta ttttgcccca  22200
tctcttaaaa ttgacgtaaa acgcgttggt gaaacatcta gcacattaga aattataaga  22260
aatgcacaga tagccccttt gaatattaat ggtattcaaa aaaacaccat gaaattaact  22320
ttcaaggtgt ctcctaatgg aaaagatgat tacacaacgg acactggtcc tgcctctggt  22380
gaatggttaa gcatttcaag ccttgtcaat tcacctgcta atttagctgg tatatatgca  22440
gctaataaat cgtgggaagt tttggcaatt ttggaagaca aattcacatc cacgagcttt  22500
aaggcacaag ttcctgttga aagtgttgtg ctgtcctatg accgtgatgg tcttggtatt  22560
ggtaaaatac gtgagtttgg aactcttgac gtggatggtg atatctatgc taataacagt  22620
cagattcaac aatatcagct aaccagtaat aacggtggtc ccaaagggaa tgttgacaat  22680
gcaaacaacc tttatgaacc gggacaatac tgccttggcc catcggcacc gggaaatcct  22740
```

-continued

```
aatggtcagt ggggatttct attccattac agctacaatg gaaataatac tgacggtata  22800
aaagaagcca tccagacatt ctggagcaac aacggtcaga tgtttttcag gcatcaccga  22860
tggtcgaaga taatcgacga ttgggaaccg tggattgatt acacacctaa gaaagagaaa  22920
cctgttgtta agaaagaaat cgagattgga tggtttttga aggcaaacat cgtaaggaaa  22980
tcaaatgtag taactctcag cttgataagg gacgtacata ctgtaccacc aggagagtac  23040
aggagtttgg atgagaaaat tccatacggg ttcagacctt gcgtacagac acatttagtt  23100
atcaataaaa acgtagcaaa ttttcataaa gaatgtgcag tatggcatct tgaacctagt  23160
ggtaatatgt tttattcaaa ccagaatatg gatgccgaag tatatactgg aacagtaact  23220
tacattactg aagacgaata tccaaacaat taagaaatga ggaaaaattt atgaaatttg  23280
agtacgaatc aaaatcaaaa gaatatgacg ctagtggtgc agcatacgcc acaaaagtag  23340
ttttgagaaa ccgagatggc gcttacgtac ccgtcttttt gccagtcgag aaaatcgact  23400
tatcaaacac tgacctccta aatgaagcgt tagaggttat ttatcaagag aatttcccac  23460
agcgtgctga gaatgagaaa tttaacaaaa ttgaagaaca aattaagaaa catcaagatg  23520
tatcaaaagc agcacaagta acgttgatgg atatcattga taagctttat gaaaaaaaag  23580
tgttgagcga tgaagacttg actgattcta aaaaataata gaaagaggaa tagatatgat  23640
tgttaaatta tttgcaatta atgtagccaa tggaaactac ccatttaaac gcgttcctga  23700
agttttgaaa ccaaaagtta aagagaaaat agctgctatt gttaatgacg aggagctatt  23760
agcacaactt acacaagaat agtcgaggag ggttgtttta tgggaccaca aaacgagaca  23820
gatttgatga actggcttat tacggttatt ctccccattt ccatttcaag tgcgagtttc  23880
tatttttcta gtcaatcacg cgcctctcga ttagaacaca gaatcactaa attagaggtc  23940
tttgaccatg aaatcgagaa aattattgaa acccacaatc agcgcctcga caaacatcaa  24000
gaggaccaaa aaataattct agctctagtc caaaggatgg accattttaa tgagaacctt  24060
gttgagctaa aaggaaacat taaagaagtt agatcgaaac ttgagaggat aataataaaa  24120
tgattaattt taaattacgt ttgcaaaata aaactacact agtagctctt atctcagcag  24180
tattccttat gctgcaacaa ttagggcttc atatccctag caacattcaa gagggagtaa  24240
atacttttgt gggaatttta gtgattctcg gaattgttac cgacccaact actaagggta  24300
tcggtgacag tgaacaggct ttgagttacc aagagccaaa agaataataa aatatagaaa  24360
ggagtgttag gtgtgactac taaaacacaa ctattgaaca ctcttgacag tctcgttaat  24420
caacgtgtta cggttcctac taatcctttt ggtgggcaat gtattgcatt gatagacaat  24480
gttttgcagt atcaaggatt gtttaacctt gatttcagct acttaaatgc catcgatgcc  24540
ttaagccgtg ctgaaagtct agggctaaaa gtaacacgat ttaacggggc taacaatcca  24600
acagtgggta gtgtttgggt gactaactgc ttgccttacc atcaatttgg tcatatcggt  24660
tttgtgtacg cagaaaaccc agacggaaca gtcaccacga ttgaacagaa tatcgatggc  24720
aacgctgatt ccctttataa tggtggatgg actcgcaagg ttacaagaaa cctcgatagt  24780
gctggtaatt ttagctatat tgattggaat gccccaaccc agcaaatggt agggtggttt  24840
gaattgccat tagatggcat ggaaaaagat aattacttta tcgacgtttc cgcttatcag  24900
ccaggcgact taacagctat ctgccaagct agtggcacta acaacactgt tattaaagtg  24960
accgagggtg tgggctgggt tagtccagta gccgctcaac aaactaacac aagtaattgt  25020
atcgggtact atcactttgc tcggtttggt ggggatgtgg caactgcaca agctgaagct  25080
```

aactacttta tcagtaactt gccatcgcat ccacgctatc tagtgtgtga ctacgaagat 25140
ggggctagta gtgataaaca agcgaatact aatgcagtcc tagcgtttat ggatatctgt 25200
aaggcgaatg gttttgaacc tatctattat agttacaagc cttacacact agctaatgta 25260
tatgtagatc aaatcactgc acgctaccca aatagcttat ggattgcagc gtatccggat 25320
tatgaggtac gcccagagcc atattggggc gtgtatccaa acatggaaca cacacgctgg 25380
tggcagttta catcaaccgg cttagctggt ggattggata agaacatagt cattattaat 25440
gatgacgaca atttagtgaa tcagaaagag gaagaagata ttatgaattt tgtagtacgt 25500
agtgaaagcg gtaaagaagg ttgggtagca gtcgttaacg gccgtgtgtt tggtatcggc 25560
tcaatgggga cagtagacgc tctcgaagcc actggagcta aacgtttgca actagaagat 25620
gcagacttca atcgtttcct atacagtcaa tcaaacgaca cggcagcagt ggcaaaagcc 25680
attgatgaag ctagcgcctc agtagttaag gctatcgaag aacgtgcaca agctacacaa 25740
ggtcaaactg gaaaataatt agaccacgaa aactataaat tgaaaaggag tatatcacct 25800
cccctaacac tgcaataggg ataccatggc agtagtggtc gaagcctcag cattatgctg 25860
gggctttttt tgtttgcttt tttttaacct aacagcccgt aattccccca cctctaaggt 25920
ggcgggatgt aagggcttcg gtctagtgca gtgacttgct ccctgtgcgt taccgacaat 25980
aaagaggatt ggcaagtttt tgactttcct tttgtcttat gataaaataa agtcagttat 26040
atttagtgaa aggttgttat atcaatgaaa ttagatacaa atgctcattc agtctttctg 26100
cttcattacc atctcattct tgttgtgaaa tatcgccgcc aagtattcac tgatgagatt 26160
tcggaacgtg caaaagaaat atttcttac atagcaccca gttacaaaat tgagttagtg 26220
gaatggaatc acgataaaga ccacgttcac attctattca aaggacaacc taaaacagaa 26280
atgagtaaat tcatcaatgc ttacaaatct gctagtagtc gattactaaa gaaagagttc 26340
cctattattc gccaaaaact ctggaaagaa atgttctggt ctcaatcttt ctgtctccta 26400
tctagtggtg gagcccctat tgaagttatc aaagaatata tcgaaaatca aggacaaaag 26460
aaatgacagt taggcaaaaa tcttataagt tcagaatata tccaactaaa gaacaaactg 26520
ttatgttctc taaaacattt ggctgttgta gggctatctg gaatatgatg ttagctgata 26580
aaatcaagca ctatgaagaa acaggacaaa cactaaaaaa tacgccagct caatacaaga 26640
aagagttcga gtggctaaaa gaagttgata gccttgcatt agctaatgta caactcaatc 26700
tccaaaaagc ctataaatct ttcttccaat ctggatttgg ttttccaaaa ttcaagaaaa 26760
aacgtcatcg tcaatcttac aaaacaaaca accaaaacgg gacaattact gtacttgatg 26820
gaaaagtcaa gctccctaaa attgggtggg tgaaactcaa ccaacataga gaaatgtctg 26880
gtgttatcaa gagtgctact atctcaatga cagaaacagg taaatacttt atttcgattt 26940
tgtgtgaaac tgaaatctat ccactcccaa aaacagggga gcatgtaggg attgaccttg 27000
ggttgtctga tttcgctatt ctatcaactg gagaaaagat tggaaatgag aaatttctcc 27060
aaaatctctc caagaaacta gctaaagagc agaaaatctt ttctcgtaga gccttggttg 27120
ctaaaaaatc tggtaagaag ttatctgaaa gtatgaacta tcagaaacaa cgtatcaagg 27180
tagctaatat ccacgagaag atagctaaca aacgcagaga ttttctcaat aagttaagta 27240
cggaaattgt caagaaccac gatattatct gtattgaaga cttatccagt aaaaatctga 27300
tgaaaaatca taaattggct agggctatcg gagatgtctc ttggtctgaa tttgtgagaa 27360
tgttagagta caaggctgaa tggtacgaaa aacaagtatc aaaaattagc cgttggtatg 27420
cttcatctca aatctgttca gattgtggct tcgcttcagg taaaaagcca ctctcaatca 27480
gagaatggac ttgtgaaaat tgtggtagtc atcacgatag agacatcaat gcaagtatca 27540
atattctaaa cgaagggcta cgcttagcct aacaaataaa gtgaaccgta ggaactacgg 27600
ggatagcttg gtaaacttgt gtaaccgctg ttggttagaa agctaatcat caagtaagca 27660
cattacccaa gaagctccta catctaagcg atagcgtagg taggagtggt tcactataaa 27720
tgctactata ttaatggata cagttaaaag ctgagtcttc gataaactct ctctcaccct 27780
gacttgaatt agtcagggtt tttgttttgc aaaaaaatat atattttttt tataaaaaca 27840
gtttccgtct ggtcgccaaa atagactaga atggattgag agcaacttgg aaaacattcg 27900
ataaaaaata aaaaacaatg gatacataca aagaacaata tatagtatgt tttactaatt 27960
ttcaagatgt ttaataaaaa aatcaagaaa acttgaaaaa aaatcaagaa aactgttgac 28020
gttgaatttt gtttaagcta taatatgttt gtaagttagt taggaaggag gaacaaaatg 28080
acagaagtag ttccaaaaat tacaatcaaa gaactccgag cacgtcacga tttgacacaa 28140
gaggagtttg ctaaaagcgt tggtactaca cctcaaacgg tgagtgcatg ggagaagaat 28200
gtactttcta tttctcctaa gaatatggca aatatttgta ataaatacca ccttcaagcg 28260
tctgatttgt atggcttttg attttaaaac ttgaattaaa ttcaagatga acgaaatagc 28320
aacaaatgat tttgactact cttttctcga tgcaaagacg aaagaattct tagaagaacg 28380
tgccaatatc atctacggca tccaaagcaa gagtgcttac aaaataggga aacaacttgc 28440
caaagctcaa aaagggcttt cgactagagg ttatggttgc ttcgaagaat ggtatagaag 28500
tttagggttt aaaaaaacca aagcttatga atatatcaat cattacaatt tcgtttgttc 28560
gcaaaacgaa caagcaaata ttgaaaaatt cgaaagtttg cctaaaacgt tacaagctca 28620
agtatctaaa ccatctgcca atccagaggt taatcaagca gtatttaatg gagatatcaa 28680
aactcacaaa gaatataaag agcttgagcg tcgcctaaaa ctcaaagatc aagcattgga 28740
agcggtcaag ggtgagttgg aacgtgtcaa acgaaactaa catcaaacac gttgaagctg 28800
agaaggcagt taaattcttg gaaagtctat cttatgacga tttcacaccg tttgaaattc 28860
gtgagacacc aaaacaaaaa gagattatag ctcttgaaaa aaatgagtga ctgaaagcat 28920
tataatgttg agggtttcaa taaaagataa aaaactttaa aaaaatagaa taaaattgtt 28980
gacaaaataa aaaatatggt ttaaaataaa accataaagt taaaaaagga gaaaagaatg 29040
gagtttaaat acgataaatt aaaaggacgt attaaagaaa aatacggaac tcaagaaaat 29100
tttgcgaaag ctattggaaa agctcaaacc acaacatctt ttaaaatcaa tggaaaaaga 29160
ttgtggaatc aagatgaaat cgttaaggcg attgagttat tagatctttc aaaagatgat 29220
attgtagaat acttctttaa ctactaatag aaagggtcac aatttggagt ttatagtaat 29280
ggtgaattac tgaactaata ttttaaagga gaaacaacaa tgaaaatttt taactggatt 29340
ttttcaaaca agaaaacaga agcagaattt ccaaaaatgga cttttgaaaa aaatgggtca 29400
gagcatagcc gtgatcgata caacaaaatt cacggattag gaaagacatt aatttgaaac 29460
atataaagta atatcgttag tcgtttcaat ccgtagccac ggcctcaccg tggagtgtat 29520
cttataccaa tttctttatc ccaaagataa atttacttta gccacacatc ttttctaaaa 29580
acatatttac aaagcggttg ggctatgggt gcgggttgaa gcactaaaaa aagcacaggt 29640
aatggcctat gcttaataaa aaatcttaaa aaggagtata ccatgaaaac atttaaaatt 29700
acaacaatta gggagggtag gaattaaata tggcaacttt atatgagtta acaggtcagt 29760
ttctagagat ttataacatg gaaattgacg atgaaacgaa actcgacaca ctagagtcta 29820

-continued

```
ttgaatggac tagcgattat gaaaataagg tagaaggata tgtaaaagtc attaagtcgc  29880
ttgaggcaga cattgaagct cgaaaaaacg aaaagaaacg tttagacgga ttaaataagt  29940
ctgatcaatc aaaaattgac aaactaaaag cagcgcttgc gattagtatg actgaaactg  30000
gtcaaaccag agttgatacc actctattta agattggttt tcataaatct aaagcggtag  30060
ttgttaacga agagaaactt ccaaaggaat atcaaatagc gacttataag ccagacaaga  30120
aaacactcaa agagttactt aaatctggaa agcatattga gggagctact cttgaagaaa  30180
ggagaaacct taacataaga tgagaattat cagagcaaaa gatatccagc gaaccaagaa  30240
ttggcgaata ctgatttatg gtaaggctgg attagggaaa acgtccctga taaaaaacat  30300
gcctggaaaa actttggtgt tgtcgttaga taattcttca aaagtgctag ctggcactga  30360
gaacgtggat atcatagatt ttgaccgtga gcatccaact gaatttatca cagagtttct  30420
aacccaagca gataacttaa tcaaaaacta tgaaaacctt gttatcgata acatttcaag  30480
ttttcaatca gattggttta ttgagcaagg tcgcaagtca aagaacggta tcagtaatga  30540
gcttcaacat tactctcaat ggacaaatta cttcttaaga gtattgactg ttatctacag  30600
caagcctatc aatatttatg tgacagcttg ggaagacacc cacgaactca atttagaaac  30660
tggtcagatt ttaactcagt atgtaccaca gattagggct agtgtactca accaactatt  30720
agggcttacc gatgtcgttg gacgtattgt tgttaatgct aaaacaggtg cacgtggact  30780
tattttggaa ggcagcgaag gtacttacgc taagaatcgc ctcgataatc gaacagcttg  30840
caagattgaa gacctcttta aatttggtga tttagatgga actaaggaat taccagagtg  30900
accttgttaa tgatatcaag caatcaatct taagaggtaa taagcgtatc atggtgcagt  30960
caccacctag aagcggtaaa accgtggtga tggctcacat tgccaaaggt gcgacagata  31020
aaggtaacac tattctgttc tttagtcatc gaaaagaaat caatgaacaa gtagttaata  31080
cctttaagcg taacggcgtt gacatgaact tagtaaccat tgatagtgtt actaagatag  31140
cacgaaacct agataggata caagagcctt cgattatatt aattgacgaa gctcaccacg  31200
ttaaagctaa aacctatctc aaaattatcg aatactattc taatagcatt gttctcatgt  31260
ttactggtac acctgcccga ttagatggca gtgggtttga tgatatcgca gacgacattg  31320
ttctcggaaa gtcggttaaa tggctacagg agaacgggaa catcgcaccg tttaaatatt  31380
atgccccttc tttaatcgac accacaaact taaaaaaacg tggtggagag tttactaaga  31440
aatctgtaga cgacacaatg aaacgtgtga tttacggtga cgttataaga cactatgaga  31500
agttagccaa aggcaaacaa gctatagtat atacacatag cgtagaagct tctgagagcg  31560
tttctaacac gtttaacgag caaggctata cttctatcgc aatcagtggt aaaacgccac  31620
cagaggttcg agagagggca atgcaagcct ttagagacgg agaacttaca attatggtta  31680
attgtgagtt attcactgaa ggaattgacc tgccaaacgt tgatgtttgc atcatgttaa  31740
gaccaactca atcattatca ctctatttgc agtttgccat gagggcttta aatccaagag  31800
acggtaaaac agctattata atcgaccatg ttggaaatgt tgataggcat ggattaccaa  31860
acgctgaccg tgaatggtca ctaaagggta ttaataaaac taagaaaaaa cttaaactcg  31920
gtgaacctac cacacggacg tgtgatgaat gctacgctac gttttggagt gctgaacgta  31980
tctgtccact gtgtggccat gagaatcagc ctacaaaaga agaaattgaa ataattcgag  32040
aaatagaact cgaagaaaga cggcaagagg ttgctagtaa agttgaaaca ttcgttacta  32100
gtgaccaatg ccaaacagta gaagaactca aagagttcgc taaacaacac ggatataaac  32160
ccggttgggt ttattaccaa cagaaaaaaa ataatatatg gagataaaaa actatgttta  32220
```

```
caattgatta ctcacaagca aaagaattcg gatctatcaa agacggtact tacgaagtta  32280
ctattgattt agcaaaacaa gatgctactc aaggaggagc tgactacctt gacatccgtt  32340
ttcgtattcg caaggacttc caacaagaat tccaaaataa cattattttc tatcgcatct  32400
ttgctaaaaa agaagacgga aaatatccag tagcttctat catgaacctt gctaaagctg  32460
caggaattcc tgatggtact aaatttagta gcttggaaga ttatctcaaa cagttggaag  32520
gaaaagctct taaagttacc gttaaaaacg aaaaatctga gtggcaaggt aaaacctacg  32580
aaaatctaaa cgttaaacgt ttggaagtta ccgatatccc acttccagaa gttaatactg  32640
agatttcaga aattgacctt ccgttctaat tatgaagatg gttgattacg caatcaacta  32700
tcaacgcatg ggctattctg ttatccctat ttcaaagaat ggcaaaaccc ctcttatttc  32760
tttcgctgac aaaccaccaa tgactgaaaa cgacattctg agggtgtggc gagataatcc  32820
agatgctaac attgcactta aaaccgatac attctttgtc attgacgtgg acatgcatgg  32880
cgatgttgac ggtttaacta atttaagaaa ttgggaacat gcaagactta tacccccaac  32940
attgcaagct ataaccccca gcggtgggag acatatctac ttaaaaaaag accccaacca  33000
tcctatatcg caaaatattg ggatgattga gggagtagat atcaaggcac acgttaataa  33060
ctatatatta gttccaccgt ccaataattc caaaggatac tatgaatggg atacagtgca  33120
ttcgccaaaa gatggaagca taacagaagc acctcttgcg ttgataaaag tattgcagaa  33180
aatgaaacca gaaccattaa gctatgaagt ctcatcgttt gctagtggca gtgttagaag  33240
tacaaaaacc acaaagttat tcgagagcat cttactaggt tttggagaca aaggcggacg  33300
aaacaatgca cttgccgagt ttgtcggtgg actgctactt agaggtgttg acccagaaat  33360
cacttatcat cttgcaaata tggcaaacaa caacaccaaa gagcctttgg gcgataagga  33420
atttgaaagg acatttaaga gcatgttaga caaagaaata aggaggattg gacttgacaa  33480
cgattgattt cgattattac agagaacaat ttgcaagctc tactctctca ccaagtaaac  33540
cgagcagcag agagggaatt aagaataagc ttaaagccta ccgaaacgac tggtttgaaa  33600
aattcaagga agaaaatcca gatagcaaag aaccaaaggc attgccagaa ttagcagtag  33660
ctaaaggttt aaataaatac actcatgtta tcaccctcga aaatgggaaa gtagctatat  33720
atgatccaga gcggggatac taccaaaaag attacagata tgcctaccag cttatctata  33780
tcttagaacc tacattcaat gaaacaaaat gccgaaatgt tctattcttg ctatcaaaca  33840
tgagcaggga atatgaatat aataacatgt atatggattt tgaaccagaa tatcgagatg  33900
taagacgttt tatcctcgtc aagaatggca tctatgataa gcgaaagaag aaactgctat  33960
cgtttgacta taagtttatt aacttcagta caattgaaac agaattagtt gagaacgccc  34020
ctaaaccaat tattaatggt tgggatgtcg atagttggtt gttagatctc atgagtggcg  34080
acagtgagct tgtagaatta ctatggcaag tgattgcagc gtcacttaat ggtaaccatt  34140
cttatcgaaa atcgatttgg ttagttggta acggtaacga tggtaagggt acgtttcaac  34200
agttaattag caatttggtt ggattaaaaa acgtagcacc attaaaactt aatcaatttt  34260
ctgaacgttt cggtcttgcc attatcgaag ggaagacagt tatcattggt gacgatgtcc  34320
aagctggtat atatgtagat gaatcttcca attttaactc agtcgttact ggtgaaccag  34380
tttcaattga gaaaaaagga gaaaatcctt acttagcgca atttaagaaa acggttatcc  34440
agtctaccaa tgctatgcca gtgtttaaga ataagtcaaa cggtacatat cgacgtatcg  34500
tgattatccc attcaaaaaa acatttggca tcaatgatga caattgggca attaaggatg  34560
```

-continued

```
attacatcaa tcgtaaagaa gttttggaat atgttctttg gaaagcaatt aatttagatt  34620
ttgacaaatt caacgaacca aaagcgacac aagaacgtat gcaagagttc aaggaagaga  34680
ataacacagt ttataaattc cttaatgaat acttgtcaga tgtcgtttcc actcgaattc  34740
cagttaggtt cttgtgggat gtataccgct catggtgtca tgagggaaat catactatac  34800
ctaaaaaatc taactttgaa aaagagctgg cacagaattt accagttggt tggactaaag  34860
agaaatggag accattagat caattcaatc caactaaaga taagccagat tattggcatg  34920
atttcaattt taattgggat gtagaaaaag atggcaaaaa aacagctgca atcatagcta  34980
agacactgtg ataccgccag acaccaagag cggtgtcctc gaaagtcctt gatagaaaag  35040
ggattgacac gctttagaca ctaagatact acttttatat atatttaaaa taaataaata  35100
aataaatata tatatatata tatatagaga gagagtcaaa aaataaggtg tctcggtgcc  35160
caaaagtgtc aaaaaccctt atatatcaag ggttttcgtg ggcactgcta agagtgtctt  35220
ggatggtgac cggtgacaaa ttaggagata tatgacaaca gaatcactaa ttcaaaatca  35280
aattcgagtg gaattatcaa aagctggcta catggtattt agaataaatg ttggaaaagt  35340
cagaatggca gatggacgtt ggtttgatac tggagctcca aaaggttttt gtgacttgtt  35400
tggatttaga ccagatggac agatattctt catcgaagtt aaaaatgaaa aaggtcgagt  35460
gagagaggac caaaagaaat ttatggaagc tatgaaaaaa cgaggggcac ttgttggagt  35520
ggcaagaagt gttaaggaag ctatgaggat agttgatggt aaaacggtgg aatgaccata  35580
tggctggcat taaatatgca cctcggccat atgacgaaca tataactgta ttagaacgtg  35640
tagagtattt caataactgg ttttatgcta cgcatcaaaa gaaaggtgca gtggcaatta  35700
agctaggtat tggtgataaa aaattgaatc gtatattgac actagagcag ttaccagacg  35760
agaaattatt gaaagagatg atagaactat gcaatataaa gtaataacat atttcgacaa  35820
catggaagac gatgtagaaa tttatgacaa taaagatgaa gctatcaaaa gattgcatca  35880
tttgagaggt gttaaatata gaaatttaaa attatataaa gtagaaatgg ttgaggtaga  35940
ataaatgaat agacttaaag aattaagaga attacggaaa attacaagag tcgagttagc  36000
cgaaaaaatt ggggttacaa aattaaccat tcttaattgg gaacatggca cccatgaaat  36060
caaaggaagt aacgctaaga agttagctga atacttcaac gtatcagttc cttacttgct  36120
tggctacgat aatacattca ctgacttaat cgcaaagatt aacgagtggg ctatcagtca  36180
tggactggat aaaggcaatc ctaaaataga atggatgaag gtaacagaag aagtcggcga  36240
gattagagat gtatttctaa aaccaaacga ttttgatgac ccagaaatgg ctctaaaaga  36300
cgctataggc gattctattg ttaccctagt ggtattatgc ctacaactcg attacgacgt  36360
tgaggagtgc cttaaaatag cttataataa cattaaggat aggcaggggg taatgattga  36420
tgggaacttc gttaaaatca gaaaatgact accttttttac attaacgtta ggatttattt  36480
tagtgcttgg gacgctagca atttatataa ctactctcaa caaacctgta gataccattg  36540
ttatctatgg aaaggtaact ggaaaactct acacaatcga ttgtggagcg tatggtaagt  36600
ttctagtcac caaggaacag tatgacaacg tacagggtta tttgaggagt tattaagaca  36660
tgaagaaata tgaatacgct gcattaacta aagagctaca tcaaaggtta actctagagt  36720
ttgatgcatt gagggaagaa catcgcagaa cactcactaa atatataatg gaaaccaaga  36780
aatgcaatag aatggaagct agaaaatatt ttcaaaggtt tgataacgtg gttaaagagc  36840
gttcgaaact atcaccttca acattggacg atatgcgcga atatcttacg gacggtctag  36900
ttaatgactt acaagagtat ctattaaaga actattcagt aagacgtggg tcatgtaaac  36960
```

-continued cagatgctga taaaactaat gcaggtctta caagagagct cttccttcaa tatcgcaagg 37020
aaatccaaga gttaagagca gcacacccta accgtaacgc agaatatatt atggaagtga 37080
aaggatgctc aaaaaatcaa gctcaaacaa tcataacagc aattaacaca gtatatacag 37140
aacttggaat tttaacgcct agaaaagtga tacaactaga agggcttctt tctagagagc 37200
tatttggcaa aatagctaaa tatgtattta ataagtatga atggccggaa agcctagata 37260
gtgaagttga tcgaatttat ttagaatatc gcactaaagg tgatataggg cttaataaag 37320
aaagtgttaa acgcacacta ttcaaagcga tttcaatggg cttgtagtgg ttcgaatcca 37380
ctacaggtca ttaattccag tcaatttaaa tttaggagga agcctatttt ctttcaatca 37440
aaacaaaatc aaagcgaggc tggtagcttt gtaagggagg tgataacagc gtaattcaaa 37500
ttctttattc ttgtttgctg tcaggggttc gactcccttg tcagtcatta gtctgtcatg 37560
actaggtaat tttttcgaca aaaaaataag atta 37594

<210> SEQ ID NO 6
<211> LENGTH: 22
<212> TYPE: DNA
<213> ORGANISM: Artificial Sequence
<220> FEATURE:
<223> OTHER INFORMATION: primer yc70
<220> FEATURE:
<221> NAME/KEY: source
<222> LOCATION: (1)..(22)
<223> OTHER INFORMATION: /organism="Artificial Sequence" /note="primer yc70" /mol_type="unassigned DNA"

<400> SEQUENCE: 6
tgctgagaca acctagtctc tc 22

<210> SEQ ID NO 7
<211> LENGTH: 20
<212> TYPE: DNA
<213> ORGANISM: Artificial Sequence
<220> FEATURE:
<223> OTHER INFORMATION: primer CR1-rev
<220> FEATURE:
<221> NAME/KEY: source
<222> LOCATION: (1)..(20)
<223> OTHER INFORMATION: /organism="Artificial Sequence" /note="primer CR1-rev" /mol_type="unassigned DNA"

<400> SEQUENCE: 7
taaacagagc ctccctatcc 20

<210> SEQ ID NO 8
<211> LENGTH: 18
<212> TYPE: DNA
<213> ORGANISM: Artificial Sequence
<220> FEATURE:
<223> OTHER INFORMATION: primer ST802CR1-gfwd
<220> FEATURE:
<221> NAME/KEY: source
<222> LOCATION: (1)..(18)
<223> OTHER INFORMATION: /organism="Artificial Sequence" /note="primer ST802CR1-gfwd" /mol_type="unassigned DNA"

<400> SEQUENCE: 8
cccggcgtat atactggc 18

<210> SEQ ID NO 9
<211> LENGTH: 18
<212> TYPE: DNA
<213> ORGANISM: Artificial Sequence

```
<220> FEATURE:
<223> OTHER INFORMATION: primer ST802CR1-g2fwd
<220> FEATURE:
<221> NAME/KEY: source
<222> LOCATION: (1)..(18)
<223> OTHER INFORMATION: /organism="Artificial Sequence" /note="primer
      ST802CR1-g2fwd" /mol_type="unassigned DNA"

<400> SEQUENCE: 9

gctgactgga ccaaatgc                                                18


<210> SEQ ID NO 10
<211> LENGTH: 18
<212> TYPE: DNA
<213> ORGANISM: Artificial Sequence
<220> FEATURE:
<223> OTHER INFORMATION: primer ST23CR1-g3fwd
<220> FEATURE:
<221> NAME/KEY: source
<222> LOCATION: (1)..(18)
<223> OTHER INFORMATION: /organism="Artificial Sequence" /note="primer
      ST23CR1-g3fwd" /mol_type="unassigned DNA"

<400> SEQUENCE: 10

gagcaagcag agggtagc                                                18


<210> SEQ ID NO 11
<211> LENGTH: 18
<212> TYPE: DNA
<213> ORGANISM: Artificial Sequence
<220> FEATURE:
<223> OTHER INFORMATION: primer 100ECR1-g4fwd
<220> FEATURE:
<221> NAME/KEY: source
<222> LOCATION: (1)..(18)
<223> OTHER INFORMATION: /organism="Artificial Sequence" /note="primer
      100ECR1-g4fwd" /mol_type="unassigned DNA"

<400> SEQUENCE: 11

cctgtcatct ctgggagt                                                18


<210> SEQ ID NO 12
<211> LENGTH: 20
<212> TYPE: DNA
<213> ORGANISM: Artificial Sequence
<220> FEATURE:
<223> OTHER INFORMATION: primer 100ECR1-g5fwd
<220> FEATURE:
<221> NAME/KEY: source
<222> LOCATION: (1)..(20)
<223> OTHER INFORMATION: /organism="Artificial Sequence" /note="primer
      100ECR1-g5fwd" /mol_type="unassigned DNA"

<400> SEQUENCE: 12

cggtgttcta tatcgaggtc                                              20


<210> SEQ ID NO 13
<211> LENGTH: 18
<212> TYPE: DNA
<213> ORGANISM: Artificial Sequence
<220> FEATURE:
<223> OTHER INFORMATION: primer CR1-grev
<220> FEATURE:
<221> NAME/KEY: source
<222> LOCATION: (1)..(18)
<223> OTHER INFORMATION: /organism="Artificial Sequence" /note="primer
      CR1-grev" /mol_type="unassigned DNA"

<400> SEQUENCE: 13

tttcacttcc tgaacccc                                                18
```

<210> SEQ ID NO 14
<211> LENGTH: 21
<212> TYPE: DNA
<213> ORGANISM: Artificial Sequence
<220> FEATURE:
<223> OTHER INFORMATION: primer CR2-fwd
<220> FEATURE:
<221> NAME/KEY: source
<222> LOCATION: (1)..(21)
<223> OTHER INFORMATION: /organism="Artificial Sequence" /note="primer
CR2-fwd" /mol_type="unassigned DNA"

<400> SEQUENCE: 14
ttagccccta ccatagtgct g 21

<210> SEQ ID NO 15
<211> LENGTH: 23
<212> TYPE: DNA
<213> ORGANISM: Artificial Sequence
<220> FEATURE:
<223> OTHER INFORMATION: primer CR2-rev
<220> FEATURE:
<221> NAME/KEY: source
<222> LOCATION: (1)..(23)
<223> OTHER INFORMATION: /organism="Artificial Sequence" /note="primer
CR2-rev" /mol_type="unassigned DNA"

<400> SEQUENCE: 15
ttagtctaac actttctgga agc 23

<210> SEQ ID NO 16
<211> LENGTH: 23
<212> TYPE: DNA
<213> ORGANISM: Artificial Sequence
<220> FEATURE:
<223> OTHER INFORMATION: primer CR3-fwd
<220> FEATURE:
<221> NAME/KEY: source
<222> LOCATION: (1)..(23)
<223> OTHER INFORMATION: /organism="Artificial Sequence" /note="primer
CR3-fwd" /mol_type="unassigned DNA"

<400> SEQUENCE: 16
ctgagattaa tagtgcgatt acg 23

<210> SEQ ID NO 17
<211> LENGTH: 23
<212> TYPE: DNA
<213> ORGANISM: Artificial Sequence
<220> FEATURE:
<223> OTHER INFORMATION: primer CR3-rev
<220> FEATURE:
<221> NAME/KEY: source
<222> LOCATION: (1)..(23)
<223> OTHER INFORMATION: /organism="Artificial Sequence" /note="primer
CR3-rev" /mol_type="unassigned DNA"

<400> SEQUENCE: 17
gctggatatt cgtataacat gtc 23

<210> SEQ ID NO 18
<211> LENGTH: 18
<212> TYPE: DNA
<213> ORGANISM: Artificial Sequence
<220> FEATURE:
<223> OTHER INFORMATION: primer 100ECR3-gfwd
<220> FEATURE:
<221> NAME/KEY: source
<222> LOCATION: (1)..(18)

<223> OTHER INFORMATION: /organism="Artificial Sequence" /note="primer 100ECR3-gfwd" /mol_type="unassigned DNA"

<400> SEQUENCE: 18
caatccgtag ccacacct 18

<210> SEQ ID NO 19
<211> LENGTH: 15
<212> TYPE: DNA
<213> ORGANISM: Artificial Sequence
<220> FEATURE:
<223> OTHER INFORMATION: primer (GTG)5
<220> FEATURE:
<221> NAME/KEY: source
<222> LOCATION: (1)..(15)
<223> OTHER INFORMATION: /organism="Artificial Sequence" /note="primer (GTG)5" /mol_type="unassigned DNA"

<400> SEQUENCE: 19
gtggtggtgg tggtg 15

<210> SEQ ID NO 20
<211> LENGTH: 28
<212> TYPE: DNA
<213> ORGANISM: Artificial Sequence
<220> FEATURE:
<223> OTHER INFORMATION: CRISPR 4 repeat
<220> FEATURE:
<221> NAME/KEY: source
<222> LOCATION: (1)..(28)
<223> OTHER INFORMATION: /organism="Artificial Sequence" /note="CRISPR 4 repeat" /mol_type="unassigned DNA"

<400> SEQUENCE: 20
gtttttcccg cacacgcggg ggtgatcc 28

<210> SEQ ID NO 21
<211> LENGTH: 36
<212> TYPE: DNA
<213> ORGANISM: Artificial Sequence
<220> FEATURE:
<223> OTHER INFORMATION: CRISPR 1 direct repeat
<220> FEATURE:
<221> NAME/KEY: source
<222> LOCATION: (1)..(36)
<223> OTHER INFORMATION: /organism="Artificial Sequence" /note="CRISPR 1 direct repeat" /mol_type="unassigned DNA"

<400> SEQUENCE: 21
gtttttgtac tctcaagatt taagtaactg tacaac 36

<210> SEQ ID NO 22
<211> LENGTH: 36
<212> TYPE: DNA
<213> ORGANISM: Artificial Sequence
<220> FEATURE:
<223> OTHER INFORMATION: CRISPR 2 terminal repeat
<220> FEATURE:
<221> NAME/KEY: source
<222> LOCATION: (1)..(36)
<223> OTHER INFORMATION: /organism="Artificial Sequence" /note="CRISPR 2 terminal repeat" /mol_type="unassigned DNA"

<400> SEQUENCE: 22
gtttttgtac tctcaagatt taagtaactg tacagt 36

<210> SEQ ID NO 23
<211> LENGTH: 36
<212> TYPE: DNA

-continued

```
<213> ORGANISM: Artificial Sequence
<220> FEATURE:
<223> OTHER INFORMATION: CRISPR 3 direct repeat
<220> FEATURE:
<221> NAME/KEY: source
<222> LOCATION: (1)..(36)
<223> OTHER INFORMATION: /organism="Artificial Sequence" /note="CRISPR 3
      direct repeat" /mol_type="unassigned DNA"

<400> SEQUENCE: 23

gatataaacc taattacctc gagaggggac ggaaac                              36


<210> SEQ ID NO 24
<211> LENGTH: 36
<212> TYPE: DNA
<213> ORGANISM: Artificial Sequence
<220> FEATURE:
<223> OTHER INFORMATION: CRISPR 3 terminal repeat
<220> FEATURE:
<221> NAME/KEY: source
<222> LOCATION: (1)..(36)
<223> OTHER INFORMATION: /organism="Artificial Sequence" /note="CRISPR 3
      terminal repeat" /mol_type="unassigned DNA"

<400> SEQUENCE: 24

gatataaacc taattacctc gagaggggac tttttt                              36


<210> SEQ ID NO 25
<211> LENGTH: 36
<212> TYPE: DNA
<213> ORGANISM: Artificial Sequence
<220> FEATURE:
<223> OTHER INFORMATION: CRISPR 3 direct repeat
<220> FEATURE:
<221> NAME/KEY: source
<222> LOCATION: (1)..(36)
<223> OTHER INFORMATION: /organism="Artificial Sequence" /note="CRISPR 3
      direct repeat" /mol_type="unassigned DNA"

<400> SEQUENCE: 25

gttttagagc tgtgttgttt cgaatggttc caaaac                              36
```

PHAGE INSENSITIVE *STREPTOCOCCUS THERMOPHILUS*

CROSS-REFERENCE TO RELATED APPLICATIONS

This application is a divisional of U.S. patent application Ser. No. 15/119,708, filed 17 Aug. 2016, now U.S. Pat. No. 10,041,135, which is a National Stage entry of International Application No. PCT/EP2015/053601, filed Feb. 20, 2015, which claims priority to European Patent Application No. 14155872.6, filed Feb. 20, 2014. The disclosures of the priority applications are incorporated in their entirety herein by reference.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-389001_ST25.txt" created on 2 Jul. 2018, and 235,192 bytes in size) is submitted concurrently with the instant application, and the entire contents of the Sequence Listing are incorporated herein by reference.

FIELD OF THE INVENTION

The present invention relates to a method for the construction of a bacteriophage insensitive mutant of a microorganism parent strain suitable for food and feed fermentation. Further, the present invention relates to a method for the construction of a bacteriophage insensitive *Streptococcus thermophilus* mutant whereby the phage resistance is conferred by a mechanism other than CRISPR.

BACKGROUND OF THE INVENTION

*Streptococcus thermophilus* is a Gram-positive thermophilic bacterium used globally as a starter culture in dairy fermentations and is widely employed for the production of cheese and yoghurt products. Despite its usefulness in starter cultures, *S. thermophilus* remains highly susceptible to (bacterio)phage predation which can lead to substandard or failed fermentations and considerable economic losses. Evidenced by these potentially considerable costs, there is a clear advantage to selecting robust starters which are less susceptible to phage attack and yet retain favourable growth and production characteristics. Combined with effective hygiene and sanitation in industrial fermentation plants, unrelated robust starters used in rotation have the potential to reduce the incidence of phage fermentation disruption.

Phages of *S. thermophilus* are, despite their narrow host ranges, the major cause of fermentation failure, due to their short latent period and large burst sizes. They are generally classified as Siphoviridae (having isometric heads and long, non-contractile tails) and usually fall into two groups (cos- and pac-type), based on their mode of DNA packaging and the number of major structural proteins present (Le Marrec et al., 1997. Applied and Environmental Microbiology 63 (8), p. 3246-3253—*Two groups of bacteriophages infecting Streptococcus thermophilus can be distinguished on the basis of mode of packaging and genetic determinants for major structural proteins*). More recently, a third group of phages infecting *S. thermophilus* was identified that represents a novel genetic lineage and highlights the genetic plasticity of these phages (Mills et al., 2011. International Dairy Journal 21, p. 963-969—*A new phage on the 'Mozzarella' block: Bacteriophage* 5093 *shares a low level of homology with other Streptococcus thermophilus phages*). Consequently, phages of *S. thermophilus* persist in dairy fermentation facilities leading to starter culture infections. In response to these infections, microorganisms such as *S. thermophilus* has evolved several mechanisms of phage resistance, some of which are more effective and stable than others.

Mutants which have become resistant to phages by means of effective and stable mechanisms may be characterised by means of DNA sequencing, morphological analyses and/or adsorption assays.

Bacteriophage resistance systems have evolved in microorganisms such as *S. thermophilus* in tandem with phage adaptation strategies to overcome these biological barriers. These systems can include those preventing phage adsorption, blocking DNA injection, restriction/modification of DNA (R/M) and abortive infection or Abi (Labrie et al. (2010) Nature reviews 8, p. 317-327—*Bacteriophage resistance mechanisms*). To date, the most intensely characterised and the most frequent of these systems in lactic streptococci, are the Clustered Regularly Interspaced Short Palindromic Repeats (CRISPR) systems, which are known to provide acquired immunity to phages through an RNA-mediated dsDNA targeting process (Barrangou et al. (2007). Science 315, p. 1709-1712—*CRISPR provides acquired resistance against viruses in prokaryotes*; Garneau et al. (2010). Nature 468, p. 67-71 —*The CRISPR/Cas bacterial immune system cleaves bacteriophage and plasmid DNA*).

Three distinct CRISPR systems (CRISPRs 1, 2 and 3), representing two distinct types (types II and III) are widespread in *S. thermophilus* and individual strains may contain multiple systems. Diversity was observed across three CRISPR loci between 124 different *S. thermophilus* strains. Specifically, CRISPR1 was ubiquitous, whereas CRISPR2 was present in 59 of 65 strains, and CRISPR3 was present in 53 of 66 strains. A total of 49 strains (39.5%) carried all three loci. (Horvath et al., 2008. Journal of Bacteriology 190 (4), p. 1401-1412—*Diversity, activity, and evolution of CRISPR loci in Streptococcus thermophilus*). Recently, a fourth CRISPR system has been described (Sinkunas et al., 2013. The European Molecular Biology Organisation journal 32, p. 385-394—*In vitro reconstitution of cascade-mediated CRISPR immunity in Streptococcus thermophilus*) although its prevalence is rare and in vivo activity is not known. Although CRISPR provides effective immunity against phages through acquired spacers which are identical to short regions of the attacking phage genomes (Barrangou et al., 2007, as above), it is known that phages can rapidly evolve to overcome these spacer additions through single nucleotide alterations in the corresponding genomic region (Deveau et al., 2008. Journal of Bacteriology 190 (4), p. 1390-1400—*Phage response to CRISPR-encoded resistance in Streptococcus thermophilus*). Furthermore, since CRISPR mutations are the most frequent mutations involved in phage resistance it is difficult to identify other more desirable mutations which provide phage resistance. Therefore, it is desirable to develop a method to obtain phage-resistant derivatives of microorganism parent strains suitable for food and feed fermentation, and especially *S. thermophilus*, where such phage resistance is due to the action of alternative phage resistance mechanisms than CRISPR. The present invention provides a method to construct and select for such phage-resistant bacteria.

SUMMARY

In a first aspect, the invention provides a method for the construction of a bacteriophage insensitive mutant (further referred to as BIM) of a microorganism parent strain suitable for food and feed fermentation comprising selecting one or more mutants which, compared to parent strain, has an increased sedimentation rate and/or an increased chain formation to provide the bacteriophage insensitive mutant.

Preferably, the invention provides a method for the construction of a non CRISPR mediated bacteriophage insensitive mutant of a microorganism parent strain, a preferably bacteriophage sensitive *S. thermophilus* parent strain.

Surprisingly, the present inventors found that an increased sedimentation rate and/or increased chain formation is predictive for the phage robustness of the derived mutants. Further, the inventors found that the frequency of CRISPR mutants is much lower in the population with altered sedimentation rate and/or chain formation compared to the parent strain, and thus selecting on these morphological characteristics provides a selective high throughput screening to generate non CRISPR BIMs.

DETAILED DESCRIPTION OF A PREFERRED EMBODIMENT

Figure 1:
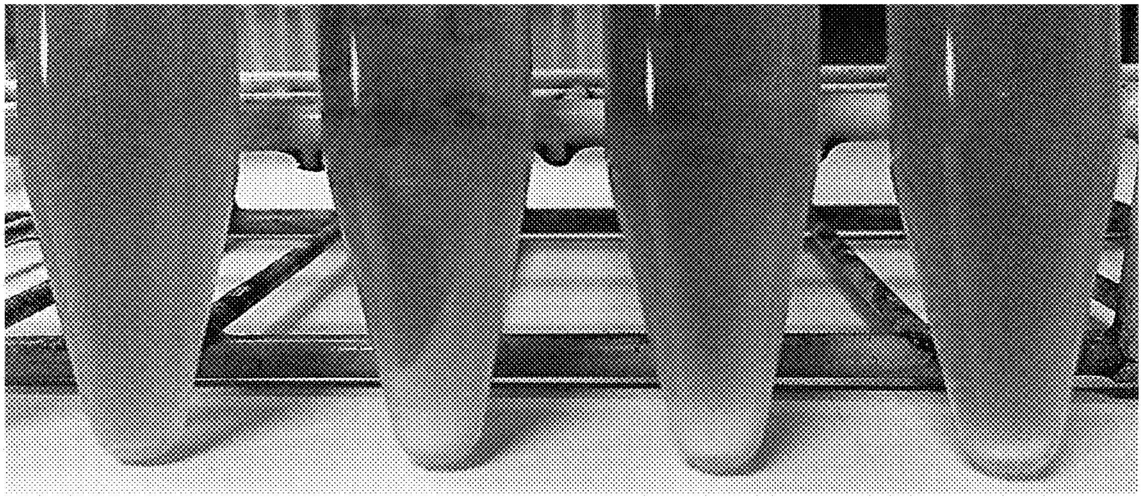
FIGS. 1-9 depict embodiments as described herein.

In the present method the mutations are naturally occurring mutations. In other words, the present method preferably does not comprise mutagenesis.

The term microorganism parent strain suitable for food and feed fermentation within the present context means microorganisms which can safely be used in the fermentative production of food and feed without causing health risk for the consumers of the food or feed. Preferably, the present microorganism parent strain suitable for food and feed fermentation is a lactic acid bacterium. For example a bacterium belonging to the genera *Lactococcus, Leuconostoc, Lactobacillus* or *Streptococcus*. More preferably, the present microorganism parent strain suitable for food and feed fermentation is a bacteriophage sensitive *S. thermophilus* parent strain.

In a first embodiment the method for the construction of a bacteriophage insensitive mutant of a bacteriophage sensitive *S. thermophilus* parent strain is comprised of the following steps:

(a) exposing the parent strain to a bacteriophage, (b) isolating single colonies of one or more bacteriophage insensitive mutant;

(c) comparing the CRISPR loci of the parent strain with the CRISPR loci of the bacteriophage insensitive mutant and (d) select the bacteriophage insensitive mutant of which the CRISPR loci is identical to the CRISPR loci of the parent strain.

In order to carry out the method of the invention, the bacteriophage-sensitive *S. thermophilus* parent strain may be cultured in a suitable medium according to methods known in the art in order to generate biomass to carry out step (a). The bacteriophages to which the bacteriophage sensitive *S. thermophilus* parent strain is exposed, may be isolated from whey samples obtained from dairy plants by any suitable method, for instance by the method described in the MATERIALS AND METHODS.

Preferably, in the present context, the term CRISPR loci means the loci of the CRISPR system 1, 2 and 3, i.e. preferably not comprising CRISPR locus 4.

Step (a)—Exposing the parent strain to a bacteriophage, may be carried out in any suitable medium, for instance in an aqueous solution such as a buffered aqueous solution or in a soft agar medium or in milk. In a preferred embodiment, exposing the parent strain to a bacteriophage is carried out in a soft agar medium. In another preferred embodiment, exposing the parent strain to a bacteriophage is carried out in milk. The milk may be incubated overnight or until clotting is observed. The parent strain used in the method of the invention may be pre-treated in order to increase the genetic diversity and to increase the number of the BIMs. This pre-treatment may be carried out by methods known in the art, such as chemical mutagenesis or by irradiation with UV-light. The—optionally pre-treated—parent strain may be exposed to one type of bacteriophage or to multiple different bacteriophages, for instance to 2, 3, 4 or 5 different bacteriophages.

Step (b)—The suspension or the incubated (clotted) milk obtained in step (a) of the method of the invention may be plated on agar plates. After incubating the agar plates at a temperature at which *S. thermophilus* may grow, colonies may appear which represent the BIMs. The colonies may be purified and preferably phenotypically verified to obtain a single strain BIM according to methods known in the art.

Step (c)—In step (c) of the method of the invention, the CRISPR loci of the BIMs obtained in step (b) of the method of the invention are analysed for their length (in base pairs) and/or sequenced and compared with the CRISPR loci of the bacteriophage sensitive parent strain.

Step (d)—In step (d) of the method of the invention only those BIMs are selected of which the CRISPR loci are identical to the CRISPR loci of the parent strain. The advantage of the method of the invention is that the selected BIMs have become phage resistant by means of a mechanism that is different from CRISPR and therefore based on an alternative phage resistance mechanism. As a result, the BIMs obtained by the method of the invention may have a more stable and/or robust phage resistance compared to a CRISPR-mediated BIM of which it is known that phages can rapidly evolve to overcome these spacer additions through single nucleotide alterations in the appropriate genomic region.

In a second embodiment, the method for the construction of a bacteriophage insensitive mutant of a microorganism parent strain, or of a bacteriophage sensitive *S. thermophilus* parent strain is comprised of the following steps:

a. exposing the microorganism parent strain and/or the bacteriophage sensitive *S. thermophilus* parent strain to a bacteriophage;

b. optionally isolating single colonies of one or more bacteriophage insensitive mutant;

c. selecting the bacteriophage insensitive mutant which, compared to the microorganisms parent strain or the bacteriophage sensitive *S. thermophilus* parent strain, exhibits:

1. an increased sedimentation rate, preferably in a liquid medium; and/or
2. an increased chain formation; and/or
3. a reduced phage adsorption d. optionally isolating single colonies of the bacteriophage insensitive mutant.

Step (a) and (b) are identical to step (a) and (b) described hereinbefore for the first embodiment of the method for the construction of a bacteriophage insensitive mutant of a bacteriophage sensitive *S. thermophilus* parent strain. Step (b) is optional because the subsequent step (c) may also be performed on multiple BIMs. In the embodiment of the method of the invention wherein step (b), isolating single colonies of the BIMs, followed by step (c), it is not necessary to perform step (d). In the alternative embodiment wherein step (b) is omitted, step (d) is preferably carried out in order to have single BIMs.

Step (c)—In step (c), BIMs are selected that have acquired one or more of the following properties:

(1) an increased sedimentation rate; and/or (2) an increased chain formation; and/or (3) a reduced phage adsorption.

Preferably, present step (c) comprises selecting the bacteriophage insensitive mutant which, compared to bacteriophage sensitive parent bacterium, exhibits an increased sedimentation rate and/or an increased chain formation. As a consequence of this selection, the selected BIMs have acquired a phage resistance mechanism that is due to one or more phage resistance or phage insensitivity mechanisms other than that mediated by the CRISPR system. Therefore, BIMs obtained by the method of the invention may have a more stable and/or robust phage resistance compared to the CRISPR mechanism of which it is known that phages can rapidly evolve to overcome these CRISPR-specific spacer additions through single nucleotide alterations in the corresponding genomic region.

Step c.1—An Increased Sedimentation Rate.

In one embodiment of the method or product of the invention (step c.1), the BIMs may have acquired an increased sedimentation rate. The sedimentation rate can be measured by any suitable method, preferably by the method described in the Materials and Methods. In order to be able to measure the difference between the sedimentation rate of a parent and a BIM, the method is preferably carried out under such conditions that only a minor fraction, for instance between 1-20%, preferably between 5-10% of the parent cells or biomass present in the suspension is collected in the pellet. The skilled person is very well capable of selecting such conditions for instance by varying the sedimentation time or the g-force, for instance when centrifugation is used. In case of a BIM with an increased sedimentation rate, between 20 and 100% of the cells or biomass present in the suspension may be collected in the pellet. Advantageously, selection based on an increased sedimentation rate provides an efficient method allowing high throughput screening of *S. thermophilus* strains and mutants thereof. CRISPR mediated BIM's do not provide an increased sedimentation rate, or at least a less increased sedimentation rate than non CRISPR BIM's, and thus could be efficiently removed from a suspension.

Differences between sedimentation rates may be established by measuring the weight of the pellet of the various BIM's after careful removal of the supernatant and then compare the pellet weight of the respective BIM with the pellet weight of the parent. The mean pellet weight increase of the BIM is preferably at least 10% of the pellet weight of the parent, more preferably at least 20%, more preferably at least 50%, more preferably at least 100%, preferably at least 150%, more preferably at least 200%, more preferably at least 250%, even more preferably at least 300% and most preferably at least 350% of the pellet weight of the parent. For instance, in case the pellet weight of the parent is 2 mg and the pellet weight of a BIM 7 mg, then the increase is 5 mg which is a 5/2*100=250% increase of the pellet weight of the parent.

In an alternative embodiment, step b) of the method of the second aspect of the invention, is not carried out, but instead, the entire suspension comprising the phage sensitive parent strain that has been exposed to the bacteriophage, resulting in a suspension with the phage sensitive parent strain as well as one or more BIMs, is subjected to the sedimentation test. The bacteria with the highest sedimentation rate may be collected and subject to further characterization, for instance via step (d) wherein single colonies of the BIM's are isolated in order to have single strains. Alternatively, the BIMs with the highest sedimentation rate may be collected, cultured in a suitable medium and subjected to step c.1. This may be repeated once or more.

Step c.2—An Increased Chain Formation

In another embodiment of the method or product of the invention (step c.2), the BIMs have acquired an increased chain formation. The increased chain formation may be measured by any suitable method, preferably by the microscopic method described in the Materials and Methods. In this method, the chain length or cells per chain (CPC) are determined by counting the individual cells per chain. By counting preferably at least 245 chains, the average number of CPC's is calculated. The average increase in chain length can then be expressed as a percentage using the following formula:

$$\frac{CPC_{mutant} - CPC_{parent}}{CPC_{parent}} * 100\%$$

The percentage increase of the averaged CPC of the BIM is preferably at least 50%, more preferably at least 100%, preferably at least 150%, more preferably at least 200%, more preferably at least 250%, even more preferably at least 300% and most preferably at least 350% of the averaged CPC of the parent. For instance, in case the averaged CPC of the parent is 3 and the averaged CPC of a BIM is 12, then the increase is 9 which is a 9/3*100=300% increase of the averaged CPC of the parent. Alternatively, the increased chain formation may be measured by a flow cytometer or FACS (fluorescence-activated cell sorter) for example as described in (Ibrahim et al., 2007, Adv Biochem Eng Biotechnol 106: p. 19-39—*Flow cytometry and cell sorting*). Using the forward scatter and sideward scatter plot visualization of the FACS, the size of the cells in the suspension becomes evident. Cells with a higher chain length will have a higher forward/sideward scatter plot then the parent bacteria.

In an alternative embodiment, step b) of the method of the second aspect of the invention, is not carried out, but instead, the entire suspension comprising the phage sensitive parent strain that has been exposed to the bacteriophage, resulting in a suspension with the phage sensitive parent strain as well as one or more BIMs, is subjected to the increased chain formation test using the FACS. A subfraction of the bacteria with the highest chain formation rate may be collected by the cell sorter by applying a selection filter and be subject to further characterization, for instance via step (d) wherein single colonies of the BIM's are isolated in order to have single strains. Alternatively, the subfraction of BIMs with the highest chain formation rate may be collected via the cell sorter, cultured in a suitable medium and subjected to step c.2. This may be repeated once or more.

Step c.3—A Reduced Phage Adsorption

In a further embodiment of the method or product of the invention (step c.3), the BIMs have acquired a reduced phage adsorption. The reduced phage adsorption may be measured by any suitable method, preferably by the method described in the Materials and Methods. In this method, a suspension of the parent strains or the BIM's was incubated for a certain time with a solution comprising phages at a certain titre (the Initial Phage Titre). Subsequently the suspension was centrifuged to give a pellet and a supernatant comprising a lower titre of phages (the Phage Titre in Supernatant), the difference being adsorbed to the bacterial cells. The phage adsorption may be expressed as the percentage of phages that are exposed to the bacterial cells which is binding to the bacterial cells. This can be calculated using the following formula:

$$\frac{[\text{Initial Phage Titre}] - [\text{Phage Titre in Supernatant}]}{[\text{Initial Phage Titre}]} * 100\%$$

The phage sensitive parent usually has a high phage adsorption percentage under the experimental conditions chosen, e.g. 80% or more, preferably 85% or more, more preferably 90% or more, more preferably 95% or more, more preferably 97% or more, preferably 98% or more, more preferably 99% or more or even 100% of the phages are binding to the phage sensitive parent. The BIMs that exhibit a reduced phage adsorption have consequently a much lower phage adsorption percentage, for example 60% or less, 55% or less, more preferably 50% or less, more preferably 45% or less, more preferably 40% or less, more preferably 30% or less, more preferably 25% or less, more preferably 20% or less, more preferably 15% or less, more preferably 10% or less and most preferably 0%, which means that the BIM completely lost the ability to bind the phage, while that is still capable of binding to the parent from which the BIM had been derived. Alternatively, the reduced phage absorption may be measured by a fluorescent scanner or plate reader using fluorescently labelled phages. This method differentiates in that of the one described in the Materials and Methods in that the phages are pre labelled with a fluorescent label (for example by incubation with a fluorescent label) and that initial phage tire and phage titre in supernatant is a function of the fluorescence.

In yet an alternative embodiment, step c.3 of the method of the second aspect of the invention, is not carried out, but instead, the entire suspension comprising the phage sensitive parent strain that has been exposed to a fluorescently labeled bacteriophage, resulting in a suspension with the phage sensitive parent strain as well as one or more BIMs, is subjected to the reduced phage absorption test using a fluorescent cell sorter (FACS). A subfraction of the bacteria with the lowest absorption rate may be collected by the cell sorter by applying a fluorescence selection filter and be subject to further characterization, for instance via step (d) wherein single colonies of the BIMs are isolated in order to have single strains. Alternatively, the subfraction of BIMs with the lowest absorption rate may be collected via the cell sorter, cultured in a suitable medium and exposed to freshly labeled phage and subjected to step c.3. This may be repeated once or more.

Preferably, the one or more BIMs which, compared to bacteriophage sensitive parent bacterium, has an increased sedimentation rate and/or an increased chain formation and/or a reduced phage adsorption is further subjected to comparing the CRISPR loci of the parent strain with the CRISPR loci of the bacteriophage insensitive mutant and selecting one or more BIMs of which the CRISPR loci is identical to the CRISPR loci of the parent strain. The advantage of comparing the CRISPR loci of the selected BIM which, compared to bacteriophage sensitive parent bacterium has an increased sedimentation rate and/or an increased chain formation, with the parent loci is that BIMs are provided having a phage resistance mechanism other than CRISPR.

In a third embodiment, the method of the invention combines the steps a-d of the first embodiment of the method of the invention followed by the steps c.1-c.3 of the second embodiment of the method of the invention. In this third embodiment, the one or more BIMs of which the CRISPR loci are identical to the CRISPR loci of the parent strain, are further subjected to selecting the bacteriophage insensitive mutant which, compared to bacteriophage sensitive parent bacterium, has an increased sedimentation rate and/or an increased chain formation; and/or a reduced phage adsorption.

In a fourth embodiment, the method of the invention combines the steps a-c of the second embodiment of the method of the invention followed by the steps c and d of the first embodiment of the method of the invention. In this fourth embodiment, the one or more BIMs which, compared to bacteriophage sensitive parent bacterium, has an increased sedimentation rate and/or an increased chain formation and/or a reduced phage adsorption is further subjected to comparing the CRISPR loci of the parent strain with the CRISPR loci of the bacteriophage insensitive mutant and selecting one or more BIMs of which the CRISPR loci is identical to the CRISPR loci of the parent strain.

Preferably, the present method, including the disclosed embodiments, further comprises culturing the one or more selected bacteriophage insensitive mutant in a culture medium, and/or recovering the bacteriophage insensitive mutant from the culture medium to provide a starter culture composition. “Starter culture” is defined herein as a preparation containing microbial cells that is intended for, or suitable for, inoculating a medium to be fermented. Such Starter cultures are generally referred to as direct vat set (DVS) or direct-to-vat inoculation (DVI) cultures or bulk starter cultures. The provision of a starter culture is advantageous since starter cultures can be inoculated directly into milk without intermediate transfer and/or propagation. Preferably, culturing is carried out at conditions such as temperature and pH control conducive to the growth of the microorganisms, or preferably *S. thermophilus* for a period of time until the desired cell concentration and activity of the culture are reached. The skilled person is able to determine the correct conditions for culturing *S. thermophilus*, or the desired microorganism.

Preferably, to the present bacteriophage insensitive mutant, or to the starter culture composition, an additive is added. For example a cryoprotectant is added. A “cryoprotectant” is defined herein as a substance used to protect cells or tissues from damage during freezing and thawing. The cryoprotectant may be any additive as long as it protects cells or tissues from damage during freezing and thawing.

Examples of cryoprotectants include, but are not limited to, sugars (e.g. sucrose, fructose, trehalose), polyalcohols (e.g. glycerol, sorbitol, mannitol), polysaccharides (e.g. celluloses, starch, gums, maltodextrin), polyethers (e.g. polypropylene glycol, polyethylene glycol, polybutylene glycol), antioxidants (e.g. natural antioxidants such as ascorbic acid, beta-carotene, vitamin E, glutathione, chemical antioxidants), oils (e.g. rapeseed oil, sunflower oil, olive oil), surfactants (e.g. Tween® 20, Tween® 80, fatty acids), peptones (e.g. soy peptones, wheat peptone, whey peptone), tryptones, vitamins, minerals (e.g. iron, manganese, zinc), hydrolysates (e.g. protein hydrolysates such as whey powder, malt extract, soy), amino acids, peptides, proteins, nucleic acids, nucleotides, nucleobases (e.g. cytosine, guanine, adenine, thymine, uracil, xanthine, hypoxanthine, inosine), yeast extracts (e.g. yeast extracts of *Saccharomyces* spp., *Kluyvermomycesa* spp., or *Torula* spp.), beef extract, growth factors, and lipids.

Preferably, the present method further comprises a step of freeze drying or freezing the present bacteriophage insensitive mutant. More preferably freeze drying to provide a dry powder. Alternatively freezing to provide a frozen matrix, such as frozen pellets. Freeze-drying is a technique well known in the art and may comprise the steps of freezing microorganisms to get frozen material and subsequently reducing the surrounding pressure while adding enough heat to allow the frozen water in the frozen material to sublime directly from the solid phase into the gas phase. Freeze-drying equipment that can be used includes, but is not limited to, rotary evaporator freeze-driers, manifold freeze-driers and tray freeze-driers. If necessary, a secondary step can be performed that aims to remove unfrozen water molecules. It is well within the experience of the person skilled in the art to establish a suitable temperature and pressure profile to achieve satisfactory freeze-drying. The freeze-dried material can be a powder or a granule.

In a second aspect, the invention provides a bacteriophage insensitive mutant of a microorganism parent strain, obtainable by the present method. Preferably the bacteriophage insensitive mutant has an increased sedimentation rate and/or an increased chain formation compared to the microorganisms parent strain. Surprisingly, the present inventors found that the BIMs provided by the present method have an increased phage robustness than CRISPR BIMs.

Preferably, the invention provides a BIM derived from a bacteriophage sensitive *S. thermophilus* parent strain. This bacteriophage insensitive mutant may be obtainable by the first, third or fourth embodiment of the method of the invention and wherein the CRISPR loci of the BIM are identical to the CRISPR loci of the parent *S. thermophilus* strain.

obtainable by the second, third or fourth embodiment of the method of the invention and wherein the BIM has an increased sedimentation rate and/or an increased chain formation and/or a reduced phage adsorption compared to the phage sensitive parent *S. thermophilus* strain.

obtainable by the third or fourth embodiment of the method of the invention and wherein the CRISPR loci of the BIM are identical to the CRISPR loci of the parent *S. thermophilus* strain and wherein the BIM has an increased sedimentation rate and/or an increased chain formation and/or a reduced phage adsorption compared to the phage sensitive parent *S. thermophilus* strain.

Preferably, the present bacteriophage insensitive mutant has a pellet weight increase of least 10% of the pellet weight of the parent, more preferably at least 20%, more preferably at least 50%, more preferably at least 100%, preferably at least 150%, more preferably at least 200%, more preferably at least 250%, even more preferably at least 300% and most preferably at least 350% of the pellet weight of the parent.

Preferably, the present bacteriophage insensitive mutant has a percentage increase of average chain length or average cells per chain (CPC) of at least 50%, more preferably at least 100%, preferably at least 150%, more preferably at least 200%, more preferably at least 250%, even more preferably at least 300% and most preferably at least 350% of the averaged CPC of the parent.

Preferably, the present bacteriophage insensitive mutant has a phage adsorption percentage of 60% or less, preferably 55% or less, more preferably 50% or less as compared to the phage adsorption of the parent.

Preferably, the present bacteriophage insensitive mutant has a reduced susceptibility to, or is insensitive for, one or more phages comprising a nucleotide sequence selected from the group consisting of SEQ ID NO 1, SEQ ID NO 2, SEQ ID NO 3, SEQ ID NO 4 and SEQ ID NO 5 or comprising a nucleotide sequence having 80%, preferably 85%, more preferably 90%, most preferably 95% or even 96%, 97%, 98% or 99% sequence identity with the nucleotide sequence selected from the group consisting of SEQ ID NO 1, SEQ ID NO 2, SEQ ID NO 3, SEQ ID NO 4 and SEQ ID NO 5. The term sequence identity is defined as the number of corresponding positions in an alignment showing an identical nucleic acid in both sequences divided by the total length of the alignment after subtraction of the total number of gaps in the alignment.

Preferably, the present bacteriophage insensitive mutant is as deposited in deposit numbers CBS136256, CBS136255 or CBS138555, or bacteriophage insensitive mutant derived from deposit CBS136256, CBS136255 or CBS138555. In other words, the present bacteriophage insensitive has preferably a sedimentation rate, an increased chain formation; and/or a reduced phage adsorption as found in CBS136256, CBS136255 or CBS138555.

In a third aspect, the invention relates to a starter culture composition comprising the present bacteriophage insensitive mutant. Preferably, the present starter culture composition is suitable for inoculation of a medium to be fermented on an industrial scale. Preferably the present starter culture composition is suitable for inoculation of milk for the production of fermented milk products. More preferably the starter culture composition comprises an additive. An example of an additive is a cryoprotectant. Additionally the starter culture composition may comprise other microorganisms or other lactic acid bacteria such as lactic acid bacteria belonging to the genera *Lactococcus, Leuconostoc* or *Lactobacillus*. More preferably the starter culture composition comprises a combination of the present bacteriophage insensitive mutant with *L. bulgaricus*, or *Lactobacillus delbrueckii* subsp. *bulgaricus*. Such a mixed starter culture is advantageous for the provision of yoghurt. Alternatively, for the provision of cheese, the present starter culture composition comprises a combination of the present bacteriophage insensitive mutant with *Lactococcus lactis*.

Preferably, the starter culture composition is frozen, preferably in the form of frozen pellets such as individual frozen pellets. Preferably the frozen pellets comprises as additive formate, such as sodium formate. Preferably the present frozen pellets have an average diameter within the range of 0.1 to 10 mm. The advantage of frozen pellets is that they will not stick and flow freely which allows a convenient dosing of the frozen pellets. Preferably the frozen pellets comprises a content of viable bacteria, preferably *S. thermophilus*, of at least $10^9$ colony forming units (CFU) per gram frozen pellets. The advantage of such concentrated frozen material is that only low amounts of frozen material is necessary to inoculate milk in industrial milk fermentation processes.

Alternatively the starter culture composition is freeze-dried. A freeze-dried starter composition may be in the form of a pellet, granule, tablet or a powder. Most preferably as a powder. The freeze-dried culture compositions can be stored and transported without refrigeration for extended periods of time under dry conditions. However, storage below 0° C. is recommended, more preferably below 15° C.

Alternatively, the present starter culture composition may be in liquid form.

In a fourth aspect, the invention relates to a container comprising the present bacteriophage insensitive mutant or comprising the present starter culture composition. The advantage of packing the present bacteriophage insensitive mutant or starter culture composition in a container is the ease of storage and transport. Preferably the present container is a commercial relevant package. An example of a commercial relevant package is a container comprising at least 50 or 500 gram frozen material when formulated in a frozen form, or comprising at least 50, 200 or at least 500 U when formulated in a freeze-dried form.

In a fifth aspect, the invention provides a process for the production of a dairy product such as a fermented milk product or cheese comprising the use of one or more of the BIM of a bacteriophage sensitive *S. thermophilus* parent strain as disclosed hereinbefore.

In a sixth aspect, the invention provides the use of the BIM of a bacteriophage sensitive *S. thermophilus* parent strain as disclosed hereinbefore in a process for the production of a dairy product, such as a fermented milk or cheese.

FIGURE LEGENDS

FIG. 1: Observed sedimentation of *S. thermophilus* strain ST802 parent (tube A) and its derived BIMs BIMST802-D1B-L-3 (non-CRISPR BIM; tube B) and BIMST802-D1B-L-6 (non-CRISPR BIM; tube C) and BIMST802-D3A-S/L-1a (CRISPR BIM; tube D).

Figure 2:
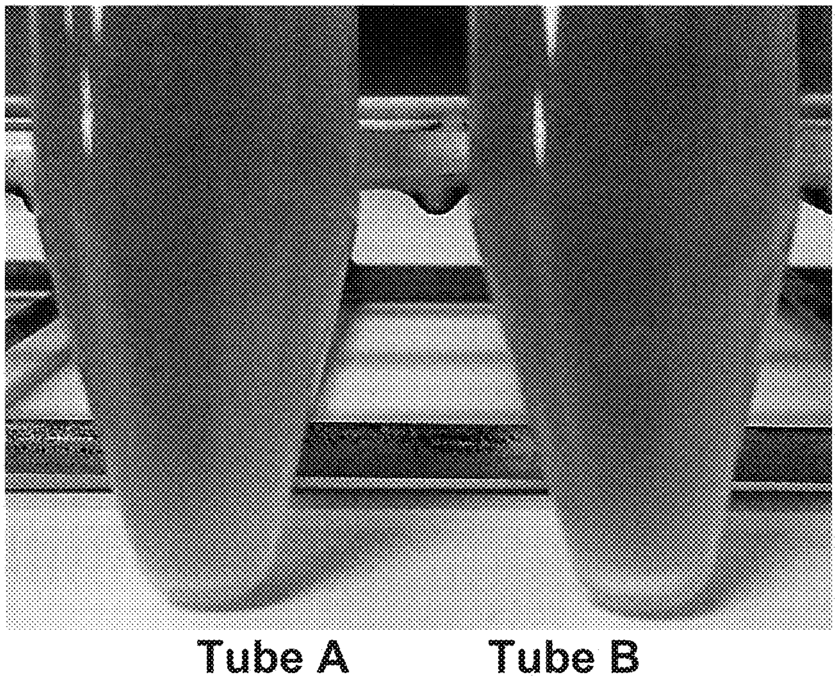

FIG. 2: Observed sedimentation of *S. thermophilus* strain ST23 parent (tube A) and its derived BIMs BIMST23-D1A-L-4 (non-CRISPR BIM; tube B).

Figure 3:
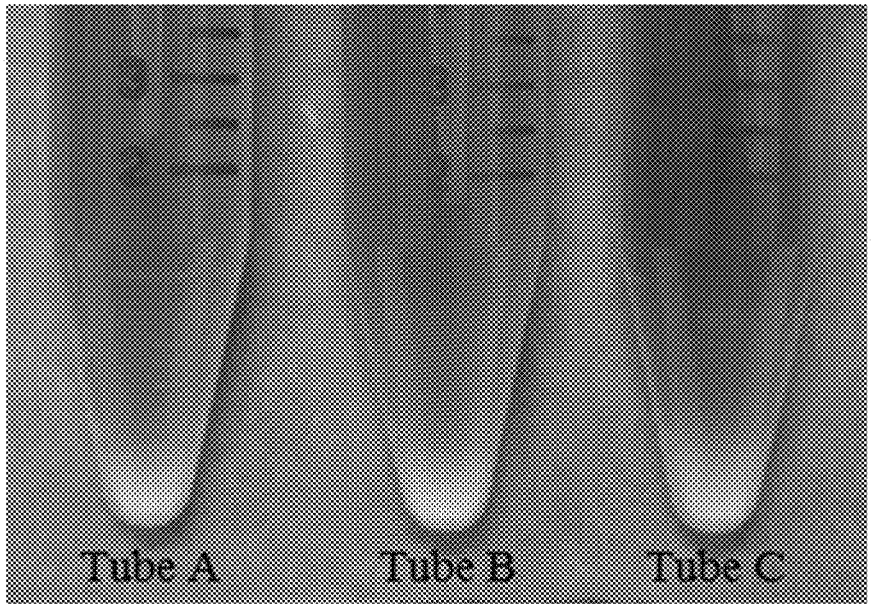

FIG. 3: Observed sedimentation of *S. thermophilus* strain 100-E parent (tube A) and its derived BIMs BIM100-E-D1A-L-7 (CRISPR BIM, tube B) and BIM100-E-D1A-L-5 (non-CRISPR BIM, tube C).

Figure 4:
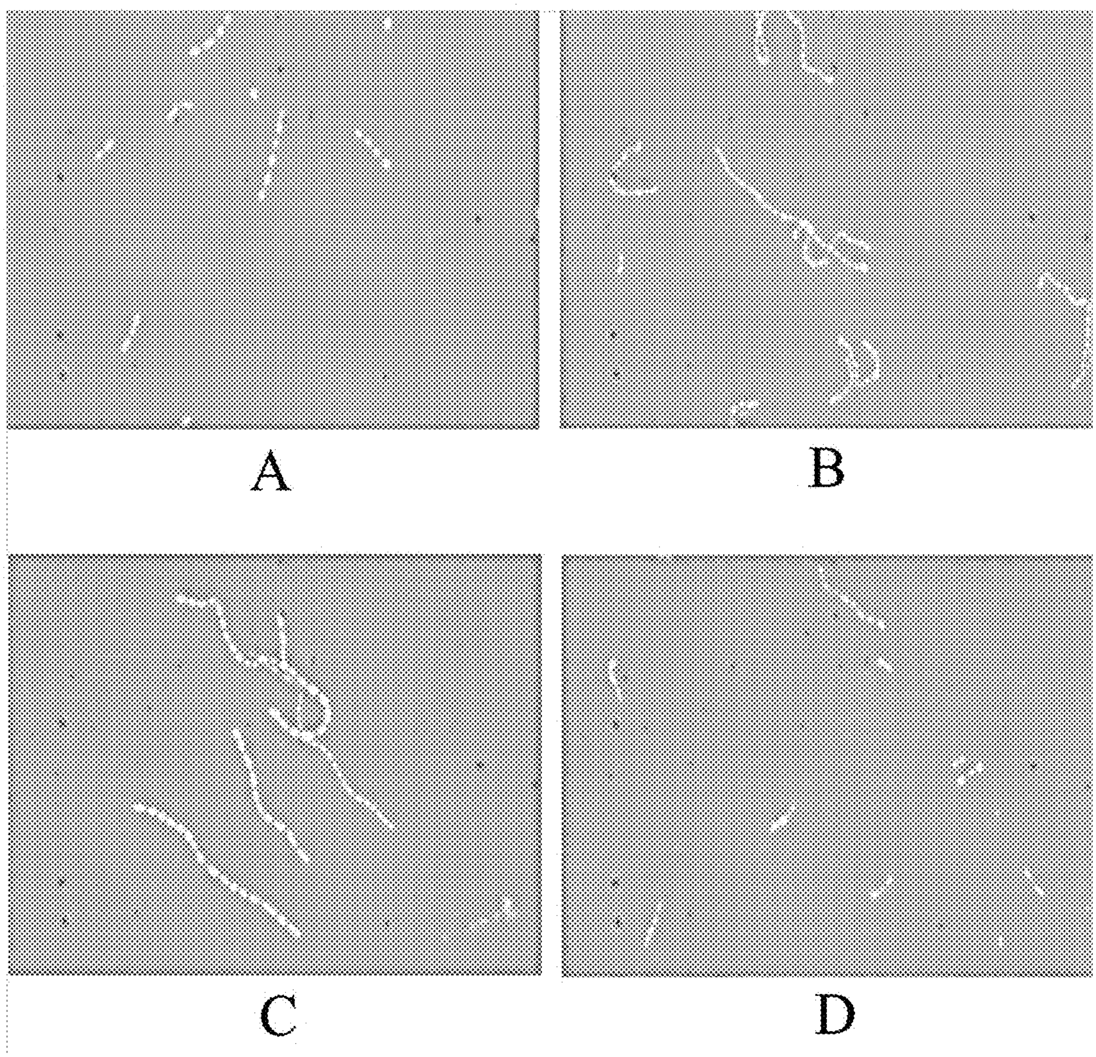

FIG. 4: Light microscope images of *S. thermophilus* strain ST802 parent (photograph A) and its derived BIMs BIMST802-D1B-L-3 (non-CRISPR BIM; photograph B), BIMST802-D1B-L-6 (non-CRISPR BIM; photograph C) and BIMST802-D3A-S/L-1a (CRISPR BIM; photograph D).

Figure 5:
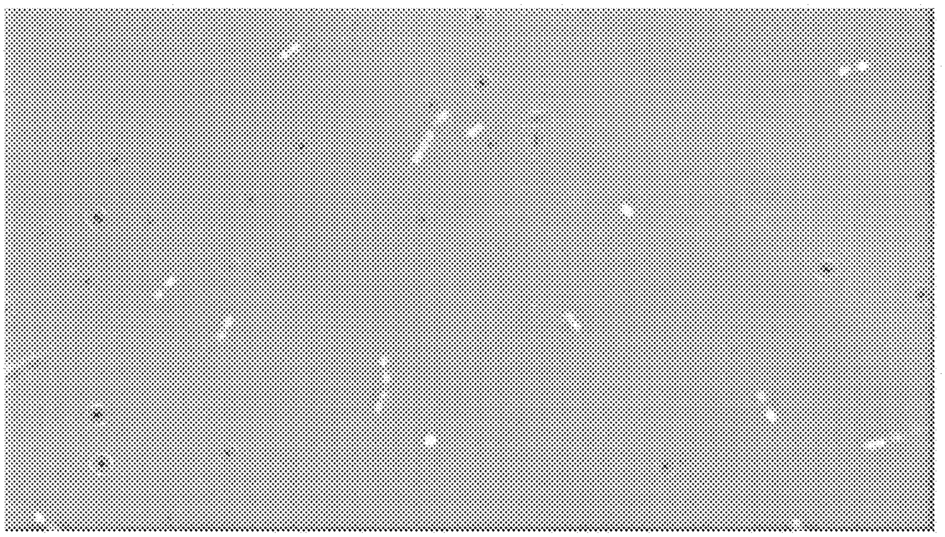
Figure 5:
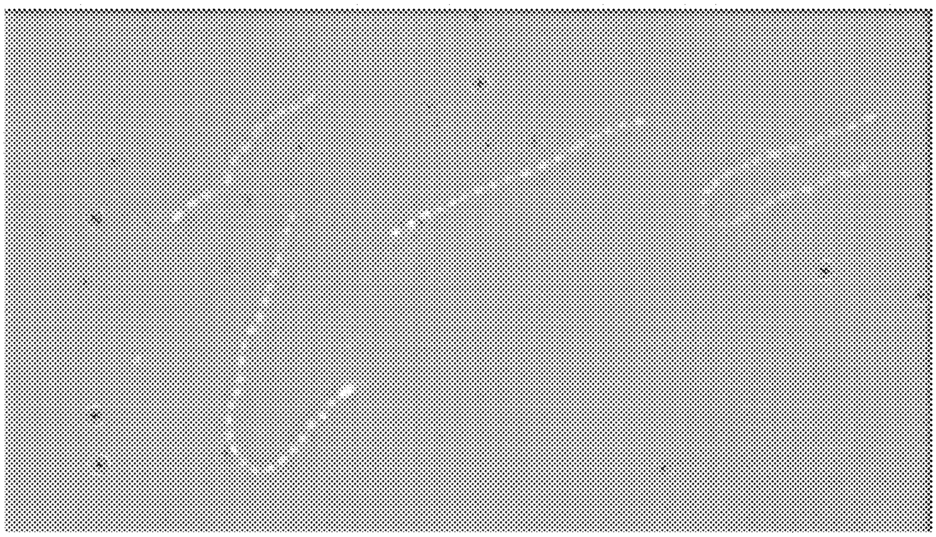

FIG. 5: Light microscope images of *S. thermophilus* strain ST23 parent (photograph A) and its derived BIMST23-D1A-L-4 (non-CRISPR BIM; photograph B).

Figure 6:
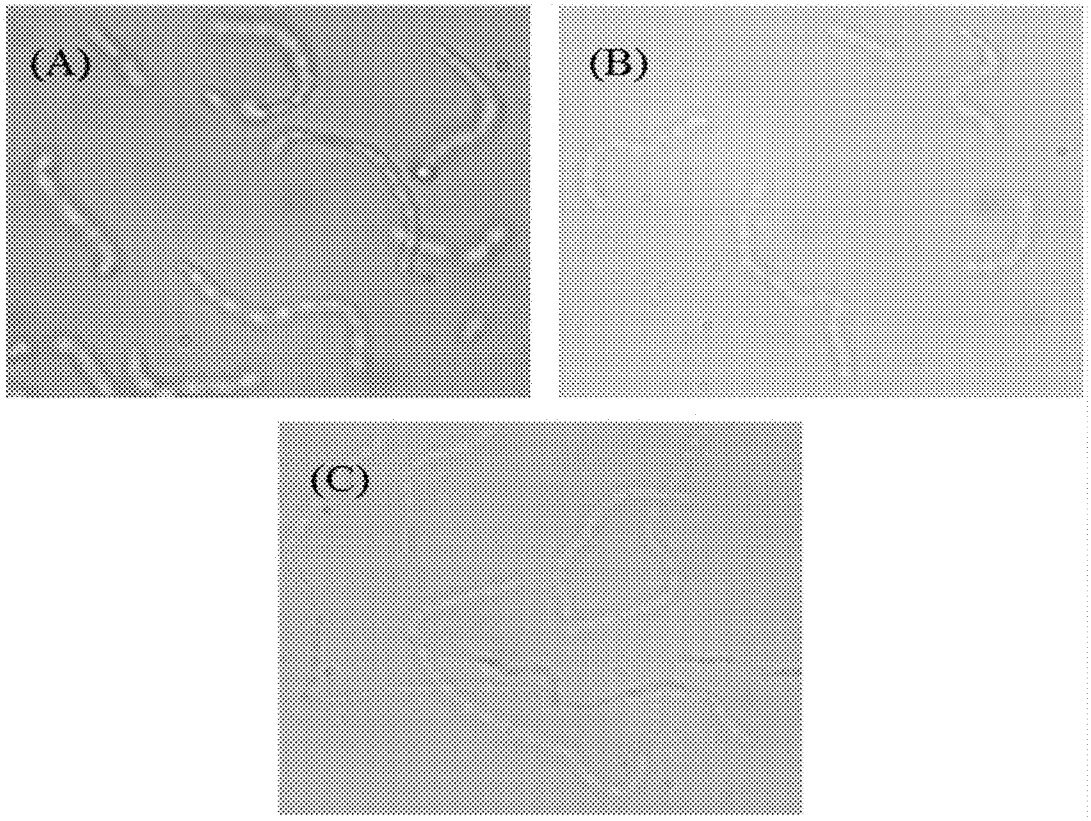

FIG. 6. Light microscopic analysis of *S. thermophilus* strain 100-E parent (photograph A) and derived BIMs BIM100-E-D1A-L-7 (CRISPR BIM, photograph B) and BIM100-E-D1A-L-5 (non-CRISPR BIM, photograph C).

Figure 7:
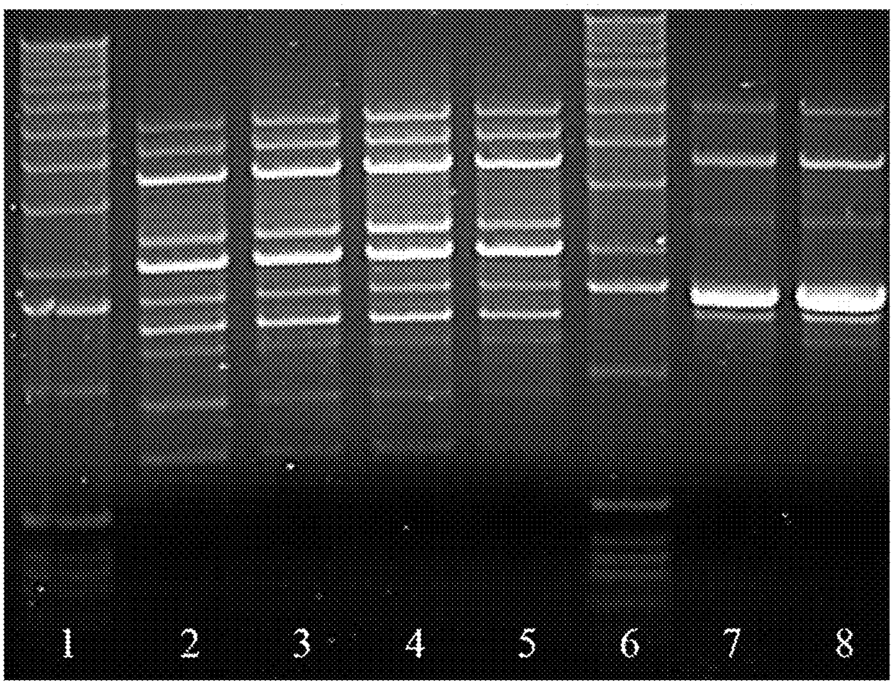

FIG. 7: PCR profiling of strains ST802, ST23 and derived BIMs. Lanes 1 and 6: Molecular weight marker X (Roche, Switzerland); lane 2: ST802 parent; lane 3: BIMST802-D1B-L-3; lane 4: BIMST802-D1B-L-6; lane 5: BIMST802-D3A-S/L-1a, lane 7: ST23 parent, lane 8: BIMST23-D1A-L-4.

Figure 8:
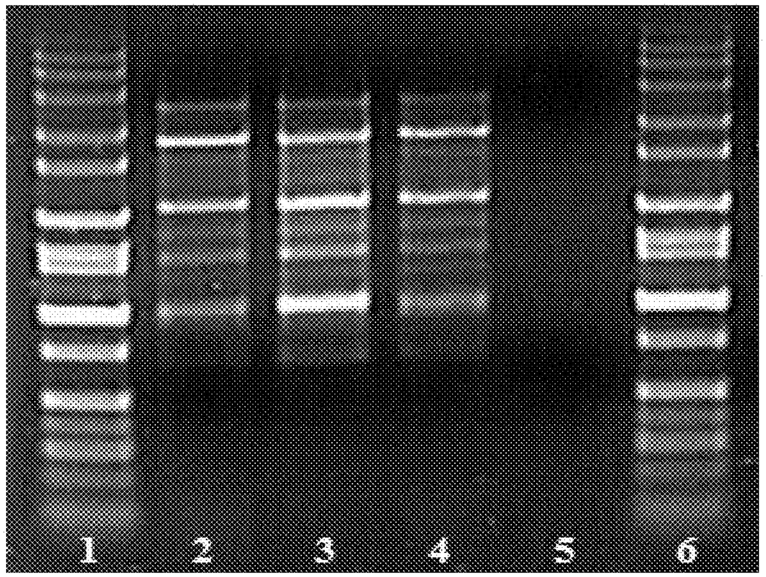

FIG. 8: PCR profiles of strain 100-E and its derived BIMs. Lanes 1 and 6: 1 kb Full Scale DNA Ladder (Fisher Scientific, U.S.A); Lane 2: *S. thermophilus* 100-E parent; Lane 3: BIM100-E-D1A-L-5 (non-CRISPR BIM); Lane 4: BIM100-E-D1A-L-7 (CRISPR BIM); Lane 5: Negative control.

Figure 9:
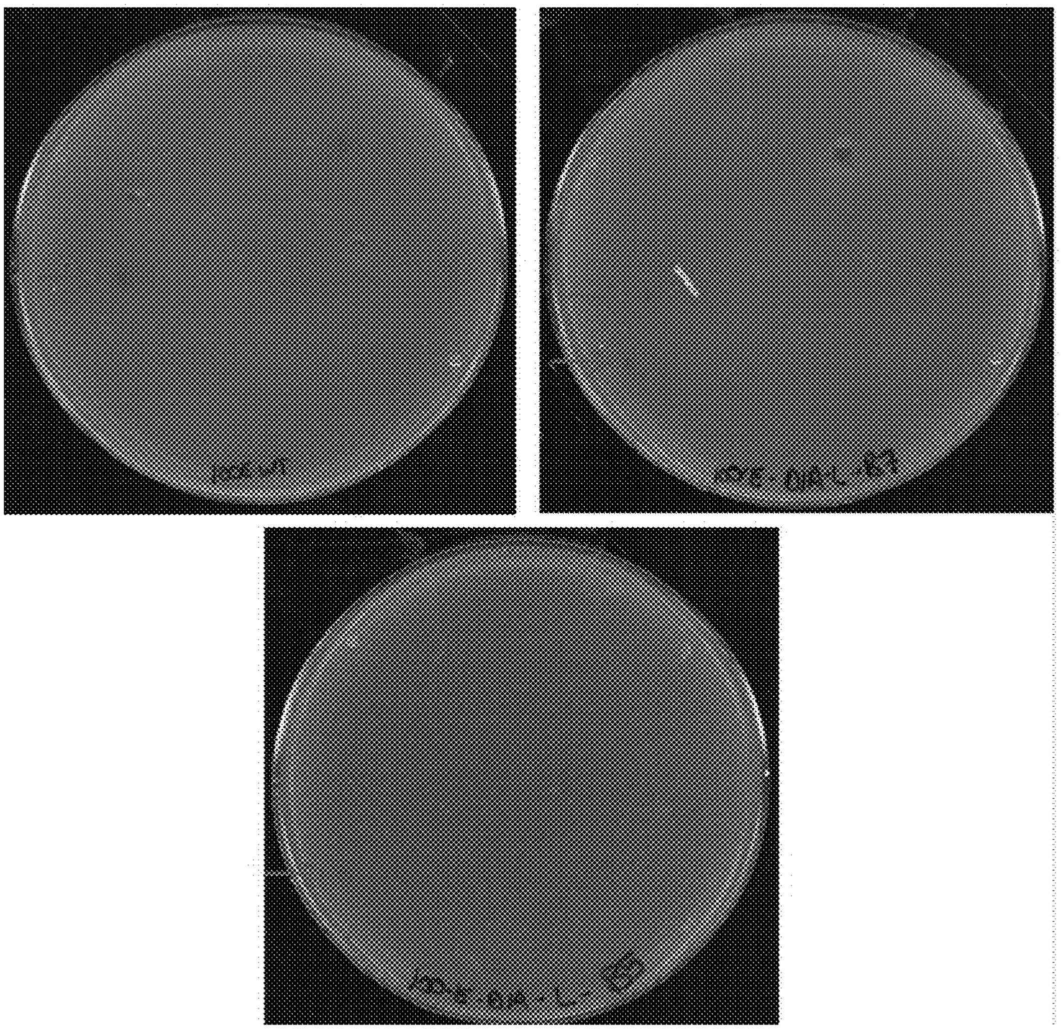

FIG. 9: Representative photograph showing phage 100-E-D1A-L plaque sizes on *S. thermophilus* 100-E parent, and its derived BIMs BIM100-E-D1A-L-7 and BIM100-E-D1A-L-5 which are labelled as 100-E-D1A-L-B7 and 100-E-D1A-L-B5, respectively.

MATERIALS AND METHODS

1. Bacterial Growth Conditions

*Streptococcus thermophilus* strains were routinely grown from 10% glycerol stocks, 20% Reconstituted Skimmed Milk (RSM) stocks or from single colonies overnight at 42° C. in M17 Broth (Oxoid, U.K.) supplemented with 0.5% lactose (LM17) or on plates using LM17 containing 10 g/L technical agar (Merck, Germany). In phage enumeration assays, adapted from D. Lillehaug, 1997 (Journal of applied microbiology 83, (1), 85-90—*"An improved plaque assay for poor plaque-producing temperate lactococcal bacteriophages"*), LM17 broth was supplemented with 0.25% glycine (Oxoid, U.K.), 10 mM $CaCl_2$) (Oxoid, U.K.) and either 10 g/L (solid agar base) or 4 g/L (semi-solid overlay) technical agar. The semi-solid agar was sterilised by autoclaving at 121° C. for 15 minutes whereas the solid agar was boiled for 7 minutes in a microwave.

2. Isolation and Selection of (Bacterio)Phages

Whey samples from dairy plants producing fermented milk products were obtained and analysed for the presence of phages against *S. thermophilus* ST802, *S. thermophilus* ST23 and *S. thermophilus* 100-E using the spot assay described below under "(Bacterio)phage assays". Single plaques were isolated by twice single plaque purification on semi-solid overlays. Phages were then propagated as follows: 10 ml LM17 broth was inoculated with 2 ml of an overnight grown culture of the host strain (*S. thermophilus* ST802, *S. thermophilus* ST23 or *S. thermophilus* 100-E) and allowed to grow for 1.5-2.0 hours. Then, a single plaque was added to the growing culture, mixed well and incubated at 42° C. for a further 2-4 hours or at 30° C. overnight. The lysed culture was centrifuged and the supernatant filtered (0.45 μm). The filtered supernatant was used as the phage stock for subsequent assays. Table 1 summarizes the phages that were obtained.

*S. thermophilus* ST802=DS67009 (CBS136256) was deposited on 2 Oct. 2013 with the Centraal Bureau for Schimmelcultures, Uppsalalaan 8, 3508 AD in Utrecht, The Netherlands.

*S. thermophilus* ST23=DS64987 (CBS136255) was deposited on 2 Oct. 2013 with the Centraal Bureau for Schimmelcultures, Uppsalalaan 8, 3508 AD in Utrecht, The Netherlands.

*S. thermophilus* 100-E=DS64990 (CBS138555) was deposited on 15 Jul. 2014 with the Centraal Bureau for Schimmelcultures, Uppsalalaan 8, 3508 AD in Utrecht, The Netherlands.

TABLE 1

A list of strains and phages used in this study.

| Parent strain | Phage | SEQ ID No. | Source |
|---|---|---|---|
| *S. thermophilus* ST802 | ϕST802-D1B-L | 1 | DSM, The Netherlands |
| *S. thermophilus* ST802 | ϕST802-D3A-S | 2 | DSM, The Netherlands |
| *S. thermophilus* ST802 | ϕST802-D3A-L | 3 | DSM, The Netherlands |
| *S. thermophilus* ST23 | ϕST23-D1A-L | — | DSM, The Netherlands |
| *S. thermophilus* ST23 | ϕST23-D2A-L | — | DSM, The Netherlands |

TABLE 1-continued

| A list of strains and phages used in this study. | | | |
|---|---|---|---|
| Parent strain | Phage | SEQ ID No. | Source |
| *S. thermophilus* 100-E | ϕ100-E-D1A-L | 4 | DSM, The Netherlands |
| *S. thermophilus* 100-E | ϕ100-E-D2A-L | 5 | DSM, The Netherlands |

3. Generation of BIMs (Bacteriophage Insensitive Mutants)

Spontaneous BIMs of the parent strains mentioned in Table 1 were generated using one of two methods.

3.1 BIMs of *Streptococcus thermophilus* ST802

BIMs of *S. thermophilus* ST802 were isolated by one of two methods.

(1) BIMs against phage ST802-D1B-L were generated by adding 400 μl fresh overnight culture of *S. thermophilus* ST802 and 10 μl of neat phage lysate (phage ST802-D1B-L isolated from a single plaque; titre approx. $1\times10^8$ pfu/ml) to 4 ml of soft LM17 agar, followed by spreading this suspension on solid agar. Colonies, representing potential BIMs, growing in the top layer were twice single colony purified and subjected to phage assays and CRISPR sequencing as described below. Two BIMs were thus obtained and characterized (see below): *S. thermophilus* BIMST802-D1B-L-3, *S. thermophilus BIMST*802-D1B-L-6.

(2) A third BIM of *S. thermophilus* ST802, namely BIMST802-D3AS/L-1A was isolated using a method as described below (to isolate *S. thermophilus* BIMST23-4) with the addition of 20 overnight passages in 10% RSM and a 1% lysate containing a mixture of phages ϕD3A-S and ϕD3A-L (titre approx. $1\times10^8$ pfu/ml).

3.2 BIMs of *Streptococcus thermophilus* ST23

BIMs of *S. thermophilus* ST23 were isolated by inoculating 1 ml of 10% (w/v) RSM with 1% of an overnight culture of *S. thermophilus* ST23 and 1% of a particular phage lysate (phages ST23 D1A-L and D2A-L, each produced from a single plaque; titer approx. $1\times10^8$ pfu/ml). The milk with the added culture and phage was then incubated at 42° C. overnight or until clotting was observed. Potential BIMs were selected on LM17 agar, twice single colony purified and subjected to phage assays and CRISPR sequencing as described below. BIMST23-D1A-L-4 was generated in this manner.

3.3 BIMs of *Streptococcus thermophilus* 100-E

BIMs of *S. thermophilus* 100-E against phage 100-E-D1A-L were isolated as described for BIMs BIMST802-D1B-L-3 and BIMST802-D1B-L-6 (section 3.1 (1) above). Two BIMs were selected for further characterization (see Example 3 below), and were designated BIM100-E-D1A-L-7 (CRISPR BIM) and BIM100-E-D1A-L-5 (non-CRISPR BIM).

4. (Bacterio)Phage Assays

Spot assays were performed by seeding the LM17 semi-solid agar overlay with 400 μl fresh overnight culture and applying 5-10 μl of phage lysate in a grid format, as described by Dupont et al. 2005 (Journal of Applied Microbiology 98, (4), 1001-1009. *"Detection of lactococcal* 936-species *bacteriophages in whey by magnetic capture hybridization PCR targeting a variable region of receptor-binding protein genes*). Plates were then allowed to dry and incubated anaerobically overnight at 42° C. A clear zone indicating lysis of the bacterial lawn by the applied phage was recorded as '+', whereas absence of lysis was recorded as '−'.

For phage enumeration, plaque assays were performed by adding 500 μl culture and 10 μl of neat or appropriately diluted phage suspension/lysate to 4 ml soft agar, followed by plating on LM17 agar plates as described above with subsequent overnight incubation at 42° C. Efficiency of plaquing (EOP) was calculated by dividing the obtained titre of a given phage on the test strain by the titre of the same phage on the parent strain.

5. Sedimentation Assays

*S. thermophilus* strains were routinely grown from 10% glycerol stocks, 20% Reconstituted Skimmed Milk (RSM) stocks or from single colonies overnight at 42° C. in LM17 broth (as described in section 1 of the MATERIALS AND METHODS). The parent strains and BIMs were treated identically and after overnight incubation at 42° C., visual assessment of the cultures was performed to observe the growth characteristic of the cultures in broth. Only if the cultures were consistently observed to sediment to the base of the tube or along the wall of the tube was the phenotype considered relevant. In all cases, the parent strain was observed to sediment to a markedly reduced degree after overnight growth. In order to measure the increase in pellet weight (and hence relative amount of sedimentation), overnight cultures of each parent and derived BIM were prepared in LM17 as described above and the supernatant carefully removed. The remaining pellet was suspended in 250 μl $sdH_2O$ and transferred to a fresh Eppendorf tube. The mixture was then made up to a volume of 500 μl using $sdH_2O$ and transferred to a section of pre-weighed blotting paper. The paper was then dried at 75° C. for 15 minutes and weighed again, with the increase in dry weight of the blotting paper taken as the pellet weight for each sample. The increase in the weight of the pellet of each derived BIM relative to the parent was then calculated. In this and all cases, the unpaired student t-test was used to determine significant differences between the parent and derived BIMs datasets.

6. Adsorption Assays

Determination of phage adsorption to parent strains and BIMs was determined as adapted from Garvey et al. 1996 (Applied environmental microbiology 62, (2), 676-679 *"The Lactococcal plasmid pNP*40 *encodes a third bacteriophage resistance mechanism, one which affects phage DNA penetration*"): 10 ml LM17 broth was inoculated with the appropriate strain from an overnight culture and grown at 42° C. until the $OD_{600\ nm}$ reached at least 0.5 but did not surpass 0.53. 700 μl of culture was transferred to a micro centrifuge tube and centrifuged at 2000 (for strains ST802 and ST23, and their derivatives) or 5000 (for strain 100-E and derivatives)×g for 10 minutes to pellet the cells. The cells were resuspended in 700 μl of ¼ strength Ringers solution (Merck, Germany) and an equal volume of the appropriate phage lysate at a titre of approximately $1\times10^5$ pfu/ml was added to the tube or to 700 μl buffer control. The mixture was incubated at 42° C. for 12 minutes, centrifuged at 15,000×g for 3 minutes and 500 μl of residual phage was immediately removed. The phage preparations were stored at 4° C. until plaque assays were performed on the parent strain, as described above. Calculation of adsorption levels (as a percentage of total number of phages present) was performed as follows: ([Control phage titre−Free phage titre in supernatant]/Control phage titre)×100%.

7. Staining & Visualisation of Cells to Determine Chain Length

Morphological assessment and comparison of the parent strains and derived BIMs was performed via wet mount. A drop of fresh overnight culture was placed on a glass slide and a cover slip immediately placed on top of the sample. Each sample was then visualised under 100× magnification using a light microscope (Leica DM1000, Germany).

Images were captured using a mounted Leica DFC290HD camera and processed using Leica Application Suite software. The percentage increase in chain length or cells per chain (CPC) of derived BIMs relative to the parent strains was calculated firstly by determining the average number of individual cells per chain in all samples by counting at least 25 chains. The average increase in length was then expressed as a percentage using the following formula: $(CPC_{mutant}-CPC_{parent})/CPC_{parent}\times100\%)$.

8. PCR Screening & CRISPR Locus Sequencing

All BIMs generated were subjected to PCR profiling to confirm their relatedness to the parent strains from which they were derived. This was performed on single colonies of each parent strain and BIM using the '(GTG)5' primer (Gevers D., Huys G. and Swing J., 2001, *Applicability of rep-PCR fingerprinting for identification of Lactobacillus species* FEMS Microb. Letters 205, 31-36 (see Table 2)). The PCR conditions were as follows: 95° C.×10 min, followed by 30 cycles of 95° C.×15 s, 40° C.×30 s and 72° C. for 8 min with a final extension step of 72° C. for 16 min.

BIMs generated were purified and the CRISPR loci amplified by PCR and sequenced to determine acquisitions or alterations to the spacer content of the BIMs. CRISPR-1, CRISPR-2 and CRISPR-3 repeat/spacer arrays for each strain were amplified individually using a single colony of the appropriate strain as template material for the PCR and primers described previously by Horvath et al. 2008 (Journal of Bacteriology 190 (4): 1401-1412 *"Diversity, activity, and evolution of CRISPR loci in Streptococcus thermophilus."*) The PCR conditions were as follows: 95° C.×10 min, followed by 30 cycles of 95° C.×15 s, 55° C.×15 s and 72° C. for either 2 min 45 s (CRISPR-1) or 1 min (CRISPR-2 and CRISPR-3) with a final extension step of 72° C. for 10 min.

The PCR generated products were visualised on a 1% agarose (Fisher Scientific, USA) gel and purified using a PCR purification spin kit (Genomed, Germany). Sequencing was performed by MWG Biotech (Eurofins, Germany), firstly using the primers used to amplify the loci, then internally using synthetic primers based on a unique spacer of each repeat/spacer array in order to complete the sequencing of the CRISPR loci, where required. CRISPRs were assembled using the Seqman program (DNAstar) and CRISPR arrays were visualised using the online CRISPR finder program from the Université of Paris sud-11 (crispr.u-psud.fr).

TABLE 2

PCR primers used in this study

| Primer name | Sequence (5' → 3') | SEQ ID NO | Reference | Target |
|---|---|---|---|---|
| yc70 | TGCTGAGACAACCTAGTCTCTC | 6 | Horvath et al. (2008) | CRISPR 1 |
| CR1-rev | TAAACAGAGCCTCCCTATCC | 7 | Horvath et al. (2008) | CRISPR 1 |
| ST802CR1-gfwd | CCCGGCGTATATACTGGC | 8 | This study | CRISPR 1 |
| ST802CR1-g2fwd | GCTGACTGGACCAAATGC | 9 | This study | CRISPR 1 |

TABLE 2-continued

PCR primers used in this study

| Primer name | Sequence (5' → 3') | SEQ ID NO | Reference | Target |
|---|---|---|---|---|
| ST23CR1-g3fwd | GAGCAAGCAGAGGGTAGC | 10 | This study | CRISPR 1 |
| 100ECR1-g4fwd | CCTGTCATCTCTGGGAGT | 11 | This study | CRISPR 1 |
| 100ECR1-g5fwd | CGGTGTTCTATATCGAGGTC | 12 | This study | CRISPR 1 |
| CR1-grev | TTTCACTTCCTGAACCCC | 13 | This study | CRISPR 1 |
| CR2-fwd | TTAGCCCCTACCATAGTGCTG | 14 | Horvath et al. (2008) | CRISPR 2 |
| CR2-rev | TTAGTCTAACACTTTCTGGAAGC | 15 | Horvath et al. (2008) | CRISPR 2 |
| CR3-fwd | CTGAGATTAATAGTGCGATTACG | 16 | Horvath et al. (2008) | CRISPR 3 |
| CR3-rev | GCTGGATATTCGTATAACATGTC | 17 | Horvath et al. (2008) | CRISPR 3 |
| 100ECR3-gfwd | CAATCCGTAGCCACACCT | 18 | This study | CRISPR 3 |
| (GTG)5 | GTGGTGGTGGTGGTG | 19 | Gevers D., Huys G. and Swing J. (2001) | Strain specific finger-print |

10. Acidification Assay

An acidification experiment was performed using a CINAC pH measurement system. For this purpose, overnight cultures of strains were generated in triplicate using 2 mL of 10% RSM with 20 μL of stock solution of the strains in 50 mL tubes with subsequent incubation at 42° C. The next day fresh 9.5% Campina QC-Milkbase was added to a final volume of 20 ml, mixed and the entire 20 mL was added to a milk bottle containing 180 mL 9.5% Campina QC-Milkbase, followed by overnight incubation at 42° C. pH was measured online (every 2 minutes) using a pH probe (Mettler Toledo HA405-DXK-08).

11. Demonstration of Non-CRISPR BIM Robustness

In order to demonstrate the relative robustness of non-CRISPR BIMs relative to CRISPR BIMs of 100-E, a phage plaque measurement and propagation experiment was performed. Firstly, the 100-E parent strain and both BIM100-E-D1A-L-5 and BIM100-E-D1A-L-7 were exposed a second time by standard plaque assay (as described in the MATERIALS AND METHODS) to the phage that was initially used in the challenge. While a high level of resistance to this phage was observed for both BIMs, phage escape mutants were also observed in the overlay agar (Table 13). Wild type and escape mutant plaques were measured using a digital callipers (Workzone, U.K.) on subsequent identical experiments, the results of which are shown in Table 17. A representative image illustrating the differences in plaque sizes on the respective strains is shown in FIG. 9.

Single plaques each of wild-type phage (exposed to 100-E parent), CRISPR-escape mutant (CEM; exposed to BIM100-E-D1A-L-7) and non-CRISPR escape mutant (NCEM; exposed to BIM100-E-D1A-L-5) were then propagated on their respective host strains. This was performed as described in the MATERIALS AND METHODS, with the following modifications to increase efficiency of propagation: a 1% inoculum of each strain was added to 10 ml of pre-warmed LM17 broth (supplemented with 10 mM $CaCl_2$ (Oxoid)) at 37° C. A single plaque of the appropriate phage was picked using a sterile pipette tip and immediately added to the tube. The propagation was allowed to proceed for 4 hours at 37° C. before filtration (0.45 μm) and plaque assay on the appropriate strain, the results of which are presented in Table 18.

A 'second round' (2°) propagation was then performed in order to confirm the non-CRISPR BIM robustness over a series of cycles. The escape mutant lysates generated from the plaque propagations (described above) were diluted to approximately $10^4$ pfu/ml. A 1% inoculum of the appropriate strain was added from a fresh overnight culture to pre-warmed LM17 broth at 42° C. and allowed to grow for 1 hour. $CaCl_2$ (Oxoid) was added to a final concentration of 10 mM. 1% of the appropriate phage lysate was added and the propagation proceeded for 4 hours at 42° C. before filtration (0.45 μm) and plaque assay (as described above) on the appropriate strain, the results of which are shown in Table 18.

EXAMPLES

Example 1

Bacteriophage Insensitive Mutants (BIMs) of *S. thermophilus* ST802

1.1 Phage Sensitivity

Bacteriophages against *S. thermophilus* ST802 were isolated as described in the MATERIALS AND METHODS. BIMs against phage ϕST802-D1B-L or against ϕST802-D3A-S and ϕST802-D3A-L were isolated, purified (by picking a single colony and growing in LM17 broth overnight at 42° C.), and subjected to spot assays. The BIM phenotype and stability was confirmed by plaque assays as described in the MATERIALS AND METHODS, the results of which are displayed in Table 3.

TABLE 3

Relative efficiencies of plaquing (EOP) of phages of *Streptococcus thermophilus* strain ST802 and derived BIMs.

| Strain/BIM | ΦST802-D1B-L | ΦST802-D3A-S | ΦST802-D3A-L |
|---|---|---|---|
| ST802 (parent) | 1 | 1 | 1 |
| BIMST802-D1B-L-3 | ≤1 × $10^{-6}$ | ≤1 × $10^{-6}$ | ≤1 × $10^{-6}$ |
| BIMST802-D1B-L-6 | ≤1 × $10^{-6}$ | ≤1 × $10^{-6}$ | ≤1 × $10^{-6}$ |
| BIMST802-D3A-S/L-1a | ≤1 × $10^{-6}$ | ≤1 × $10^{-6}$ | ≤1 × $10^{-6}$ |

Note 1:
≤ denotes the limit of detection i.e. no plaques were detected when the derived BIM was challenged with a phage lysate containing 1 × $10^6$ pfu/ml phages.
Note 2:
In derived BIM nomenclature, D1B-L or D3A-SL denotes the phage(s) against which the BIM was generated.

1.2 CRISPR Sequencing

The loci of CRISPR-1, CRISPR-2 and CRISPR-3 of *S. thermophilus* ST802 and its BIMs were sequenced as described in paragraph 8 of the Materials and Methods. Table 4 shows that the sizes of the CRISPR-1, CRISPR-2 and CRISPR-3 (2545 bp, 258 bp and 827 bp, respectively) for BIMST802-D1 B-L-3 and BIMST802-D1 B-L-6, as well as the spacer number and content were identical in the parent and BIMs. No CRISPR locus could be detected using CRISPR-4 repeat GTTTTTCCCGCACACGCGGGGGTGATCC(SEQ ID No. 20) as a consensus signature, nor by using the online CRISPR finder program from the Université of Paris sud-11 (crispr.upsud.fr).

The result shows that phage insensitivity was conferred to BIMST802-D1B-L-3 and BIMST802-D1B-L-6 by a mechanism other than CRISPR-1, CRISPR-2 or CRISPR-3. The adsorption results as well as the sedimentation results suggest that these BIMs carry mutations and/or adaptations in the cell envelope and/or phage receptor binding site. In the case of BIMST802-D3A-S/L-1a, the addition of three new spacers at the leader end of the CRISPR-1 locus and two at the leader end of the CRISPR-3 locus indicate that phage insensitivity was conferred by the CRISPR mechanism.

TABLE 4

Summary of CRISPR in *S. thermophilus* strain ST802 and derived BIMs

| Strain | CRISPR | Size | Direct repeat | # spacers | Terminal repeat |
|---|---|---|---|---|---|
| ST802 (parent) | 1 | 2543 bp | 5'-GTTTTTGTACTC | 38 | 5'-GTTTTTGTACTC |
| BIMST802-D1B-L-3 | 1 | 2543 bp | TCAAGATTTAAGT | 38 | TCAAGATTTAAGTA |
| BIMST802-D1B-L-6 | 1 | 2543 bp | AACTGTACAAC-3' | 38 | ACTGTACAGT-3' |
| BIMST802-D3A-S/L-1a | 1 | 2741 bp | (SEQ ID NO 21) | 41 | (SEQ ID NO 22) |
| ST802 (parent) | 2 | 258 bp | 5'-GATATAAACCTA | 3 | 5'-GATATAAACCTA |
| BIMST802-D1B-L-3 | 2 | 258 bp | ATTACCTCGAGAG | 3 | ATTACCTCGAGAG |
| BIMST802-D1B-L-6 | 2 | 258 bp | GGGACGGAAAC-3 | 3 | GGGACTTTTTT-3' |
| BIMST802-D3A-S/L-1a | 2 | 258 bp | (SEQ ID NO 23) | 3 | (SEQ ID NO 24) |
| ST802 (parent) | 3 | 827 bp | 5'-GTTTTAGAGCTG | 12 | Same as direct |
| BIMST802-D1B-L-3 | 3 | 827 bp | TGTTGTTTCGAATG | 12 | repeat |
| BIMST802-D1B-L-6 | 3 | 827 bp | GTTCCAAAAC-3' | 12 | |
| BIMST802-D3A-S/L-1a | 3 | 959 bp | (SEQ ID NO 25) | 14 | |

1.3 PCR Profiling

PCR profiling using the (GTG)5 primer and method described above was performed on all BIMs and their parent strains to confirm their relatedness to the parent strain from which they were derived. The results were visualised on a 1% agarose gel (shown in FIG. 5) and, taken together with the results of CRISPR locus sequencing (described above), confirm that all BIMST802-D1B-L-3 and BIMST802-D1B-L-6 are direct derivatives of the corresponding phage-sensitive *S. thermophilus* strain ST802.

1.4 Mutant Phenotype

All BIMs showed similar acidification activities compared to the parent (data not shown). While the proposed CRISPR-mediated BIM of ST802 did not appear to sediment compared to the parent (FIG. 1, Tubes A and D) proposed non-CRISPR BIMs exhibited a distinctive sedimentation phenotype relative to the parent and to each other (FIG. 1, Tubes A, B and C). The degree to which each BIM sediments relative to the parent strain is indicated by an increase in pellet weight, shown in Table 5 below. It is clear that the proposed non-CRISPR BIMs produce a heavier pellet than both the parent and CRISPR BIM strains. Morphological analysis using simple staining of cells combined with light microscopy revealed that the BIMs form cell aggregates and long chains in comparison with the parent strain (FIGS. 3A, 3B and 3C). The percentage increase in chain length is indicated in Table 6 below. This increase in chain length may also explain the observed sedimentation phenotype in FIG. 1: BIMST802-D1B-L-3 and BIMST802-D1B-L-6 sediment more than the parent strain, while BIMST802-D3A-S/L-1a does not.

TABLE 5

Pellet weights of parent and BIMs of *S. thermophilus* strain ST802.

| Strain | Pellet weight (g) | Mean pellet weight increase in g (%) | p-value |
|---|---|---|---|
| ST802 parent | .0024 ± .0005 | N/A | N/A |
| BIMST802-D1B-L-3 | .0077 ± .0019 | 0.0053 (220%) | 0.02 |
| BIMST802-D1B-L-6 | .0099 ± .0030 | 0.0075 (312%) | 0.02 |
| ST802 D3A-SL-1A | .0047 ± .0004 | .0023 (96%) | 0.007 |

TABLE 6

Relative cells per chain (CPC) of parent and BIMs of *S. thermophilus* strain ST802.

| Strain | CPC | % CPC increase versus parent | p-value |
|---|---|---|---|
| ST802 parent | 3.4 ± 2.2 | N/A | N/A |
| BIMST802-D1B-L-3 | 8.9 ± 5.9 | 161% | $5.9 \times 10^{-8}$ |
| BIMST802-D1B-L-6 | 12.8 ± 12.2 | 276% | $3.2 \times 10^{-6}$ |
| ST802 D3A-SL-1A | 4.1 ± 3.6 | 20% | 0.27 |

1.5 Adsorption of Phages

Adsorption assays were performed to determine the level of adsorption of phages to both the parent strains and the derived BIMs, the results of which are shown in Table 7. Each of the infecting phages adsorb efficiently to the parent strain (adsorption levels are ≈80%). In contrast, phage adsorption to two of the BIMs is markedly reduced which indicates that in two out of three cases the BIMs confer resistance through an adsorption blocking mechanism.

TABLE 7

Adsorption of phages to parent and BIMs of *S. thermophilus* strain ST802.

| Strain | Long chain formation? | ΦST802-D1B-L | ΦST802-D3A-S | ΦST802-D3A-L |
|---|---|---|---|---|
| ST802 (parent) | No | 89 ± 3% | 89 ± 9% | 94 ± 2% |
| BIMST802-D1B-L-3 | Yes | 32 ± 10% | 47 ± 15% | 25 ± 17% |
| p-value | | 0.0013 | 0.014 | 0.0009 |
| BIMST802-D1B-L-6 | Yes | 6 ± 1% | 29 ± 25% | 15 ± 5% |
| p-value | | $3.12 \times 10^{-6}$ | 0.029 | $3.22 \times 10^{-5}$ |
| BIMST802-D3A-S/L-1a | No | 100 ± 0% | 99 ± 0% | 99 ± 0% |
| p-value | | 0.006 | 0.12 | 0.030 |

Example 2

Bacteriophage Insensitive Mutants of *S. thermophilus* ST23

2.1. Phage Sensitivity

Bacteriophages against *S. thermophilus* ST23 were isolated as described in the MATERIALS AND METHODS. A BIM against phage ϕST23-D1A-L was isolated, purified (by picking a single colony and growing in LM17 broth overnight at 42° C.) and subjected to spot assays and confirmatory plaque assays as described in the MATERIALS AND METHODS, the results of which are shown in Table 8.

TABLE 8

Relative efficiencies of plaquing (EOP) of phages of *Streptococcus thermophilus* strain ST23 and derived BIM.

| Strain | φST23-D1A-L | φST23-D2A-L |
|---|---|---|
| ST23 (parent) | 1 | 1 |
| BIMST23-D1A-L-4 | $\leq 1 \times 10^{-9}$ | $1 \times 10^{-3}$* |

Note:
≤ denotes the limit of detection i.e. no plaques were detected when the derived BIM was challenged with a phage lysate containing $1 \times 10^{9}$ pfu/ml phages.
*A reduction in plaque size (by approximately 50%) and an increase in plaque haziness was also observed.

2.2 CRISPR Sequencing

PCR-generated CRISPR-1, CRISPR-2 and CRISPR-3 size profiles (1952 bp, 843 bp and 1289 bp respectively) of ST23 and its derivatives indicated that no additions were made to the arrays and this result was confirmed by sequencing: both spacer number and content were identical to those of the parent-see Table 9. No CRISPR locus could be detected using CRISPR-4 repeat GTTTTTCCCGCACACGCGGGGGTGATCC (SEQ ID No. 20) as a consensus signature, nor by using the online CRISPR finder program from the Université of Paris sud-11 (crispr.upsud.fr).

TABLE 9

Summary of CRISPR in *S. thermophilus* strain ST23 and derived BIMs

| Strain | CRISPR | Size | Direct repeat | # spacers | Terminal repeat |
|---|---|---|---|---|---|
| ST23 (parent) | 1 | 1952 bp | 5'-GTTTTTGTACTCT | 29 | 5'-GTTTTTGTACTC |
| BIMST23-D1A-L-4 | 1 | 1952 bp | CAAGATTTAAGTA | 29 | TCAAGATTTAAGT |
| | | | ACTTACAAC-3' | | AACTGTACAGT-3' |
| ST23 (parent) | 2 | 843 bp | 5'-GATATAAACCTAA | 11 | 5'-GATATAAACCTA |
| BIMST23-D1A-L-4 | 2 | 843 bp | TTACCTCGAGAGG | 11 | ATTACCTCGAGAG |
| | | | GGACGGAAAC-3' | | GGGACTTTTTT-3' |
| ST23 (parent) | 3 | 1289 bp | 5'-GTTTTAGAGCTGT | 19 | As direct repeat |
| BIMST23-D1A-L-4 | 3 | 1289 bp | GTTGTTTCGAATG | 19 | As direct repeat |
| | | | GTTCCAAAAC-3' | | |

The result in Example 2 shows that phage resistance was conferred to BIMST23-D1A-L-4 by a mechanism other than CRISPR. The adsorption results (section 2.5) suggest mutations and/or adaptations in the cell wall and/or phage receptor binding site.

2.3 PCR Profiling

PCR profiling using the (GTG)5 primer and method described above was performed on all BIMs and their parents to confirm their relatedness to the parent strains from which they were derived. The results were visualised on a 1% agarose gel (shown in FIG. 5) and, taken together with the results of CRISPR locus sequencing (described above), confirm that BIMST23-D1A-L-4 is a direct derivative of the corresponding phage-challenged *S. thermophilus* strain ST23.

2.4 Mutant Phenotype

*S. thermophilus* BIMST23-D1A-L-4 was shown to exhibit similar acidification activities compared to the parent (data not shown). Furthermore, BIMST23-D1A-L-4 also aggregates and forms longer cell chains than the parent, as shown in FIGS. 4A and 4B, respectively. The proposed non-CRISPR BIM exhibited a distinctive sedimentation phenotype relative to the parent (FIG. 2—Tubes A and B). The degree to which the BIM sediments relative to the parent strain is indicated by an increase in pellet weight, shown in Table 10 below. The percentage increase in chain length is indicated in Table 11.

TABLE 10

Pellet weights of parent and BIM of *S. thermophilus* strain ST23.

| Strain/BIM | Pellet weight (g) | Mean pellet weight increase in g (%) | p-value |
|---|---|---|---|
| ST23 | 0.0036 ± 0.0001 | N/A | N/A |
| BIMST23-D1A-L-4 | 0.0044 ± 0.0002 | 0.0008 (22%) | 0.009 |

TABLE 11

Relative cells per chain (CPC) of BIM of *S. thermophilus* strain ST23.

| Strain | CPC | % CPC increase versus parent | p-value |
|---|---|---|---|
| ST23 parent | 2.8 ± 0.4 | N/A | N/A |
| BIMST23-D1A-L-4 | 5.6 ± 1.1 | 100 | $1.6 \times 10^{-10}$ |

2.5 Adsorption of Phages

Adsorption assays were performed to determine the level of adsorption of phages to both the parent strains and the derived BIM, the results of which are shown in Table 7. Each of the infecting phages adsorb optimally to the parent strain (adsorption levels are ≈80%). In contrast, phage adsorption to the BIM is markedly reduced and indicates that the BIM confers resistance through an adsorption blocking mechanism.

TABLE 12

Adsorption of phages to parent and BIM of *S. thermophilus* strain ST23.

| Strain | Long chain formation | φST23-D1A-L | φST23-D2A-L |
|---|---|---|---|
| ST23 (parent) | No | 94 ± 4% | 97 ± 1% |
| BIMST23-D1A-L-4 | Yes | 18 ± 12% | 32 ± 2% |
| p-value | | 0.0005 | $1.5 \times 10^{-7}$ |

Example 3

Bacteriophage Insensitive Mutants of *S. thermophilus* 100-E 3.1 Phage Sensitivity Bacteriophages against *S. thermophilus* 100-E were isolated as described in the MATERIALS AND METHODS section. BIMs against phage ϕ100-E-D1A-L were isolated, purified (by picking a single colony and growing in LM17 broth overnight at 42° C.) and subjected to spot assays and confirmatory plaque assays as described in the MATERIALS AND METHODS, the results of which are shown in Table 13. BIM100-E-D1A-L-7 showed a high level of resistance to the phage that was used in the challenge only, while BIM100-E-D1A-L-5 appeared insensitive to this phage as well as a distinct phage (phage 100-E-D2A-L; Table 13).

TABLE 13

Relative efficiencies of plaquing (EOP) of phages of *Streptococcus thermophilus* strain 100-E and derived BIMs.

| Strain | φ100-E-D1A-L | φ100-E-D2A-L |
|---|---|---|
| 100-E (parent) | 1 | 1 |
| BIM100-E-D1A-L-7 | $9.7 \times 10^{-7}$ | 0.6 |
| BIM100-E-D1A-L-5 | $2.9 \times 10^{-6}$ | $\leq 1.2 \times 10^{-7}$ |

3.2 CRISPR Sequencing

PCR-generated CRISPR-1, CRISPR-2 and CRISPR-3 size profiles (2409/2476 bp, 115 bp and 1358 bp respectively) of 100-E and its derivative BIMs indicated that no additions were made to the arrays of BIMIOO-E-DIAL-5. This result was confirmed by sequencing: both spacer number and content were identical to those of the parent see Table 14. In the case of BIMIO E-DIA-L-7, the addition of a spacer at the leader end of the CRISPRI locus indicates that the observed phage resistance was conferred by the CRISPR mechanism_No CRISPR locus could be detected using CRISPR-4 repeat GTTTTTCCCGCACACGCGGGGGTGATCC (SEQ ID No. 20) as a consensus signature, nor by using the online CRISPR finder program from the Université of Paris sud-11 (crispr.upsud.fr).

TABLE 14

Summary of CRISPR in *S. thermophilus* strain 100-E and derived BIMs

| Parent/BIM | CRISPR | Size (bp) | Direct repeat | # spacers | Terminal repeat |
|---|---|---|---|---|---|
| 100-E (parent)<br>BIM100-E-D1A-L5<br>BIM100-E-D1A-L7 | 1 | 2409<br>2409<br>2476 | 5'-GTTTTT GTACTCTCA AGATTTAAG TAACTGTAC AAC-3' | 36<br>36<br>37 | 5'-GTTTTT GTACTCTCA AGATTTAAG TAACTGTAC AGT-3' |
| 100-E (parent)<br>BIM100-E-D1A-L5<br>BIM100-E-D1A-L7 | 2 | 115 | 5'-GATATA AACCTAATT ACCTCGAGA GGGGACGGA AAC-3' | 1 | 5'-GATATA AACCTAATT ACCTCGAGA GGGGACTTT TTT-3' |
| 100-E (parent)<br>BIM100-E-D1A-L5<br>BIM100-E-D1A-L7 | 3 | 1358 | 5'-GTTTTA GAGCTGTGT TGTTTCGAA TGGTTCCAA AAC-3' | 20 | As direct repeat |

The result in Example 3 shows that phage resistance was conferred to BIM100-E-D1A-L5 by a mechanism other than CRISPR. The adsorption results (section 3.5) suggest that the observed phage resistance or insensitivity is due to an inability of the phage to efficiently recognize and bind to its host.

3.3 PCR Profiling

PCR profiling using the (GTG)5 primer method described above was performed on both BIMs and their parent to confirm their relatedness to the parent strain from which they were derived. The results were visualized on a 1% agarose gel (FIG. 8) and, taken together with the results of CRISPR locus sequencing (described above), confirm that both BIM100-E-D1A-L5 and BIM100-E-D1A-L7 are direct derivatives of the corresponding phage-challenged *S. thermophilus* parent strain 100-E.

3.4 Mutant Phenotype

*S. thermophilus* 100-E and its derived BIMs were examined for sedimentation phenotypes as described in the MATERIALS AND METHODS. While the proposed CRISPR-mediated BIM of 100-E (BIM100-E-D1A-L-7) did not appear to sediment compared to the parent (FIG. 3, Tubes A and B), the proposed non-CRISPR BIM (BIM100-E-D1A-L-5) was shown to exhibit a distinctive sedimentation phenotype relative to the parent (FIG. 3, Tube C). Morphological analysis using light microscopy revealed that BIM100-E-D1A-L-5 forms cell aggregates and long chains in comparison with the parent strain, while BIM100-E-D1A-L-7 resembles the parent strain in its sedimentation profile (FIGS. 6A, B and C). The percentage increase in chain lengths are indicated in Table 15 below. This increase in chain length may also explain the observed sedimentation phenotype in FIG. 3.

TABLE 15

Relative cells per chain (CPC) of BIMs of *S. thermophilus* strain 100-E.

| Strain | CPC | % CPC increase versus parent | p-value |
|---|---|---|---|
| 100-E parent | 6.4 ± 3.9 | N/A | N/A |
| BIM100-E-D1A-L-7 | 6.7 ± 4.5 | 4.5% | 0.72 |
| BIM100-E-D1A-L-5 | 16.8 ± 9.3 | 162.7% | $1 \times 10^{-11}$ |

3.5 Adsorption of Phages

Adsorption assays were performed to determine the level of adsorption of both phages to both the parent strains and the derived BIMs of 100-E, the results of which are shown in Table 16. Each of the infecting phages adsorb optimally to the parent strain (adsorption levels are ≈80%), and to the CRISPR BIM (BIM100-E-D1A-L-7) In contrast, phage 100-E-D1A-L adsorption to BIM100-E-D1A-L-5 is markedly reduced and indicates that the insensitivity of the BIM to this phage is conferred by an adsorption blocking mechanism.

TABLE 16

Adsorption of phages to parent and BIM of *S. thermophilus* strain 100-E.

| Strain | Long chain formation? | φ100-E-D1A-L | φ100-E-D2A-L |
|---|---|---|---|
| 100-E (parent) | No | 79.9 ± 13.6% | 91.1 ± 1.0% |
| BIM100-E-D1A-L-7 | No | 83.2 ± 1.8% | 92.0 ± 2.2% |
| p-value | | 0.76 | 0.62 |
| BIM100-E-D1A-L-5 | Yes | 10.2 ± 8.2% | 87.4 ± 3.9% |
| p-value | | 0.0034 | 0.26 |

3.6 Non-CRISPR BIM Robustness

In order to demonstrate that non-CRISPR BIMs are more phage robust than CRISPR-mediated BIMs, four parameters were measured: 1) efficiency of plaquing of two phages on each BIM, 2) range of phage resistance (i.e. number of non-identical phages to which the BIM is resistant), 3) phage escape mutant plaque size and 4) phage escape mutant propagation ability.

Firstly, it is clear from the results shown in Table 13 that BIM100-E-D1A-L-5 (non-CRISPR) has an approximately equal and high level of resistance to phage 100-E-D1A-L as BIM100-E-D1A-L-7 (CRISPR), and has a broader range of resistance compared to BIM100-E-D1A-L-7, being resistant to both infecting phages of 100-E. The CRISPR-mediated resistance of BIM100-E-D1A-L-7 renders this BIM insensitive to one phage only (i.e. the phage that was used in the challenge to generate the BIM). This trend is also upheld for all four phages infecting 100-E in the DSM collection, with BIM100-E-D1A-L-7 being sensitive to three of four phages and BIM100-E-D1A-L-5 being resistant to all four phages (data not shown).

Secondly, as well as exhibiting a broader phage resistance/insensitivity, phage escape mutants capable of producing plaques on BIM100-E-D1A-L-5 (NCEMs) are less virulent than those obtained on BIM100-E-D1A-L-7 (CEMs), using plaque size and propagation ability as measures of virulence, as shown in table 17.

TABLE 17

Plaque sizes of wild type phage 100-E-D1A-L and escape mutants on *S. thermophilus* 100-E parent and derived BIMs.

| Strain | Phage | EOP | Plaque size (mm) | p value |
|---|---|---|---|---|
| 100-E (parent) | 100-E-D1A-L (wild type) | 1 | 1.39 ± 0.35 (n = 10) | |
| BIM100-E-D1A-L-7 | 100-E-D1A-L (CEM) | $9.7 \times 10^{-7}$ | 1.35 ± 0.11 (n = 3) | 0.85 |
| BIM100-E-D1A-L-5 | 100-E-D1A-L (NCEM) | $2.9 \times 10^{-6}$ | 0.88 ± 0.19 (n = 5) | 0.01 |

Table 17 above shows the plaque sizes of wild type phage 100-E-D1A-L and both NCEM and CEM phages. It is clear that OEMs approximately maintain the plaque size of the wild type phage, whereas NCEMs have a markedly reduced plaque size. This phenomenon is also illustrated in FIG. 9.

TABLE 18

Relative EOP of wild type phage 100-E-D1A-L and escape mutants on *S. thermophilus* 100-E parent and derived BIMs.

| Strain | Phage | EOP (1° propagation) | EOP (2° propagation) |
|---|---|---|---|
| 100-E (parent) | 100-E-D1A-L (wild type) | 1 | 1 |
| BIM100-E-D1A-L-7 | 100-E-D1A-L (CEM) | 3.2 | 0.5 |
| BIM100-E-D1A-L-5 | 100-E-D1A-L (NCEM) | $1.2 \times 10^{-4}$ | $6.0 \times 10^{-7}$ |

Table 18 above details the relative EOP of the wild type phage on 100-E (parent) and phage escape mutants BIM100-E-D1A-L-5 and BIM100-E-D1A-L-7 on their respective hosts, over the course of two phage propagations (as outlined in the MATERIALS AND METHODS). It is clear that while the CEM phage could quickly overcome the CRISPR based resistance to propagate to wild type phage levels, the NCEM phage was unable to do so. In fact, while a relatively low level of propagation was achieved from a plaque in the first round, it appears that none was achieved in the second round, with the reduction in detected phage approximately reflecting the dilution factor in the second propagation. Taken together, these data clearly show the higher level of robustness of non-CRISPR BIMs against phage challenges relative to those utilising CRISPR.

The invention claimed is:

1. A bacteriophage insensitive mutant of a parent strain of *Streptococcus thermophilus*, wherein the bacteriophage insensitive mutant is generated by exposing the *Streptococcus thermophilus* parent strain to an isolated bacteriophage wherein the bacteriophage insensitive mutant is suitable for use in food or feed, and wherein the bacteriophage insensitive mutant has an increased sedimentation rate and/or an increased chain formation compared to the parent strain, wherein the parent strain is deposited as CBS136255, CBS136256 or CBS138555.

2. The bacteriophage insensitive mutant according to claim 1, having a phage adsorption percentage of 60% or less, 55% or less, or 50% or less compared to the phage adsorption of the parent strain.

3. The bacteriophage insensitive mutant according claim 2, wherein the bacteriophage comprises at least one nucleotide sequence selected from the group consisting of SEQ ID NO: 1, SEQ ID NO: 2, SEQ ID NO: 3, SEQ ID NO: 4 and SEQ ID NO: 5.

4. A starter culture composition suitable for inoculation of a medium to be fermented on an industrial scale comprising the bacteriophage insensitive mutant according to claim 1.

5. The starter culture composition according to claim 4, wherein the starter culture composition is frozen, freeze dried, or in liquid form.

6. A container comprising the bacteriophage insensitive mutant according to claim 1, or comprising a starter culture composition comprising the mutant of claim 1.

7. The bacteriophage insensitive mutant of claim 1, which has reduced phage adsorption, compared to the phage adsorption of the parent strain, to one or more phages that comprise a nucleotide sequence selected from the group consisting of SEQ ID NO: 1, SEQ ID NO: 2, SEQ ID NO: 3, SEQ ID NO: 4 and SEQ ID NO: 5 or that comprise a nucleotide sequence having at least 80% sequence identity with the nucleotide sequence selected from the group consisting of SEQ ID NO: 1, SEQ ID NO: 2, SEQ ID NO: 3, SEQ ID NO: 4 and SEQ ID NO: 5.

8. The bacteriophage insensitive mutant of claim 7, which has reduced phage adsorption, compared to the phage adsorption of the parent strain, to one or more that comprise a nucleotide sequence having at least 85% sequence identity with the nucleotide sequence selected from the group consisting of SEQ ID NO: 1, SEQ ID NO: 2, SEQ ID NO: 3, SEQ ID NO: 4 and SEQ ID NO: 5.

9. The bacteriophage insensitive mutant of claim 8, wherein the parent strain is bacteriophage sensitive.

10. The bacteriophage insensitive mutant of claim 9, which mutant has CRISPR loci which is identical to the CRISPR loci of the bacteriophage sensitive *Streptococcus thermophilus* parent strain.

11. The starter culture composition of claim 4, in combination with further comprising a cryoprotectant.

12. The starter culture composition of claim 4, further comprising *L. bulgaricus* or *Lactobacillus delbrueckii* subsp. *bulgaricus.*

13. The bacteriophage insensitive mutant of claim 1 which has an increased sedimentation rate compared to the parent strain.

14. The bacteriophage insensitive mutant of claim 1 which has an increased chain formation compared to the parent strain.

15. A starter culture composition suitable for inoculation of a medium to be fermented on an industrial scale comprising the bacteriophage insensitive mutant according to claim 7.

16. The starter culture composition of claim 15, further comprising *L. bulgaricus* or *Lactobacillus delbrueckii* subsp. *bulgaricus.*

17. A dairy product comprising the starter culture composition of claim 4.

18. A dairy product comprising the starter culture composition of claim 5.

19. The dairy product of claim 17, which is a fermented milk product or cheese.

20. The dairy product of claim 18, which is a fermented milk product or cheese.

* * * * *